United States Patent
Shoji et al.

(10) Patent No.: US 11,208,421 B2
(45) Date of Patent: Dec. 28, 2021

(54) 2-CARBOXYPENAM COMPOUND OR SALT THEREOF, PHARMACEUTICAL COMPOSITION CONTAINING NOVEL 2-CARBOXYPENAM COMPOUND OR SALT THEREOF, AND APPLICATIONS THEREOF

(71) Applicant: FUJIFILM Corporation, Tokyo (JP)

(72) Inventors: Muneo Shoji, Toyama (JP); Kentaro Furuya, Toyama (JP); Kei Matsuura, Toyama (JP); Hiromi Hayashi, Toyama (JP); Tetsuya Matsushita, Toyama (JP); Hirofumi Omura, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 20 days.

(21) Appl. No.: 16/839,563

(22) Filed: Apr. 3, 2020

(65) Prior Publication Data

US 2020/0239495 A1 Jul. 30, 2020

Related U.S. Application Data

(63) Continuation of application No. PCT/JP2018/037355, filed on Oct. 5, 2018.

(30) Foreign Application Priority Data

Oct. 5, 2017 (JP) .............................. JP2017-194763

(51) Int. Cl.
C07D 499/897 (2006.01)
(52) U.S. Cl.
CPC ................................ *C07D 499/897* (2013.01)
(58) Field of Classification Search
CPC .................................................. C07D 499/897
See application file for complete search history.

(56) References Cited

U.S. PATENT DOCUMENTS

| 5,300,497 | A | 4/1994 | Ochiai et al. |
| 5,506,225 | A | 4/1996 | Iwata et al. |
| 2014/0162995 | A1 | 6/2014 | Bhagwat et al. |
| 2014/0249126 | A1 | 9/2014 | Liao et al. |

FOREIGN PATENT DOCUMENTS

| EP | 0 421 752 A2 | 4/1991 |
| JP | 62-000088 A | 1/1987 |
| JP | 63-183588 A | 7/1988 |
| JP | 3-271292 A | 12/1991 |
| JP | 4-74182 A | 3/1992 |
| JP | 6-504760 A | 6/1994 |
| JP | 10-182654 A | 7/1998 |
| JP | 2014-514305 A | 6/2014 |
| JP | 2014-528965 A | 10/2014 |
| WO | 2013/052568 A1 | 4/2013 |

OTHER PUBLICATIONS

Office Action dated May 11, 2021 in Japanese Application No. 2019-547029.
Extended European Search Report dated Aug. 6, 2020, from the European Patent Office in European Application No. 18864010.6.
Livermore, "Multiple Mechanisms of Antimicrobial Resistance in *Pseudomonas aeruginosa*: Our Worst Nightmare?", Antimicrobial Resistance, Clinical Infectious Diseases, vol. 34, 2002, pp. 634-640.
Tojo et al. "Dissemination in Japan of multidrug-resistant *Pseudomonas aeruginosa* isolates producing IMP-type metallo-β-lactamases and AAC(6')-Iae/AAC(6')-Ib", Journal of Infection and Chemotherapy, vol. 20, 2014, pp. 586-588.
"Surveillance on *Pseudomonas aeruginosa* Isoltaed in GIFU Prefecture (2004)", The Japanese Journal of Antibiotics, vol. 59, No. 5, 2006, pp. 355-363.
Farrell et al., "Ceftolozane/tazobactam activity tested against Gram-negative bacterial isolates from hospitalised patients with pneumonia in US and European medical centres (2012)", International Journal of Antimicrobial Agents, vol. 43, 2014, pp. 533-539.
Huband et al., "In Vitro Activity of Ceftazidime-Avibactam against Contemporary *Pseudomonas aeruginosa* Isolates from U.S. Medical Centers by Census Region, 2014", Antimicrobial Agents and Chemotherapy, vol. 60, No. 4, Apr. 2016, pp. 2537-2541.
International Search Report dated Dec. 18, 2018 from the International Searching Authority in International Application No. PCT/JP2018/037355.
International Preliminary Report on Patentability dated Apr. 8, 2020 from the International Bureau in International Application No. PCT/JP2018/037355.
Written Opinion dated Dec. 18, 2018 from the International Bureau in International Application No. PCT/JP2018/037355.

*Primary Examiner* — Paul V Ward
(74) *Attorney, Agent, or Firm* — Sughrue Mion, PLLC

(57) ABSTRACT

An object of the present invention is to provide a compound and a pharmaceutical composition which exhibit strong antibacterial activity against Gram-negative bacteria and drug-resistant Gram-negative bacteria. According to the present invention, a compound represented by General Formula [1] (the reference signs in the formula have the same definitions as those described in the present specification) or a salt thereof has strong antibacterial activity against Gram-negative bacteria such as *Pseudomonas aeruginosa* and drug-resistant Gram-negative bacteria including multidrug-resistant *Pseudomonas aeruginosa*, and the pharmaceutical composition containing the compound or a salt thereof is useful as an antibacterial agent.

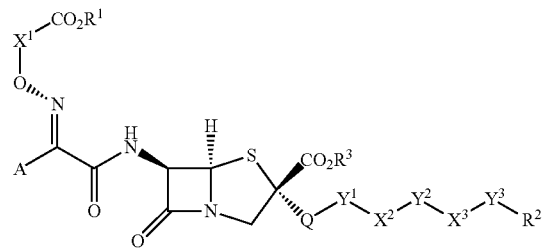

14 Claims, No Drawings

2-CARBOXYPENAM COMPOUND OR SALT THEREOF, PHARMACEUTICAL COMPOSITION CONTAINING NOVEL 2-CARBOXYPENAM COMPOUND OR SALT THEREOF, AND APPLICATIONS THEREOF

CROSS-REFERENCE TO RELATED APPLICATIONS

This application is a Continuation of PCT International Application No. PCT/JP2018/037355 filed on Oct. 5, 2018, which claims priority under 35 U.S.C. § 119(a) to Japanese Patent Application No. 2017-194763 filed on Oct. 5, 2017. Each of the above application(s) is hereby expressly incorporated by reference, in its entirety, into the present application.

BACKGROUND OF THE INVENTION

1. Field of the Invention

The present invention relates to a novel 2-carboxypenam derivative or a salt thereof exhibiting strong antibacterial activity against Gram-negative bacteria, particularly, *Pseudomonas aeruginosa*, a pharmaceutical composition containing the novel 2-carboxypenam derivative or a salt thereof, and applications thereof.

2. Description of the Related Art

Gram-negative bacteria have an outer membrane formed of a lipid bilayer that is not found in Gram-positive bacteria, and are difficult for drugs to penetrate. Therefore, drug resistance of the Gram-negative bacteria tends to be stronger than that of Gram-positive bacteria. Gram-negative bacteria have a plurality of drug efflux proteins which are involved in drug resistance (Clinical Infectious Diseases (Clin Infect Dis), 2002, No. 34, pp. 634-640).

It is known that among Gram-negative bacteria, *Pseudomonas aeruginosa* particularly has a strong tendency to exhibit natural resistance to various antibacterial agents. *Pseudomonas aeruginosa* is an attenuated bacterium that is widely resident in the natural environment and living environment, and usually does not exhibit pathogenicity to healthy individuals. However, for patients with serious underlying diseases, patients immunosuppressed by transplantation or the like (immunocompromised host), and patients who underwent medical catheterization, tracheal intubation, surgical operation, and the like, *Pseudomonas aeruginosa* is a pathogen that causes severe acute infections such as sepsis. That is, *Pseudomonas aeruginosa* is one of the main causative bacteria of opportunistic infections and nosocomial infections.

Conventionally, infections caused by *Pseudomonas aeruginosa* have been treated with drugs having activity against *Pseudomonas aeruginosa*, such as carbapenem-based drugs, quinolone-based drugs, and/or aminoglycoside-based drugs.

However, in recent years, *Pseudomonas aeruginosa* which has acquired resistance to these drugs has been clinically isolated in medical practice (Journal of Infection and Chemotherapy, 2014, No. 20, pp. 586-588), and multidrug-resistant *Pseudomonas aeruginosa* which has acquired resistance to all of the above three kinds of drugs has also been isolated (The Japanese Journal of Antibiotics (Jpn. J. Antibiotics), 2006, No. 59, pp. 355-363). Furthermore, bacteria have been isolated which are resistant to ceftolozan/tazobactam or ceftazidime/avibactam improved in terms of the activity against *Pseudomonas aeruginosa* by using cephalosporin-based drugs (International Journal of Antimicrobial Agents (Int. J. Antimicrob. Agents), 2014, No. 43, pp. 533-539, Antimicrobial Agents and Chemotherapy, 2016, No. 60, pp. 2537-2541).

SUMMARY OF THE INVENTION

Infections caused by multidrug-resistant *Pseudomonas aeruginosa* have few effective therapeutic agents and are a major problem worldwide as intractable diseases.

It is desired to provide compounds and pharmaceutical compositions that exhibit strong antibacterial activity against Gram-negative bacteria and drug-resistant Gram-negative bacteria. Furthermore, it is desired to provide compounds and pharmaceutical compositions that exhibit strong antibacterial activity against drug-resistant *Pseudomonas aeruginosa*, particularly, multidrug-resistant *Pseudomonas aeruginosa*.

Under these circumstances, the inventors of the present invention have conducted intensive studies. As a result, the inventors have found that a compound represented by General Formula [1] or a salt thereof has excellent solubility in water and exhibits strong antibacterial activity against gram-negative bacteria such as *Pseudomonas aeruginosa* and drug-resistant gram-negative bacteria including multidrug-resistant *Pseudomonas aeruginosa*, and have accomplished the present invention.

The present invention provides the following.

<1> A compound represented by General Formula [1] or a salt thereof.

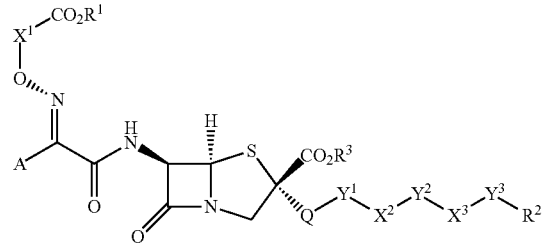

General Formula [1]
"In the formula,
$R^1$ represents a hydrogen atom or a carboxyl protecting group;
$R^2$ represents an aryl group which may be substituted or a heterocyclic group which may be substituted;
$R^3$ represents a hydrogen atom or a carboxyl protecting group;
$X^1$ represents a $C_{1-6}$ alkylene group which may be substituted, a $C_{2-6}$ alkenylene group which may be substituted, a $C_{2-6}$ alkynylene group which may be substituted, a divalent cyclic hydrocarbon group which may be substituted, or a divalent monocyclic saturated heterocyclic group which may be substituted;
A represents a heterocyclic group which may be substituted;
Q represents a thio group;
$Y^1$ represents a $C_{1-6}$ alkylene group which may be substituted, a $C_{2-6}$ alkenylene group which may be substituted, a $C_{2-6}$ alkynylene group which may be substituted, a group represented by Formula —N=CH—CH=N—, or a bond;

$X^2$ represents a group represented by General Formula —NR$^4$— (where, R$^4$ represents a hydrogen atom, a $C_{1-6}$ alkyl group which may be substituted, or a hydroxyl group which may be protected), a group represented by General Formula —N$^+$R$^5$R$^6$— (where, R$^5$ and R$^6$ are the same as or different from each other and each represent a $C_{1-6}$ alkyl group which may be substituted, or in combination represent a $C_{2-6}$ alkylene group which may be substituted or a $C_{2-6}$ alkenylene group which may be substituted), a group represented by General Formula —NR$^7$—C(=O)—NR$^8$— (where, R$^7$ and R$^8$ are the same as or different from each other and each represent a hydrogen atom, a $C_{1-6}$ alkyl group which may be substituted, or a hydroxyl group which may be protected), a divalent cyclic amino group which may be substituted, or a bond;

$Y^2$ represents a $C_{1-6}$ alkylene group which may be substituted, a $C_{2-6}$ alkenylene group which may be substituted, a $C_{2-6}$ alkynylene group which may be substituted, or a bond;

$X^3$ represents a group represented by General Formula —NR$^9$— (where, R$^9$ represents a hydrogen atom, a $C_{1-6}$ alkyl group which may be substituted or a hydroxyl group which may be protected) or a bond; and $Y^3$ represents a group represented by —C(=O)— or —C(=O)—C(=O)—, a group represented by General Formula —C(=O)—C(=NR$^{10}$)— (where, R$^{10}$ represents a hydrogen atom, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, a cyclic amino group which may be substituted, an amino group which may be substituted, an amino group which may be protected, or a hydroxyl group which may be protected), or a divalent heterocyclic group which may be substituted."

<2> The compound or a salt thereof according to <1>, wherein R$^2$ represents an aryl group which may be substituted.

<3> The compound or a salt thereof according to <1> or <2>, wherein A represents a monocyclic heterocyclic group which may be substituted.

<4> The compound or a salt thereof according to any one of <1> to <3>, wherein X$^1$ represents a $C_{1-6}$ alkylene group which may be substituted.

<5> The compound or a salt thereof according to any one of <1> to <4>, wherein Y$^1$ represents a $C_{1-6}$ alkylene group which may be substituted, a $C_{2-6}$ alkenylene group which may be substituted, a group represented by Formula —N=CH—CH=N—, or a bond.

<6> The compound or a salt thereof according to any one of <1> to <5>, wherein X$^2$ represents a group represented by General Formula —NR$^{4a}$— (where, R$^{4a}$ represents a hydrogen atom), a group represented by General Formula —N$^+$R$^{5a}$R$^{6a}$— (where, R$^{5a}$ and R$^{6a}$ in combination represent a $C_{2-6}$ alkylene group which may be substituted), a group represented by General Formula —NR$^{7a}$—C(=O)—NR$^{8a}$— (where, R$^{7a}$ and R$^{8a}$ are the same as or different from each other and each represent a hydrogen atom or a hydroxyl group which may be protected), a divalent cyclic amino group which may be substituted, or a bond.

<7> The compound or a salt thereof according to any one of <1> to <6>, wherein Y$^2$ represents a $C_{1-6}$ alkylene group which may be substituted or a bond.

<8> The compound or a salt thereof according to any one of <1> to <7>, wherein X$^3$ represents a group represented by General Formula —NR$^{9a}$— (where, R$^{9a}$ represents a hydrogen atom) or a bond.

<9> The compound or a salt thereof according to any one of <1> to <8>, wherein Y$^3$ represents a group represented by Formula —C(=O)— or —C(=O)—C(=O)—, a group represented by General Formula —C(=O)—C(=NR$^{10a}$)— (where, R$^{10a}$ represents a $C_{1-6}$ alkylamino group which may be substituted, a cyclic amino group which may be substituted, an amino group which may be substituted, or a hydroxyl group which may be protected), or a divalent heterocyclic group which may be substituted.

<10> The compound or a salt thereof according to any one of <1> to <9>, wherein R$^3$ represents a hydrogen atom.

<11> The compound or a salt thereof according to any one of <1> to <10>, wherein R$^1$ represents a hydrogen atom.

<12> The compound or a salt thereof according to any one of <1> to <11>, wherein R$^2$ represents a phenyl group which may be substituted;

A represents a monocyclic nitrogen and sulfur-containing heterocyclic group which may be substituted;

$X^1$ represents a $C_{1-3}$ alkylene group which may be substituted;

$Y^1$ represents a $C_{1-6}$ alkylene group which may be substituted, a $C_{2-6}$ alkenylene group which may be substituted, or a bond;

$X^2$ represents a group represented by General Formula —NR$^{4a}$— (where, R$^{4a}$ represents a hydrogen atom), a group represented by General Formula —N$^+$R$^{5a}$R$^{6a}$— (where, R$^{5a}$ and R$^{6a}$ in combination represent a $C_{2-6}$ alkylene group which may be substituted), a divalent cyclic amino group which may be substituted, or a bond; and $Y^2$ represents a $C_{1-3}$ alkylene group or a bond.

<13> A pharmaceutical composition comprising the compound or a salt thereof according to any one of <1> to <12>.

<A> A method for treating infections caused by Gram-negative bacteria or drug-resistant Gram-negative bacteria, comprising administering the compound or a salt thereof according to any one of <1> to <12> to a subject.

<B> The compound or a salt thereof according to any one of <1> to <12> that is used for treating infections caused by Gram-negative bacteria or drug-resistant Gram-negative bacteria.

<C> Use of the compound or a salt thereof according to any one of <1> to <12> for manufacturing a pharmaceutical composition.

<D> Use of the compound or a salt thereof according to any one of <1> to <12> for manufacturing a pharmaceutical composition for treating infections caused by Gram-negative bacteria or drug-resistant Gram-negative bacteria.

The compound according to an embodiment of the present invention or a salt thereof exhibits strong antibacterial activity against Gram-negative bacteria and drug-resistant Gram-negative bacteria, and is useful as a medicine. The pharmaceutical composition according to an embodiment of the present invention exhibits strong antibacterial activity against Gram-negative bacteria and drug-resistant Gram-negative bacteria.

DESCRIPTION OF THE PREFERRED EMBODIMENTS

Hereinafter, the present invention will be specifically described.

In the present specification, unless otherwise specified, "%" means "% by mass".

In the present specification, unless otherwise specified, each term has the following meaning.

The halogen atom means a fluorine atom, a chlorine atom, a bromine atom, or an iodine atom.

The $C_{1-6}$ alkyl group means, for example, a linear or branched $C_{1-6}$ alkyl group such as a methyl, ethyl, propyl, isopropyl, butyl, sec-butyl, isobutyl, tert-butyl, pentyl, isopentyl, or hexyl group.

The $C_{1-3}$ alkyl group means a methyl, ethyl, propyl, or isopropyl group.

The $C_{2-6}$ alkenyl group means, for example, a linear or branched $C_{2-6}$ alkenyl group such as a vinyl, allyl, propenyl, isopropenyl, butenyl, isobutenyl, 1,3-butadienyl, pentenyl, or hexenyl group.

The $C_{2-6}$ alkynyl group means a linear or branched $C_{2-6}$ alkynyl group such as an ethynyl, propynyl, butynyl, pentynyl, or hexynyl group.

The $C_{3-8}$ cycloalkyl group means a $C_{3-8}$ cycloalkyl group such as a cyclopropyl, cyclobutyl, cyclopentyl, or cyclohexyl group.

The aryl group means, for example, a $C_{6-18}$ aryl group such as a phenyl or naphthyl group.

The aryl $C_{1-6}$ alkyl group means, for example, an aryl $C_{1-6}$ alkyl group such as a benzyl, diphenylmethyl, trityl, phenethyl, or naphthylmethyl group.

The $C_{1-6}$ alkylene group means a linear or branched $C_{1-6}$ alkylene group such as a methylene, ethylene, propylene, butylene, or hexylene group.

The $C_{1-3}$ alkylene group means a methylene, ethylene, or propylene group.

The $C_{2-6}$ alkylene group means a linear or branched $C_{2-6}$ alkylene group such as an ethylene, propylene, butylene, or hexylene group.

The $C_{2-6}$ alkenylene group means a linear or branched $C_{2-6}$ alkenylene group such as a vinylene, propenylene, butenylene, or pentenylene group.

The $C_{2-6}$ alkynylene group means a linear or branched $C_{2-6}$ alkynylene group such as an ethynylene, propynylene, butynylene, or pentynylene group.

The $C_{1-6}$ alkoxy group means, for example, a linear or branched $C_{1-6}$ alkoxy group such as a methoxy, ethoxy, propoxy, isopropoxy, butoxy, isobutoxy, sec-butoxy, tert-butoxy, pentyloxy, or hexyloxy group.

The $C_{1-6}$ alkoxy $C_{1-6}$ alkyl group means, for example, a $C_{1-6}$ alkyloxy $C_{1-6}$ alkyl group such as a methoxymethyl or 1-ethoxyethyl group.

The $C_{2-12}$ alkanoyl group means, for example, a linear or branched $C_{2-12}$ alkanoyl group such as an acetyl, propionyl, valeryl, isovaleryl, or pivaloyl group.

The aroyl group means, for example, a benzoyl or naphthoyl group.

The acyl group means, for example, a formyl group, a succinyl group, a glutaryl group, a maleoyl group, a phthaloyl group, a $C_{2-12}$ alkanoyl group, or an aroyl group.

The $C_{1-6}$ alkoxycarbonyl group means, for example, a linear or branched $C_{1-6}$ alkyloxycarbonyl group such as a methoxycarbonyl, ethoxycarbonyl, isopropoxycarbonyl, tert-butoxycarbonyl, or 1,1-dimethylpropoxycarbonyl group.

The aryl $C_{1-6}$ alkoxycarbonyl group means, for example, an ar$C_{1-6}$ alkyloxycarbonyl group such as a benzyloxycarbonyl or phenethyloxycarbonyl group.

The aryloxycarbonyl group means, for example, a phenyloxycarbonyl or naphthyloxycarbonyl group.

The $C_{1-6}$ alkylamino group means a linear or branched $C_{1-6}$ alkylamino group such as a methylamino, ethylamino, propylamino, isopropylamino, butylamino, sec-butylamino, tert-butylamino, pentylamino, or hexylamino group.

The di($C_{1-6}$ alkyl) amino group means a linear or branched di($C_{1-6}$ alkyl) amino group such as a dimethylamino, diethylamino, dipropylamino, diisopropylamino, dibutylamino, di(tert-butyl) amino, dipentylamino, dihexylamino, (ethyl)(methyl) amino, or (methyl)(propyl) amino group.

The $C_{1-6}$ alkylthio group means, for example, a $C_{1-6}$ alkylthio group such as a methylthio, ethylthio, or propylthio group.

The $C_{1-6}$ alkylsulfonyl group means, for example, a $C_{1-6}$ alkylsulfonyl group such as a methylsulfonyl, ethylsulfonyl, or propylsulfonyl group.

The arylsulfonyl group means, for example, a benzenesulfonyl, p-toluenesulfonyl, or naphthalenesulfonyl group.

The $C_{1-6}$ alkylsulfonyloxy group means, for example, a $C_{1-6}$ alkylsulfonyloxy group such as a methylsulfonyloxy an ethylsulfonyloxy group.

The arylsulfonyloxy group means a benzenesulfonyloxy or p-toluenesulfonyloxy group.

The silyl group means, for example, a trimethylsilyl, triethylsilyl, or tributylsilyl group.

The cyclic amino group means a cyclic amino group which contains one or more nitrogen atoms as hetero atoms forming a ring, such as a aziridinyl, azetidinyl, pyrrolyl, dihydropyrrolyl, pyrrolidinyl, tetrahydropyridyl, piperidinyl, homopiperidinyl, pyrazolyl, pyrazolinyl, pyrazolidinyl, imidazolyl, imidazolinyl, imidazolidinyl, thiazolinyl, thiazolidinyl, dihydrothiadiazolyl, piperazinyl, homopiperazinyl, morpholinyl, homomorpholinyl, or thiomorpholinyl group, and may further contain one or more oxygen atoms or sulfur atoms.

The monocyclic nitrogen-containing heterocyclic group means a monocyclic nitrogen-containing heterocyclic group containing only nitrogen atoms as hetero atoms forming a ring. Examples of the monocyclic nitrogen-containing heterocyclic group include an azetidinyl group; a 5-membered nitrogen-containing heterocyclic group such as a pyrrolidinyl, pyrrolinyl, pyrrolyl, imidazolidinyl, imidazolinyl, imidazolyl, pyrazolidinyl, pyrazolinyl, pyrazolyl, triazolyl, or tetrazolyl group; a 6-membered nitrogen-containing heterocyclic group such as piperidyl, tetrahydropyridyl, pyridyl, piperazinyl, pyrazinyl, pyridazinyl, pyrimidinyl, or homopiperazinyl group; a 7-membered nitrogen-containing heterocyclic group such as a homopiperidinyl group; and an 8-membered nitrogen-containing heterocyclic group such as an octahydroazocinyl group.

The monocyclic oxygen-containing heterocyclic group means a monocyclic oxygen-containing heterocyclic group containing only oxygen atoms as hetero atoms forming a ring. Examples of the monocyclic oxygen-containing heterocyclic group include a 5-membered oxygen-containing heterocyclic group such as a tetrahydrofuranyl or furanyl group; and a 6-membered oxygen-containing heterocyclic group such as a tetrahydropyranyl or pyranyl group.

The monocyclic sulfur-containing heterocyclic group means a thienyl group or the like.

The monocyclic nitrogen and oxygen-containing heterocyclic group means a monocyclic nitrogen and oxygen-containing heterocyclic group containing only a nitrogen atom and an oxygen atom as hetero atoms forming a ring. Examples of the monocyclic nitrogen and oxygen-containing heterocyclic group include a 5-membered nitrogen and oxygen-containing heterocyclic group such as an oxazolyl, oxazolidinyl, isoxazolyl, or oxadiazolyl group; and a and a 6-membered nitrogen and oxygen-containing heterocyclic group such as a homomorpholinyl group.

The monocyclic nitrogen and sulfur-containing heterocyclic group means a monocyclic nitrogen and sulfur-containing heterocyclic group containing only a nitrogen atom and a sulfur atom as hetero atoms forming a ring. Examples of the monocyclic nitrogen and sulfur-containing heterocyclic group include a 5-membered nitrogen and sulfur-containing heterocyclic group such as a thiazolyl, isothiazolyl, or thiadiazolyl group; and a 6-membered nitrogen and sulfur-containing heterocyclic group such as a thiomorpholinyl, 1-oxidethiomorpholinyl, or 1,1-dioxidethiomorpholinyl group.

The monocyclic heterocyclic group means a monocyclic nitrogen-containing heterocyclic group, a monocyclic oxygen-containing heterocyclic group, a monocyclic sulfur-containing heterocyclic group, a monocyclic nitrogen and oxygen-containing heterocyclic group, or a monocyclic nitrogen and sulfur-containing heterocyclic group.

The monocyclic saturated heterocyclic group means a monocyclic heterocyclic group not containing a multiple bond. Examples of the monocyclic saturated heterocyclic group include aziridinyl, azetidinyl, pyrrolidinyl, piperidinyl, imidazolidinyl, pyrazolidinyl, piperazinyl, tetrahydrofuranyl, tetrahydropyranyl, and morpholinyl groups.

The bicyclic nitrogen-containing heterocyclic group means a bicyclic nitrogen-containing heterocyclic group which contains only nitrogen atoms as hetero atoms forming a ring such as an indolinyl, indolyl, isoindolinyl, isoindolyl, benzimidazolyl, indazolyl, benzotriazolyl, quinolyl, tetrahydroquinolinyl, quinolyl, tetrahydroisoquinolinyl, isoquinolinyl, quinolizinyl, cinnolinyl, phthalazinyl, quinazolinyl, dihydroquinoxalinyl, quinoxalinyl, naphthyridinyl, purinyl, pyrrolopyridinyl, dihydrocyclopentapyridinyl, pteridinyl, or quinuclidinyl group.

The bicyclic oxygen-containing heterocyclic group means a bicyclic oxygen-containing heterocyclic group containing only oxygen atoms as hetero atoms forming a ring such as a 2,3-dihydrobenzofuranyl, benzofuranyl, isobenzofuranyl, chromanyl, chromenyl, isochromanyl, 1,3-benzodioxolyl, 1,3-benzodioxanyl, or 1,4-benzodioxanyl group.

The bicyclic sulfur-containing heterocyclic group means a bicyclic sulfur-containing heterocyclic group containing only sulfur atoms as hetero atoms forming a ring such as a 2,3-dihydrobenzothienyl or benzothienyl group.

The bicyclic nitrogen and oxygen-containing heterocyclic group means a bicyclic nitrogen and oxygen-containing heterocyclic group containing only a nitrogen atom and an oxygen atom as hetero atoms forming a ring such as a benzoxazolyl, benzisoxazolyl, benzoxadiazolyl, benzomorpholinyl, dihydropyranopyridyl, dihydrodioxynopyridyl, or dihydropyridoxazinyl group.

The bicyclic nitrogen and sulfur-containing heterocyclic group means a bicyclic nitrogen and sulfur-containing heterocyclic group containing a nitrogen atom and a sulfur atom as hetero atoms forming a ring such as a benzothiazolyl, benzisothiazolyl, or benzothiadiazolyl group.

The bicyclic heterocyclic group means a bicyclic nitrogen-containing heterocyclic group, a bicyclic oxygen-containing heterocyclic group, a bicyclic sulfur-containing heterocyclic group, a bicyclic nitrogen and oxygen-containing heterocyclic group, or a bicyclic nitrogen and sulfur-containing heterocyclic group.

The heterocyclic group means a monocyclic heterocyclic group or a bicyclic heterocyclic group.

The divalent cyclic hydrocarbon group means a group formed by removing two hydrogen atoms, which are bonded to two adjacent atoms, from cyclic hydrocarbon such as cyclopropane-1,2-diyl, cyclobutane-1,3-diyl, cyclobutene-1,3-diyl, cyclopentane-1,3-diyl, cyclopentene-1,3-diyl, cyclopentadiene-1,3-diyl, cyclohexane-1,3-diyl, cyclohexane-1,4-diyl, cyclohexene-1,3-diyl, cyclohexene-1,4-diyl, cyclohexadiene-1,3-diyl, cyclohexadiene-1,4-diyl, cycloheptane-1,3-diyl, cycloheptene-1,4-diyl, cyclooctane-1,3-diyl, benzene-1,3-diyl, and benzene-1,4-diyl.

The divalent monocyclic saturated heterocyclic group is a divalent group formed by further removing any one hydrogen atom from the aforementioned monocyclic heterocyclic group not containing a multiple bond. For example, the divalent monocyclic saturated heterocyclic group means a group formed by further removing any one hydrogen atom from an aziridinyl, azetidinyl, pyrrolidinyl, piperidinyl, imidazolidinyl, pyrazolidinyl, piperazinyl, tetrahydrofuranyl, tetrahydropyranyl, or morpholinyl group, and the like.

The divalent heterocyclic group is a divalent group formed by further removing any one hydrogen atom from the aforementioned heterocyclic group. The divalent heterocyclic group includes a divalent monocyclic heterocyclic group and a divalent bicyclic heterocyclic group.

The divalent monocyclic heterocyclic group is a divalent group formed by further removing any one hydrogen atom from the aforementioned monocyclic heterocyclic group. The divalent monocyclic heterocyclic group includes a divalent monocyclic nitrogen-containing heterocyclic group, a divalent monocyclic oxygen-containing heterocyclic group, a divalent monocyclic sulfur-containing heterocyclic group, a divalent monocyclic nitrogen and oxygen-containing heterocyclic group, and a divalent monocyclic nitrogen and sulfur-containing heterocyclic group.

The divalent bicyclic heterocyclic group is a divalent group formed by further removing any one hydrogen atom from the aforementioned bicyclic heterocyclic group. The divalent bicyclic heterocyclic group includes a divalent bicyclic nitrogen-containing heterocyclic group, a divalent bicyclic oxygen-containing heterocyclic group, a divalent bicyclic sulfur-containing heterocyclic group, a divalent bicyclic nitrogen and oxygen-containing heterocyclic group, and a divalent bicyclic nitrogen and sulfur-containing heterocyclic group.

The divalent cyclic amino group is a divalent group formed by further removing any one hydrogen atom from the aforementioned cyclic amino group. Examples of the divalent cyclic amino group include a divalent group formed by removing any two hydrogen atoms from aziridine, azetidine, pyrrole, dihydropyrrole, pyrrolidine, tetrahydropyridine, piperidine, homopiperidine, pyrazolyl, pyrazoline, pyrazolidine, imidazole, imidazoline, imidazolidine, thiazoline, thiazolidine, dihydrothiadiazole, piperazine, homopiperazine, morpholine, homomorpholine, and thiomorpholine.

Examples of the leaving group include a halogen atom, a $C_{1-6}$ alkylsulfonyloxy group, and an arylsulfonyloxy group. The $C_{1-6}$ alkylsulfonyloxy group or the arylsulfonyloxy group may have a substituent.

The hydroxyl protecting group includes all groups that can be used as a protecting group of general hydroxyl groups. Examples of the hydroxyl protecting group include the groups described in "Protective Groups in Organic Synthesis, W. Greene et al., 4th Edition, pp. 16-299, 2007, John Wiley & Sons, INC". Specifically, examples thereof include a $C_{1-6}$ alkyl group, a $C_{2-6}$ alkenyl group, an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, a $C_{1-6}$ alkylsulfonyl group, an arylsulfonyl group, a silyl group, a tetrahydrofuranyl group, and a tetrahydropyranyl group. These groups may be substituted with one or more groups selected from a substituent group A1.

The amino protecting group includes all groups that can be used as a protecting group of general amino groups. Examples of the amino protecting group include the groups described in "Protective Groups in Organic Synthesis, W. Greene et al., 4th Edition, pp. 696-926, 2007, John Wiley & Sons, INC". Specifically, examples thereof include an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, an aryloxycarbonyl group, a $C_{1-6}$ alkylsulfonyl group, an arylsulfonyl group, and a silyl group. These groups may be substituted with one or more groups selected from the substituent group A1.

The imino protecting group includes all groups that can be used as a protecting group of general imino groups. Examples of the imino protecting group include the groups described in "Protective Groups in Organic Synthesis, W. Greene et al., 4th Edition, pp. 696-868, 2007, John Wiley & Sons, INC". Specifically, examples thereof include an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, an aryloxycarbonyl group, a $C_{1-6}$ alkylsulfonyl group, an arylsulfonyl group, and a silyl group. These groups may be substituted with one or more groups selected from the substituent group A1.

The carboxyl protecting group includes all groups that can be used as a protecting group of general carboxyl groups. Examples of the carboxyl protecting group include the groups described in "Protective Groups in Organic Synthesis, W. Greene et al., 4th Edition, pp. 533-643, 2007, John Wiley & Sons, INC". Specifically, examples thereof include a $C_{1-6}$ alkyl group, a $C_{2-6}$ alkenyl group, an aryl $C_{1-6}$ alkyl group, a $C_{1-6}$ alkoxy $C_{1-6}$ alkyl group, and a silyl group. These groups may be substituted with one or more groups selected from the substituent group A1.

Examples of aliphatic hydrocarbons include pentane, hexane, cyclohexane, heptane, and decahydronaphthalene.

Examples of halogenated hydrocarbons include methylene chloride, chloroform, and dichloroethane.

Examples of alcohols include methanol, ethanol, propanol, 2-propanol, butanol, and 2-methyl-2-propanol.

Examples of ethers include diethyl ether, diisopropyl ether, dioxane, tetrahydrofuran, anisole, ethylene glycol dimethyl ether, diethylene glycol dimethyl ether, and diethylene glycol diethyl ether.

Examples of ketones include acetone, 2-butanone, and 4-methyl-2-pentanone.

Examples of esters include methyl acetate, ethyl acetate, propyl acetate, and butyl acetate.

Examples of amides include N,N-dimethylformamide, N,N-dimethylacetamide, and 1-methyl-2-pyrrolidone.

Examples of nitriles include acetonitrile and propionitrile.

Examples of aromatic hydrocarbons include benzene, toluene, and xylene.

In the present specification, the substituent group means the following.

Substituent group A1:
a hydrogen atom,
a halogen atom,
a cyano group,
a nitro group,
an oxo group,
a $C_{1-6}$ alkyl group which may be substituted with one or more groups selected from a substituent group B2,
a $C_{2-6}$ alkenyl group which may be substituted with one or more groups selected from the substituent group B2,
a $C_{2-6}$ alkynyl group which may be substituted with one or more groups selected from the substituent group B2,
a $C_{1-6}$ alkoxy group which may be substituted with one or more groups selected from the substituent group B2,
an aryloxy group which may be substituted with one or more groups selected from a substituent group B1,
an acyl group which may be substituted with one or more groups selected from the substituent group B1,
a $C_{1-6}$ alkylamino group which may be substituted with one or more groups selected from the substituent group B2,
a di($C_{1-6}$ alkyl)amino group which may be substituted with one or more groups selected from the substituent group B2,
an imino group which may be protected or substituted with one or more groups selected from the substituent group B1,
a $C_{1-6}$ alkylthio group which may be substituted with one or more groups selected from the substituent group B2,
an arylthio group which may be substituted with one or more groups selected from the substituent group B1,
a $C_{1-6}$ alkylsulfonyl group which may be substituted with one or more groups selected from the substituent group B2,
an arylsulfonyl group which may be substituted with one or more groups selected from the substituent group B1,
a $C_{3-8}$ cycloalkyl group which may be substituted with one or more groups selected from the substituent group B1,
an aryl group which may be substituted with one or more groups selected from the substituent group B1,
a heterocyclic group which may be substituted with one or more groups selected from the substituent group B1,
a carbamoyl group which may be substituted with one or more groups selected from the substituent group B1,
a sulfamoyl group which may be substituted with one or more groups selected from the substituent group B1,
a hydroxyl group which may be protected,
an amino group which may be protected, and
a carboxyl group which may be protected.

Substituent group A2:
a hydrogen atom,
a halogen atom,
a cyano group,
a nitro group,
an oxo group,
a $C_{1-6}$ alkoxy group which may be substituted with one or more groups selected from the substituent group B2,
an aryloxy group which may be substituted with one or more groups selected from the substituent group B1,
an acyl group which may be substituted with one or more groups selected from the substituent group B1,
a $C_{1-6}$ alkylamino group which may be substituted with one or more groups selected from the substituent group B2,
a di($C_{1-6}$ alkyl)amino group which may be substituted with one or more groups selected from the substituent group B2,
a $C_{1-6}$ alkylthio group which may be substituted with one or more groups selected from the substituent group B2,
an arylthio group which may be substituted with one or more groups selected from the substituent group B1,
a $C_{1-6}$ alkylsulfonyl group which may be substituted with one or more groups selected from the substituent group B2, an arylsulfonyl group which may be substituted with one or more groups selected from the substituent group B1,
a $C_{3-8}$ cycloalkyl group which may be substituted with one or more groups selected from the substituent group B1,
an aryl group which may be substituted with one or more groups selected from the substituent group B1,
a heterocyclic group which may be substituted with one or more groups selected from the substituent group B1,
a carbamoyl group which may be substituted with one or more groups selected from the substituent group B1,
a sulfamoyl group which may be substituted with one or more groups selected from the substituent group B1,
a hydroxyl group which may be protected,
an amino group which may be protected, and
a carboxyl group which may be protected.
Substituent group B1:
a hydrogen atom,
a halogen atom,
a cyano group,
a nitro group,
an oxo group,
a $C_{1-6}$ alkyl group which may be substituted with one or more groups selected from a substituent group C,
a $C_{2-6}$ alkenyl group which may be substituted with one or more groups selected from the substituent group C,
a $C_{2-6}$ alkynyl group which may be substituted with one or more groups selected from the substituent group C,
a $C_{1-6}$ alkoxy group which may be substituted with one or more groups selected from the substituent group C,
an aryloxy group which may be substituted with one or more groups selected from the substituent group C,
an acyl group which may be substituted with one or more groups selected from the substituent group C,
a $C_{1-6}$ alkylamino group which may be substituted with one or more groups selected from the substituent group C,
a di($C_{1-6}$ alkyl)amino group which may be substituted with one or more groups selected from the substituent group C,
a $C_{1-6}$ alkylthio group which may be substituted with one or more groups selected from the substituent group C,
an arylthio group which may be substituted with one or more groups selected from the substituent group C,
a $C_{1-6}$ alkylsulfonyl group which may be substituted with one or more groups selected from the substituent group C,
an arylsulfonyl group which may be substituted with one or more groups selected from the substituent group C,
a $C_{3-8}$ cycloalkyl group which may be substituted with one or more groups selected from the substituent group C,
an aryl group which may be substituted with one or more groups selected from the substituent group C,
a heterocyclic group which may be substituted with one or more groups selected from the substituent group C,
a carbamoyl group which may be substituted with one or more groups selected from the substituent group C,
a sulfamoyl group which may be substituted with one or more groups selected from the substituent group C,
a hydroxyl group which may be protected,
an amino group which may be protected, and
a carboxyl group which may be protected.
Substituent group B2:
a hydrogen atom,
a halogen atom,
a cyano group,
a nitro group,
an oxo group,
a $C_{1-6}$ alkoxy group which may be substituted with one or more groups selected from the substituent group C,
an aryloxy group which may be substituted with one or more groups selected from the substituent group C,
an acyl group which may be substituted with one or more groups selected from the substituent group C,
a $C_{1-6}$ alkylamino group which may be substituted with one or more groups selected from the substituent group C,
a di($C_{1-6}$ alkyl)amino group which may be substituted with one or more groups selected from the substituent group C,
a $C_{1-6}$ alkylthio group which may be substituted with one or more groups selected from the substituent group C,
an arylthio group which may be substituted with one or more groups selected from the substituent group C,
a $C_{1-6}$ alkylsulfonyl group which may be substituted with one or more groups selected from the substituent group C,
an arylsulfonyl group which may be substituted with one or more groups selected from the substituent group C,
a $C_{3-8}$ cycloalkyl group which may be substituted with one or more groups selected from the substituent group C,
an aryl group which may be substituted with one or more groups selected from the substituent group C,
a heterocyclic group which may be substituted with one or more groups selected from the substituent group C,
a carbamoyl group which may be substituted with one or more groups selected from the substituent group C,
a sulfamoyl group which may be substituted with one or more groups selected from the substituent group C,
a hydroxyl group which may be protected,
an amino group which may be protected, and
a carboxyl group which may be protected.
Substituent group C:
a halogen atom,
a cyano group,
a carbamoyl group,
a $C_{1-6}$ alkyl group,
a $C_{1-6}$ alkoxy group,
an amino which may be protected,
an imino which may be protected,
a hydroxyl group which may be protected, and
a carboxyl group which may be protected.

The $C_{1-6}$ alkylene group, the $C_{2-6}$ alkenylene group, and the $C_{2-6}$ alkynylene group represented by $X^1$, $Y^1$, and $Y^2$ may be substituted with one or more groups selected from the substituent group A2.

The $C_{2-6}$ alkylene or $C_{2-6}$ alkenylene group that $R^5$ and $R^6$ form in combination may be substituted with one or more groups selected from the substituent group A1.

The $C_{1-6}$ alkyl group represented by $R^4$, $R^5$, $R^6$, $R^7$, $R^8$, $R^9$, and $R^{10}$ may be substituted with one or more groups selected from the substituent group A2.

The $C_{2-6}$ alkylene and $C_{2-6}$ alkenylene groups that $R^5$ and $R^6$ form in combination may be substituted with one or more groups selected from the substituent group A1.

The $C_{2-6}$ alkylene group that $R^{5a}$ and $R^{6a}$ form in combination may be substituted with one or more groups selected from the substituent group A1.

The $C_{1-6}$ alkoxy group, the $C_{1-6}$ alkylamino group, the di($C_{1-6}$ alkyl)amino group, and the amino group represented by $R^{10}$ may be substituted with one or more groups selected from the substituent group A2.

The $C_{1-6}$ alkylamino group and the amino group represented by $R^{10}$ may be substituted with one or more groups selected from the substituent group A2.

The cyclic amino group represented by $R^{10}$ and $R^{10a}$ may be substituted with one or more groups selected from the substituent group A1.

The aryl group and the heterocyclic group represented by $R^2$ may be substituted with one or more groups selected from the substituent group A1.

The heterocyclic group represented by A may be substituted with one or more groups selected from the substituent group A1.

The divalent cyclic hydrocarbon group represented by $X^1$ may be substituted with one or more groups selected from the substituent group A1.

The divalent monocyclic saturated heterocyclic group represented by $X^1$ may be substituted with one or more groups selected from the substituent group A1.

The divalent heterocyclic group represented by $Y^3$ may be substituted with one or more groups selected from the substituent group A1.

The divalent cyclic amino group represented by $X^2$ may be substituted with one or more groups selected from the substituent group A1.

As the compound according to the embodiment of the present invention, for example, the following compounds are preferable.

A compound in which $R^1$ represents a hydrogen atom is preferable.

A compound in which $R^2$ represents an aryl group that may be substituted is preferable, and a compound in which $R^2$ represents a phenyl group that may be substituted is more preferable.

As the substituent of the aryl group or the heterocyclic group represented by $R^2$, one or more groups selected from a halogen atom and a hydroxyl group which may be protected are preferable.

A compound in which $R^3$ represents a hydrogen atom is preferable.

$X^1$ is preferably a $C_{1-6}$ alkylene group which may be substituted or a divalent monocyclic saturated heterocyclic group which may be substituted, more preferably a $C_{1-6}$ alkylene group which may be substituted, and even more preferably a $C_{1-3}$ alkylene group which may be substituted.

A compound in which A represents a monocyclic heterocyclic group which may be substituted is preferable. A is more preferably a monocyclic nitrogen-containing heterocyclic group which may be substituted or a monocyclic nitrogen and sulfur-containing heterocyclic group which may be substituted, even more preferably a monocyclic nitrogen and sulfur-containing heterocyclic group, and particularly preferably 2-aminothiazol-4-yl.

$Y^1$ is preferably a $C_{1-6}$ alkylene group which may be substituted, a $C_{2-6}$ alkenylene group which may be substituted, a group represented by Formula —N=CH—CH=N—, or a bond, and more preferably a $C_{1-6}$ alkylene group which may be substituted, a $C_{2-6}$ alkenylene group which may be substituted, or a bond.

$X^2$ is preferably a group represented by General Formula —$NR^{4a}$— (where, $R^{4a}$ represents a hydrogen atom), a group represented by General Formula —$N^+R^{5a}R^{6a}$— (where, $R^{5a}$ and $R^{6a}$ are the same as or different from each other and in combination represent a $C_{2-6}$ alkylene group which may be substituted), a group represented by General Formula —$NR^7$—C(=O)—$NR^8$— (where, $R^{7a}$ and $R^{8a}$ are the same as or different from each other and each represent a hydrogen atom or a hydroxyl group which may be protected), a divalent cyclic amino group which may be substituted, or a bond, and more preferably a group represented by General Formula —$NR^{4a}$— (where, $R^{4a}$ represents a hydrogen atom), a group represented by General Formula —$N^+R^{5a}R^{6a}$— (where, $R^{5a}$ and $R^{6a}$ in combination represent a $C_{2-6}$ alkylene group which may be substituted), a divalent cyclic amino group which may be substituted, or a bond.

$Y^2$ is preferably a $C_{1-6}$ alkylene group which may be substituted or a bond, and more preferably a $C_{1-3}$ alkylene group or a bond.

$X^3$ is preferably a group represented by General Formula —$NR^{9a}$— (where, $R^{9a}$ represents a hydrogen atom) or a bond.

$Y^3$ is preferably a group represented by —C(=O)— or —C(=O)—C(=O)—, a group represented by General Formula —C(=O)—C(=$NR^{10a}$)— (where, $R^{10a}$ represents a $C_{1-6}$ alkylamino group which may be substituted, a cyclic amino group which may be substituted, an amino group which may be substituted, or a hydroxyl group which may be protected), or a divalent heterocyclic group which may be substituted.

More specifically, the following compounds are preferable.

(3R,5R,6R)-6-((Z)-2-(2-aminothiazol-4-yl)-2-(((2-carboxypropan-2-yl)oxy)imino)acetamide)-3-(((R)-2-(2-(2-chloro-3,4-dihydroxyphenyl)-2-oxoacetamide)-3-methoxypropyl)thio)-7-oxo-4-thia-1-azabicyclo[3.2.0]heptane-3-carboxylic acid (compound of Example 3)

(3R,5R,6R)-6-((Z)-2-(2-aminothiazol-4-yl)-2-(((2-carboxypropan-2-yl)oxy)imino)acetamide)-3-(((S)-3-(2-(2-chloro-3,4-dihydroxyphenyl)-2-oxoacetamide)-2-methoxypropyl)thio)-7-oxo-4-thia-1-azabicyclo[3.2.0]heptane-3-carboxylic acid (compound of Example 6)

(3R,5R,6R)-6-((Z)-2-(2-aminothiazol-4-yl)-2-(((2-carboxypropan-2-yl)oxy)imino)acetamide)-3-((2-((Z)-2-(2-chloro-3,4-dihydroxyphenyl)-2-(2-methylhydrazono)acetamide)ethyl)thio)-7-oxo-4-thia-1-azabicyclo[3.2.0]heptane-3-carboxylic acid (compound of Example 8)

(3R,5R,6R)-6-((Z)-2-(2-aminothiazol-4-yl)-2-(((2-carboxypropan-2-yl)oxy)imino)acetamide)-3-((1-((Z)-2-(2-carbamoylhydrazono)-2-(2-chloro-3,4-dihydroxyphenyl)acetyl)azetidin-3-yl)thio)-7-oxo-4-thia-1-azabicyclo[3.2.0]heptane-3-carboxylic acid (compound of Example 11)

(3R,5R,6R)-6-((Z)-2-(2-aminothiazol-4-yl)-2-(((2-carboxypropan-2-yl)oxy)imino)acetamide)-3-((2-(2-chloro-3,4-dihydroxybenzamide)ethyl)thio)-7-oxo-4-thia-1-azabicyclo[3.2.0]heptane-3-carboxylic acid (compound of Example 18)

(3R,5R,6R)-6-((Z)-2-(2-aminothiazol-4-yl)-2-(((2-carboxypropan-2-yl)oxy)imino)acetamide)-3-(((R)-2-(2-chloro-3,4-dihydroxybenzamide)-3-methoxypropyl)thio)-7-oxo-4-thia-1-azabicyclo[3.2.0]heptane-3-carboxylic acid (compound of Example 19)

(3R,5R,6R)-6-((Z)-2-(2-aminothiazol-4-yl)-2-(((2-carboxypropan-2-yl)oxy)imino)acetamide)-3-(((((R)-4-(2-chloro-3,4-dihydroxybenzoyl)morpholin-3-yl)methyl)thio)-7-oxo-4-thia-1-azabicyclo[3.2.0]heptane-3-carboxylic acid (compound of Example 20)

(3R,5R,6R)-6-((Z)-2-(2-aminothiazol-4-yl)-2-(((2-carboxypropan-2-yl)oxy)imino)acetamide)-3-((2-(2-chloro-3,4-dihydroxy-N-methylbenzamide)ethyl)thio)-7-oxo-4-thia-1-azabicyclo[3.2.0]heptane-3-carboxylic acid (Compound of Example 25)

(3R,5R,6R)-6-((Z)-2-(2-aminothiazol-4-yl)-2-(((2-carboxypropan-2-yl)oxy)imino)acetamide)-3-(((((S)-4-(2-chloro-3,4-dihydroxybenzoyl)morpholin-3-yl)methyl)thio)-7-oxo-4-thia-1-azabicyclo[3.2.0]heptane-3-carboxylic acid (compound of Example 27)

(3R,5R,6R)-6-((Z)-2-(2-aminothiazol-4-yl)-2-(((2-carboxypropan-2-yl)oxy)imino)acetamide)-3-((2-(2-(2-chloro-3, 4-dihydroxybenzoyl)hydradienyl)ethyl)thio)-7-oxo-4-thia-1-azabicyclo[3.2.0]heptane-3-carboxylic acid (compound of Example 28)

Examples of the salt of the compound represented by General Formula [1] include salts in a basic group such as a generally known amino group or in an acidic group such as a hydroxyl or carboxyl group.

Examples of the salts in the basic group include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salts in the acidic group include salts with alkali metals such as sodium and potassium; salts with alkaline earth metals such as calcium and magnesium; ammonium salts; salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine, and the like.

Among the above salts, for example, pharmacologically acceptable salts are preferable.

In a case where the compound represented by General Formula [1] or a salt thereof has isomers (for example, an optical isomer, a geometric isomer, a tautomer, and the like), the present invention includes the isomers as well as solvates, hydrates, and various forms of crystals.

The compound according to the embodiment of the present invention or a salt thereof can be made into a pharmaceutical composition (pharmaceutical formulation) by being combined with one or two or more pharmaceutically acceptable carriers, excipients, or diluents.

The carriers, excipients, and diluents include, for example, water, lactose, dextrose, fructose, sucrose, sorbitol, mannitol, polyethylene glycol, propylene glycol, starch, gum, gelatin, alginate, calcium silicate, calcium phosphate, cellulose, aqueous syrup, methylcellulose, polyvinylpyrrolidone, alkyl parahydroxybenzosorbate, talc, magnesium stearate, stearic acid, glycerin, various oils such as sesame oil, olive oil, and soybean oil, and the like.

Furthermore, if necessary, by being mixed with the aforementioned carriers, excipients, and diluents as well as additives such as a bulking agent, a binder, a disintegrant, a pH adjuster, and a solubilizing agent that are generally used, the compound or a salt thereof can be made into oral or parenteral medicines such as tablets, pills, capsules, granules, powders, solutions, emulsions, suspensions, ointments, injections, or skin patches through commonly used formulation techniques.

The administration method, dosage, and number of doses of the compound according to the embodiment of the present invention or a salt thereof or the pharmaceutical composition according to the embodiment of the present invention can be appropriately selected according to the age, body weight, and symptom of the patient. Usually, for an adult, the compound according to the embodiment of the present invention may be orally or parenterally administered (for example, by means of injection, infusion, administration to the rectal site, and the like) at a dose of 0.01 to 1,000 mg/kg once a day or in divided portions a day.

The compound according to the embodiment of the present invention or a salt thereof or the pharmaceutical composition according to the embodiment of the present invention is preferably administered as an injection.

The pharmaceutical composition containing the compound according to the embodiment of the present invention or a salt thereof is preferably manufactured as a solution, a frozen solution, or a lyophilized formulation. The pharmaceutical composition is more preferably a lyophilized formulation.

Next, a method for manufacturing the compound according to the embodiment of the present invention will be described.

The compound according to the embodiment of the present invention is manufactured by combining known methods. For example, the compound can be manufactured according to a manufacturing method described below.

[Manufacturing Method 1]

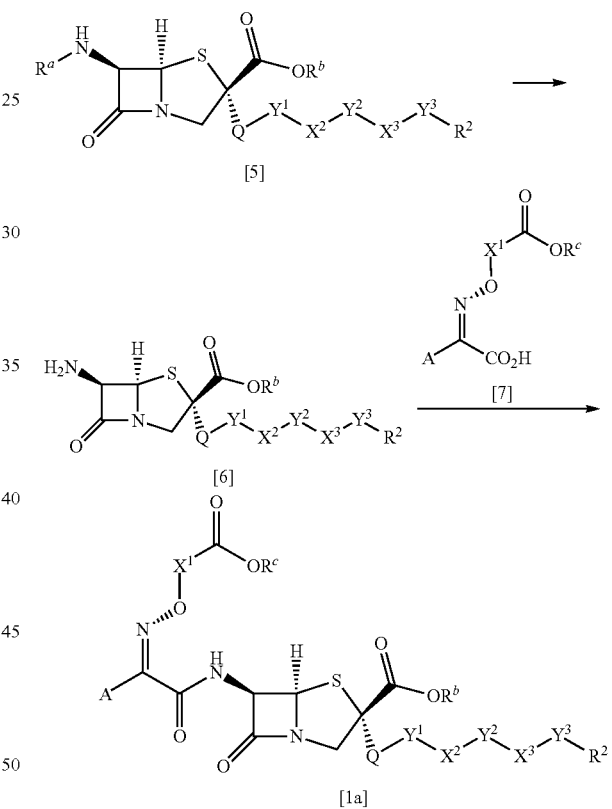

"In the formula, $R^a$ represents an amino protecting group; $R^b$ and $R^c$ each represent a carboxyl protecting group; and $R^2$, Q, $Y^1$, $Y^2$, $Y^3$, $X^1$, $X^2$, $X^3$ and A have the same definition as $R^2$, Q, $Y^1$, $Y^2$, $Y^3$, $X^1$, $X^2$, $X^3$, and A described above."

(1-1) Deprotection

The compound represented by the General Formula [6] can be manufactured by deprotecting the compound represented by General Formula [5] by the method described, for example, in "Protective Groups in Organic Synthesis, W. Greene et al., 4th edition, pp. 696-926, 2007, John Wiley & Sons, INC." and the like.

The compound represented by General Formula [6] may be used for the next reaction without being isolated.

(1-2) Amidation

As the compound represented by General Formula [7], for example, (Z)-2-(2-aminothiazol-4-yl)-2-(((1-(tert-butoxy)-2-methyl-1-oxopropan-2-yl)oxy)imino) acetic acid and the like are known.

The compound represented by General Formula [Ia] can be manufactured by reacting the compound represented by General Formula [6] with the compound represented by General Formula [7] in the presence of a condensing agent or an acid halide or in the presence of a base.

Furthermore, the compound represented by General Formula [Ia] can also be manufactured by reacting the compound represented by General Formula [6] with a benzothiazolyl ester as the compound represented by General Formula [7].

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

As the solvent, for example, halogenated hydrocarbons, ethers, esters, and amides are preferable. Among these, halogenated hydrocarbons and amides are more preferable.

The amount of the solvent used is not particularly limited, but may be 1 to 500 times (v/w) the amount of the compound represented by General Formula [6].

Examples of the base used in this reaction include an inorganic base and an organic base.

As the base, for example, an organic base is preferable. As the organic base, triethylamine, N,N-diisopropylethylamine, and 4-methylmorpholine are more preferable, and N,N-diisopropylethylamine and 4-methylmorpholine are even more preferable.

The amount of the base used may be 1 to 50 times and preferably 1 to 10 times the molar amount of the compound represented by General Formula [6].

Examples of the condensing agent used in this reaction include carbodiimides such as N,N'-diisopropylcarbodiimide (DIC), N,N'-di-(tert-butyl)carbodiimide, N,N'-dicyclohexylcarbodiimide (DCC), N-(tert-butyl)-N'-ethylcarbodiimide (BEC), N-cyclohexyl-N'-(2-morpholinoethyl)carbodiimide (CMC), and 1-ethyl-3-(3-dimethylaminopropyl)carbodiimide (EDC); imidazoliums such as 1,1'-carbonyldiimidazole (CDI) and 1,1'-carbonyl di(1,2,4-triazole) (CDT); acid azides such as diphenylphosphoryl azide; acid cyanides such as diethylphosphoryl cyanide; 2-ethoxy-1-ethoxycarbonyl-1,2-dihydroquinoline; and uroniums such as O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O-(benzotriazol-1-yl)-N,N,N',N'-bis(tetramethylene)uronium hexafluorophosphate (HBPyU), O-(benzotriazol-1-yl)-N,N,N',N'-bis(pentamethylene)uronium hexafluorophosphate (HBPipU), O-(6-chlorobenzotriazol-1-yl)-N,N,N',N'-tetramethyluronium hexafluorophosphate (HCTU), O-(3,4-dihydro-4-oxo-1,2,3-benzotriazin-3-yl)-N,N,N',N'-tetramethyluronium hexafluorophosphate (HDBTU), O-(2-oxo-1 (2H)pyridyl)-N,N,N',N'-tetramethyluronium hexafluorophosphate (TPTU), O-((ethoxycarbonyl)cyanomethyleneamino)-N,N,N',N'-tetramethyluronium hexafluorophosphate (HOTU), O-((ethoxycarbonyl)cyanomethyleneamino)-N,N,N',N'-tetramethyluronium tetrafluoroborate (TOTU), N,N,N',N'-tetramethyl-O—(N-succinimidyl)uronium hexafluorophosphate (HSTU), N,N,N',N'-tetramethyl-O—(N-succinimidyl)uronium tetrafluoroborate (TSTU), dipyrrolidino(N-succinimidyloxy)carbenium hexafluorophosphate (HSPyU), and S-(1-oxide-2-pyridyl)-N,N,N',N'-tetramethylthiouronium tetrafluoroborate (TOTT).

As the condensing agent, for example, carbodiimides are preferable, and EDC is more preferable.

The amount of the condensing agent used may be 1 to 50 times and preferably 1 to 5 times the molar amount of the compound represented by General Formula [6].

In a case where carbodiimides are used as the condensing agent, it is preferable to add additives thereto.

Examples of the additives include 1-hydroxybenzotriazole (HOBT), 1-hydroxy-7-azabenzotriazole (HOAT), and ethyl(hydroxyimino) cyanoacetate. Among these, HOBT and ethyl(hydroxyimino) cyanoacetate are preferable.

The amount of the additive used may be 0.01 to 10 times and preferably 0.1 to 1 time the molar amount of the compound represented by General Formula [6].

In a case where an acid halide is used, examples of the acid halide used include oxalyl chloride; carboxylic acid halides such as acetyl chloride and trifluoroacetyl chloride; sulfonic acid halides such as methanesulfonyl chloride and tosyl chloride; chloroformic acid esters such as ethyl chloroformate and isobutyl chloroformate; halides of sulfites such as thionyl chloride and thionyl bromide; and halides of phosphate such as phosphorus oxychloride, phosphorus oxybromide, phosphorus trichloride, and phosphorus pentachloride.

The amount of the compound represented by General Formula [7] used is not particularly limited, but may be 1 to 10 times the molar amount of the compound represented by General Formula [6].

This reaction may be carried out at −30° C. to 150° C. preferably at 0° C. to 100° C. for 30 minutes to 48 hours.

[Manufacturing Method 2]

General Formula [1]

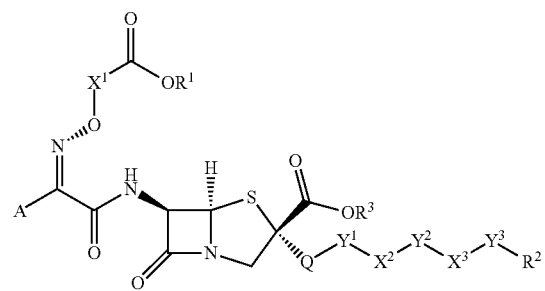

[1]

"In the formula, $R^1$, $R^2$, $R^3$, Q, $Y^1$, $Y^2$, $Y^3$, $X^1$, $X^2$, $X^3$, and A have the same definition as $R^1$, $R^2$, $R^3$, Q, $Y^1$, $Y^2$, $Y^3$, $X^1$, $X^2$, $X^3$, and A described above."

The compound represented by General Formula [1] in which either or both of $R^1$ and $R^3$ represent a protecting group can be manufactured by protecting the compound represented by General Formula [1] in which either or both of $R^1$ and $R^3$ represent a hydrogen atom by, for example, the method described in "Protective Groups in Organic Synthesis, W. Greene et al., 4th edition, pp. 533-643, 2007, John Wiley & Sons. Sons, INC." and the like.

[Manufacturing Method 3]
General Formula [1]

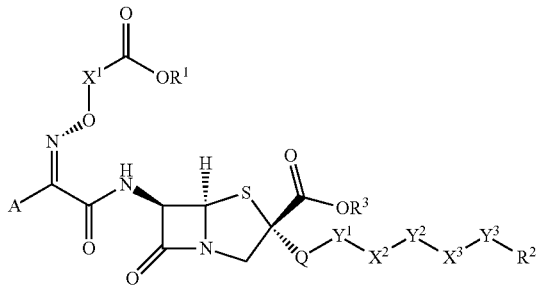

"In the formula, $R^1$, $R^2$, $R^3$, Q, $Y^1$, $Y^2$, $Y^3$, $X^1$, $X^2$, $X^3$, and A have the same definition as $R^1$, $R^2$, $R^3$, Q, $Y^1$, $Y^2$, $Y^3$, $X^1$, $X^2$, $X^3$, and A described above."

The compound represented by General Formula [1] can be manufactured based on the method described, for example, in JP1992-74182A (JP-H04-074182A), pp. 9-14.

[Manufacturing Method 4]

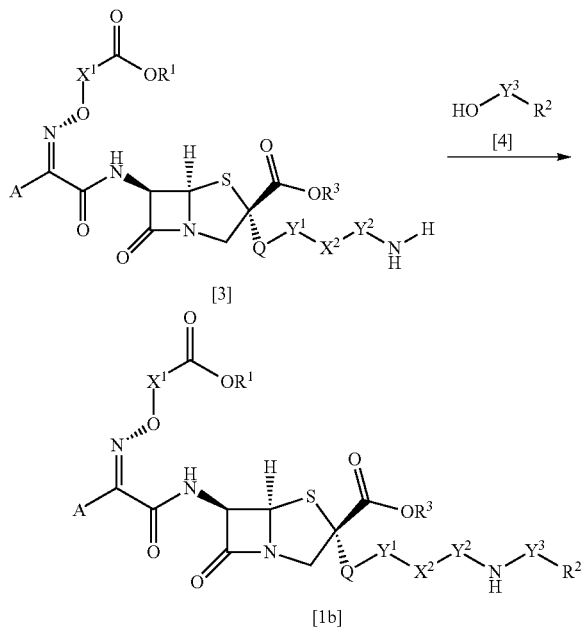

"In the formula, $R^1$, $R^2$, $R^3$, Q, $Y^1$, $Y^2$, $Y^3$, $X^1$, $X^2$, $X^3$, and A have the same definition as $R^1$, $R^2$, $R^3$, Q, $Y^1$, $Y^2$, $Y^3$, $X^1$, $X^2$, $X^3$, and A described above."

The compound represented by General Formula [1b] can be manufactured by reacting the compound represented by General Formula [3] with the compound represented by General Formula [4] in the presence of a condensing agent or an acid halide or in the presence of a base.

The amount of the compound represented by General Formula [4] used is not particularly limited, but may be 1 to 10 times the molar amount of the compound represented by General Formula [3].

The amount of the solvent used is not particularly limited, but may be 1 to 500 times (v/w) the amount of the compound represented by General Formula [3].

The amount of the base used may be 1 to 50 times and preferably 1 to 10 times the molar amount of the compound represented by General Formula [3].

This reaction may be carried out at −30° C. to 150° C. and preferably at 0° C. to 100° C., for 30 minutes to 48 hours.

The solvent used in this reaction is not particularly limited as long as it does not affect the reaction. Examples thereof include halogenated hydrocarbons, ethers, esters, amides, nitriles, sulfoxides, aromatic hydrocarbons, and water. These solvents may be used by being mixed together.

In a case where a condensing agent is used, as the solvent, dimethylacetamide and DMF are preferable.

In a case where an acid halide is used, as the solvent, for example, tetrahydrofuran, acetonitrile, and water are preferable. As the solvent, a mixed solvent of tetrahydrofuran and water is more preferable.

Examples of the base used in this reaction include an inorganic base and an organic base.

In a case where a condensing agent is used, as the base, for example, an organic base is preferable, and N-methylmorpholine is more preferable.

In a case where an acid halide is used, as the base, for example, an inorganic base is preferable. The base is preferably sodium hydrogen carbonate.

In a case where a condensing agent is used, as the condensing agent, for example, the condensing agent described in the manufacturing method 1 is preferable.

As the condensing agent, for example, carbodiimides are preferable, and EDC and HATU are more preferable.

In a case where a condensing agent is used, the amount of the condensing agent used may be 1 to 50 times and preferably 1 to 5 times the molar amount of the compound represented by General Formula [3].

In a case where carbodiimides are used as a condensing agent, it is preferable to further add additives thereto.

Examples of the additives include 1-hydroxybenzotriazole (HOBT), 1-hydroxy-7-azabenzotriazole (HOAT), and ethyl(hydroxyimino) cyanoacetate. Among these, HOBT and ethyl(hydroxyimino) cyanoacetate are preferable.

The amount of the additives used may be 0.01 to 10 times and preferably 0.1 to 1 time the molar amount of the compound represented by General Formula [3].

In a case where an acid halide is used, examples of the acid halide used include the acid halide described in the manufacturing method 1.

As the acid halide, for example, oxalyl chloride is preferable.

The amount of the acid halide used may be 0.9 to 3 times and preferably 0.9 to 1.5 times the molar amount of the compound represented by General Formula [4].

Next, a method for manufacturing raw materials for manufacturing the compound according to the embodiment of the present invention will be described.

[Manufacturing Method A]

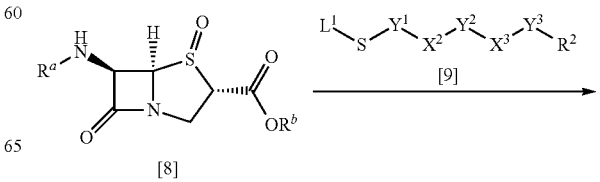

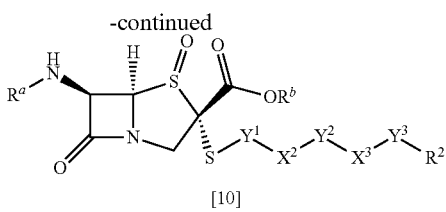

[10]

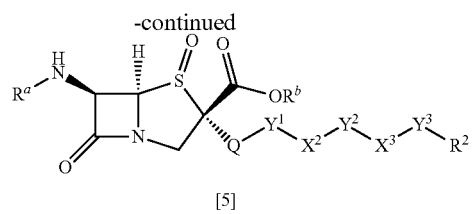

[5]

"In the formula, L¹ represents a leaving group; $R^a$ represents an amino protecting group; $R^b$ represents a carboxyl protecting group; and $Y^1$, $Y^2$, $Y^3$, $X^2$, $X^3$, an $R^2$ have the same definition as $Y^1$, $Y^2$, $Y^3$, $X^2$, $X^3$, an $R^2$ described above".

The compound represented by General Formula [10] can be manufactured by reacting the compound represented by General Formula [8] with the compound represented by General Formula [9] in the presence of a base.

Examples of the compound represented by General Formula [8] include benzhydryl(3 S,5R,6R)-7-oxo-6-(2-phenylacetamide)-4-thia-1-azabicyclo[3.2.0]heptane-3-carb oxylate 4-oxide.

In a case where $L^1$ in the compound represented by General Formula [9] is a tosyl group, the compound represented by General Formula [9] can be manufactured, for example, by reacting a compound represented by General Formula $L^2$-$Y^1$—$X^2$—$Y^2$—$X^3$—$Y^3$—$R^2$ (where, $L^2$ represents a halogen atom; and $Y^1$, $Y^2$, $Y^3$, $X^2$, $X^3$, and $R^2$ have the same definition as $Y^1$, $Y^2$, $Y^3$, $X^2$, $X^3$, and $R^2$ described above" with potassium p-toluenethiosulfonate.

The solvent used in this reaction is not particularly limited as long as it does not negatively affect the reaction. Examples of the solvent include aliphatic hydrocarbons, halogenated hydrocarbons, alcohols, ethers, ketones, esters, amides, aromatic hydrocarbons, sulfoxides, nitriles, water, and the like. These may be used by being mixed together.

The amount of the solvent used is not particularly limited, but may be preferably 1 to 150 times (v/w) the amount of the compound represented by General Formula [8].

Examples of the base used in this reaction include inorganic bases such as sodium hydroxide, potassium hydroxide, lithium hydroxide, sodium hydrogen carbonate, sodium carbonate, potassium carbonate, and cesium carbonate, and organic bases such as 1,8-diazabicyclo[5.4.0]-7-undecene, sodium methoxide, sodium ethoxide, potassium tert-butoxide, triethylamine, N,N-diisopropylethylamine, and pyridine.

The amount of the base used may be 1 to 50 times and preferably 1 to 2 times the molar amount of the compound represented by General Formula [8].

The amount of the compound represented by General Formula [9] used may be 1 to 50 times and preferably 1 to 2 times the molar amount of the compound represented by General Formula [8].

This reaction may be carried out at −40° C. to temperature equal to or lower than the boiling point of the solvent and preferably −40° C. to 5° C., for 1 minute to 24 hours.

[Manufacturing Method B]

"In the formula, $R^a$, $R^b$, Q, $Y^1$, $Y^2$, $Y^3$, $X^2$, $X^3$, and $R^2$ have the same definition as $R^a$, $R^b$, Q, $Y^1$, $Y^2$, $Y^3$, $X^2$, $X^3$, and $R^2$ described above."

The compound represented by General Formula [5] can be manufactured by reducing the compound represented by General Formula [10].

Examples of the reduction reaction include reduction by a phosphorus compound.

The solvent used in this reaction is not particularly limited as long as it does not negatively affect the reaction. Examples of the solvent include aliphatic hydrocarbons, halogenated hydrocarbons, ethers, ketones, esters, amides, aromatic hydrocarbons, sulfoxides, nitriles, and the like. These may be used by being mixed together.

The amount of the solvent used is not particularly limited, but may be preferably 1 to 150 times (v/w) the amount of the compound represented by General Formula [10].

Examples of the phosphorus compound used in this reaction include phosphorus tribromide.

The amount of the phosphorus compound used may be 5 to 50 times and preferably 5 to 15 times the molar amount of the compound represented by General Formula [10].

This reaction may be carried out at −40° C. to 70° C. and preferably at −30° C. to 5° C. for 30 minutes to 48 hours.

Among the compounds used in the aforementioned manufacturing methods, for the compounds having a protectable substituent such as an amino group, a hydroxyl group, or a carboxyl group, these groups can be protected in advance with general protecting groups, and the protecting groups can be eliminated by known methods after the reaction.

[Manufacturing Method C]

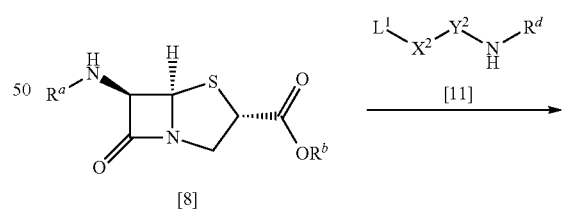

[8]     [11]

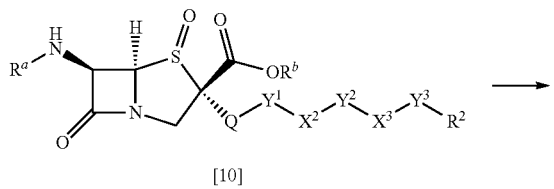

[10]

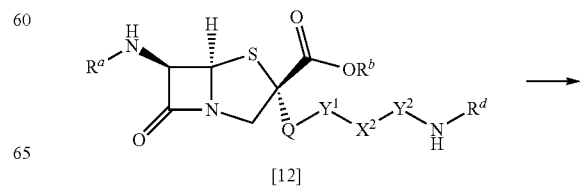

[12]

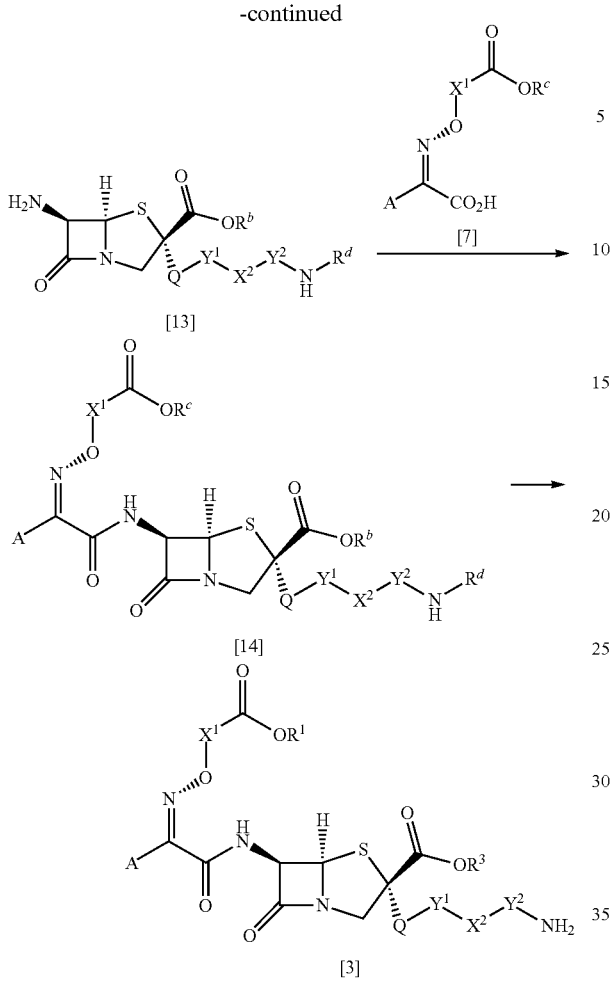

"In the formula, $R^d$ represents an amino protecting group, and $L^1$, $R^1$, $R^3$, $R^a$, $R^b$, $R^c$, Q, $Y^1$, $Y^2$, $X^1$, $X^2$, and A have the same definition as $L^1$, $R^1$, $R^3$, $R^a$, $R^b$, $R^c$, Q, $Y^1$, $Y^2$, $X^1$, $X^2$, and A described above."

The compound represented by General Formula [12] can be manufactured by reacting the compound represented by General Formula [8] with the compound represented by General Formula [11] in the presence of a base.

This reaction may be carried out by the same manufacturing method as the manufacturing method of the compound represented by General Formula [10] in the manufacturing method A.

The compound represented by General Formula [13] can be obtained by deprotecting the compound represented by General Formula [12].

This reaction may be carried out by the same manufacturing method as the manufacturing method of the compound represented by General Formula [6] in the manufacturing method 1.

The compound represented by General Formula [14] is obtained by reacting the compound represented by General Formula [13] with the compound represented by General Formula [7] in the presence of a condensing agent or an acid halide or in the presence of a base.

This reaction may be carried out by the same manufacturing method as the manufacturing method of the compound represented by General Formula [Ia] in the manufacturing method 1.

The compound represented by General Formula [3] can be obtained by deprotecting the compound represented by General Formula [14].

This reaction may be carried out by the same manufacturing method as the manufacturing method of the compound represented by General Formula [6] in the manufacturing method 1.

EXAMPLES

Next, the present invention will be described based on examples and reference examples, but the present invention is not limited thereto.

Unless otherwise specified, silica gel column chromatography is flash column chromatography in which B. W. Silica gel, BW-300 manufactured by Fuji Silysia Chemical, Ltd. is used as a carrier.

In the medium-pressure reverse-phase silica gel column chromatography, Isolera SV or Isolera LSV manufactured by Biotage Japan Ltd. was used. Furthermore, as a carrier, SNAP Ultra $C_{18}$ Cartridge manufactured by Biotage Japan Ltd. was used.

The mixing ratio in the eluent is a volume ratio.

The NMR spectrum shows proton NMR, and the internal standard is as follows. The δ value is expressed as ppm.

Deuterated chloroform ($CDCl_3$): Tetramethylsilane (0.00 ppm)

Deuterated methanol ($CD_3OD$): methanol ($CH_3OH$) (3.30 ppm)

Deuterated dimethyl sulfoxide ($CD_3SOCD_3$): Tetramethylsilane (0.00 ppm)

Heavy water ($D_2O$): water (4.65 ppm)

The abbreviation in each of the examples and reference examples has the following meaning.

Alloc: allyloxycarbonyl, BH: diphenylmethyl, Boc: tert-butoxycarbonyl, Cbz: benzyloxycarbonyl, DBU: 1,8-diazabicyclo[5.4.0]-7-undecene, DMAC: N,N-dimethylacetamide, DMAP: 4-(dimethylamino)pyridine, DMF: N,N-dimethylformamide, ESI: electrospray ionization method, Et: ethyl, HOBt: 1-hydroxybenzotriazole monohydrate, HATU: O-(7-azabenzotriazol-1-yl)-N,N,N',N'-tetramethyluronium hexafluorophosphate, IPE: diisopropyl ether, Me: methyl, Moz: 4-methoxybenzyloxycarbonyl, Ms: methanesulfonyl, MTBE: tert-butyl methyl ether, NMM: N-methylmorpholine, NMP: 1-methyl-2-pyrrolidone, PMB: 4-methoxybenzyl, PNZ: p-nitrobenzyloxycarbonyl, SEM: 2-(trimethylsilyl)ethoxymethyl, TBDPS: tert-butyldiphenylsilyl, TBS: tert-butyldimethylsilyl, tBu: tert-butyl, THF: tetrahydrofuran, THP: tetrahydro-2H-pyran-2-yl, Tr: triphenylmethyl, Ts: p-toluenesulfonyl, WSC: 1-ethyl-3-(3-dimethylaminopropyl)carbodiimide hydrochloride, s: singlet, brs: broad singlet, d: doublet, dd: double doublet, dt: doublet triplet, m: multiplet, t: triplet In the NMR spectrum, for example, the description of [1.45] 1.46 (3H, s) means that peaks derived from each isomer of the mixture of geometric isomers are observed as singlets at 1.45 and 1.46, and the total number of protons is 3.

Reference Example 1

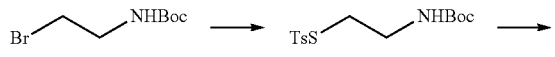

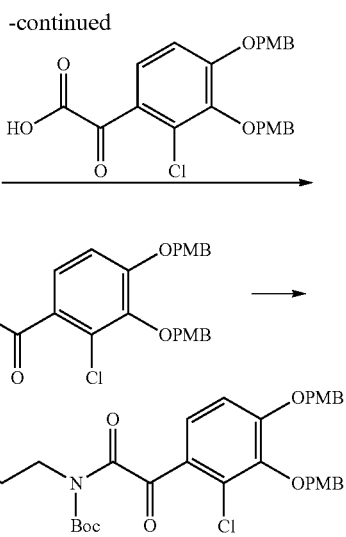

Reference Example 1 (1)

DMF (460 mL) and potassium p-toluenethiosulfonate (112 g, 493 mmol) were added to tert-butyl (2-bromoethyl)carbamate (92.0 g, 411 mmol), and the mixture was stirred. The reaction mixture was heated to 70° C. and stirred at the same temperature for 40 minutes. The reaction mixture was cooled to room temperature, and water (1.50 L) was added thereto such that solids were precipitated. IPE (150 mL) was added to the reaction mixture, the mixture was stirred for 70 minutes, and then the solids were collected by filtration. The solids were washed sequentially with water and IPE and then dried, thereby obtaining a target substance (90.5 g) as white solids.

Reference Example 1 (2)

A 4 mol/L hydrochloric acid/dioxane solution (241 mL), the compound (80.0 g, 241 mmol) obtained in Reference Example 1 (1), and methanol (8.00 mL) were sequentially added to a reaction vessel, and the mixture was stirred at room temperature. After solids were precipitated, the reaction mixture was diluted with IPE (500 mL), and the solids were collected by filtration. The solids were dried, thereby obtaining a target substance (51.2 g) as white solids.

Reference Example 1 (3)

The compound obtained in Reference Example 1 (2) (6.83 g, 25.5 mmol), DMAC (106 mL), NMM (8.96 mL, 81.2 mmol), 2-(2-chloro-3,4-bis((4-methoxybenzyl)oxy)phenyl)-2-oxoacetic acid (10.6 g, 23.2 mmol), WSC (5.34 g, 27.8 mmol), and HOBt (711 mg, 4.64 mmol) were sequentially added to a reaction vessel at room temperature, and the mixture was stirred overnight. Ethyl acetate (200 mL) and water (300 mL) were added to the reaction mixture, and then 6 mol/L hydrochloric acid was added thereto so as to adjust the pH to 2.2. The organic layers were separated, and the aqueous layer was extracted using ethyl acetate (100 mL). The organic layers were combined and washed sequentially with a 1% aqueous sodium chloride solution (300 mL), a saturated aqueous sodium hydrogen carbonate solution (200 mL), and a 10% aqueous sodium chloride solution (200 mL). The organic layer was dehydrated and dried over anhydrous magnesium sulfate, and then the solvent was distilled away under reduced pressure. The residue was purified by silica gel column chromatography [eluent; ethyl acetate:hexane=45:55], thereby obtaining a target substance (10.5 g) as a yellow oily substance.

$^1$H-NMR (400 MHz, CDCl$_3$) δ value: 2.44 (3H, s), 3.21 (2H, t, J=6.6 Hz), 3.64-3.73 (2H, m), 3.80 (3H, s), 3.84 (3H, s), 4.96 (2H, s), 5.12 (2H, s), 6.83 (2H, d, J=8.8 Hz), 6.91-6.97 (3H, m), 7.20-7.39 (6H, m), 7.59 (2H, d, J=8.4 Hz), 7.85 (2H, d, J=8.4 Hz)

Reference Example 1 (4)

The compound (10.5 g, 15.7 mmol) obtained in Reference Example 1 (3), THF (105 mL), and Boc$_2$O (6.84 g, 31.3 mmol) were added to a reaction vessel, and the mixture was stirred. DMAP (1.91 g, 15.7 mmol) was added to the reaction mixture, and the mixture was stirred for 20 minutes. Then, ethyl acetate (300 mL) and 1 mol/L hydrochloric acid (100 mL) were added to the reaction mixture, and the organic layer was separated. The organic layer was washed with a saturated aqueous sodium chloride solution (100 mL) and then dehydrated and dried over anhydrous magnesium sulfate, and then the solvent was distilled away under reduced pressure. The residue was purified by silica gel column chromatography [eluent; ethyl acetate:hexane=40:60], thereby obtaining S-(2-(N-(tert-butoxycarbonyl)-2-(2-chloro-3,4-bis)((4-methoxybenzyl)oxy)phenyl)-2-oxoacetamide)ethyl) 4-methylbenzenesulfonothioate (9.94 g) as a yellow oily substance.

Reference Example 2

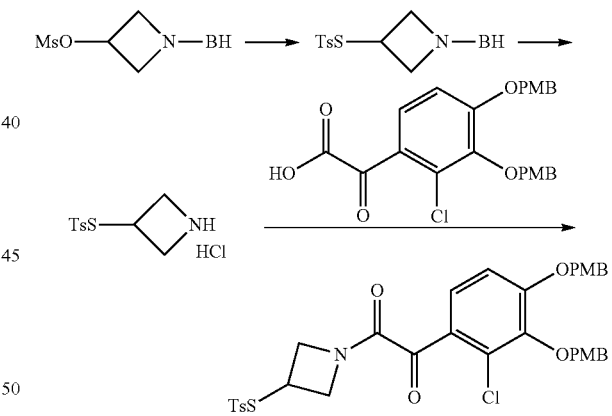

Reference Example 2 (1)

DMF (375 mL) and potassium p-toluenethiosulfonate (74.1 g, 327 mmol) were added to 1-benzhydrylazetidin-3-yl methanesulfonate (75.0 g, 236 mmol), and the mixture was stirred. The reaction mixture was heated to 72° C. and stirred at the same temperature for 4 hours and 40 minutes. The reaction mixture was cooled to room temperature, water (700 mL) and ethyl acetate (700 mL) were added thereto, and the organic layer was separated. The organic layer was washed sequentially with a 2.5% aqueous sodium chloride solution (700 mL) and a 5.0% aqueous sodium chloride solution (500 mL). The organic layer was dehydrated and dried over anhydrous magnesium sulfate, and then the solvent was distilled away under reduced pressure. Ethyl acetate:hexane=1:9 (300 mL) were added to the residue, and solids were collected by filtration. The solids were dried, thereby obtaining a target substance (72.9 g) as light yellow solids.

Reference Example 2 (2)

Dichloromethane (600 mL) was added to the compound (60.0 g, 146 mmol) obtained in Reference Example 2 (1), and then 1-chloroethylchloroformate (25.1 g, 176 mmol) was added dropwise thereto for 10 minutes. The reaction mixture was heated and stirred for 5 hours under reflux and then cooled to room temperature. The reaction solvent was distilled away under reduced pressure, methanol (600 mL) was added to the obtained oily substance, and the mixture was heated under reflux for 2 hours and 10 minutes. The reaction mixture was cooled, acetonitrile (200 mL) was added thereto, and the solvent was distilled away under reduced pressure. IPE (100 mL) was added to the obtained residue, the lower layer was separated, acetonitrile (100 mL) was added thereto, and the mixture was allowed to stand in a freezer overnight. The precipitated solids were collected by filtration, washed with acetonitrile, and then dried, thereby obtaining a target substance (28.4 g) as light brown solids.

$^1$H-NMR (400 MHz, DMSO-$d_6$) δ value: 2.45 (3H, s), 3.85-3.96 (2H, m), 4.25-4.37 (3H, m), 7.52 (2H, d, J=8.2 Hz), 7.84 (2H, d, J=8.2 Hz), 9.22 (1H, s)

Reference Example 2 (3)

The compound obtained in Reference Example 2 (2) (2.10 g, 7.51 mmol), DMAC (20 mL), NMM (2.10 mL, 18.8 mmol), 2-(2-chloro-3,4-bis((4-methoxybenzyl)oxy)phenyl)-2-oxoacetic acid (3.43 g, 7.51 mmol), WSC (1.73 g, 9.01 mmol), and HOBt (1.01 g, 7.51 mmol) were sequentially added to a reaction vessel at room temperature, and the mixture was stirred at room temperature for 4 hours. Ethyl acetate, 1 mol/L hydrochloric acid, and water were added to the reaction mixture, and the organic layer was separated. The organic layer was washed sequentially with 1 mol/L hydrochloric acid, a saturated aqueous sodium hydrogen carbonate solution, and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=60:40], thereby obtaining S-(1-(2-(2-chloro-3,4-bis ((4-methoxybenzyl)oxy))phenyl)-2-oxoacetyl)azetidin-3-yl) 4-methylbenzenesulfonothioate (2.29 g) as light yellow solids.

$^1$H-NMR (400 MHz, CDCl$_3$) δ value: 2.47 (3H, s), 3.81 (3H, s), 3.83 (3H, s), 3.95-4.04 (1H, m), 4.21-4.32 (2H, m), 4.44-4.54 (1H, m), 4.68-4.79 (1H, m), 4.95 (2H, s), 5.11 (2H, s), 6.83 (2H, d, J=8.4 Hz), 6.89-7.00 (3H, m), 7.30-7.42 (6H, m), 7.51 (1H, d, J=8.8 Hz), 7.80 (2H, d, J=8.0 Hz)

Reference Example 3

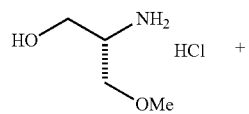

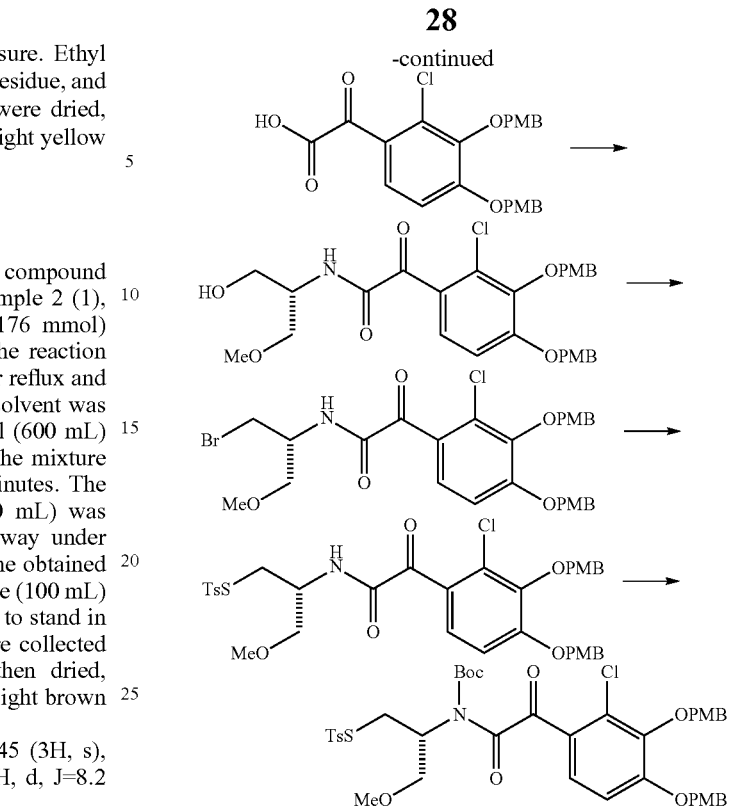

Reference Example 3 (1)

(S)-2-amino-3-methoxypropan-1-ol hydrochloride (3.80 g, 26.8 mmol), DMAC (38 mL), NMM (7.40 mL, 67.1 mmol), 2-(2-chloro-3,4-bis((4-methoxybenzyl)oxy)phenyl)-2-oxoacetic acid (11.0 g, 24.2 mmol), WSC (6.17 g, 32.2 mmol), and HOBt (3.26 g, 24.2 mmol) were sequentially added to a reaction vessel at room temperature, and the mixture was stirred at room temperature for 4 hours. Ethyl acetate (130 mL) and water (130 mL) were added to the reaction mixture, and the organic layer was separated. The organic layer was washed twice with water and then with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=80:20], thereby obtaining a target substance (6.73 g) as a light yellow oily substance.

$^1$H-NMR (400 MHz, DMSO-$d_6$) δ value: 3.27 (3H, s), 3.40-3.50 (4H, m), 3.74 (3H, s), 3.78 (3H, s), 4.82 (1H, t, J=5.6 Hz), 4.90 (2H, s), 5.23 (2H, s), 6.80-6.90 (2H, m), 6.95-7.04 (2H, m), 7.24-7.31 (2H, m), 7.32 (1H, d, J=8.8 Hz), 7.40-7.50 (2H, m), 7.54 (1H, d, J=8.8 Hz), 8.68 (1H, d, J=8.4 Hz)

Reference Example 3 (2)

THF (135 mL) was added to the compound (6.73 g, 12.4 mmol) obtained in Reference Example 3 (1), and the reaction mixture was stirred. Triphenylphosphine (4.22 g, 16.1 mmol) and carbon tetrabromide (5.33 g, 16.1 mmol) were sequentially added to the reaction mixture under ice cooling, and then the mixture was stirred at room temperature for 1 hour and 30 minutes. Triphenylphosphine (4.22 g, 16.1 mmol) and carbon tetrabromide (5.33 g, 16.1 mmol) were sequentially added to the reaction mixture, and the mixture was stirred at room temperature for 2 hours. The reaction mixture was filtered, and the solvent was distilled away under reduced pressure. The obtained residue was purified by silica gel column chromatography [eluent; ethyl acetate:hexane=40:60], thereby obtaining a target substance (7.10 g) as a light yellow oily substance.

Reference Example 3 (3)

DMF (71 mL) and potassium p-toluenethiosulfonate (3.18 g, 14.0 mmol) were added to the compound (7.10 g, 11.7 mmol) obtained in Reference Example 3 (2), and the mixture was stirred. The reaction mixture was heated to 60° C. and stirred at the same temperature for 3 hours. Then, potassium p-toluenethiosulfonate (1.32 g, 5.85 mmol) was added to the reaction mixture, and the mixture was stirred at 70° C. for 1 hour. Thereafter, potassium p-toluenethiosulfonate (794 mg, 3.51 mmol) was added to the reaction mixture, and the mixture was stirred at 70° C. for 1 hour and 20 minutes. Furthermore, potassium p-toluenethiosulfonate (529 mg, 2.34 mmol) was added to the reaction mixture, and the mixture was stirred at 70° C. for 20 minutes. The reaction mixture was cooled to room temperature, water (210 mL) and ethyl acetate (210 mL) were added thereto, and the organic layer was separated. The organic layer was washed twice with water and then with a saturated aqueous sodium chloride solution. The organic layer was dehydrated and dried over anhydrous magnesium sulfate, and then the solvent was distilled away under reduced pressure. The residue was purified by silica gel column chromatography [eluent; ethyl acetate:hexane=40:60], thereby obtaining a target substance (5.04 g) as a yellow oily substance.

Reference Example 3 (4)

The compound (5.04 g, 7.06 mmol) obtained in Reference Example 3 (3), THF (50 mL), and Boc$_2$O (4.62 g, 21.2 mmol) were added to a reaction vessel, and the mixture was stirred. DMAP (862 mg, 7.06 mmol) was added to the reaction mixture at room temperature, and the mixture was stirred at the same temperature for 1 hour. Then, the reaction solvent was distilled away under reduced pressure, and the residue was purified by silica gel column chromatography [eluent; ethyl acetate:hexane=35:65], thereby obtaining (R)—S-(2-(N-(tert-butoxy)carbonyl)-2-(2-chloro-3,4-bis ((4-methoxybenzyl)oxy)phenyl)-2-oxoacetamide)-3-methoxypropyl) 4-methylbenzenesulfonothioate (1.23 g) as a light yellow oily substance.

$^1$H-NMR (400 MHz, CDCl$_3$) δ value: 1.31 (9H, s), 2.44 (3H, s), 3.45 (3H, s), 3.36-3.50 (2H, m), 3.60-3.78 (2H, m), 3.80 (3H, s), 3.84 (3H, s), 4.89-5.02 (1H, m), 4.94 (2H, s), 5.13 (2H, s), 6.78-6.85 (2H, m), 6.86-6.97 (2H, m), 7.02 (1H, d, J=8.8 Hz), 7.29-7.39 (7H, m), 7.81-7.87 (2H, m)

Reference Example 4

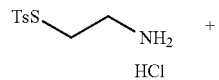

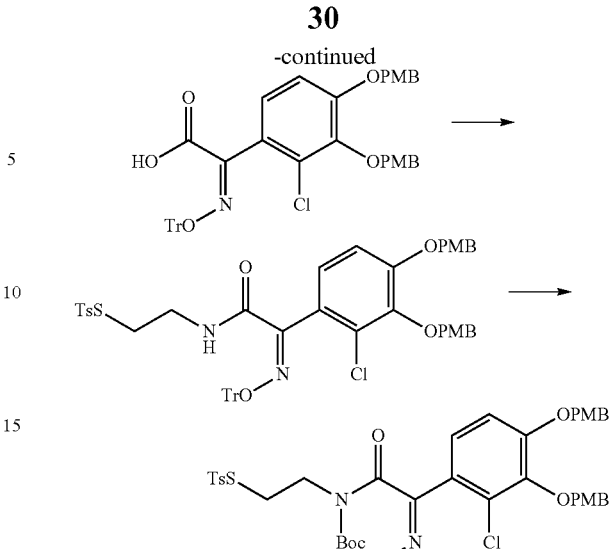

Reference Example 4 (1)

(Z)-2-(2-chloro-3,4-bis((4-methoxybenzyl)oxy)phenyl)-2-((trityloxy)imino)acetic acid (18.9 g, 26.4 mmol), DMAC (188 mL), NMM (9.34 g, 92.4 mmol), S-(2-aminoethyl) 4-methylbenzenesulfonothioate hydrochloride (7.78 g, 29.0 mmol), WSC (6.07 g, 31.7 mmol), and HOBt (808 mg, 5.28 mmol) were sequentially added to a reaction vessel at room temperature, and the mixture was stirred at room temperature for 2 hours and 45 minutes. Water (200 mL) and ethyl acetate (150 mL) were added to the reaction mixture, and then 6 mol/L hydrochloric acid was added thereto so as to adjust the pH to 3.0. The organic layer was separated and washed with a saturated aqueous sodium hydrogen carbonate solution (100 mL), a 2.5% aqueous sodium chloride solution (100 mL), and a 5.0% aqueous sodium chloride solution (100 mL). The organic layer was dehydrated and dried over anhydrous magnesium sulfate, and then the solvent was distilled away under reduced pressure. The residue was purified by silica gel column chromatography [eluent; ethyl acetate:hexane=50:50], thereby obtaining a target substance (18.9 g) as a light yellow oily substance.

Reference Example 4 (2)

The compound (16.0 g, 17.3 mmol) obtained in Reference Example 4 (1), THF (80 mL), and Boc$_2$O (7.55 g, 34.6 mmol) were added to a reaction vessel, and the mixture was stirred. DMAP (2.11 g, 17.3 mmol) was added to the reaction mixture, and the mixture was stirred at room temperature. Then, the reaction mixture was then stirred at 38° C. for 1 hour and 20 minutes. The reaction mixture was cooled to room temperature and added to a mixture of ethyl acetate and water. The pH of the reaction mixture was adjusted to 3 from 2, and the organic layer was separated. The organic layer was washed with a saturated aqueous sodium chloride solution and then dehydrated and dried over anhydrous magnesium sulfate, and then the solvent was distilled away under reduced pressure. The residue was purified by silica gel column chromatography [eluent; ethyl acetate:hexane=40:60], thereby obtaining (Z)— S-(2-(N-(tert-butoxycarbonyl)-2-(2-chloro-3,4-bis((4-methoxybenzyl)oxy)phenyl)-2-((trityloxy)imino)acetamide)ethyl) 4-methylbenzenesulfonothioate (11.9 g) as a light yellow oily substance.

$^1$H-NMR (400 MHz, DMSO-d$_6$) δ value: 1.25 (9H, s), 2.40 (3H, s), 2.95-2.98 (2H, m), 3.70 (3H, s), 3.75-3.77 (2H, m), 3.78 (3H, s), 4.92 (2H, s), 5.20 (2H, s), 6.83 (2H, d, J=6.8 Hz), 6.99 (2H, d, J=6.8 Hz), 7.00-7.15 (6H, m), 7.24-7.27 (11H, m), 7.28-7.48 (6H, m), 7.77 (2H, d, J=8.4 Hz)

Reference Example 5

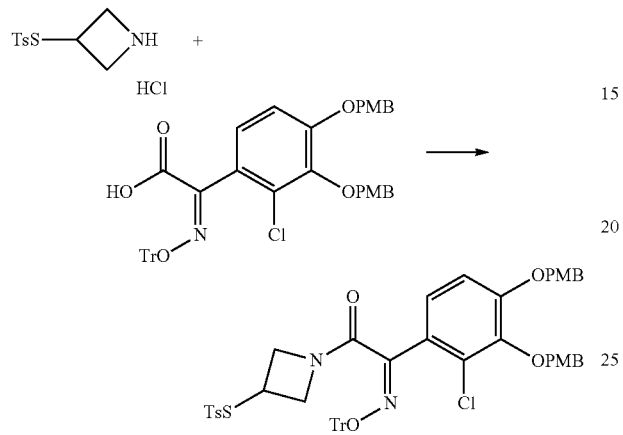

(Z)-2-(2-chloro-3,4-bis((4-methoxybenzyl)oxy)phenyl)-2-((trityloxy)imino)acetic acid (2.55 g, 3.57 mmol), DMAC (10 mL), NMM (904 mg, 8.93 mmol), the compound obtained in Reference Example 2 (2) (1.00 g, 3.57 mmol), WSC (822 mg, 4.29 mmol), and HOBt (483 mg, 3.57 mmol) were sequentially added to a reaction vessel at room temperature, and the mixture was stirred at the same temperature for 4 hours. Water, ethyl acetate, and 1 mol/L hydrochloric acid were sequentially added to the reaction mixture, and the organic layer was separated. The organic layer was washed with a saturated aqueous sodium hydrogen carbonate solution and then twice with a 5% aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=60:40], thereby obtaining (Z)—S-(1-(2-(2-chloro-3,4-bis((4-methoxybenzyl)oxy)phenyl)-2-((trityloxy)imino)acetyl)azetidin-3-yl) 4-methylbenzenesulfonothioate (2.48 g) as white solids.

$^1$H-NMR (400 MHz, CDCl$_3$) δ value: 2.45 (3H, s), 3.38-3.48 (1H, m), 3.66-3.72 (1H, m), 3.74 (3H, s), 3.83 (3H, s), 3.86-3.96 (2H, m), 4.17-4.26 (1H, m), 4.97 (2H, s), 5.09 (2H, s), 6.78 (2H, d, J=8.4 Hz), 6.92 (2H, d, J=8.4 Hz), 6.95-7.07 (2H, m), 7.14-7.42 (21H, m), 7.73 (2H, d, J=8.4 Hz)

Reference Example 6

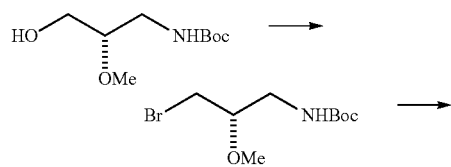

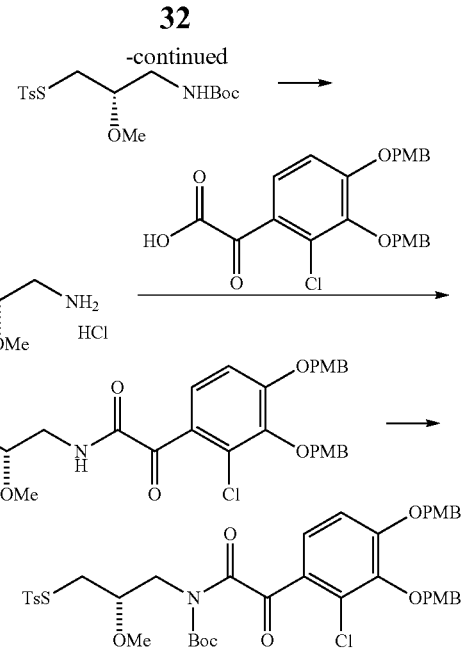

Reference Example 6 (1)

THF (270 mL) was added to tert-butyl (S)-(3-hydroxy-2-methoxypropyl) carbamate (13.4 g, 65.3 mmol), and the reaction mixture was stirred. Triphenylphosphine (22.3 g, 84.9 mmol) and carbon tetrabromide (28.1 g, 84.9 mmol) were sequentially added to the reaction mixture under ice cooling, and then the mixture was stirred at room temperature for 1 hour and 50 minutes. The reaction mixture was filtered, and the residue was washed with THF. The solvent was distilled away under reduced pressure, and the obtained residue was purified by silica gel column chromatography [eluent; ethyl acetate:hexane=20:80], thereby obtaining a target substance (16.0 g) as a light yellow oily substance.

Reference Example 6 (2)

DMF (160 mL) and potassium p-toluenethiosulfonate (22.4 g, 99.0 mmol) were added to the compound (16.0 g, 59.7 mmol) obtained in Reference Example 6 (1), and the mixture was stirred. The reaction mixture was heated and stirred at a temperature of 50° C. to 70° C. for 4 hours and 50 minutes. The reaction mixture was cooled to room temperature, and water (300 mL) and ethyl acetate (300 mL) were added thereto. A saturated aqueous sodium hydrogen carbonate solution was added to the reaction mixture so as to adjust the pH to 6.2, and then water (200 mL) was added thereto. The organic layer was separated and washed sequentially with a 2% aqueous sodium chloride solution (200 mL) and a 5% aqueous sodium chloride solution (200 mL). The organic layer was dehydrated and dried over anhydrous magnesium sulfate, and then the solvent was distilled away under reduced pressure. The residue was purified by silica gel column chromatography [eluent; ethyl acetate:hexane=40:60], thereby obtaining a target substance (17.1 g) as a colorless oily substance.

Reference Example 6 (3)

1,4-Dioxane (17 mL), methanol (0.85 mL) and a 4 mol/L hydrochloric acid/dioxane solution (23 mL) were sequentially added to the compound (8.50 g, 23.0 mmol) obtained in Reference Example 6 (2), and the mixture was stirred at room temperature for 1 hour and 50 minutes. IPE (300 mL) was added to the reaction mixture, and an oily substance was separated. Acetonitrile (25 mL) was added to the oily substance, and the solvent was distilled away under reduced pressure, thereby obtaining a target substance as colorless foamy solids.

$^1$H-NMR (400 MHz, CD$_3$OD) δ value: 1.85 (2H, s), 2.75 (1H, dd, J=13.8, 9.2 Hz), 2.96-3.01 (1H, m), 3.06-3.09 (2H. m), 3.11-3.14 (2H, m), 3.21 (3H, s), 3.47 (1H, s), 3.55-3.63 (1H, m), 7.29 (2H, d, J=8.0 Hz), 7.67 (2H, d, J=8.4 Hz)

Reference Example 6 (4)

The compound obtained in Reference Example 6 (3) (7.18 g, 23.0 mmol), DMAC (88 mL), NMM (7.76 g, 76.7 mmol), 2-(2-chloro-3,4-bis((4-methoxybenzyl)oxy)phenyl)-2-oxoacetic acid (8.76 g, 19.2 mmol), WSC (4.41 g, 23.0 mmol), and HOBt (587 mg, 3.83 mmol) were sequentially added to a reaction vessel at room temperature, and the mixture was stirred at room temperature overnight. Water (400 mL) and ethyl acetate (400 mL) were added to the reaction mixture, and then 6 mol/L hydrochloric acid was added thereto so as to adjust the pH to 2.2. The organic layer was separated and washed sequentially with a 2.5% aqueous sodium chloride solution (400 mL) and a 5.0% aqueous sodium chloride solution (200 mL). The organic layer was dehydrated and dried over anhydrous magnesium sulfate, and then the solvent was distilled away under reduced pressure. The residue was purified by silica gel column chromatography [eluent; ethyl acetate:hexane=45:55], thereby obtaining a target substance (10.2 g) as a yellow oily substance.

Reference Example 6 (5)

The compound (10.0 g, 14.0 mmol) obtained in Reference Example 6 (4), THF (50 mL), and Boc$_2$O (6.11 g, 28.0 mmol) were added to a reaction vessel, and the mixture was stirred. DMAP (1.71 g, 14.0 mmol) was added to the reaction mixture, and the mixture was stirred for 25 minutes. Ethyl acetate (30 mL) and water (20 mL) were added to the reaction mixture, and then 6 mol/L hydrochloric acid was added thereto so as to adjust the pH to 1.8. The organic layer was separated, washed with a saturated aqueous sodium chloride solution (5 mL), and then dehydrated and dried over anhydrous magnesium sulfate. Thereafter, the solvent was distilled away under reduced pressure. The residue was purified by silica gel column chromatography [eluent; ethyl acetate:hexane=30:70], thereby obtaining (S)—S-(3-(N-(tert-butoxycarbonyl)-2-(2-chloro-3,4-bis((4-methoxybenzyl)oxy)phenyl)-2-oxoacetamide)-2-methoxypropyl) 4-methylbenzenesulfonothioate (7.9 g) as a yellow oily substance.

$^1$H-NMR (400 MHz, DMSO-d$_6$) δ value: 1.26 (9H, s), 3.12-3.28 (1H, m), 3.58-3.63 (1H, m), 3.65-3.73 (2H, m), 3.73 (3H, s), 3.78 (3H, s), 3.81-3.92 (1H, m), 4.93 (2H, s), 5.27 (2H, s), 6.83 (2H, d, J=8.4 Hz), 7.00 (2H, d, J=8.8 Hz), 7.26 (2H, d, J=8.8 Hz), 7.41 (1H, d, J=8.8 Hz), 7.48 (4H, d, J=8.0 Hz), 7.79 (1H, d, J=9.2 Hz), 7.83 (2H, d, J=8.4 Hz)

Reference Example 7

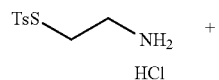

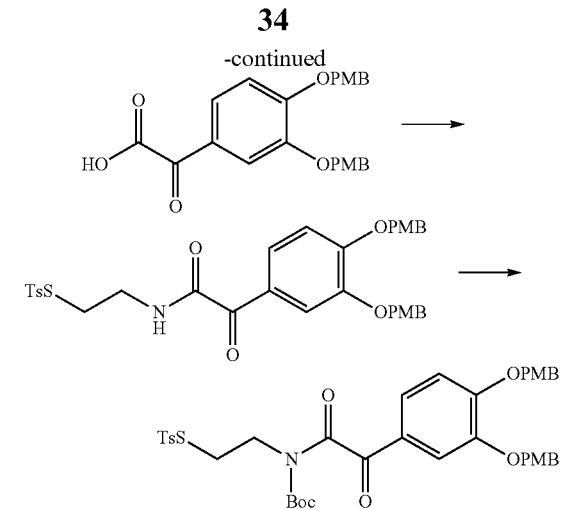

Reference Example 7 (1)

2-(3,4-Bis((4-methoxybenzyl)oxy)phenyl)-2-oxoacetic acid (13.0 g, 30.8 mmol), DMAC (130 mL), NMM (10.9 g, 108 mmol), S-(2-aminoethyl) 4-methylbenzenesulfonothioate hydrochloride (9.07 g, 33.9 mmol), WSC (7.08 g, 36.9 mmol), and HOBt (943 mg, 6.15 mmol) were sequentially added to a reaction vessel at room temperature, and the mixture was stirred at room temperature overnight. Water (300 mL) and ethyl acetate (300 mL) were added to the reaction mixture, and then 6 mol/L hydrochloric acid was added thereto so as to adjust the pH to 1.8. The organic layer was separated and washed with a 2.5% aqueous sodium chloride solution (300 mL) and a 5.0% aqueous sodium chloride solution (200 mL). The organic layer was dehydrated and dried over anhydrous magnesium sulfate, and the solvent was distilled away under reduced pressure. Ethyl acetate (10 mL) was added to the residue such that solids were precipitated, and the solids were diluted with MTBE (100 mL). The solids were collected by filtration and washed with MTBE. The solids were dried, thereby obtaining a target substance (12.7 g) as yellow solids.

Reference Example 7 (2)

The compound (12.0 g, 18.4 mmol) obtained in Reference Example 7 (1), THF (60 mL), and Boc$_2$O (8.04 g, 36.8 mmol) were added to a reaction vessel, and the mixture was stirred. DMAP (2.25 g, 18.4 mmol) was added to the reaction mixture, and the mixture was stirred at room temperature. The reaction mixture was then stirred at 40° C. for 30 minutes. The reaction mixture was cooled to room temperature, and ethyl acetate (200 mL) and water (200 mL) were added to the reaction mixture. The pH of the reaction mixture was adjusted to 1.8, and the organic layer was separated. The organic layer was washed with a saturated sodium chloride aqueous solution (100 mL) and then dehydrated and dried over anhydrous magnesium sulfate, and then the solvent was distilled away under reduced pressure. The residue was purified by silica gel column chromatography [eluent; ethyl acetate:hexane=40:60], thereby obtaining S-(2-(2-(3,4-bis((4-methoxybenzyl)oxy)phenyl)-N-(tert-butoxycarbonyl)-2-oxoacetamide)ethyl) 4-methylbenzenesulfonothioate (10.7 g) as a yellow oily substance.

¹H-NMR (400 MHz, DMSO-d₆) δ value: 1.19 (9H, s), 2.42 (3H, s), 3.25-3.33 (1H, m), 3.74 (3H, s), 3.75 (3H, s), 3.98-4.06 (2H, m), 5.10 (2H, s), 5.18 (2H, s), 6.91 (2H, d, J=8.4 Hz), 6.94 (2H, d, J=8.4 Hz), 7.21 (2H, d, J=8.8 Hz), 7.29-7.46 (2H, m), 7.33 (2H, d, J=8.4 Hz), 7.50 (2H, d, J=8.0 Hz), 7.65 (2H, d, J=8.4 Hz), 7.86 (2H, d, J=8.4 Hz)

Reference Example 8

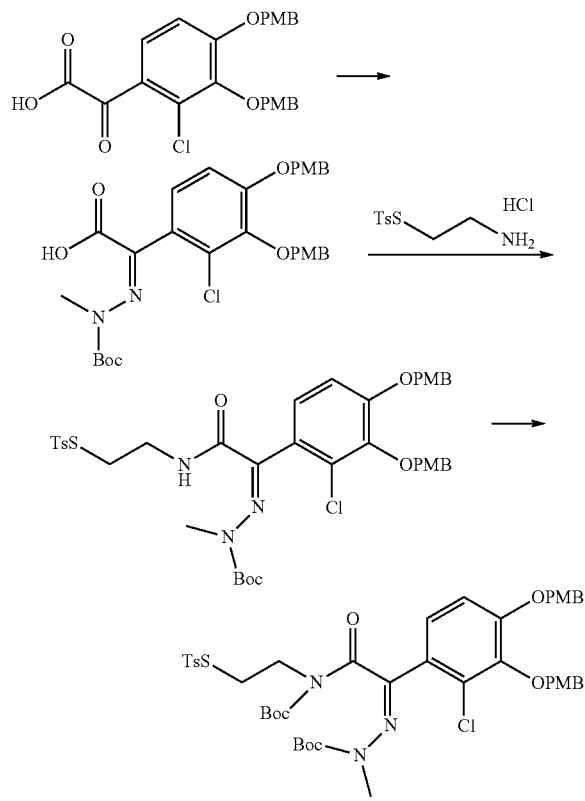

Reference Example 8 (1)

Ethanol (50 mL) and 1-Boc-1-methylhydrazine (880 mg, 6.02 mmol) were added to 2-(2-chloro-3,4-bis((4-methoxybenzyl)oxy)phenyl)-2-oxoacetic acid (2.50 g, 5.47 mmol), and the mixture was stirred at room temperature overnight. The solvent was distilled away under reduced pressure, ethyl acetate and 1 mol/L hydrochloric acid were added to the residue, and the organic layer was separated. The organic layer was washed with a saturated aqueous sodium chloride solution and then dehydrated and dried over anhydrous magnesium sulfate. The solvent was distilled away under reduced pressure, thereby obtaining a target substance (3.38 g) as light yellow solids.

Reference Example 8 (2)

The compound obtained in Reference Example 8 (1) (3.38 g, 5.43 mmol), DMAC (13 mL), NMM (1.25 g, 12.3 mmol), S-(2-aminoethyl) 4-methylbenzenesulfonothioate hydrochloride (1.32 g, 4.93 mmol), WSC (1.13 g, 5.91 mmol), and HOBt (666 mg, 4.93 mmol) were sequentially added to a reaction vessel at room temperature, and the mixture was stirred at the same temperature for 3 hours. Ethyl acetate and 1 mol/L hydrochloric acid were sequentially added to the reaction mixture, and the organic layer was separated. The organic layer was washed sequentially with water, a saturated aqueous sodium hydrogen carbonate solution, and a 5% aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=60:40], thereby obtaining a target substance (3.42 g) as white solids.

Reference Example 8 (3)

The compound (3.42 g, 4.28 mmol) obtained in Reference Example 8 (2), THF (34 mL), and Boc₂O (1.03 g, 4.71 mmol) were added to a reaction vessel, and the mixture was stirred. DMAP (550 mg, 4.50 mmol) was added to the reaction mixture at room temperature, and the mixture was stirred at the same temperature for 2 hours. Then, Boc₂O (1.03 g, 4.71 mmol) and DMAP (550 mg, 4.50 mmol) were added to the reaction mixture, and the mixture was stirred at the same temperature for 4 hours. Water, ethyl acetate, and 1 mol/L hydrochloric acid were sequentially added to the reaction mixture, and the organic layer was separated. The organic layer was washed with a saturated aqueous sodium chloride solution and then dehydrated and dried over anhydrous sodium sulfate, and then the solvent was distilled away under reduced pressure. The residue was purified by silica gel column chromatography [eluent; ethyl acetate:hexane=40:60], thereby obtaining tert-butyl (Z)-2-(1-(2-chloro-3,4-bis((4-methoxybenzyl)oxy)phenyl)-2-oxo-2-((2-(tosylthio)ethyl)amino) ethylidene)-1-methylhydrazine-1-carboxylate (1.72 g) as white solids.

¹H-NMR (400 MHz, CDCl₃) δ value: 1.46 (9H, s), 1.47 (9H, s), 2.43 (3H, s), 2.81 (3H, s), 3.24 (2H, t, J=7.2 Hz), 3.80 (3H, s), 3.84 (3H, s), 3.92 (2H, t, J=7.2 Hz), 5.02 (2H, s), 5.07 (2H, s), 6.78-6.84 (2H, m), 6.89 (1H, d, J=8.4 Hz), 6.91-6.96 (2H, m), 7.00 (1H, d, J=8.4 Hz), 7.32 (4H, d, J=8.8 Hz), 7.36 (2H, d, J=8.4 Hz), 7.84 (2H, d, J=8.4 Hz)

Reference Example 9

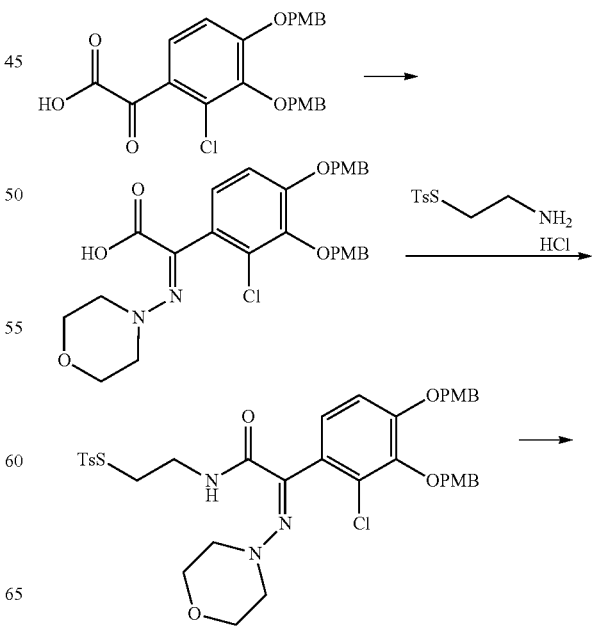

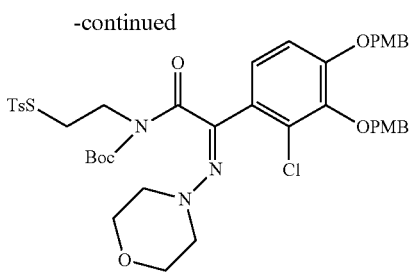

Reference Example 9 (1)

Ethanol (50 mL) and 4-aminomorpholine (838 mg, 8.21 mmol) were added to 2-(2-chloro-3,4-bis((4-methoxybenzyl)oxy)phenyl)-2-oxoacetic acid (2.50 g, 5.47 mmol), and the mixture was stirred at room temperature overnight. Ethyl acetate was added to the reaction mixture, and solids were collected by filtration. The solids were washed with ethyl acetate and then dried, thereby obtaining a target substance (2.00 g) as white solids.

Reference Example 9 (2)

The compound obtained in Reference Example 9 (1) (2.00 g, 3.70 mmol), DMAC (9 mL), NMM (850 mg, 8.40 mmol), S-(2-aminoethyl) 4-methylbenzenesulfonothioate hydrochloride (900 mg, 3.36 mmol), WSC (733 mg, 4.03 mmol), and HOBt (454 mg, 3.36 mmol) were sequentially added to a reaction vessel at room temperature, and the mixture was stirred at the same temperature for 5 hours. Ethyl acetate and 1 mol/L hydrochloric acid were sequentially added to the reaction mixture, and the organic layer was separated. The organic layer was washed sequentially with water, a saturated aqueous sodium hydrogen carbonate solution, and a 5% aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=60:40], thereby obtaining a target substance (2.45 g) as white solids.

Reference Example 9 (3)

The compound (2.45 g, 3.25 mmol) obtained in Reference Example 9 (2), THF (25 mL), and $Boc_2O$ (0.78 g, 3.57 mmol) were added to a reaction vessel, and the mixture was stirred. DMAP (417 mg, 3.41 mmol) was added to the reaction mixture at room temperature, and the mixture was stirred at the same temperature for 2 hours and 30 minutes. Then, $Boc_2O$ (0.78 g, 3.57 mmol) and DMAP (417 mg, 3.41 mmol) were added to the reaction mixture, and the mixture was stirred at the same temperature for 30 minutes. The reaction mixture was heated and stirred at a temperature of 50° C. to 60° C. for 45 minutes. The reaction mixture was cooled to room temperature and stirred for 2 hours and 30 minutes. $Boc_2O$ (0.78 g, 3.57 mmol) was added to the reaction mixture, and the mixture was stirred at a temperature of 50° C. to 60° C. for 2 hours. The reaction mixture was cooled to room temperature, ethyl acetate and 1 mol/L hydrochloric acid were sequentially added thereto, and the organic layer was separated. The organic layer was washed with a saturated aqueous sodium chloride solution and then dehydrated and dried over anhydrous sodium sulfate, and then the solvent was distilled away under reduced pressure.

The residue was purified by silica gel column chromatography [eluent; ethyl acetate:hexane=50:50], thereby obtaining (Z)—S-(2-(N-(tert-butoxycarbonyl)-2-(2-chloro-3,4-bis((4-methoxybenzyl)oxy)phenyl)-2-(morpholinoimino)acetamide)ethyl) 4-methylbenzenesulfonothioate (685 mg) as light yellow solids.

$^1$H-NMR (400 MHz, $CDCl_3$) δ value: 1.52 (9H, s), 2.43 (3H, s), 3.04-3.12 (4H, m), 3.22 (2H, t, J=7.2 Hz), 3.55-3.63 (4H, m), 3.79 (3H, s), 3.84 (3H, s), 3.90 (2H, t, J=7.2 Hz), 5.01 (2H, s), 5.06 (2H, s), 6.79-6.85 (2H, m), 6.89 (1H, d, J=8.4 Hz), 6.90-6.96 (2H, m), 7.04 (1H, d, J=8.4 Hz), 7.30-7.39 (6H, m), 7.83 (2H, d, J=8.4 Hz)

Reference Example 10

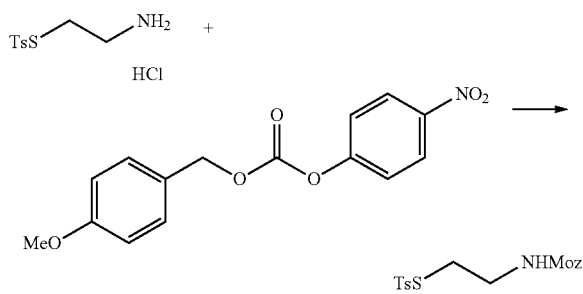

Acetonitrile (270 mL), triethylamine (21.3 g, 210 mmol), and 4-methoxybenzyl (4-nitrophenyl) carbonate (31.9 g, 105 mmol)) were added to S-(2-aminoethyl) 4-methylbenzenesulfonothioate hydrochloride (26.8 g, 100 mmol), and the mixture was stirred at room temperature for 1 hour. Water and ethyl acetate were added to the reaction mixture, and the organic layer was separated. The organic layer was washed sequentially with water and saturated sodium chloride. The organic layer was dehydrated and dried over anhydrous sodium sulfate, and then the solvent was distilled away under reduced pressure. The residue was purified by silica gel column chromatography [eluent; ethyl acetate:hexane=40:60], thereby obtaining S-(2-((((4-methoxybenzyl)oxy)carbonyl)amino)ethyl) 4-methylbenzenesulfonothioate (34.6 g) as a colorless oily substance.

$^1$H-NMR (400 MHz, $CDCl_3$) δ value: 2.45 (3H, s), 3.12 (2H, t, J=6.4 Hz), 3.38-3.54 (2H, m), 3.81 (3H, s), 5.01 (2H, s), 5.09 (1H, s), 6.86-6.91 (2H, m), 7.27-7.31 (2H, m), 7.34 (2H, d, J=8.0 Hz), 7.81 (2H, d, J=8.0 Hz)

Reference Example 11

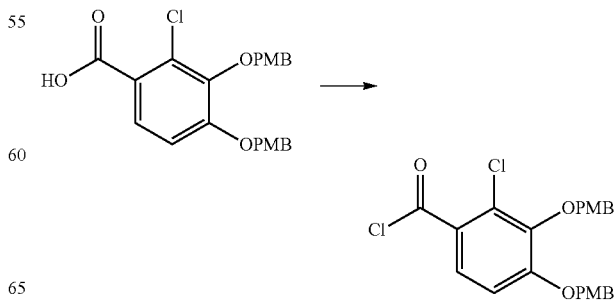

THF (400 mL) was added to 2-chloro-3,4-bis((4-methoxybenzyl)oxy)benzoic acid (40.0 g, 93.3 mmol), and the mixture was stirred under ice cooling. DMF (361 μL, 4.66 mmol) was added to the reaction mixture at the same temperature, and then oxalyl dichloride (14.2 g, 112 mmol) was added dropwise thereto. The reaction mixture was stirred at room temperature for 1 hour, and then oxalyl dichloride (14.2 g, 112 mmol) was added dropwise thereto. The reaction mixture was stirred at room temperature overnight, and then IPE (400 mL) was added to the reaction mixture. Solids were collected by filtration and washed with IPE. The solids were dried, thereby obtaining 2-chloro-3,4-bis((4-methoxybenzyl)oxy)benzoyl chloride (30 g) as white solids.

$^{1}$H-NMR (400 MHz, DMSO-$d_6$) δ value: 3.74 (3H, s), 3.78 (3H, s), 4.88 (2H, s), 5.18 (2H, s), 6.82-6.89 (2H, m), 6.95-7.02 (2H, m), 7.23 (1H, d, J=9.2 Hz), 7.26-7.33 (2H, m), 7.41-7.49 (2H, m), 7.62 (1H, d, J=8.4 Hz)

Reference Example 12

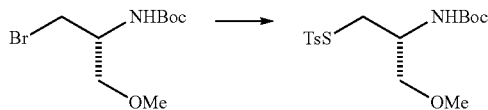

DMF (400 mL) and potassium p-toluenethiosulfonate (44.1 g, 195 mmol) were added to tert-butyl (R)-(1-bromo-3-methoxypropan-2-yl) carbamate (43.5 g, 162 mmol), and the mixture was stirred. The reaction mixture was heated and stirred at a temperature of 60° C. to 70° C. for 2 hours. The reaction mixture was cooled to room temperature, and MTBE (200 mL), ethyl acetate (300 mL), and water (500 mL) were added thereto. The organic layer was separated and washed sequentially with water (500 mL) and a saturated aqueous sodium chloride solution (200 mL). The organic layer was dehydrated and dried over anhydrous magnesium sulfate, and then the solvent was distilled away under reduced pressure. The residue was purified by silica gel column chromatography [eluent; ethyl acetate:hexane=35:65], thereby obtaining (R)—S-(2-((tert-butoxycarbonyl)amino-3-methoxypropyl) 4-methylbenzenesulfonothioate (21.1 g) as a light yellow oily substance.

$^{1}$H-NMR (400 MHz, CDCl$_3$) δ value: 1.44 (9H, s), 2.45 (3H, s), 3.13-3.21 (2H, m), 3.30 (3H, s), 3.33-3.39 (1H, m), 3.51 (1H, dd, J=9.8, 3.4 Hz), 3.92-4.03 (1H, m), 4.91-5.04 (1H, m), 7.32-7.38 (2H, m), 7.82-7.88 (2H, m)

Reference Example 13

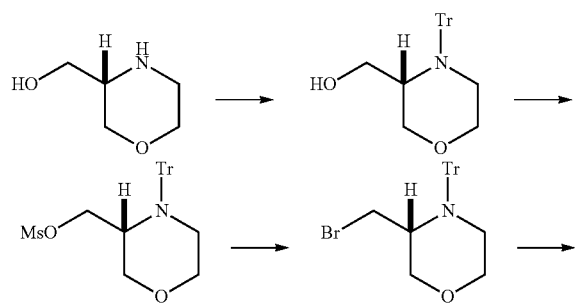

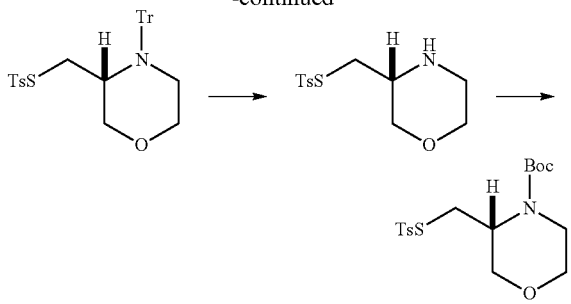

Reference Example 13 (1)

DMF (100 mL) was added to (S)-morpholin-3-yl methanol (10.2 g, 87.1 mmol), and the mixture was stirred. Under ice cooling, triethylamine (10.6 g, 104 mmol) and triphenylmethyl chloride (24.3 g, 87.1 mmol) were added to the reaction mixture, and the mixture was stirred at room temperature for 4 hours. The reaction mixture was diluted with ethyl acetate, a saturated aqueous sodium hydrogen carbonate solution was added thereto, and the organic layer was separated. The organic layer was washed sequentially with a saturated aqueous sodium hydrogen carbonate solution, water, and a saturated aqueous sodium chloride solution, and then dehydrated and dried over anhydrous sodium sulfate. Thereafter, the solvent was distilled away under reduced pressure. The residue was purified by silica gel column chromatography [eluent; ethyl acetate:hexane=40:60], thereby obtaining a target substance (24.1 g) as a light yellow oily substance.

Reference Example 13 (2)

Dichloromethane (240 mL) was added to the compound (24.1 g, 67.0 mmol) obtained in Reference Example 13 (1), and the mixture was stirred. Under ice cooling, triethylamine (13.6 g, 134 mmol) and methanesulfonyl chloride (9.22 g, 80.5 mmol) were sequentially added to the reaction mixture, and the mixture was stirred at the same temperature for 30 minutes. The reaction mixture was stirred at room temperature for 30 minutes, then water (250 mL) was added thereto, and the organic layer was separated. The organic layer was washed with water and then dehydrated and dried over anhydrous sodium sulfate. The solvent was distilled away under reduced pressure, thereby obtaining a yellow oily substance containing a target substance.

Reference Example 13 (3)

DMF (290 mL) and lithium bromide (8.72 g, 100 mmol) were sequentially added to the yellow oily substance obtained in Reference Example 13 (2), and the mixture was stirred at a temperature of 60° C. to 70° C. for 40 minutes. The reaction mixture was diluted with ethyl acetate, water was added thereto, and the organic layer was separated. The organic layer was washed twice with water and then with a saturated aqueous sodium chloride solution. The organic layer was dehydrated and dried over anhydrous magnesium sulfate, and then the solvent was distilled away under reduced pressure, thereby obtaining a yellow oily substance containing a target substance.

Reference Example 13 (4)

DMF (280 mL) and potassium p-toluenethiosulfonate (22.8 g, 101 mmol) were added to the yellow oily substance obtained in Reference Example 13 (3), and the mixture was stirred. The reaction mixture was heated to 70° C. and stirred at the same temperature for 3 hours. The reaction mixture was cooled to room temperature, and water was added thereto such that solids were precipitated. Then, the solids were collected by filtration and washed with IPE. The solids were dried, thereby obtaining a target substance (22.2 g) as white solids.

Reference Example 13 (5)

Ethyl acetate (220 mL) and 1,4-dioxane (110 mL) were added to the compound (22.2 g, 41.9 mmol) obtained in Reference Example 13 (4), and the mixture was stirred. The reaction mixture was cooled on ice, a 4 mol/L hydrochloric acid/dioxane solution (21.0 mL) was added thereto, and the mixture was stirred at room temperature for 1 hour. The solvent was distilled away under reduced pressure, thereby obtaining a target substance (12.0 g) as white solids.

Reference Example 13 (6)

Dichloromethane (120 mL) was added to the compound (12.0 g, 41.8 mmol) obtained in Reference Example 13 (5), and the mixture was stirred. Under ice cooling, triethylamine (21.1 g, 209 mmol) and Boc$_2$O (18.2 g, 83.5 mmol) were added to the reaction mixture, and the mixture was stirred at room temperature for 2 hours. Water was added to the reaction mixture, and the organic layer was separated. The organic layer was washed with water and then dehydrated and dried over anhydrous sodium sulfate, and then the solvent was distilled away under reduced pressure. The residue was purified by silica gel column chromatography [eluent; ethyl acetate:hexane=40:60], thereby obtaining tert-butyl (R)-3-((tosylthio)methyl)morpholine-4-carboxylate (12.3 g) as a yellow oily substance.

$^1$H-NMR (400 MHz, CDCl$_3$) δ value: 1.49 (9H, s), 2.46 (3H, s), 2.80-3.13 (1H, m), 3.20 (1H, dd, J=13.2, 8.0 Hz), 3.31 (1H, dd, J=13.2, 8.0 Hz), 3.37-3.48 (1H, m), 3.54 (1H, dd, J=12.0, 2.8 Hz), 3.63-3.93 (3H, m), 4.20-4.30 (1H, m), 7.35 (2H, d, J=8.8 Hz), 7.85 (2H, d, J=7.6 Hz)

Reference Example 14

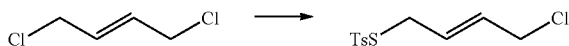

DMF (100 mL) and potassium p-toluenethiosulfonate (7.00 g, 30.9 mmol) were added to (E)-1,4-dichlorobut-2-ene (25.1 g, 201 mmol), and the mixture was stirred at room temperature for 3 hours and 45 minutes. The reaction mixture was cooled to room temperature, and water, ethyl acetate, and hexane were added thereto. The organic layer was separated, washed three times with water, and then washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate: hexane=10:90], thereby obtaining (E)-S-(4-chlorobut-2-en-1-yl) 4-methylbenzenesulfonothioate (7.30 g) as a yellow oily substance.

$^1$H-NMR (400 MHz, CDCl$_3$) δ value: 2.46 (3H, s), 3.66-3.71 (2H, m), 3.90-3.95 (2H, m), 5.62-5.81 (2H, m), 7.32-7.38 (2H, m), 7.78-7.83 (2H, m)

Reference Example 15

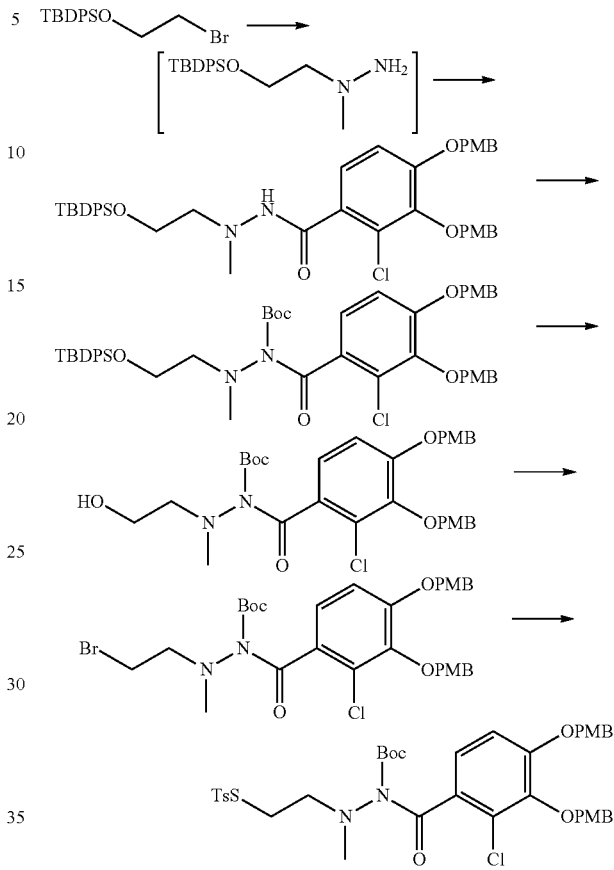

Reference Example 15 (1)

Acetonitrile (75 mL) and methylhydrazine (3.27 mL, 61.9 mmol) were added to (2-bromoethoxy) (tert-butyl) diphenylsilane (7.50 g, 20.6 mmol), and the mixture was heated and stirred under reflux for 1 hour. The reaction mixture was cooled to room temperature, and ethyl acetate and water were added thereto. The organic layer was separated and washed with a saturated aqueous sodium chloride solution. The organic layer was dehydrated and dried over anhydrous sodium sulfate, and then the solvent was distilled away under reduced pressure. 2-Chloro-3,4-bis((4-methoxybenzyl)oxy)benzoic acid (8.85 g, 20.6 mmol), DMAC (75 mL), HOBt (3.16 g, 20.6 mmol), and WSC (4.75 g, 24.8 mmol) were sequentially added to the obtained yellow oily substance, and the mixture was stirred at room temperature for 2 hours. Water and ethyl acetate were added to the reaction mixture, and solids were filtered. The organic layer was separated and washed sequentially with 1 mol/L hydrochloric acid, a saturated aqueous sodium hydrogen carbonate solution, and a saturated aqueous sodium chloride solution. The organic layer was dehydrated and dried over anhydrous sodium sulfate, and then the solvent was distilled away under reduced pressure. Ethyl acetate and IPE were added to the residue, and the mixture was stirred at room temperature for 1 hour. Solids were collected by filtration, thereby obtaining a target substance (8.55 g) as white solids.

Reference Example 15 (2)

THF (50 mL), Boc₂O (3.30 mL, 14.6 mmol), and DMAP (1.31 g, 10.7 mmol) were added to the compound (7.22 g, 9.77 mmol) obtained in Reference Example 15 (1), and the mixture was stirred at room temperature for 3 hours. Boc₂O (2.42 mL, 10.7 mmol) and DMAP (1.31 g, 10.7 mmol) were added to the reaction mixture, and the mixture was stirred at room temperature for 5 hours and 10 minutes. The solvent was distilled away under reduced pressure, ethyl acetate, and 1 mol/L hydrochloric acid were added to the residue, and the organic layer was separated. The organic layer was washed with a saturated aqueous sodium chloride solution and then dehydrated and dried over anhydrous magnesium sulfate, and the solvent was distilled away under reduced pressure. The residue was purified by silica gel column chromatography [eluent; ethyl acetate:hexane=50:50], thereby obtaining a target substance (8.62 g) as a light yellow oily substance.

Reference Example 15 (3)

THF (50 mL) was added to the compound (8.62 g, 9.77 mmol) obtained in Reference Example 15 (2), and the mixture was stirred under ice cooling. Acetic acid (4.5 mL, 78.2 mmol) and a 1 mol/L tetra-n-butylammonium fluoride/THF solution (39.0 mL, 39.0 mmol) were sequentially added to the reaction mixture at the same temperature, and the mixture was stirred at room temperature for 5 hours. The solvent was distilled away under reduced pressure, ethyl acetate and an aqueous sodium hydrogen carbonate solution (6.56 g of sodium hydrogen carbonate/100 mL of water) were added to the residue, and the organic layer was separated. The organic layer was washed with a saturated aqueous sodium hydrogen carbonate solution and a saturated aqueous sodium chloride solution and then dehydrated and dried over anhydrous magnesium sulfate, and then the solvent was distilled away under reduced pressure. The residue was purified by silica gel column chromatography [eluent; ethyl acetate:hexane=50:50], thereby obtaining a target substance (5.76 g) as a colorless oily substance.

¹H-NMR (400 MHz, CDCl₃) δ value: 1.22 (9H, s), 2.97 (3H, s), 3.17-3.30 (2H, m), 3.51-3.57 (2H, m), 3.80 (3H, s), 3.83 (3H, s), 3.85-3.93 (1H, m), 4.93 (2H, s), 5.09 (2H, s), 6.84 (2H, d, J=8.8 Hz), 6.88-6.97 (3H, m), 7.08 (1H, d, J=8.4 Hz), 7.35 (4H, d, J=8.4 Hz)

Reference Example 15 (4)

THF (100 mL) was added to the compound (5.60 g, 9.32 mmol) obtained in Reference Example 15 (3), and the mixture was stirred. Under ice cooling, triphenylphosphine (2.93 g, 11.2 mmol) and carbon tetrabromide (3.71 g, 11.2 mmol) were sequentially added to the reaction mixture, and the mixture was stirred at room temperature for 65 minutes. The reaction mixture was cooled on ice, triphenylphosphine (2.93 g, 11.2 mmol) and carbon tetrabromide (3.71 g, 11.2 mmol) were sequentially added thereto, and the mixture was stirred at room temperature for 45 minutes. The reaction mixture was filtered, the residue was washed with THF, and the solvent was distilled away under reduced pressure. The residue was purified by silica gel column chromatography [eluent; ethyl acetate:hexane=25:75], thereby obtaining a target substance (6.18 g) as a colorless oily substance.

Reference Example 15 (5)

DMF (60.0 mL) and potassium p-toluenethiosulfonate (2.53 g, 11.2 mmol) were added to the compound (6.18 g, 9.31 mmol) obtained in Reference Example 15 (4), and the mixture was stirred. The reaction mixture was heated and stirred at a temperature of 70° C. to 80° C. for 2 hours and 30 minutes. The reaction mixture was cooled to room temperature, and water, ethyl acetate, and hexane were added thereto. The organic layer was washed twice with water and then with a saturated aqueous sodium chloride solution. The organic layer was dehydrated and dried over anhydrous magnesium sulfate, and then the solvent was distilled away under reduced pressure. The residue was purified by silica gel column chromatography [eluent; ethyl acetate:hexane=40:60], thereby obtaining tert-butyl 1-(2-chloro-3,4-bis((4-methoxybenzyl)oxy)benzoyl)-2-methyl-2-(2-(tosylthio)ethyl)hydrazine-1-carboxylate (6.87 g) as a light yellow oily substance.

¹H-NMR (400 MHz, CDCl₃) δ value: 1.25 (9H, s), 2.43 (3H, s), 2.85 (3H, s), 3.09 (2H, t, J=6.8 Hz), 3.26-3.49 (2H, m), 3.80 (3H, s), 3.83 (3H, s), 4.92 (2H, s), 5.08 (2H, s), 6.81-6.87 (2H, m), 6.88-6.95 (3H, m), 7.03 (1H, d, J=8.8 Hz), 7.29-7.38 (6H, m), 7.77-7.84 (2H, m)

Reference Example 16

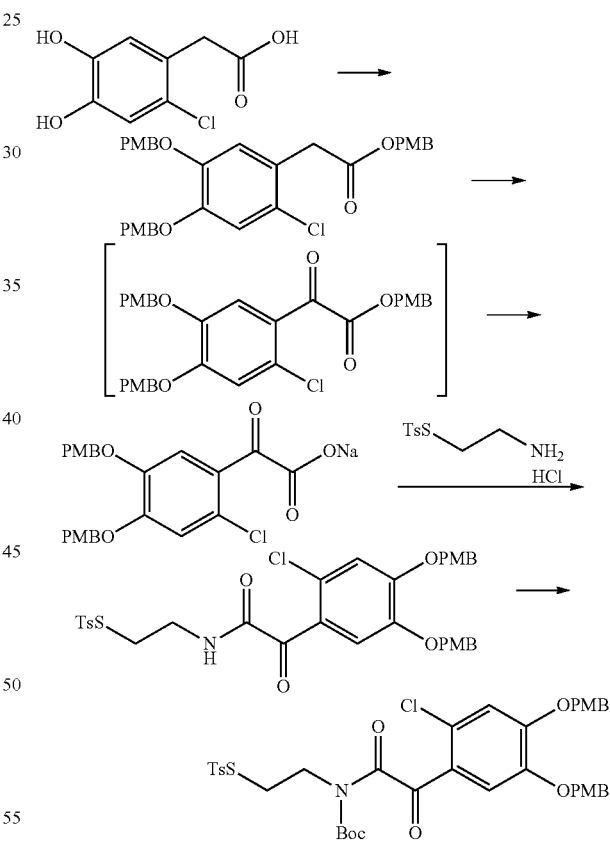

Reference Example 16 (1)

2-(2-Chloro-4,5-dihydroxyphenyl) acetic acid (35.2 g, 173.7 mmol), DMF (134 mL), potassium carbonate (120.0 g), and p-methoxybenzyl chloride (89.8 g, 573.4 mmol) were sequentially added to a reaction vessel, and the mixture was stirred at room temperature for 4 hours. Ethyl acetate (600 mL) and a saturated aqueous sodium hydrogen carbonate solution (300 mL) were added to the reaction mixture, and the organic layer was separated. The organic layer was washed twice with water (300 mL) and with a saturated aqueous sodium chloride solution and then dehydrated and dried over anhydrous sodium sulfate. The solvent was distilled away under reduced pressure, and ethyl acetate (50 mL) and IPE (25 mL) were added to the residue. Solids were collected by filtration and dried, thereby obtaining a target substance (57.0 g) as a white powder.

Reference Example 16 (2)

The compound (55.0 g, 97.7 mmol) obtained in Reference Example 16 (1) and pyridine (550 mL) were added to a reaction vessel, and the mixture was stirred at room temperature. Selenium dioxide (27.1 g, 244.2 mmol) was added to the reaction mixture, and the mixture was heated. The reaction mixture was stirred at 85° C. for 48 hours. After being cooled to room temperature, the reaction mixture was filtered through celite. Ethyl acetate (550 mL) and water (550 mL) were added to the filtrate, and 6 mol/L hydrochloric acid was added thereto so as to adjust the pH to 2.2. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate], and ethyl acetate (700 mL), hexane (350 mL), and water (700 mL) were added thereto. An 8 mol/L aqueous sodium hydroxide solution and a saturated aqueous sodium hydrogen carbonate solution were added to the obtained mixture so as to adjust the pH to 8.2. The reaction mixture was stirred at room temperature for 1 hour, and then solids were collected by filtration and dried, thereby obtaining a target substance (42.0 g) as a white powder.

Reference Example 16 (3)

The compound obtained in Reference Example 16 (2) (24.0 g, 50.1 mmol), DMAC (240 mL), triethylamine (31.4 mL, 225.5 mmol), the compound (20.1 g, 75.2 mmol) obtained in Reference Example 1 (2), and HATU (24.8 g, 65.2 mmol) were sequentially added to a reaction vessel at room temperature, and the mixture was stirred at the same temperature for 1 hour. Ethyl acetate and water were sequentially added to the reaction mixture, and the organic layer was separated. The organic layer was washed sequentially with a saturated aqueous sodium hydrogen carbonate solution and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate], thereby obtaining a target substance (11.3 g) as a colorless oily substance.

Reference Example 16 (4)

By using the compound (11.3 g, 16.8 mmol) obtained in Reference Example 16 (3), in the same manner as in Reference Example 1 (4), S-(2-(N-(tert-butoxycarbonyl)-2-(2-chloro-4,5-bis((4-methoxybenzyl)oxy)phenyl)-2-oxoacetamide)ethyl) 4-methylbenzenesulfonothioate (11.2 g) was obtained as a light yellow oily substance.

$^1$H-NMR (400 MHz, CDCl$_3$) δ value: 1.33 (9H, s), 2.45 (3H, s), 3.21 (2H, t, J=7.2 Hz), 3.81 (3H, s), 3.82 (3H, s), 4.04 (2H, t, J=7.2 Hz), 5.10 (2H, s), 5.12 (2H, s), 6.85-6.94 (5H, m), 7.30-7.38 (6H, m), 7.67 (1H, s), 7.88 (2H, d, J=8.4 Hz)

Reference Example 17

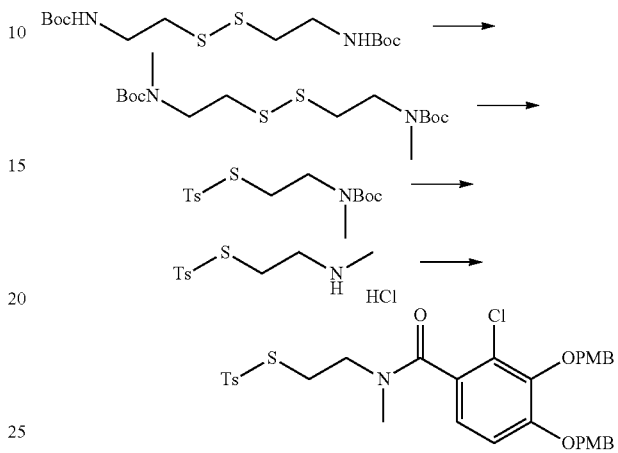

Reference Example 17 (1)

Di-tert-butyl (disulfadinylbis(ethane-2,1-diyl)) dicarbamate (2.8 g, 7.9 mmol) and DMF (30 mL) were added to a reaction vessel, and the mixture was stirred in a nitrogen atmosphere under ice cooling. At the same temperature, sodium hydride (60% mineral oil suspension, 794 mg, 19.9 mmol) was added to the reaction mixture, and the mixture was stirred at room temperature for 30 minutes. Methyl iodide (11.3 g, 79.4 mmol) was added to the reaction mixture at the same temperature, and the mixture was stirred for 2 hours and 30 minutes. Ethyl acetate and water were added to the reaction mixture, and the organic layers were separated. The aqueous layer was extracted using ethyl acetate, and the organic layers were combined and washed sequentially with water and a saturated aqueous sodium chloride solution. The organic layer was dehydrated and dried over anhydrous sodium sulfate, and the solvent was distilled away under reduced pressure. The residue was purified by silica gel column chromatography [eluent; ethyl acetate: hexane=20:80], thereby obtaining a target substance (1.37 g) as a light yellow oily substance.

Reference Example 17 (2)

At room temperature, dichloromethane (13.4 mL), potassium p-toluenethiosulfonate (2.01 g, 11.3 mmol), and iodine (1.88 g, 7.39 mmol) were added to the compound (1.34 g, 3.52 mmol) obtained in Reference Example 17 (1), and the mixture was stirred overnight. A 1 mol/L aqueous sodium thiosulfate solution was added to the reaction mixture, and the organic layer was separated. The organic layer was dehydrated and dried over anhydrous sodium sulfate, and the solvent was distilled away under reduced pressure. The residue was purified by silica gel column chromatography [eluent; ethyl acetate:hexane=20:80], thereby obtaining a target substance (1.77 g) as a yellow oily substance.

Reference Example 17 (3)

By using the compound (1.77 g, 5.12 mmol) obtained in Reference Example 17 (2), in the same manner as in Reference Example 1 (2), a target substance (1.25 g) was obtained as white solids.

Reference Example 17 (4)

The compound obtained in Reference Example 17 (3) (1.25 g, 4.44 mmol), DMF (12.5 mL), N,N-diisopropylethylamine (1.93 mL, 11.1 mmol), 2-chloro-3,4-bis((4-methoxybenzyl)oxy) benzoic acid (1.90 g, 4.44 mmol), and HATU (2.19 g, 5.77 mmol) were sequentially added to a reaction vessel at room temperature, and the mixture was stirred overnight. Ethyl acetate (25 mL) and water (25 mL) were added to the reaction mixture, and then a saturated aqueous sodium hydrogen carbonate solution was added thereto so as to adjust the pH to 8.2. The organic layer was separated and washed sequentially with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=60:40], thereby obtaining S-(2-(2-chloro-3,4-bis((4-methoxybenzyl)oxy)-N-methylbenzamide)ethyl) 4-methylbenzenesulfonothioate (2.56 g) as light yellow solids.

$^1$H-NMR (400 MHz, CDCl$_3$) δ value: 2.41 (1H, s), 2.46 (3H, s), 2.84 (3H, s), 3.07 (1H, s), 3.30 (2H, t, J=6.8 Hz), 3.80 (3H, s), 3.83 (3H, s), 4.90-5.12 (4H, m), 6.78-6.86 (3H, m), 6.88-6.98 (6H, m), 7.27-7.40 (2H, m), 7.60-7.68 (1H, m), 7.82-7.90 (2H, m)

Reference Example 18

Reference Example 18 (1)

By using 2-(2-chloro-3,4-bis((4-methoxybenzyl)oxy)phenyl)-2-oxoacetic acid (2.50 g, 5.47 mmol) and tert-butylcarbazate (723 mg, 5.47 mmol), in the same manner as in Reference Example 8 (1), a target substance (3.25 g) was obtained as light yellow solids.

Reference Example 18 (2)

By using the compound (3.25 g, 5.46 mmol) obtained in Reference Example 18 (1), a target substance (1.24 g) was obtained as white solids in the same manner as in Reference Example 8 (2).

Reference Example 18 (3)

By using the compound (1.24 g, 1.58 mmol) obtained in Reference Example 18 (2), in the same manner as in Reference Example 8 (3), di-tert-butyl (Z)-2-(2((tert-butoxycarbonyl) (2-(tosylthio)ethyl)amino)-1-(2-chloro-3,4-bis((4-methoxybenzyl)oxy)phenyl)-2-oxoethylidene)hydrazine-1,1-dicarboxylate (983 mg) was obtained as white solids.

$^1$H-NMR (400 MHz, CDCl$_3$) δ value: 1.33 (9H, s), 1.48 (18H, s), 2.43 (3H, s), 3.11-3.23 (2H, m), 3.80 (3H, s), 3.84 (3H, s), 4.00-4.09 (2H, m), 4.89 (2H, s), 5.11 (2H, s), 6.78-7.01 (5H, m), 7.28-7.39 (6H, m), 7.89 (2H, d, J=8.4 Hz), 8.09 (1H, d, J=8.8 Hz)

Reference Example 19

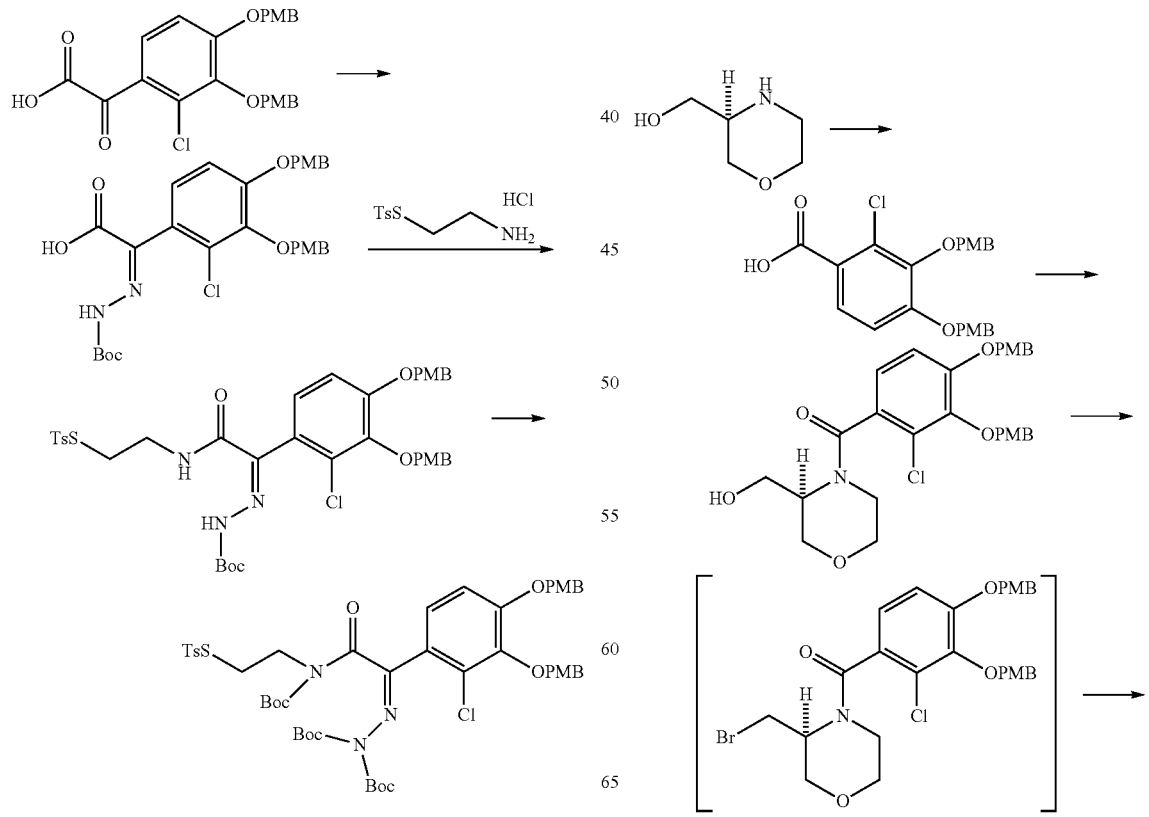

49

-continued

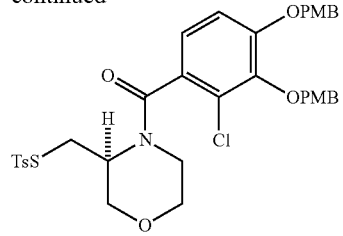

Reference Example 19 (1)

By using ((3R)-morpholin-3-yl) methanol (3.73 g, 31.9 mmol) and 2-chloro-3,4-bis((4-methoxybenzyl)oxy)benzoic acid (14.1 g, 32.8 mmol), in the same manner as in Reference Example 17 (3), a target substance (13.6 g) was obtained as white solids.

Reference Example 19 (2)

The compound (13.6 g, 25.7 mmol) obtained in Reference Example 19 (1) and dichloromethane (643 mL) were added to a reaction vessel, and the mixture was stirred under ice cooling. At the same temperature, carbon tetrabromide (14.5 g, 43.7 mmol) and triphenylphosphine (11.5 g, 43.7 mmol) were added to the reaction mixture, and the mixture was stirred for 10 minutes. The solvent was distilled away under reduced pressure, and the residue was purified by silica gel column chromatography [eluent; ethyl acetate:hexane=60:40], thereby obtaining a target substance (6.89 g) as a light brown oily substance.

Reference Example 19 (3)

By using the compound obtained in Reference Example 19 (2), in the same manner as in Reference Example 13 (4), (S)—S-((4-(2-chloro-3,4-bis((4-methoxybenzyl)oxy)benzoyl)morpholin-3-yl)methyl) 4-methylbenzenesulfonothioate (7.24 g) was obtained as white solids.

$^1$H-NMR (400 MHz, CDCl$_3$) δ value: 2.45 [2.46] (3H, s), 2.86-3.02 (1H, m), 3.05-3.58 (4H, m), 3.59-3.75 (2H, m), 3.76-3.93 (7H, m), 4.74-4.88 (1H, m), 4.92-5.14 (4H, m), 6.77-6.85 (2H, m), 6.87-7.10 (4H, m), 7.27-7.44 (5H, m), 7.59-7.66 (1H, m), 7.87 [7.93](2H, d, J=8.4 Hz)

Example 1

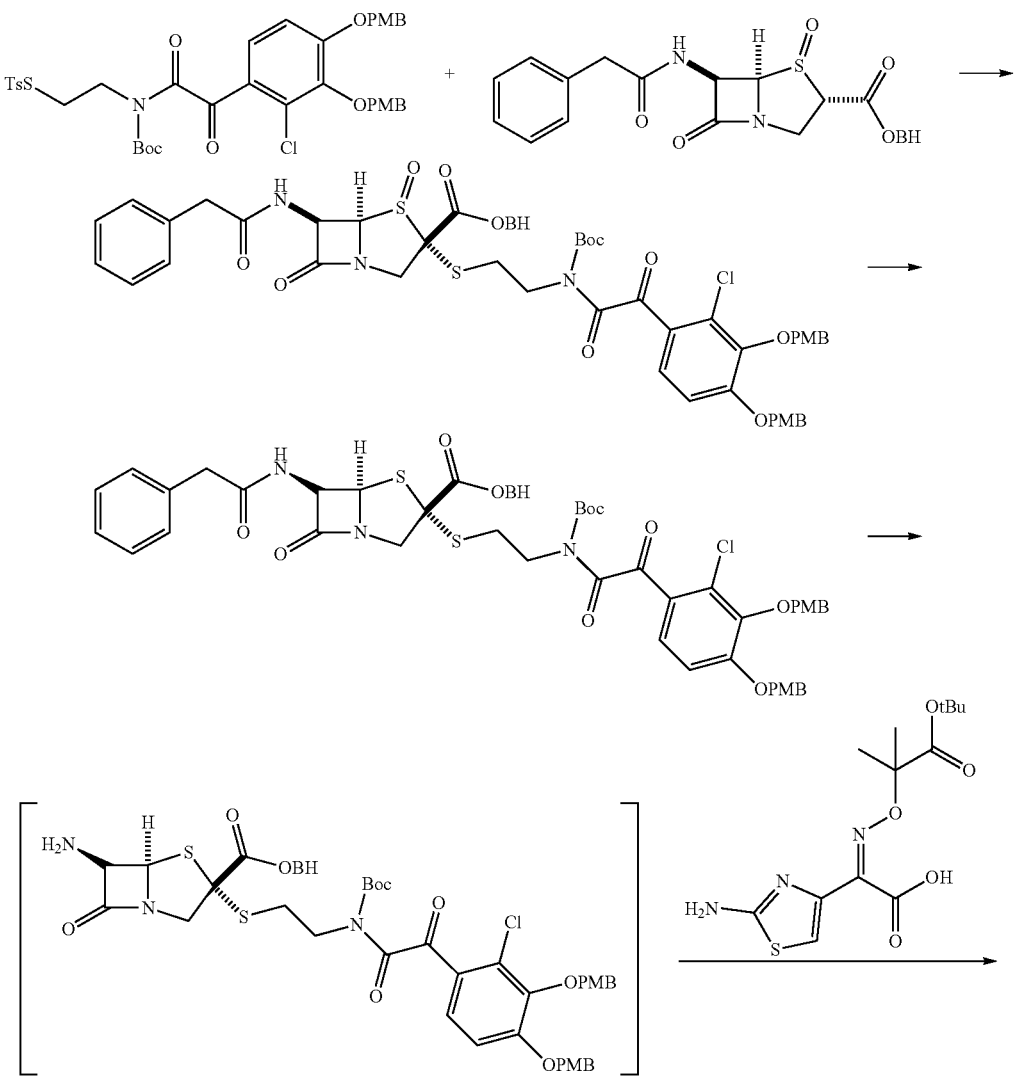

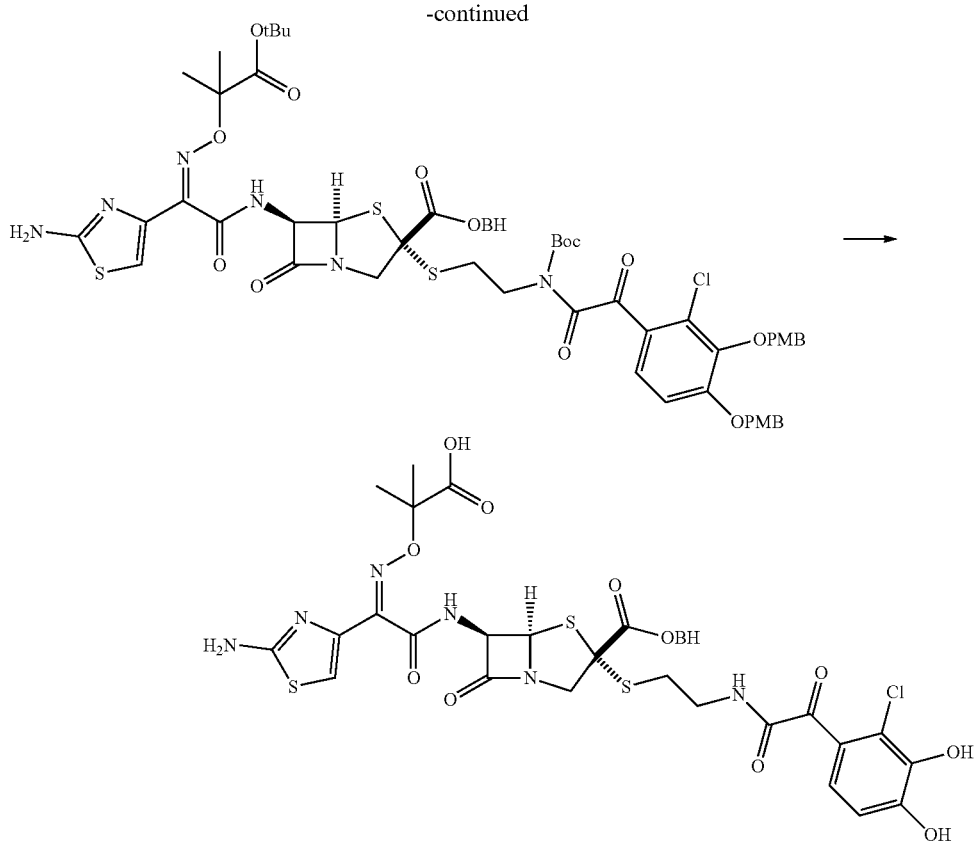

-continued

Example 1 (1)

Benzhydryl (3S,5R,6R)-7-oxo-6-(2-phenylacetamide)-4-thia-1-azabicyclo[3.2.0]heptane-3-carboxylate 4-oxide (6.35 g, 13.0 mmol) and dichloromethane (50 mL) were added to S-(2-(N-(tert-butoxycarbonyl)-2-(2-chloro-3,4-bis ((4-methoxybenzyl)oxy)phenyl)-2-oxoacetamide)ethyl) 4-methylbenzenesulfonothioate (9.98 g, 13.0 mmol), and the mixture was stirred. The reaction mixture was cooled to −20° C., and at the same temperature, a solution of DBU (1.88 g, 12.3 mmol) in dichloromethane (10 mL) was added dropwise to the reaction mixture for 15 minutes. The reaction mixture was stirred at the same temperature for 30 minutes. Then, the reaction mixture was added to a mixture of dichloromethane (47 mL), water (70 mL), and 1 mol/L hydrochloric acid (6.5 mL). The organic layer was separated from the reaction mixture and washed with a saturated aqueous sodium chloride solution (50 mL). The organic layer was dehydrated and dried over anhydrous magnesium sulfate, and then the solvent was distilled away under reduced pressure. The residue was purified by silica gel column chromatography [eluent; ethyl acetate:hexane=50:50], thereby obtaining a target substance (14.9 g) as a white foamy substance.

Example 1 (2)

Ethyl acetate (10 mL) and NMP (48 mL) were added to the compound (10.8 g, 9.79 mmol) obtained in Example 1 (1), and the mixture was stirred. The reaction mixture was cooled to −20° C., and a solution of phosphorus tribromide (21.2 g, 78.3 mmol) in ethyl acetate (6 mL) was added dropwise to the reaction mixture at the same temperature for 10 minutes. The reaction mixture was heated to −10° C. and stirred at the same temperature for 2 hours. Then, the reaction mixture was cooled to −20° C. The cooled reaction mixture was added to a mixture of ethyl acetate (100 mL) and an aqueous potassium hydrogen carbonate solution (29.3 g of potassium hydrogen carbonate/270 mL of water) at a temperature equal to or lower than 20° C. for 20 minutes. The organic layer was separated from the reaction mixture and washed three times with a 2% aqueous sodium chloride solution (200 mL). The organic layer was dehydrated and dried over anhydrous magnesium sulfate, and then the solvent was distilled away under reduced pressure. The residue was purified by silica gel column chromatography [eluent; ethyl acetate:hexane=50:50], thereby obtaining a target substance (6.09 g) as a yellow foamy substance.

$^1$H-NMR (400 MHz, DMSO-$d_6$) δ value: 1.23 (9H, s), 2.81-3.01 (2H, m), 3.41-3.52 (2H, m), 3.64-3.88 (1H, m), 3.71 (3H, s), 3.78 (3H, s), 4.44 (1H, d, J=12.8 Hz), 4.92 (2H, s), 5.26 (2H, s), 5.46 (1H, d, J=3.8 Hz), 5.55 (1H, dd, J=7.4, 3.8 Hz), 6.82 (2H, d, J=8.8 Hz), 6.75-6.83 (1H, m), 6.94-7.04 (1H, m), 7.00 (2H, d, J=8.4 Hz), 7.27-7.53 (33H, m), 7.80 (1H, d, J=8.8 Hz), 9.04 (1H, d, J=7.2 Hz)

Example 1 (3)

Dichloromethane (10 mL) was added to the compound (1.00 g, 0.92 mmol) obtained in Example 1 (2), and the mixture was cooled to −30° C. At the same temperature, N,N-dimethylaniline (0.41 mL, 3.22 mmol) and phosphorus pentachloride (287 mg, 1.38 mmol) were sequentially added to the reaction mixture, and the mixture was stirred at a temperature equal to or lower than −30° C. for 60 minutes. Then, the reaction mixture was added to methanol (5 mL) under ice cooling and stirred for 10 minutes. Ethyl acetate (50 mL) and an aqueous sodium hydrogen carbonate solution (1.0 g of sodium hydrogen carbonate/30 mL of water) were added to the reaction mixture, and the organic layer was separated. The organic layer was washed sequentially with water and a saturated aqueous sodium chloride solution and then dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (333 mg, 1.01 mmol), HATU (385 mg, 1.01 mmol), 2,6-lutidine (236 μL, 2.02 mmol), and DMF (10 mL) were added to the filtrate. The reaction mixture was stirred at room temperature under reduced pressure until it became a solution. Ethyl acetate (30 mL) and water (30 mL) were added to the reaction mixture, and the organic layer was separated. Water (30 mL) and a saturated aqueous sodium hydrogen carbonate solution were added to the organic layer so as to adjust the pH to 7.1. The organic layer was separated and dehydrated and dried over anhydrous sodium sulfate, and then the solvent was distilled away under reduced pressure. The residue was purified by silica gel column chromatography [eluent; ethyl acetate:hexane=60:40], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino) acetamide)-3-((2-(N-(tert-butoxycarbonyl)-2-(2-chloro-3,4-bis((4-methoxybenzyl)oxy)phenyl)-2-oxoacetamide)ethyl) thio)-7-oxo-4-thia-1-azabicyclo[3.2.0]heptane-3-carboxylate (460 mg) as light yellow solids.

$^1$H-NMR (400 MHz, CDCl$_3$) δ value: 1.29 (9H, s), 1.34 (9H, s), 1.52 (3H, s), 1.53 (3H, s), 2.83-2.99 (2H, m), 3.35 (1H, d, J=12.0 Hz), 3.78 (3H, s), 3.84-3.88 (2H, m), 3.84 (3H, s), 4.58 (1H, d, J=12.0 Hz), 4.95 (2H, s), 5.14 (2H, s), 5.57 (1H, d, J=4.4 Hz), 5.88 (1H, dd, J=9.2, 3.6 Hz), 5.95 (1H, s), 6.80-6.83 (3H, m), 6.87 (1H, s), 6.94 (2H, d, J=8.8 Hz), 7.04 (1H, d, J=9.2 Hz), 7.25-7.41 (15H, m), 7.58 (1H, d, J=8.8 Hz), 7.88 (1H, d, J=8.8 Hz)

Example 1 (4)

Dichloromethane (6 mL) was added to the compound (400 mg, 0.31 mmol) obtained in Example 1 (3), and the mixture was cooled to −20° C. At the same temperature, anisole (1.36 mL), nitromethane (2 mL), and aluminum chloride (208 mg, 1.56 mmol) were sequentially added to the reaction mixture. The reaction mixture was stirred at the same temperature for 2 hours and 10 minutes. The reaction mixture was added to a mixture of acetonitrile (10 mL), water (10 mL), and trisodium citrate dihydrate (827 mg, 2.81 mmol) and washed sequentially with acetonitrile (15 mL) and water (15 mL). A saturated aqueous sodium hydrogen carbonate solution was added to the reaction mixture so as to adjust the pH to 6.0, and aqueous layers were separated. The organic layer was extracted twice by using water (20 mL), and the aqueous layers were combined and concentrated under reduced pressure. The residue was purified by medium-pressure reverse-phase silica gel column chromatography [eluent; water:acetonitrile=100:0→75:25], and the aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamide)-3-((2-(2-(2-chloro-3,4-dihydroxyphenyl)-2-oxoacetamide)ethyl)thio)-7-oxo-4-thia-1-azabicyclo[3.2.0] heptane-3-carboxylic acid (75 mg) as white solids.

$^1$H-NMR (400 MHz, DMSO-d$_6$) δ value: 1.39 (3H, s), 1.42 (3H, s), 2.75-2.90 (2H, m), 3.00 (1H, d, J=12.2 Hz), 3.27-3.43 (2H, m), 4.30 (1H, d, J=12.2 Hz), 5.43 (1H, d, J=4.2 Hz), 5.63 (1H, dd, J=9.6, 4.2 Hz), 6.05-6.18 (1H, brs), 6.36 (1H, d, J=8.8 Hz), 6.77 (1H, s), 7.01 (1H, s), 7.15 (1H, d, J=8.8 Hz), 7.26 (2H, s), 7.64 (1H, s), 8.63-8.75 (1H, m), 10.06 (1H, s);

MS (ESI): 717.00 [M+H]$^+$, 715.10 [M−H]$^−$

Example 2

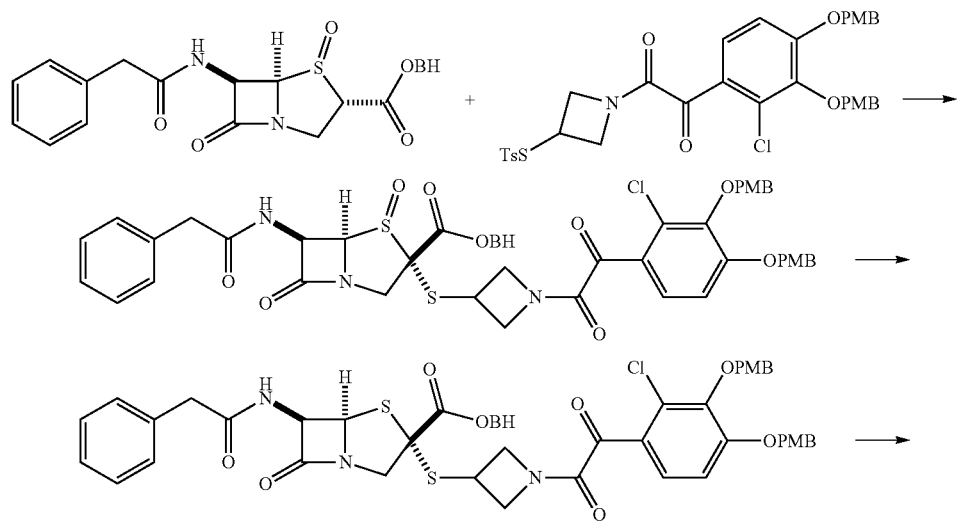

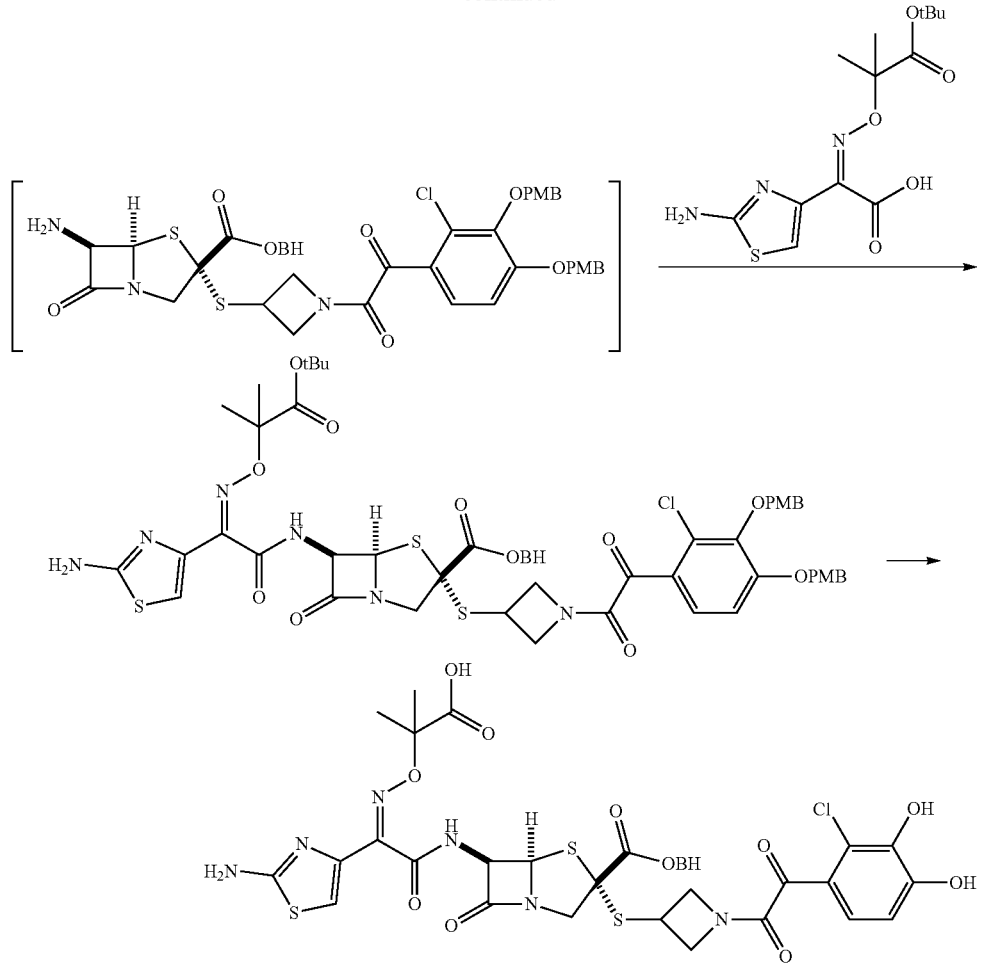

Example 2 (1)

S-(1-(2-(2-chloro-3,4-bis((4-methoxybenzyl)oxy)phenyl)-2-oxoacetyl)azetidin-3-yl) 4-methylbenzenesulfonothioate (2.30 g, 3.38 mmol) and dichloromethane (15 mL) were added to benzhydryl (3 S,5R,6R)-7-oxo-6-(2-phenylacetamide)-4-thia-1-azabicyclo[3.2.0]heptane-3-carboxylate 4-oxide (1.50 g, 3.07 mmol), and the mixture was stirred. The reaction mixture was cooled on ice, and a solution of DBU (0.47 g, 3.07 mmol) in dichloromethane (7 mL) was added dropwise thereto. The reaction mixture was stirred at the same temperature for 45 minutes. Then, the reaction mixture was added to a mixture of chloroform (22 mL), water (22 mL), and 1 mol/L hydrochloric acid (2.2 mL). The organic layer was separated from the reaction mixture and washed sequentially with a saturated aqueous sodium hydrogen carbonate solution and a saturated aqueous sodium chloride solution. The organic layer was dehydrated and dried over anhydrous magnesium sulfate, and then the solvent was distilled away under reduced pressure. The residue was purified by silica gel column chromatography [eluent; ethyl acetate:hexane=30:70], thereby obtaining a target substance (2.90 g) as white solids.

Example 2 (2)

Ethyl acetate (2.9 mL) and NMP (14.3 mL) were added to the compound (2.91 g, 2.87 mmol) obtained in Example 2 (1), and the mixture was stirred. The reaction mixture was cooled to −20° C., and a solution of phosphorus tribromide (6.21 g, 22.9 mmol) in ethyl acetate (1.1 mL) was added dropwise to the reaction mixture. The reaction mixture was stirred at the same temperature for 3 hours. Then, the reaction mixture was added to a mixture of aqueous potassium hydrogen carbonate solution (8.6 g of potassium hydrogen carbonate/38 mL of water). Ethyl acetate (80 mL) was added to the reaction mixture, and then a saturated aqueous sodium hydrogen carbonate solution was added thereto so as to adjust the pH to 6.0. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=60:40], thereby obtaining a target substance (1.2 g) as light yellow solids.

$^1$H-NMR (400 MHz, CDCl$_3$) δ value: 3.16 (1H, dd, J=13.0, 1.0 Hz), 3.52 (1H, dd, J=6.2, 3.8 Hz), 3.74-3.86 (1H, m), 3.80 (3H, s), 3.83 (3H, s), 3.94-3.98 (1H, m), 4.09-4.15 (1H, m), 4.23-4.44 (2H, m), 4.54-4.61 (1H, m), 4.97 (2H, d, J=2.8 Hz), 5.12 (2H, d, J=3.6 Hz), 5.40 (1H, dd, J=4.0, 2.8 Hz), 5.67 (1H, dd, J=9.2, 4.0 Hz), 6.26 (1H, d, J=8.8 Hz), 6.78 (1H, d, J=7.2 Hz), 6.84 (2H, d, J=8.4 Hz), 6.93 (2H, d, J=8.4 Hz), 6.97 (1H, dd, J=8.8, 4.0 Hz), 7.20-7.41 (19H, m), 7.53 (1H, d, J=8.8 Hz)

Example 2 (3)

Dichloromethane (12 mL) and N,N-dimethylaniline (510 mg, 4.21 mmol) were added to the compound (1.20 g, 1.20 mmol) obtained in Example 2 (2), and the mixture was stirred. The reaction mixture was cooled to −40° C., phosphorus pentachloride (375 mg, 1.80 mmol) was added thereto, and the mixture was stirred at the same temperature for 30 minutes. Then, the reaction mixture was added to methanol (6 mL) and stirred for 10 minutes. Ethyl acetate (70 mL) and an aqueous sodium hydrogen carbonate solution (1.31 g of sodium hydrogen carbonate/40 mL of water) were added to the reaction mixture, and the organic layer was separated. The organic layer was washed sequentially with water and a saturated aqueous sodium chloride solution and then dehydrated and dried over anhydrous sodium sulfate. Solids were filtered, and the filtrate was diluted with ethyl acetate such that the total volume thereof became 110 mL. (Z)-2-(2-aminothiazol-4-yl)-2-(((1-(tert-butoxy)-2-methyl-1-oxopropan-2-yl)oxy)imino)acetic acid (217 mg, 0.66 mmol), HATU (251 mg, 0.66 mmol), 2,6-lutidine (154 µL, 1.32 mmol), and DMF (5.3 mL) were added to the obtained solution (55 mL). The reaction mixture was stirred at room temperature under reduced pressure until it became a solution. Water (30 mL) and ethyl acetate (30 mL) were added to the reaction mixture, and the organic layer was separated. Water (30 mL) was added to the organic layer, and then a saturated aqueous sodium hydrogen carbonate solution was added thereto so as to adjust the pH to 7.3. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=90:10], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-((1-(2-(2-chloro-3,4-bis((4-methoxybenzyl)oxy)phenyl)-2-oxoacetyl)azetidin-3-yl)thio)-7-oxo-4-thia-1-azabicyclo[3.2.0]heptane-3-carboxylate (339 mg) as light yellow solids.

$^1$H-NMR (400 MHz, CDCl$_3$) δ value: 1.30-1.38 (9H, m), 1.50-1.57 (6H, m), 3.27 (1H, d, J=12.6 Hz), 3.62-3.70 (1H, m), 3.80 (3H, s), 3.83 (3H, s), 3.86-4.00 (2H, m), 4.16-4.48 (2H, m), 4.57 (1H, d, J=12.6 Hz), 4.93-5.00 (2H, m), 5.10-5.16 (2H, m), 5.49 (1H, t, J=4.2 Hz), 5.82 (1H, s), 5.88 (1H, dd, J=8.7, 4.1 Hz), 6.86-7.00 (9H, m), 7.23-7.41 (12H, m), 7.52 (1H, d, J=8.7 Hz), 7.75 (1H, t, J=9.2 Hz)

Example 2 (4)

Dichloromethane (5.1 mL) was added to the compound (339 mg, 0.28 mmol) obtained in Example 2 (3), and the mixture was cooled to −20° C. At the same temperature, anisole (1.24 mL) and aluminum chloride (303 mg, 2.28 mmol) were sequentially added to the reaction mixture. The reaction mixture was stirred at the same temperature for 1 hour and 20 minutes. The reaction mixture was added to a mixture of acetonitrile (10 mL), water (10 mL), and trisodium citrate dihydrate (1.00 g, 3.41 mmol) and washed sequentially with acetonitrile (2 mL) and water (2 mL). Then, a saturated aqueous sodium hydrogen carbonate solution was added to the reaction mixture so as to adjust the pH to 5.2, and the aqueous layer was separated. The aqueous layer was purified by medium-pressure reverse-phase silica gel column chromatography [eluent; water:acetonitrile=100:0→75:25], the aqueous solution containing a target substance was concentrated and then lyophilized, thereby obtaining (3R,5R,6R)-6-((Z)-2-(2-aminothiazol-4-yl)-2-(((2-carboxypropan-2-yl)oxy)imino)acetamide)-3-((1-(2-(2-chloro-3,4-dihydroxyphenyl)-2-oxoacetyl)azetidin-3-yl)thio)-7-oxo-4-thia-1-azabicyclo[3.2.0]heptane-3-carboxylic acid (75 mg) as yellow solids.

$^1$H-NMR (400 MHz, D$_2$O) δ value: 1.39-1.54 (6H, m), 3.21-3.32 (1H, m), 4.03-4.30 (4H, m), 4.36-4.49 (1H, m), 4.57-4.67 (2H, m), 5.52-5.64 (1H, m), 5.74 (1H, s), 6.50-6.68 (1H, m), 6.97-7.05 (1H, m), 7.20-7.32 (1H, m), 7.41 (1H, s);

MS (ESI): 729.00 [M+H]$^+$, 726.90 [M−H]$^−$

Example 3

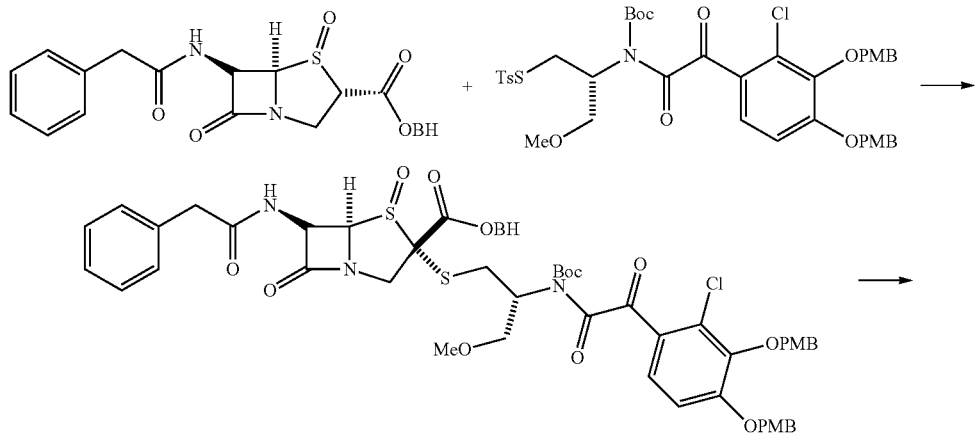

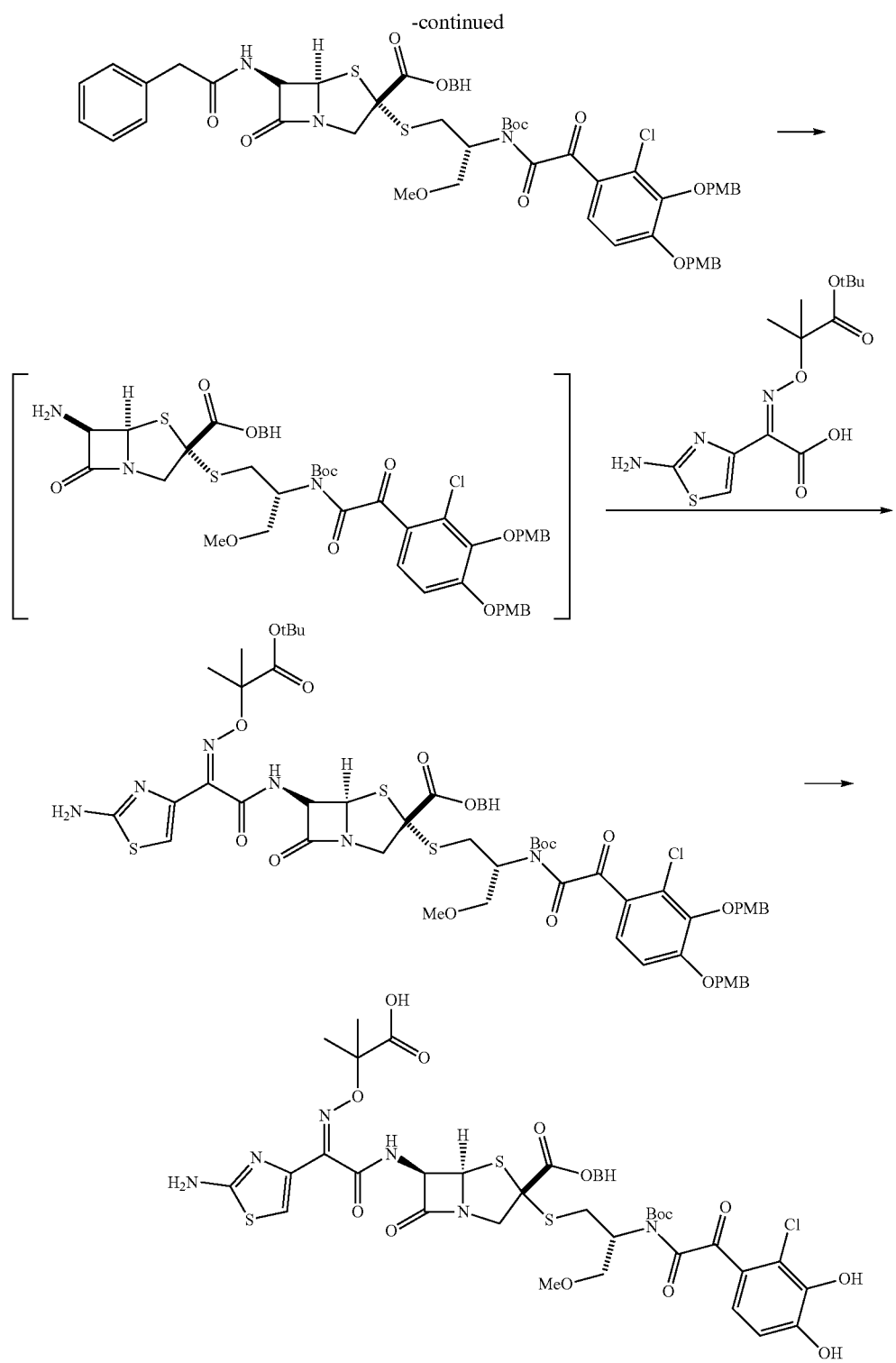

Example 3 (1)

Dichloromethane (15 mL) and (R)—S-(2-(N-(tert-butoxycarbonyl)-2-(2-chloro-3,4-bis((4-methoxybenzyl)oxy)phenyl))-2-oxoacetamide)-3-methoxypropyl) 4-methylbenzenesulfonothioate (1.19 g, 1.46 mmol) were sequentially added to benzhydryl (3 S,5R,6R)-7-oxo-6-(2-phenylacetamide)-4-thia-1-azabicyclo[3.2.0]heptane-3-carboxylate 4-oxide (650 mg, 1.33 mmol), and the mixture was stirred. The reaction mixture was cooled on ice, and then a solution of DBU (0.20 g, 1.33 mmol) in dichloromethane (7 mL) was added dropwise thereto at the same temperature. The reaction mixture was stirred at the same temperature for 45 minutes. The reaction mixture was then added to a mixture of chloroform (22 mL), water (22 mL), and 1 mol/L hydrochloric acid (2.2 mL). The organic layer was separated and washed sequentially with a saturated aqueous sodium hydrogen carbonate solution and a saturated aqueous sodium chloride solution. The organic layer was dehydrated and dried over anhydrous magnesium sulfate, and then the solvent was distilled away under reduced pressure. The residue was purified by silica gel column chromatography [eluent; ethyl acetate:hexane=50:50], thereby obtaining a target substance (1.2 g) as white solids.

Example 3 (2)

Ethyl acetate (6 mL) and NMP (12 mL) were added to the compound (1.2 g, 1.0 mmol) obtained in Example 3 (1), and the mixture was stirred. The reaction mixture was cooled to −20° C., and phosphorus tribromide (2.3 g, 8.4 mmol) was added dropwise to the reaction mixture at the same temperature. The reaction mixture was stirred at a temperature of −15° C. to −10° C. for 3 hours and 50 minutes. Then, the reaction mixture was added to a mixture of an aqueous potassium hydrogen carbonate solution (3.1 g of potassium hydrogen carbonate/20 mL of water). The reaction mixture was extracted twice using ethyl acetate (10 mL), and the organic layer was washed twice with a 5% aqueous sodium chloride solution (50 mL). The organic layer was dehydrated and dried over anhydrous magnesium sulfate, and then the solvent was distilled away under reduced pressure. The residue was purified by silica gel column chromatography [eluent; ethyl acetate:hexane=50:50], thereby obtaining a target substance (740 mg) as white solids.

$^1$H-NMR (400 MHz, CDCl$_3$) δ value: 1.27 (9H, s), 2.97 (1H, dd, J=13.2, 5.6 Hz), 3.23 (1H, d, J=12.9 Hz), 3.26-3.36 (1H, m), 3.34 (3H, s), 3.45-3.52 (1H, m), 3.50 (2H, d, J=2.6 Hz), 3.55-3.63 (1H, m), 3.72-3.82 (1H, m), 3.77 (3H, s), 3.84 (3H, s), 4.55 (1H, d, J=12.9 Hz), 4.94 (3H, s), 5.13 (3H, s), 5.47 (1H, d, J=4.0 Hz), 5.68 (1H, dd, J=9.2, 4.0 Hz), 6.29 (1H, d, J=9.2 Hz), 6.76-6.82 (3H, m), 6.93 (2H, d, J=8.7 Hz), 7.02 (1H, d, J=8.9 Hz), 7.18-7.42 (14H, m), 7.86 (1H, d, J=8.9 Hz)

Example 3 (3)

Dichloromethane (7.4 mL) and N,N-dimethylaniline (278 mg, 2.29 mmol) were added to the compound (740 mg, 0.65 mmol) obtained in Example 3 (2), and the mixture was stirred. The reaction mixture was cooled to −50° C., phosphorus pentachloride (220 mg, 1.05 mmol) was added thereto at the same temperature, and the mixture was stirred at a temperature of −50° C. to −45° C. for 1 hour and 10 minutes. Then, the reaction mixture was added to methanol (3.7 mL) and stirred for 8 minutes. Ethyl acetate (30 mL) and an aqueous sodium hydrogen carbonate solution (714 mg of sodium hydrogen carbonate/21 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. (Z)-2-(2-aminothiazol-4-yl)-2-(((1-(tert-butoxy)-2-methyl-1-oxopropan-2-yl)(oxy)imino)acetic acid (128 mg, 0.39 mmol), HATU (148 mg, 0.39 mmol), 2,6-lutidine (45 μL, 0.39 mmol), and DMF (3.3 mL) were added to half of the obtained solution. The reaction mixture was stirred at room temperature under reduced pressure for 70 minutes until it became a solution. Water and ethyl acetate were added to the reaction mixture, and the organic layer was separated. Water was added to the organic layer, and a saturated aqueous sodium hydrogen carbonate solution was added thereto so as to adjust the pH to 7.0. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=50:50], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-(((R)-2-(N-(tert-butoxycarbonyl)- 2-(2-chloro-3,4-bis((4-methoxybenz yl)oxy)phenyl)-2-oxoacetamide)-3-methoxypropyl)thio)-7-oxo-4-thia-1-azabicyclo[3.2.0]heptane-3-carboxylate (220 mg) as white solids.

$^1$H-NMR (400 MHz, CDCl$_3$) δ value: 1.21-1.30 (6H, m), 1.47 (9H, s), 1.67 (9H, s), 3.20-3.36 (2H, m), 3.34 (3H, s), 3.46-3.52 (1H, m), 3.55-3.62 (1H, m), 3.75-3.81 (4H, m), 3.84 (3H, s), 4.55 (1H, d, J=12.9 Hz), 4.90-4.97 (2H, m), 5.07-5.17 (2H, m), 5.47 (1H, d, J=4.1 Hz), 5.68 (1H, dd, J=9.3, 4.1 Hz), 6.29 (1H, d, J=9.3 Hz), 6.75-7.08 (8H, m), 7.16-7.44 (14H, m)

Example 3 (4)

Dichloromethane (2.2 mL) was added to the compound (220 mg, 0.17 mmol) obtained in Example 3 (3), and the mixture was cooled to −20° C. At the same temperature, anisole (0.72 mL), nitromethane (1.1 mL), and aluminum chloride (266 mg, 1.99 mmol) were sequentially added to the reaction mixture. The reaction mixture was stirred at a temperature of −20° C. to −15° C. for 45 minutes. The reaction mixture was added to a mixture of acetonitrile (15 mL), water (15 mL), and trisodium citrate dihydrate (733 mg, 2.49 mmol) and washed sequentially with acetonitrile (10 mL) and water (10 mL). Then, a saturated aqueous sodium hydrogen carbonate solution was added to the reaction mixture so as to adjust the pH to 5.5, and the aqueous layers were separated. The organic layer was extracted twice by using water (5 mL), and the aqueous layers were combined and concentrated. The obtained solution was purified by medium-pressure reverse-phase silica gel column chromatography [eluent; water:acetonitrile=100:0→70:30], and the aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamide)-3-(((R)-2-(2-(2-chloro-3,4-dihydroxyphenyl)-2-oxoacetamide)-3-methoxypropyl)thio)-7-oxo-4-thia-1-azabicyclo[3.2.0]heptane-3-carboxylic acid (38 mg) as yellow solids.

$^1$H-NMR (400 MHz, D$_2$O) δ value: 1.41 (3H, s), 1.43 (3H, s), 2.84-2.97 (1H, m), 3.01-3.10 (1H, m), 3.24 (1H, d, J=12.3 Hz), 3.36 (3H, s), 3.52-3.64 (2H, m), 3.69 (1H, dd, J=11.2, 1.7 Hz), 4.35 (1H, d, J=12.3 Hz), 5.56 (1H, d, J=3.7 Hz), 5.68 (1H, d, J=3.7 Hz), 6.54 (1H, d, J=8.4 Hz), 7.21 (1H, d, J=8.4 Hz), 7.34 (1H, s);

MS (ESI): 760.95 [M+H]$^+$, 758.85 [M−H]$^−$

Example 4
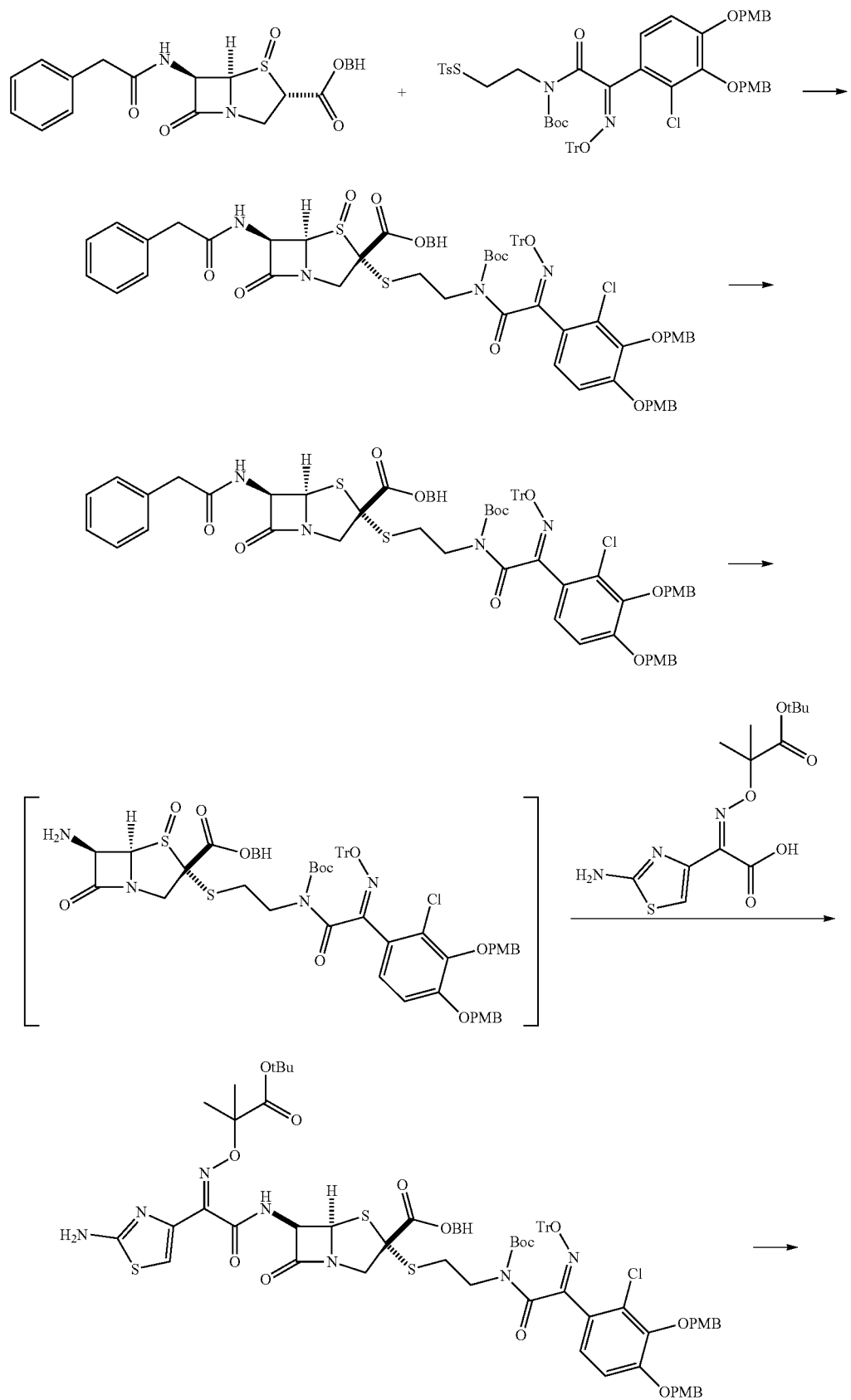

-continued

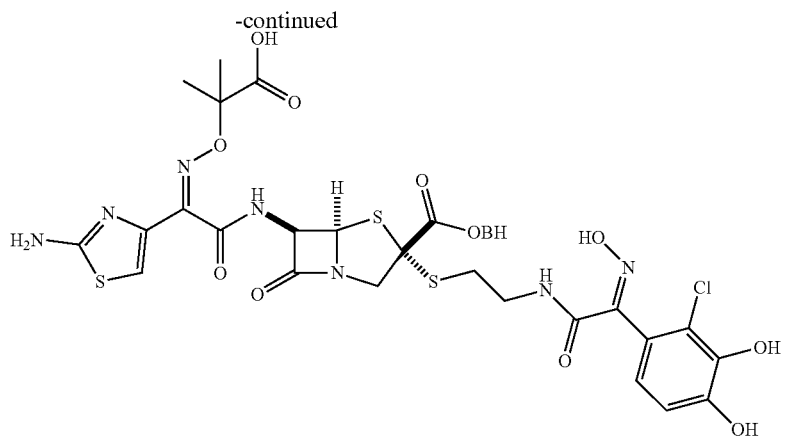

Example 4 (1)

(Z)—S-(2-(N-(tert-butoxycarbonyl)-2-(2-chloro-3,4-bis((4-methoxybenzyl)oxy)phenyl)-2-((trityloxy)imino)acetamide)ethyl 4-methylbenzenesulfonothioate (11.9 g, 11.6 mmol) and dichloromethane (51 mL) were added to benzhydryl (3 S,5R,6R)-7-oxo-6-(2-phenylacetamide)-4-thia-1-azabicyclo[3.2.0]heptane-3-carboxylate 4-oxide (5.10 g, 10.4 mmol), and the mixture was stirred. The reaction mixture was cooled to −20° C., and a solution of DBU (1.51 g, 9.92 mmol) in dichloromethane (10 mL) was added dropwise to the reaction mixture at the same temperature. The reaction mixture was stirred at the same temperature for 1 hour and then added to a mixture of dichloromethane (60 mL), water (60 mL), and 1 mol/L hydrochloric acid (6 mL) under ice cooling. The organic layer was separated from the reaction mixture and washed sequentially with water (60 mL), a 5% aqueous sodium hydrogen carbonate solution (60 mL), and a 10% aqueous sodium chloride solution (60 mL). The organic layer was dehydrated and dried over anhydrous sodium sulfate, and then the solvent was distilled away under reduced pressure. The residue was purified by silica gel column chromatography [eluent; ethyl acetate:hexane=40:60], thereby obtaining a target substance (12.2 g) as a colorless oily substance.

Example 4 (2)

Ethyl acetate (9 mL) and NMP (45 mL) were added to the compound (12.2 g, 8.93 mmol) obtained in Example 4 (1), and the mixture was stirred. The reaction mixture was cooled to −20° C., and then phosphorus tribromide (19.4 g, 71.5 mmol) was added dropwise to the reaction mixture at the same temperature. The reaction mixture was stirred at a temperature of −15° C. to −5° C. for 3 hours. Then, the reaction mixture was added to a mixture of ethyl acetate (130 mL) and an aqueous potassium hydrogen carbonate solution (26.8 g of potassium hydrogen carbonate/119 mL of water) under ice cooling. The organic layer was separated and washed twice with a 5% aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=50:50], thereby obtaining a target substance (8.53 g) as a light yellow oily substance.

$^1$H-NMR (400 MHz, CDCl$_3$) δ value: 1.26 (9H, s), 2.65 (2H, t, J=7.6 Hz), 3.09 (1H, d, J=13.6 Hz), 3.48 (2H, d, J=3.2 Hz), 3.55-3.66 (2H, m), 3.76 (3H, s), 3.83 (3H, s), 4.48 (1H, d, J=13.2 Hz), 4.97 (2H, s), 5.09 (2H, s), 5.32 (1H, d, J=4.0 Hz), 5.63 (1H, dd, J=9.2, 3.6 Hz), 6.34 (1H, d, J=9.2 Hz), 6.76 (1H, s), 6.77-6.83 (3H, m), 6.89-6.96 (4H, m), 7.15-7.39 (32H, m), 7.48 (1H, d, J=7.6 Hz)

Example 4 (3)

Dichloromethane (16 mL) and N, N-dimethylaniline (505 mg, 4.17 mmol) were added to the compound (1.60 g, 1.19 mmol) obtained in Example 4 (2), and the mixture was stirred. The reaction mixture was cooled to −50° C., phosphorus pentachloride (372 mg, 1.79 mmol) was added thereto at the same temperature, and the mixture was stirred at a temperature of −50° C. to −45° C. for 1 hour. Then, the reaction mixture was added to methanol (8 mL) and stirred for 15 minutes. Ethyl acetate and an aqueous sodium hydrogen carbonate solution (1.3 g of sodium hydrogen carbonate/39 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. The filtrate was divided into four parts, and (Z)-2-(2-aminothiazol-4-yl)-2-(((1-(tert-butoxy)-2-methyl-1-oxopropan-2-yl)oxy)imino)acetic acid (100 mg, 0.40 mmol), HATU (100 mg, 0.40 mmol), 2,6-lutidine (40 μL, 0.40 mmol), and DMF (4 mL) were added thereto. The reaction mixture was stirred at room temperature under reduced pressure for 1 hour and 45 minutes until it became a solution. Water and ethyl acetate were added to the reaction mixture, and the organic layer was separated. Water and a saturated aqueous sodium hydrogen carbonate solution were added to the organic layer so as to adjust the pH to 7.5. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=90:10], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-((2-((Z)—N-(tert)- butoxycarbonyl)-2-(2-chloro-3,4-bis((4-methoxybenz yl)oxy)phenyl)-2-((trityloxy)imino) acetamide)ethyl)thio)-7-oxo-4-thia-1-azabicyclo[3.2.0] heptane-3-carboxylate (240 mg) as light yellow solids.

$^1$H-NMR (400 MHz, CDCl$_3$) δ value: 1.25 (3H, s), 1.33 (3H, s), 1.46 (9H, s), 1.67 (9H, s), 2.57-2.78 (2H, m), 3.21

(1H, d, J=12.2 Hz), 3.57 (2H, t, J=7.3 Hz), 3.76 (3H, s), 3.83 (3H, s), 4.48 (1H, d, J=12.2 Hz), 4.97 (2H, s), 5.09 (2H, s), 5.43 (1H, d, J=4.0 Hz), 5.83 (1H, dd, J=8.8, 4.0 Hz), 6.47 (1H, s), 6.76-6.87 (2H, m), 6.90-6.99 (2H, m), 7.18-7.50 (33H, m)

Example 4 (4)

Dichloromethane (3.6 mL) was added to the compound (240 mg, 0.16 mmol) obtained in Example 4 (3), and the mixture was cooled to −20° C. At the same temperature, anisole (0.68 mL), nitromethane (1.2 mL), and aluminum chloride (167 mg, 1.25 mmol) were sequentially added to the reaction mixture. The reaction mixture was stirred at a temperature of −20° C. to −15° C. for 1 hour and 25 minutes. The reaction mixture was added to a mixture of acetonitrile (15 mL), water (15 mL), and trisodium citrate dihydrate (551 mg, 1.87 mmol) and washed sequentially with acetonitrile (10 mL) and water (10 mL). Then, a saturated aqueous sodium hydrogen carbonate solution was added to the reaction mixture so as to adjust the pH to 5.5, and the aqueous layers were separated. The organic layer was extracted twice by using water (5 mL), the aqueous layers were combined and concentrated. The obtained solution was purified by medium-pressure reverse-phase silica gel column chromatography [eluent; water:acetonitrile=100:0→75:25], and the aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamide)-3-((2-((Z)-2-(2-chloro-3,4-dihydroxyphenyl)-2-(hydroxyimino)acetamide)ethyl)thio)-7-oxo-4-thia-1-azabicyclo[3.2.0]heptane-3-carboxylic acid (17 mg) as yellow solids.

$^1$H-NMR (400 MHz, DMSO-d$_6$) δ value: 1.38 (3H, s), 1.42 (3H, s), 2.72-2.89 (2H, m), 2.98 (1H, d, J=12.4 Hz), 3.52-3.61 (2H, m), 4.27 (1H, d, J=12.4 Hz), 5.32-5.48 (2H, brs), 5.61 (1H, dd, J=9.6, 4.0 Hz), 6.47 (1H, d, J=8.2 Hz), 6.73 (1H, d, J=8.2 Hz), 6.75 (1H, s), 7.01 (1H, s), 7.24 (2H, s), 7.64 (1H, s), 8.08 (1H, t, J=6.0 Hz), 11.83 (1H, s);

MS (ESI): 732.00 [M+H]$^+$, 730.10 [M−H]$^−$

Example 5

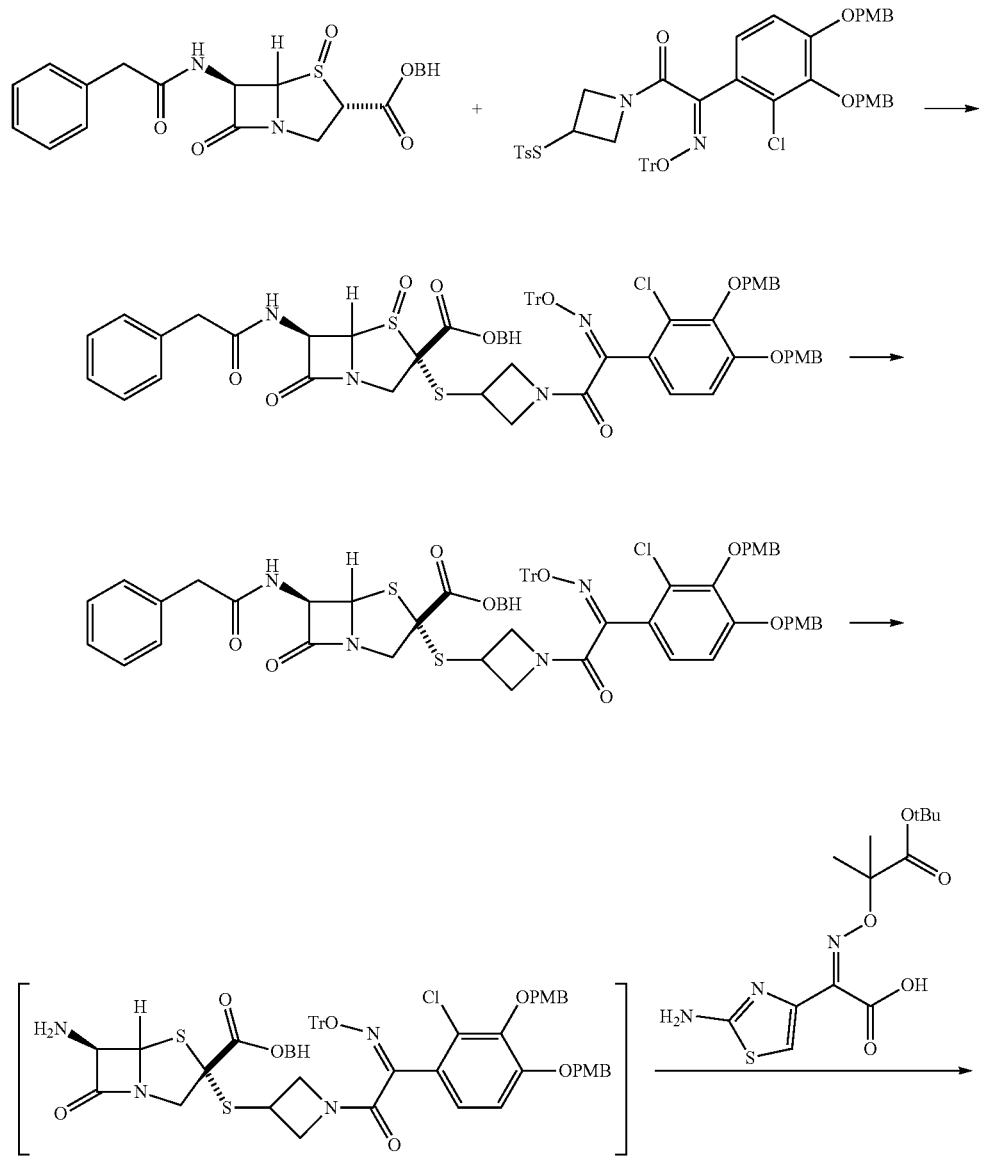

-continued

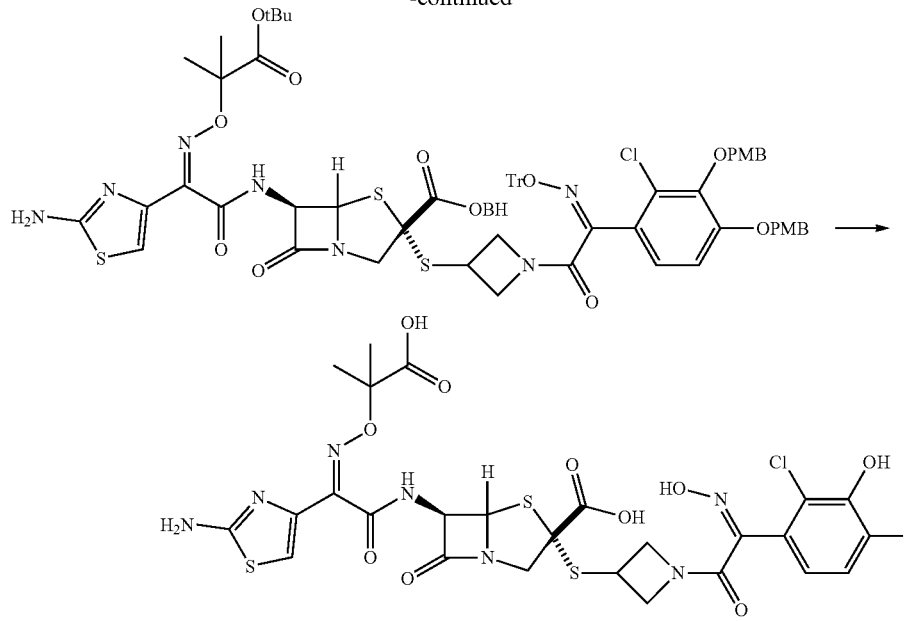

Example 5 (1)

(Z)—S-(1-(2-(2-chloro-3,4-bis((4-methoxybxyenzyl)oxy)phenyl)-2-(((trityloxy)imino)acetyl)azetidin-3-yl) 4-methylbenzenesulfonothioate (2.43 g, 2.59 mmol) and dichloromethane (15 mL) were added to benzhydryl (3 S,5R,6R)-7-oxo-6-(2-phenylacetamide)-4-thia-1-azabicyclo [3.2.0]heptane-3-carboxylate 4-oxide (1.15 g, 2.35 mmol), and the mixture was stirred under ice cooling. At the same temperature, a solution of DBU (358 mg, 2.35 mmol) in dichloromethane (7 mL) was added dropwise to the reaction mixture. The reaction mixture was stirred at the same temperature for 45 minutes. Then, the reaction mixture was added to a mixture of chloroform (22 mL), water (22 mL), and 1 mol/L hydrochloric acid (2.2 mL). The organic layer was separated from the reaction mixture and washed sequentially with a saturated aqueous sodium hydrogen carbonate solution and a saturated aqueous sodium chloride solution. The organic layer was dehydrated and dried over anhydrous magnesium sulfate, and then the solvent was distilled away under reduced pressure. The residue was purified by silica gel column chromatography [eluent; ethyl acetate:hexane=30:70], thereby obtaining a target substance (3.00 g) as light yellow solids.

Example 5 (2)

Ethyl acetate (2.4 mL) and NMP (12 mL) were added to the compound (3.00 g, 2.36 mmol) obtained in Example 5 (1), and the mixture was stirred. The reaction mixture was cooled to −20° C., and a solution of phosphorus tribromide (5.11 g, 18.9 mmol) in ethyl acetate (1.6 mL) was added dropwise to the reaction mixture. The reaction mixture was stirred at a temperature of −20° C. to −10° C. for 3 hours, and then added to a mixture of an aqueous potassium hydrogen carbonate solution (7.08 g of potassium hydrogen carbonate/31 mL of water). Ethyl acetate (20 mL) was added to the reaction mixture, and then a saturated aqueous sodium hydrogen carbonate solution was added thereto so as to adjust the pH to 6.3. The organic layer was separated from the reaction mixture and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=55:45], thereby obtaining a target substance (1.75 g) as white solids.

$^1$H-NMR (400 MHz, CDCl$_3$) δ value: 2.96 (1H, dd, J=19.8, 12.6 Hz), 3.32-3.65 (5H, m), 3.73 (3H, s), 3.77-3.81 (1H, m), 3.84 (3H, s), 4.07-4.19 (1H, m), 4.51 (1H, dd, J=12.8, 10.8 Hz), 4.98 (2H, s), 5.10 (2H, s), 5.36 (1H, dd, J=20.8, 4.0 Hz), 5.69 (1H, ddd, J=9.8, 9.8, 3.8 Hz), 6.35 (1H, dd, J=9.0, 5.4 Hz), 6.76-6.79 (3H, m), 6.92-7.07 (5H, m), 7.17-7.38 (33H, m)

Example 5 (3)

Dichloromethane (17.5 mL) and N,N-dimethylaniline (591 mg, 4.88 mmol) were added to the compound (1.75 g, 1.39 mmol) obtained in Example 5 (2), and the mixture was stirred. The reaction mixture was cooled to −40° C., phosphorus pentachloride (435 mg, 2.09 mmol) was added thereto at the same temperature, and the mixture was stirred at a temperature of −40° C. to −35° C. for 30 minutes. Then, the reaction mixture was added to methanol (8.8 mL) and stirred for 1 hour and 10 minutes. Ethyl acetate (90 mL) and an aqueous sodium hydrogen carbonate solution (1.52 g of sodium hydrogen carbonate/50 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. The filtrate was diluted with ethyl acetate such that the total volume thereof became 120 mL. (Z)-2-(2-aminothiazol-4-yl)-2-(((1-(tert-butoxy)-2-methyl-1-oxopropan-2-yl)oxy) imino) acetic acid (252 mg, 0.77 mmol), HATU (291 mg, 0.77 mmol), 2,6-lutidine (178 μL, 1.53 mmol), and DMF (7.9 mL) were added to the obtained solution (60 mL). The reaction mixture was stirred at room temperature under reduced pressure until it became a solution. Water (40 mL) and ethyl acetate (40 mL) were added to the reaction mixture, and the organic layer was separated. Water (40 mL) was added to the organic layer, and then a saturated aqueous sodium hydrogen carbonate solution was added thereto so as to adjust the pH to 6.8. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=70:30], thereby obtaining benzhydryl (3R, 5R,6R)-6-((Z)-2-(2-aminothiazol-4-yl)-2-(((1-(tert-butoxy)-2-methyl-1-oxopropan-2-yl)oxy)imino)acetamide)-3-((1-((Z)-2-(2-chloro- 3,4-bis((4-methoxybenzyl)oxy)phenyl)-2-((trityloxy)imino)acetyl)azetidin-3-yl)thio)-7-oxo-4-thia-1-azabicyclo[3.2.0]heptane-3-carboxylate (535 mg) as light yellow solids.

$^1$H-NMR (400 MHz, CDCl$_3$) δ value: 1.34 (9H, d, J=2.0 Hz), 1.52 (3H, d, J=4.0 Hz), 1.55 (3H, d, J=3.2 Hz), 3.11 (1H, dd, J=16.6, 12.6 Hz), 3.31-3.45 (2H, m), 3.52-3.65 (1H, m), 3.74 (3H, d, J=2.4 Hz), 3.79-3.88 (1H, m), 3.84 (3H, s), 4.01-4.19 (1H, m), 4.50 (1H, dd, J=12.6, 11.4 Hz), 4.98 (2H, s), 5.10 (2H, s), 5.37-5.50 (1H, m), 5.89-5.94 (2H, m), 6.03 (1H, s), 6.76-6.79 (3H, m), 6.87-7.06 (6H, m), 7.16-7.38 (28H, m), 7.53-7.78 (1H, m)

Example 5 (4)

Dichloromethane (8 mL) was added to the compound (535 mg, 0.37 mmol) obtained in Example 5 (3), and the mixture was cooled to −20° C. At the same temperature, anisole (1.6 mL) and aluminum chloride (591 mg, 4.43 mmol) were sequentially added to the reaction mixture. The reaction mixture was stirred at the same temperature for 1 hour and 40 minutes. The reaction mixture was added to a mixture of acetonitrile (15 mL), water (15 mL), and trisodium citrate dihydrate (1.95 g, 6.65 mmol) and washed sequentially with acetonitrile (2 mL) and water (2 mL). Then, a saturated aqueous sodium hydrogen carbonate solution was added to the reaction mixture so as to adjust the pH to 5.1, and the aqueous layer was separated. The aqueous layer was purified by medium-pressure reverse-phase silica gel column chromatography [eluent; water:acetonitrile=100: 0→75:25], and the aqueous solution containing a target substance was concentrated and then lyophilized, thereby obtaining a compound (3R,5R,6R)-6-((Z)-2-(2-aminothiazol-4-yl)-2-(((2-carboxypropan-2-yl)oxy)imino)acetamide)-3-((1-((Z)-2-(2-chloro-3,4-dihydroxyphenyl)-2-(hydroxyimino)acetyl)azetidin-3-yl)thio)-7-oxo-4-thia-1-azabicyclo[3.2.0]heptane-3-carboxylic acid (78 mg) as light yellow solids.

$^1$H-NMR (400 MHz, D$_2$O) δ value: 1.48 (3H, d, J=5.6 Hz), 1.51 (3H, s), 3.28 (1H, d, J=12.8 Hz), 3.99-4.14 (2H, m), 4.25-4.29 (1H, m), 4.41 (1H, dd, J=12.0, 12.0 Hz), 4.53-4.60 (2H, m), 5.57 (1H, dd, J=15.8, 3.8 Hz), 5.76 (1H, ddd, J=10.7, 3.7, 0.7 Hz), 6.88 (1H, dd, J=8.0, 7.2 Hz), 6.96 (1H, d, J=8.4 Hz), 7.02 (1H, s);

MS (ESI): 744.00 [M+H]$^+$, 742.00 [M−H]$^−$

Example 6

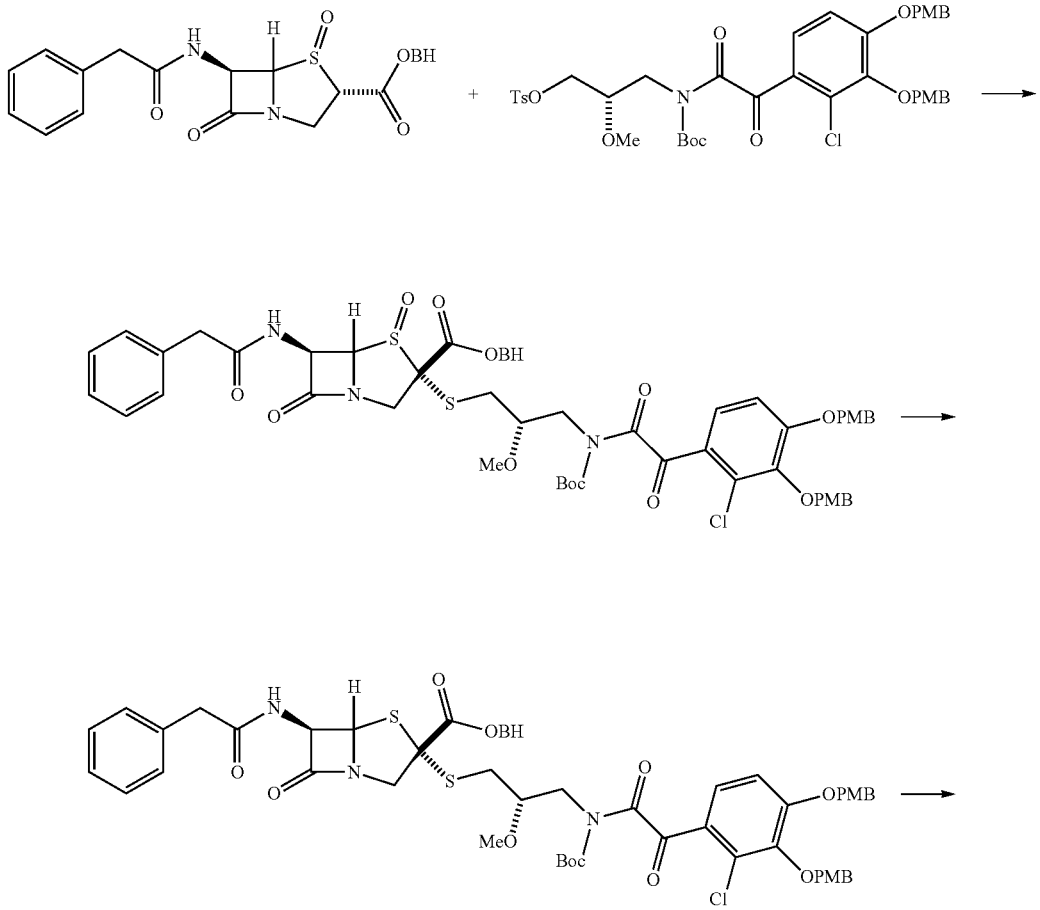

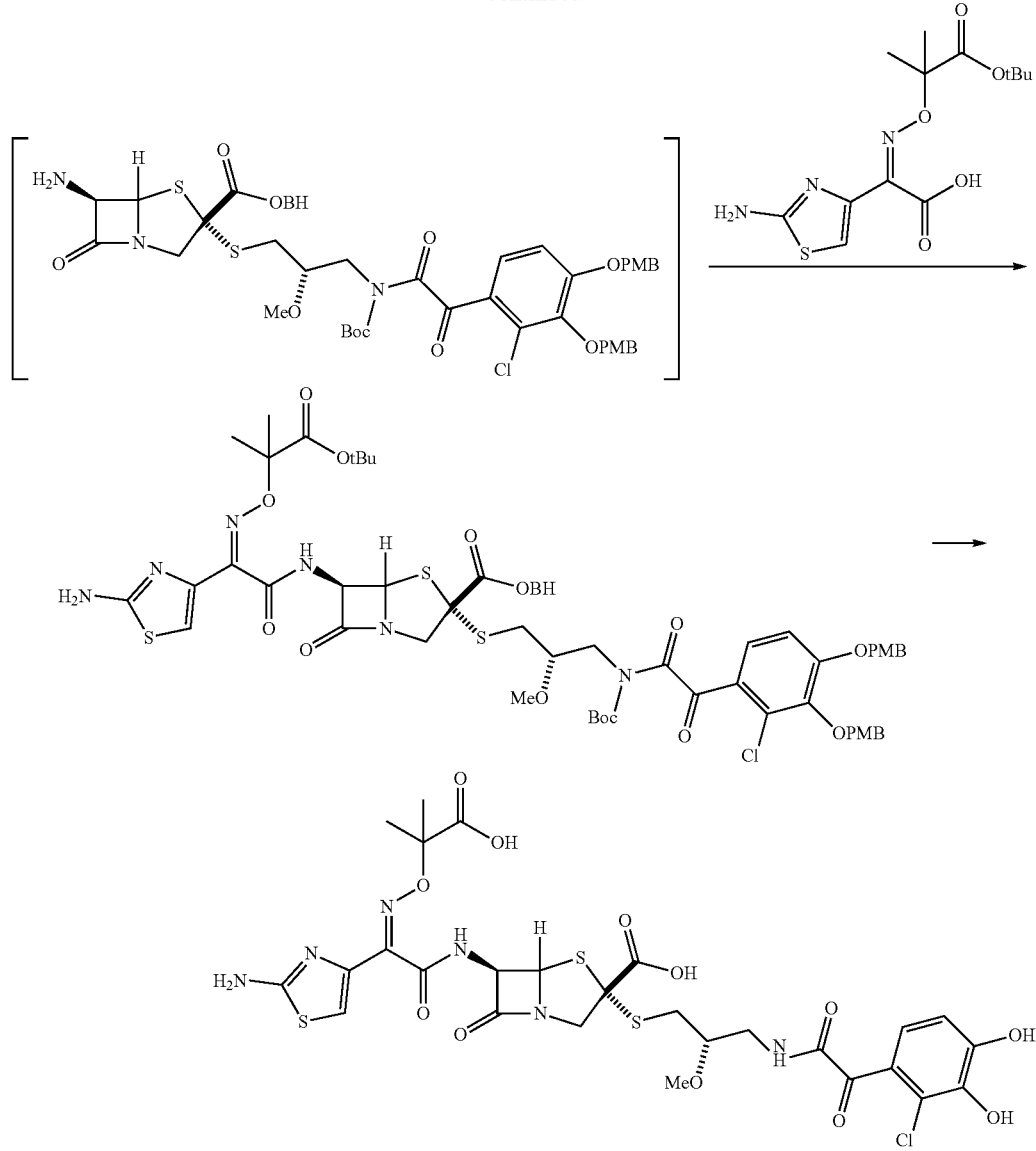

Example 6(1)

(S)—S-(3-(N-(tert-butoxycarbonyl)-2-(2-chloro-3,4-bis ((4-methoxybenzyl)oxy)phenyl)-2-oxoacetamide)-2-methoxypropyl) 4-methylbenzenesulfonothioate (7.88 g, 9.67 mmol) and dichloromethane (45 mL) were added to benzhydryl (3 S, 5R,6R)-7-oxo-6-(2-phenylacetamide)-4-thia-1-azabicyclo[3.2.0]heptane-3-carboxylate 4-oxide (4.50 g, 9.21 mmol), and the mixture was stirred. The reaction mixture was cooled to −20° C., and at the same temperature, a solution of DBU (1.33 g, 8.75 mmol) in dichloromethane (10 mL) was added dropwise to the reaction mixture. The reaction mixture was stirred at the same temperature for 30 minutes. Then, under ice cooling, the reaction mixture was added to a mixture of water (30 mL) and 1 mol/L hydrochloric acid (4.1 mL). The organic layer was separated from the reaction mixture and dehydrated and dried over anhydrous sodium sulfate, and then the solvent was distilled away under reduced pressure. The residue was purified by silica gel column chromatography [eluent; ethyl acetate:hexane=55:45], thereby obtaining a target substance (9.90 g) as yellow solids.

Example 6 (2)

Ethyl acetate (9 mL) and NMP (43 mL) were added to the compound (9.90 g, 8.63 mmol) obtained in Example 6 (1), and the mixture was stirred. The reaction mixture was cooled to −20° C., and a solution of phosphorus tribromide (18.7 g, 69.1 mmol) in ethyl acetate (6 mL) was added dropwise to the reaction mixture at the same temperature. The reaction mixture was stirred at a temperature of −20° C. to −10° C. for 6 hours and 30 minutes. Under ice cooling, the reaction mixture was added to a mixture of an aqueous potassium hydrogen carbonate solution (25.9 g of potassium hydrogen carbonate/115 mL of water). Ethyl acetate (200 mL) was added to the reaction mixture, and the organic layer was separated. Water (150 mL), ethyl acetate (100 mL), and an aqueous sodium chloride solution (10 mL) were added to the organic layer, and the organic layer was separated. The organic layer was dehydrated and dried over anhydrous sodium sulfate, and then the solvent was distilled away under reduced pressure. The residue was purified by silica gel column chromatography [eluent; ethyl acetate: hexane=55:45], thereby obtaining a target substance (6.84 g) as white solids.

$^1$H-NMR (400 MHz, CDCl$_3$) δ value: 1.30 (9H, s), 2.77 (1H, dd, J=13.2, 6.4 Hz), 2.83 (1H, dd, J=13.2, 4.8 Hz), 3.25 (1H, d, J=12.8 Hz), 3.32 (3H, s), 3.48 (2H, d, J=2.4 Hz), 3.60-3.66 (1H, m), 3.73-3.78 (1H, m), 3.78 (3H, s), 3.84 (3H, s), 3.93 (1H, dd, J=13.8, 6.6 Hz), 4.56 (1H, d, J=13.2 Hz), 4.95 (2H, s), 5.14 (2H, s), 5.46 (1H, d, J=4.0 Hz), 5.65 (1H, dd, J=9.2, 4.0 Hz), 6.38 (1H, d, J=9.2 Hz), 6.81 (2H, d, J=8.8 Hz), 6.81 (1H, s), 6.94 (2H, d, J=8.4 Hz), 7.05 (1H, d, J=8.8 Hz), 7.19-7.22 (3H, m), 7.25-7.42 (16H, m), 7.88 (1H, d, J=8.8 Hz)

Example 6 (3)

Dichloromethane (15 mL) was added to the compound (1.50 g, 1.33 mmol) obtained in Example 6 (2), and the mixture was stirred. The reaction mixture was cooled to a temperature equal to or lower than −30° C., N,N-dimethylaniline (563 mg, 4.64 mmol) and phosphorus pentachloride (414 mg, 1.99 mmol) were sequentially added thereto, and the mixture was stirred at the same temperature for 30 minutes. Then, the reaction mixture was added to methanol (7.5 mL), and the mixture was stirred under ice cooling for 10 minutes. Ethyl acetate (60 mL) and an aqueous sodium hydrogen carbonate solution (1.45 g of sodium hydrogen carbonate/40 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (481 mg, 1.46 mmol), HATU (555 mg, 1.46 mmol), 2,6-lutidine (340 μL, 2.92 mmol), and DMF (15 mL) were added to the filtrate. The reaction mixture was stirred at room temperature under reduced pressure until it became a solution. Water (50 mL) and ethyl acetate (50 mL) were added to the reaction mixture, and the organic layer was separated. Water (50 mL) was added to the organic layer, and then a saturated aqueous sodium hydrogen carbonate solution was added thereto so as to adjust the pH to 6.5. The organic layer was separated and dehydrated and dried over anhydrous sodium sulfate, and then the solvent was distilled away under reduced pressure. The residue was purified by silica gel column chromatography [eluent; ethyl acetate:hexane=60:40], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-(((S)-3-(N-(tert-butoxycarbonyl)-2-(2-chloro-3,4-bis((4-methoxybenzyl)oxy)phenyl)-2-oxoacetamide)-2-methoxypropyl)thio)-7-oxo-4-thia-1-azabicyclo[3.2.0]heptane-3-carboxylate (770 mg) as light yellow solids.

$^1$H-NMR (400 MHz, CDCl$_3$) δ value: 1.30 (9H, s), 1.34 (9H, s), 1.51 (3H, s), 1.52 (3H, s), 2.78-2.87 (2H, m), 3.28 (1H, d, J=12.8 Hz), 3.29 (3H, s), 3.61-3.67 (1H, m), 3.73 (1H, dd, J=14.0, 4.8 Hz), 3.79 (3H, s), 3.84 (3H, s), 3.93 (1H, dd, J=13.8, 7.0 Hz), 4.57 (1H, d, J=12.8 Hz), 4.95 (2H, s), 5.14 (2H, s), 5.56 (1H, d, J=4.0 Hz), 5.87 (1H, dd, J=9.0, 3.8 Hz), 6.26 (1H, s), 6.81 (2H, d, J=8.4 Hz), 6.84 (1H, s), 6.93 (2H, d, J=8.8 Hz), 7.04 (1H, d, J=8.8 Hz), 7.27-7.43 (17H, m), 7.87 (1H, d, J=9.2 Hz)

Example 6 (4)

A dichloromethane (12 mL) solution was added to the compound (770 mg, 0.58 mmol) obtained in Example 6 (3), and the mixture was cooled to −20° C. At the same temperature, anisole (2.5 mL) and aluminum chloride (620 mg, 4.65 mmol) were sequentially added to the reaction mixture. The reaction mixture was stirred at the same temperature for 1 hour. The reaction mixture was added to a mixture of acetonitrile (15 mL), water (15 mL), and trisodium citrate dihydrate (2.05 g, 6.98 mmol) under ice cooling, and washed with a 50% aqueous acetonitrile solution (2 mL). Then, a saturated aqueous sodium hydrogen carbonate solution was added to the reaction mixture so as to adjust the pH to 5.2, and the aqueous layer was separated. The aqueous layer was concentrated under reduced pressure, and the residue was purified by medium-pressure reverse-phase silica gel column chromatography [eluent; water:acetonitrile=100:0→90:10]. The aqueous solution containing a target substance was lyophilized, thereby obtaining (3R,5R,6R)-6-((Z)-2-(2-aminothiazol-4-yl)-2-(((2-carboxypropane-2-yl)oxy)imino)acetamide)-3-(((S)-3-(2-(2-chloro-3,4-dihydroxyphenyl)-2-oxoacetamide)-2-methoxypropyl)thio)-7-oxo-4-thia-1-azabicyclo[3.2.0]heptane-3-carboxylic acid (223 mg) as yellow solids.

$^1$H-NMR (400 MHz, D$_2$O) δ value: 1.47 (3H, s), 1.49 (3H, s), 3.00 (1H, dd, J=13.4, 6.2 Hz), 3.06 (1H, dd, J=13.6, 5.6 Hz), 3.31 (1H, d, J=12.4 Hz), 3.47 (3H, s), 3.54 (1H, dd, J=14.2, 6.2 Hz), 3.67 (1H, dd, J=14.2, 4.6 Hz), 3.81-3.87 (1H, m), 4.44 (1H, d, J=12.4 Hz), 5.60 (1H, d, J=4.0 Hz), 5.73 (1H, d, J=3.2 Hz), 6.59 (1H, d, J=8.4 Hz), 7.02 (1H, s), 7.22 (1H, d, J=8.4 Hz);

MS (ESI): 761.05 [M+H]$^+$, 758.80 [M−H]$^−$

Example 7

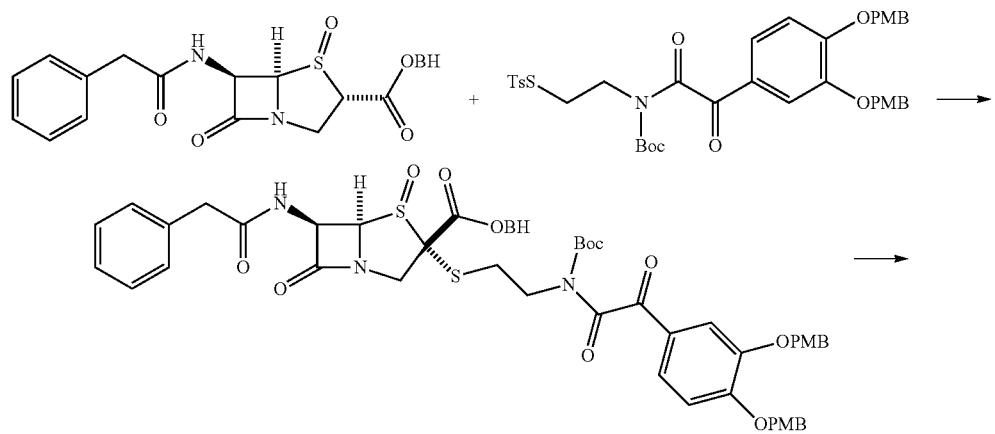

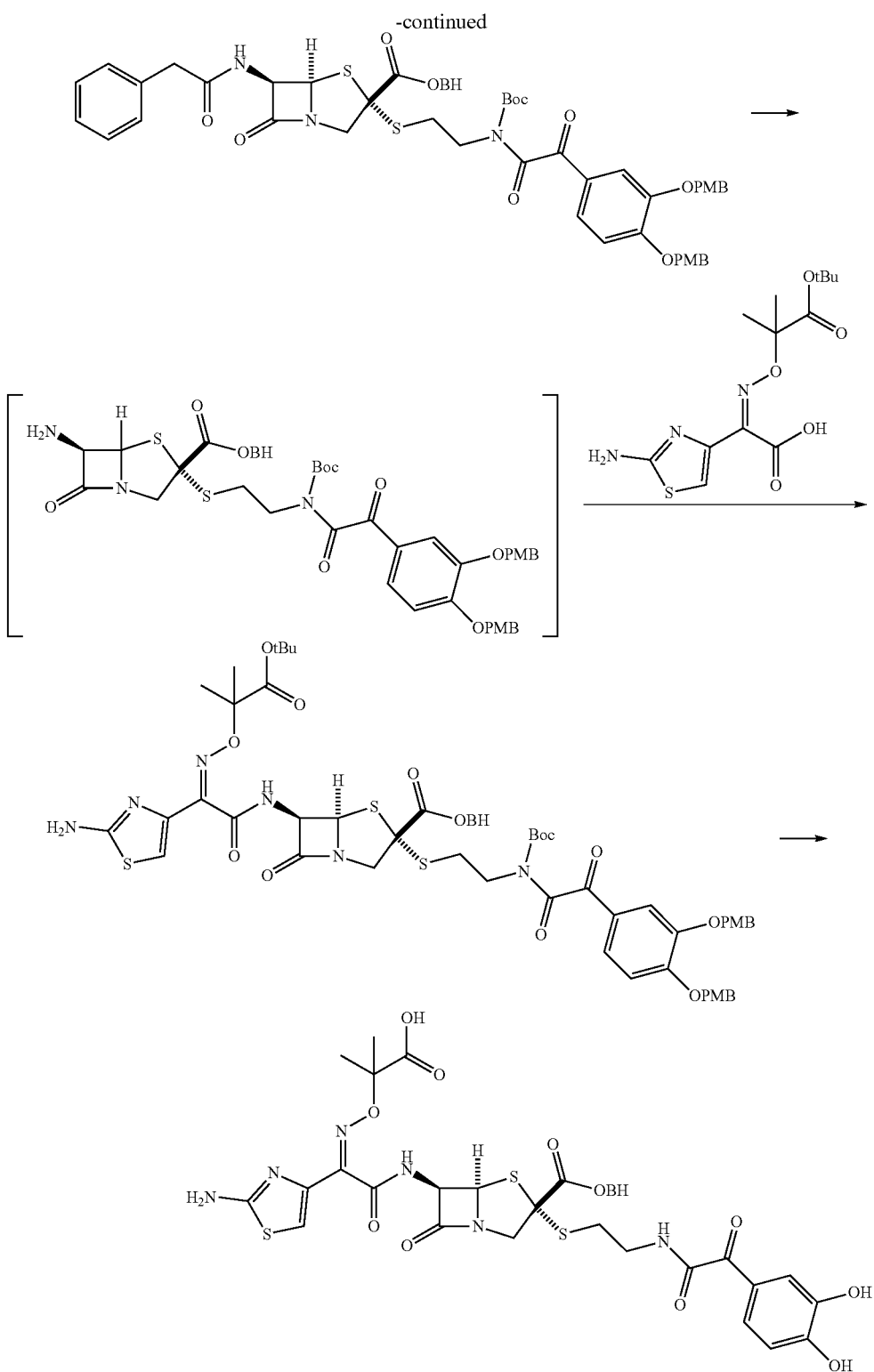

Example 7 (1)

S-(2-(2-(3,4-bis((4-methoxybenzyl)oxy)phenyl)-N-(tert-butoxycarbonyl)-2-oxoacetamide)ethyl) 4-methylbenzenesulfonothioate (10.3 g, 13.8 mmol) and dichloromethane (64 mL) were added to benzhydryl (3 S,5R,6R)-7-oxo-6-(2-phenylacetamide)-4-thia-1-azabicyclo[3.2.0]heptane-3-carboxylate 4-oxide (6.40 g, 13.1 mmol), and the mixture was stirred. The reaction mixture was cooled to −20° C., and at the same temperature, a solution of DBU (1.89 g, 12.4 mmol) in dichloromethane (8 mL) was added dropwise to the reaction mixture. The reaction mixture was stirred at the same temperature for 1 hour. Then, the reaction mixture was added to a mixture of dichloromethane (60 mL), water (60 mL), and 1 mol/L hydrochloric acid (5.9 mL) under ice cooling. The organic layer was separated from the mixture and dehydrated and dried over anhydrous sodium sulfate, and then the solvent was distilled away under reduced pressure. The residue was purified by silica gel column chromatography [eluent; ethyl acetate:hexane=70:30], thereby obtaining a target substance (14.6 g) as light yellow solids.

Example 7 (2)

Ethyl acetate (13 mL) and NMP (66 mL) were added to the compound (14.0 g, 13.1 mmol) obtained in Example 7 (1), and the mixture was stirred. The reaction mixture was cooled to −20° C., and a solution of phosphorus tribromide (28.4 g, 105 mmol) in ethyl acetate (9 mL) was added dropwise to the reaction mixture at the same temperature. The reaction mixture was stirred at a temperature of −25° C. to −10° C. for 3 hours. Then, the reaction mixture was added to a mixture of an aqueous potassium hydrogen carbonate solution (39.3 g of potassium hydrogen carbonate/175 mL of water) under ice cooling. Ethyl acetate (200 mL) was added to the reaction mixture, and the organic layer was separated. Water, ethyl acetate (100 mL), and a saturated aqueous sodium chloride solution (10 mL) were added to the organic layer, and the organic layer was washed. The organic layer was washed with a saturated aqueous sodium chloride solution and dehydrated and dried over anhydrous sodium sulfate, and then the solvent was distilled away under reduced pressure. The residue was purified by silica gel column chromatography [eluent; ethyl acetate:hexane=65:35], thereby obtaining a target substance (8.11 g) as light yellow solids.

$^1$H-NMR (400 MHz, CDCl$_3$) δ value: 1.19 (9H, s), 2.83-2.97 (2H, m), 3.23 (1H, d, J=12.8 Hz), 3.49 (2H, d, J=2.4 Hz), 3.80 (3H, s), 3.81 (3H, s), 3.91 (1H, dd, J=7.1, 3.5 Hz), 3.92 (1H, dd, J=7.1, 3.5 Hz), 4.57 (1H, d, J=12.8 Hz), 5.11 (2H, s), 5.15 (2H, s), 5.44 (1H, d, J=4.0 Hz), 5.65 (1H, dd, J=9.2, 4.0 Hz), 6.34 (1H, d, J=9.2 Hz), 6.80 (1H, s), 6.86-6.94 (7H, m), 7.19-7.22 (3H, m), 7.25-7.39 (15H, m), 7.52 (1H, d, J=2.0 Hz)

Example 7 (3)

Dichloromethane (10 mL) was added to the compound (1.00 g, 0.95 mmol) obtained in Example 7 (2), and the mixture was stirred. The reaction mixture was cooled to a temperature equal to or lower than −30° C., N,N-dimethylaniline (403 mg, 3.33 mmol) and phosphorus pentachloride (297 mg, 1.43 mmol) were sequentially added thereto, and the mixture was stirred at the same temperature for 1 hour. Then, the reaction mixture was added to methanol (5 mL), and the mixture was stirred for 10 minutes under ice cooling. Ethyl acetate (50 mL) and an aqueous sodium hydrogen carbonate solution (1.04 g of sodium hydrogen carbonate/30 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (344 mg, 1.05 mmol), HATU (397 mg, 1.05 mmol), 2,6-lutidine (243 μL, 2.09 mmol), and DMF (10 mL) were added to the filtrate. The reaction mixture was stirred at room temperature under reduced pressure until it became a solution. Water (30 mL) and ethyl acetate (30 mL) were added to the reaction mixture, and the organic layer was separated. Water (30 mL) was added to the organic layer, and then a saturated aqueous sodium hydrogen carbonate solution was added thereto so as to adjust the pH to 6.9. The organic layer was separated and dehydrated and dried over anhydrous sodium sulfate, and then the solvent was distilled away under reduced pressure. The residue was purified by silica gel column chromatography [eluent; ethyl acetate:hexane=60:40], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-((2-(2-(3,4-bis((4-methoxybenzyl)oxy)phenyl)-N-(tert-butoxycarbonyl)-2-oxoacetamide)ethyl)thio)-7-oxo-4-thia-1-azabicyclo[3.2.0]heptane-3-carboxylate (519 mg) as light yellow solids.

$^1$H-NMR (400 MHz, CDCl$_3$) δ value: 1.19 (9H, s), 1.34 (9H, s), 1.51 (3H, s), 1.52 (3H, s), 2.83-3.02 (2H, m), 3.34 (1H, d, J=12.8 Hz), 3.80 (3H, s), 3.81 (3H, s), 3.90 (2H, t, J=7.0 Hz), 4.58 (1H, d, J=12.8 Hz), 5.11 (2H, s), 5.15 (2H, s), 5.55 (1H, d, J=4.0 Hz), 5.85 (1H, dd, J=8.8, 4.0 Hz), 6.25 (1H, s), 6.83-6.95 (8H, m), 7.25-7.36 (14H, m), 7.49 (1H, d, J=9.2 Hz), 7.53 (1H, d, J=2.0 Hz)

Example 7 (4)

Dichloromethane (7.8 mL) was added to the compound (519 mg, 0.42 mmol) obtained in Example 7 (3), and the mixture was cooled to −20° C. At the same temperature, anisole (1.8 mL) and aluminum chloride (445 mg, 3.33 mmol) were sequentially added to the reaction mixture. The reaction mixture was stirred at the same temperature for 1 hour. The reaction mixture was added to a mixture of acetonitrile (32 mL), water (24 mL), and trisodium citrate dihydrate (1.47 g, 5.00 mmol) under ice cooling, and washed with a 50% aqueous acetonitrile solution (2 mL). Then, a saturated aqueous sodium hydrogen carbonate solution was added to the reaction mixture so as to adjust the pH to 5.1, and the aqueous layer was separated. The aqueous layer was concentrated under reduced pressure, and the residue was purified by medium-pressure reverse-phase silica gel column chromatography [eluent; water:acetonitrile=100:0→90:10]. The aqueous solution containing a target substance was lyophilized, thereby obtaining (3R,5R,6R)-6-((Z)-2-(2-aminothiazol-4-yl)-2-(((2-carboxypropane-2-yl)oxy)imino)acetamide)-3-((2-(2-(3,4-dihydroxyphenyl)-2-oxoacetamide)ethyl)thio)-7-oxo-4-thia-1-azabicyclo[3.2.0]heptane-3-carboxylic acid (110 mg) as yellow solids.

$^1$H-NMR (400 MHz, D$_2$O) δ value: 1.43 (3H, s), 1.46 (3H, s), 3.07 (2H, t, J=6.4 Hz), 3.30 (1H, d, J=12.4 Hz), 3.59-3.73 (1H, m), 4.39 (1H, d, J=12.4 Hz), 5.55 (1H, d, J=4.0 Hz), 5.70 (1H, d, J=3.6 Hz), 6.93 (1H, s), 7.01 (1H, d, J=8.4 Hz), 7.58 (1H, d, J=2.0 Hz), 7.64 (1H, dd, J=8.6, 2.2 Hz);

MS (ESI): 683.05 [M+H]$^+$, 680.85 [M−H]$^−$

Example 8
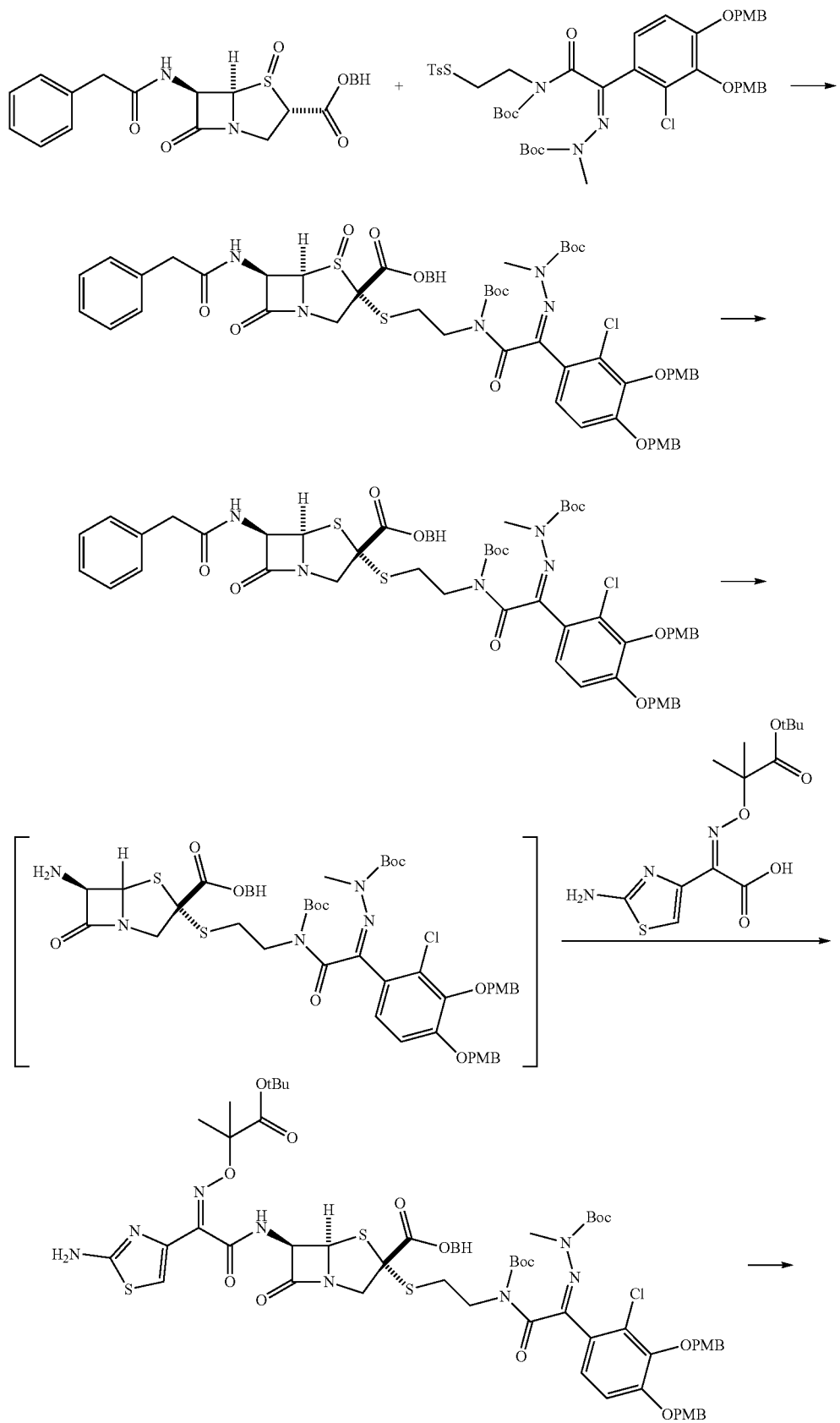

-continued

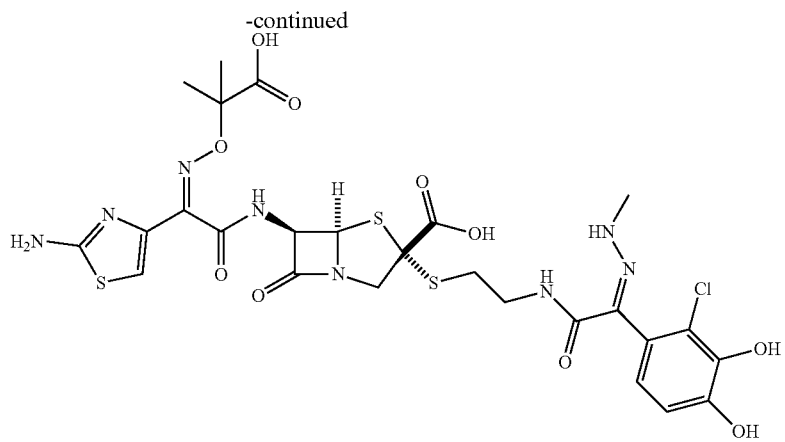

Example 8 (1)

Tert-butyl (Z)-2-(1-(2-chloro-3,4-bis((4-methoxybenzyl)oxy)phenyl)-2-oxo-2-((2-(tosylthio)ethyl)amino) ethylidene)-1-methylhydrazine-1-carboxylate (1.71 g, 1.90 mmol) and dichloromethane (17 mL) were added to benzhydryl (3 S,5R,6R)-7-oxo-6-(2-phenylacetamide)-4-thia-1-azabicyclo[3.2.0]heptane-3-carboxylate 4-oxide (846 mg, 1.73 mmol), and the mixture was stirred under ice cooling. At the same temperature, a solution of DBU (264 mg, 1.73 mmol) in dichloromethane (2 mL) was added dropwise to the reaction mixture. The reaction mixture was stirred at the same temperature for 1 hour. Then, the reaction mixture was added to a mixture of dichloromethane (10 mL), water (15 mL), and 1 mol/L hydrochloric acid (0.86 mL). The organic layer was separated from the reaction mixture and dehydrated and dried over anhydrous magnesium sulfate, and then the solvent was distilled away under reduced pressure. The residue was purified by silica gel column chromatography [eluent; ethyl acetate:hexane=65:35], thereby obtaining a target substance (1.99 g) as light yellow solids.

Example 8 (2)

Ethyl acetate (1.6 mL) and NMP (8 mL) were added to the compound (1.99 g, 1.62 mmol) obtained in Example 8 (1), and the mixture was stirred. The reaction mixture was cooled to −20° C. At the same temperature, a solution of phosphorus tribromide (3.50 g, 12.9 mmol) in ethyl acetate (1.1 mL) was added dropwise to the reaction mixture. The reaction mixture was stirred at a temperature of −20° C. to −10° C. for 3 hours, and then added to a mixture of an aqueous potassium hydrogen carbonate solution (4.86 g of potassium hydrogen carbonate/22 mL of water). Ethyl acetate (20 mL) and a saturated aqueous sodium chloride solution were added to the reaction mixture, and the organic layer was separated. The organic layer was washed with a saturated aqueous sodium chloride solution and dehydrated and dried over anhydrous sodium sulfate, and then the solvent was distilled away under reduced pressure. The residue was purified by silica gel column chromatography [eluent; ethyl acetate:hexane=55:45], thereby obtaining a target substance (1.63 g) as light yellow solids.

$^1$H-NMR (400 MHz, CDCl$_3$) δ value: 1.42 (9H, s), 1.47 (9H, s), 2.81 (3H, s), 2.86-2.95 (2H, m), 3.19 (1H, d, J=13.1 Hz), 3.48 (1H, d, J=2.5 Hz), 3.75-3.90 (2H, m), 3.79 (3H, s), 3.83 (3H, s), 4.51 (1H, d, J=13.1 Hz), 5.01 (2H, s), 5.06 (2H, s), 5.40 (1H, d, J=3.9 Hz), 5.64 (1H, dd, J=9.2, 3.9 Hz), 6.36 (1H, d, J=9.2 Hz)), 6.74-7.04 (8H, m), 7.14-7.42 (18H, m)

Example 8 (3)

Dichloromethane (11 mL) and N,N-dimethylaniline (384 mg, 3.17 mmol) were added to the compound (1.10 g, 0.91 mmol) obtained in Example 8 (2), and the mixture was stirred. The reaction mixture was cooled to −50° C., phosphorus pentachloride (282 mg, 1.36 mmol) was added thereto at the same temperature, and the mixture was stirred at a temperature of −50° C. to −45° C. for 65 minutes. Then, the reaction mixture was added to methanol (5.5 mL) and stirred for 8 minutes. Ethyl acetate (30 mL) and an aqueous sodium hydrogen carbonate solution (989 mg of sodium hydrogen carbonate/33 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (178 mg, 0.54 mmol), HATU (205 mg, 0.54 mmol), 2,6-lutidine (63 µL, 0.54 mmol), and DMF (4.9 mL) were added to half of the filtrate. The reaction mixture was stirred at room temperature under reduced pressure for 70 minutes until it became a solution. Water and ethyl acetate were added to the reaction mixture, and the organic layer was separated. Water was added to the organic layer, and then a saturated aqueous sodium hydrogen carbonate solution was added thereto so as to adjust the pH to 7.0. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=50:50], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-((2-((Z)—N-(tert- butoxycarbonyl)-2-(2-(tert-butoxycarbonyl)-2-methyl hydrazono)-2-(2-chloro-3,4-bis((4-methoxybenzyl)oxy)phenyl)acetamide)ethyl)thio)7-oxo-4-thia-1-azabicyclo[3.2.0]heptane-3-carboxylate (170 mg) as light yellow solids.

$^1$H-NMR (400 MHz, CDCl$_3$) δ value: 1.44 (9H, s), 1.45-1.50 (15H, m), 2.82 (3H, s), 2.80-3.04 (2H, m), 3.27-3.35 (1H, m), 3.74-3.94 (2H, m), 3.78 (3H, s), 3.82 (3H, s), 4.56 (1H, d, J=12.8 Hz), 5.02 (2H, s), 5.06 (2H, s), 5.29 (1H, s), 5.54 (1H, d, J=3.9 Hz), 5.86 (1H, dd, J=9.1, 3.9 Hz), 6.78-7.10 (8H, m), 7.15-7.55 (14H, m)

Example 8 (4)

Dichloromethane (2.6 mL) was added to the compound (170 mg, 0.12 mmol) obtained in Example 8 (3), and the mixture was cooled to −20° C. At the same temperature, anisole (0.53 mL), nitromethane (0.85 mL), and aluminum chloride (129 mg, 0.97 mmol) were sequentially added to the reaction mixture. The reaction mixture was stirred at the same temperature for 1 hour. The reaction mixture was added to a mixture of acetonitrile (15 mL), water (15 mL), and trisodium citrate dihydrate (426 mg, 1.45 mmol), and washed sequentially with acetonitrile (10 mL) and water (10 mL). Then, a saturated aqueous sodium hydrogen carbonate solution was added to the reaction mixture so as to adjust the pH to 5.5, and the aqueous layers were separated. The organic layer was extracted twice by using water (5 mL), the aqueous layers were combined and concentrated under reduced pressure. The concentrated aqueous solution was purified by medium-pressure reverse-phase silica gel column chromatography [eluent; water:acetonitrile=100: 0→70:30], and the aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamide)-3-((2-((Z)-2-(2-chloro-3,4-dihydroxyphenyl)-2-(2-methylhydrazono)acetamide)ethyl)thio)-7-oxo-4-thia-1-azabicyclo[3.2.0]heptane-3-carboxylic acid (32 mg) as white solids.

$^1$H-NMR (400 MHz, DMSO-$d_6$) δ value: 1.36 (3H, s), 1.45 (3H, s), 2.83 (2H, t, J=7.1 Hz), 2.93 (3H, d, J=2.8 Hz), 3.02 (1H, d, J=12.2 Hz), 3.35-3.65 (2H, m), 4.28 (1H, d, J=12.2 Hz), 5.29 (1H, d, J=3.8 Hz), 5.63 (1H, dd, J=8.8, 3.8 Hz), 6.29 (1H, d, J=8.0 Hz), 6.42 (1H, s), 6.65-6.73 (1H, m), 6.72 (1H, s), 7.61 (1H, t, J=6.0 Hz), 11.3 (1H, s);

MS (ESI): 745.00 [M+H]$^+$, 742.95 [M−H]$^−$

Example 9

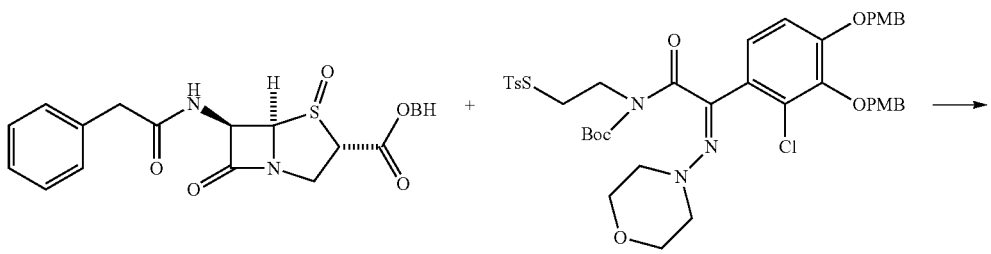

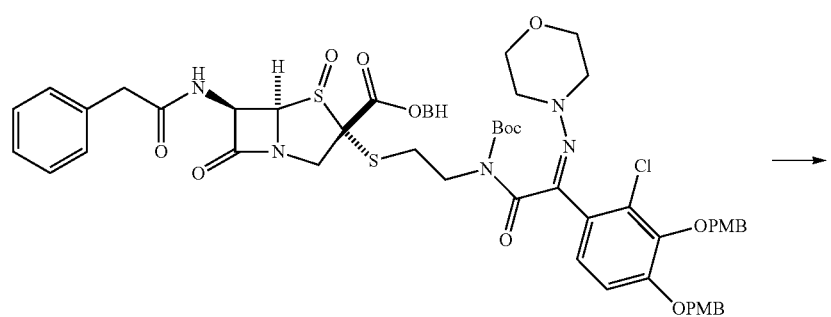

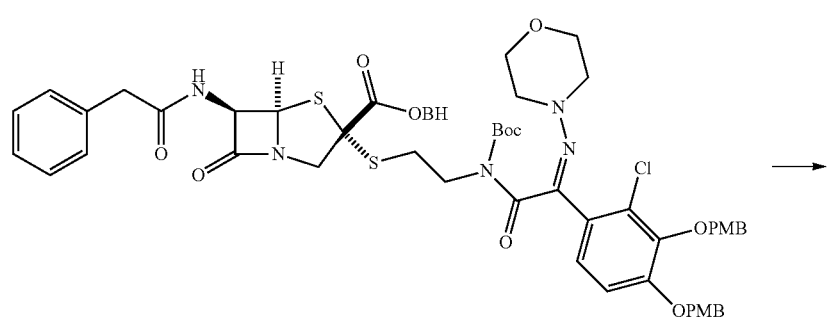

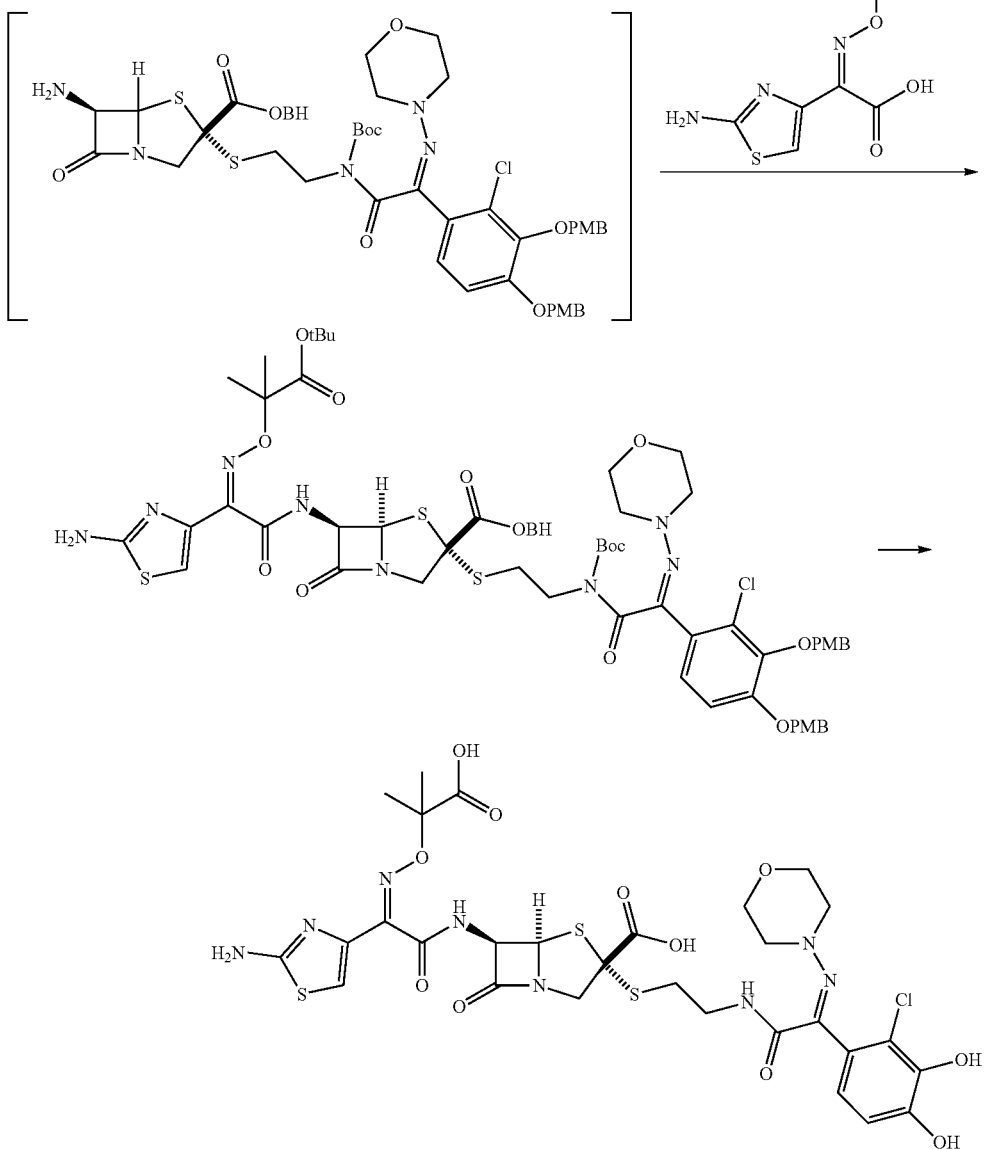

Example 9 (1)

(Z)— S-(2-(N-(tert-butoxycarbonyl)-2-(2-chloro-3,4-bis ((4-methoxybenzyl)oxy)phenyl)-2-(morpholinoimino)acetamide)ethyl) 4-methylbenzenesulfonothioate (680 mg, 0.80 mmol) and dichloromethane (6.80 mL) were added to benzhydryl (3 S,5R,6R)-7-oxo-6-(2-phenylacetamide)-4-thia-1-azabicyclo[3.2.0]heptane-3-carboxylate 4-oxide (354 mg, 0.72 mmol), and the mixture was stirred. The reaction mixture was cooled on ice, and a solution of DBU (110 mg, 0.72 mmol) in dichloromethane (2 mL) was added dropwise to the reaction mixture at the same temperature. The reaction mixture was stirred at the same temperature for 1 hour and 30 minutes. Then, the reaction mixture was added to a mixture of dichloromethane (5 mL), water (5 mL), and 1 mol/L hydrochloric acid (0.36 mL) under ice cooling. The organic layer was separated from the reaction mixture and dehydrated and dried over anhydrous sodium sulfate, and then the solvent was distilled away under reduced pressure. The residue was purified by silica gel column chromatography [eluent; ethyl acetate:hexane=60:40], thereby obtaining a target substance (633 mg) as light yellow solids.

Example 9 (2)

Ethyl acetate (0.53 mL) and NMP (2.7 mL) were added to the compound (633 mg, 0.53 mmol) obtained in Example 9 (1), and the mixture was stirred. The reaction mixture was cooled to −20° C., and a solution of phosphorus tribromide (1.16 g, 4.27 mmol) in ethyl acetate (0.36 mL) was added dropwise to the reaction mixture at the same temperature. The reaction mixture was stirred at a temperature of −20° C. to −10° C. for 3 hours and 30 minutes. Then, the reaction mixture was added to a mixture of an aqueous potassium hydrogen carbonate solution (1.60 g of potassium hydrogen carbonate/7 mL of water) under ice cooling. Ethyl acetate (10 mL) and a saturated aqueous sodium chloride solution were added to the reaction mixture, and the organic layer was separated. The organic layer was washed with an aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=55:45], thereby obtaining a target substance (367 mg) as light yellow solids.

$^1$H-NMR (400 MHz, CDCl$_3$) δ value: 1.49 (9H, s), 2.81-2.95 (2H, m), 3.06 (4H, t, J=4.6 Hz), 3.20 (1H, d, J=12.9 Hz), 3.48 (2H, d, J=2.4 Hz), 3.58 (4H, t, J=4.6 Hz), 3.70-3.82 (2H, m), 3.79 (3H, s), 3.83 (3H, s), 4.51 (1H, d, J=12.9 Hz), 5.00 (2H, s), 5.05 (2H, s), 5.41 (1H, d, J=3.9 Hz), 5.65 (1H, dd, J=9.2, 3.8 Hz), 6.36 (1H, d, J=9.2 Hz), 6.75-6.97 (8H, m), 7.03 (1H, d, J=7.0 Hz), 7.16-7.48 (17H, m)

Example 9 (3)

Dichloromethane (3.7 mL) was added to the compound (367 mg, 0.31 mmol) obtained in Example 9 (2), and the mixture was stirred. The reaction mixture was cooled to a temperature equal to or lower than −30° C., N,N-dimethylaniline (133 mg, 1.10 mmol) and phosphorus pentachloride (98.0 mg, 0.47 mmol) were sequentially added thereto, and the mixture was stirred at a temperature of −40° C. to −35° C. for 1 hour. Then, the reaction mixture was added to methanol (1.8 mL) and stirred for 10 minutes under ice cooling. Ethyl acetate (20 mL) and an aqueous sodium hydrogen carbonate solution (0.34 g of sodium hydrogen carbonate/20 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. Ethyl acetate was added to the filtrate such that the total volume thereof became 50 mL. (Z)-2-(2-aminothiazol-4-yl)-2-(((1-(tert-butoxy)-2-methyl-1-oxopropane-2-yl)oxy)imino)acetic acid (56.9 mg, 0.17 mmol), HATU (65.7 mg, 0.17 mmol), 2,6-lutidine (40 μL, 0.35 mmol), and DMF (1.7 mL) were added to the obtained ethyl acetate solution (25 mL). The reaction mixture was stirred at room temperature under reduced pressure until it became a solution. Water (10 mL) and ethyl acetate (10 mL) were added to the reaction mixture, and the organic layer was separated. Water (10 mL) was added to the organic layer, and then a saturated aqueous sodium hydrogen carbonate solution was added thereto so as to adjust the pH to 6.9. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate: hexane=60:40], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-((2-((Z)—N-(tert-butoxycarbonyl)-2-(2-chloro-3,4-bis((4-methoxybenzyl)oxy)phenyl)-2-(morpholinoimino)acetamide)ethyl)thio)-7-oxo-4-thia-1-azabicyclo[3.2.0]heptane-3-carboxylate (64 mg) as light yellow solids.

$^1$H-NMR (400 MHz, CDCl$_3$) δ value: 1.33 (9H, s), 1.49 (9H, s), 1.51 (3H, s), 1.52 (3H, s), 2.78-2.90 (1H, m), 2.92-3.04 (1H, m), 3.07 (4H, t, J=4.5 Hz), 3.30 (1H, d, J=12.7 Hz), 3.59 (4H, t, J=4.5 Hz), 3.71-3.81 (2H, m), 3.79 (3H, s), 3.83 (3H, s), 4.51 (1H, d, J=12.7 Hz), 5.00 (2H, s), 5.03 (2H, s), 5.52 (1H, d, J=3.9 Hz), 5.69 (1H, s), 5.85 (1H, dd, J=9.0, 3.9 Hz), 6.76-6.96 (8H, m), 7.07 (1H, d, J=8.5 Hz), 7.22-7.40 (12H, m), 7.53 (1H, d, J=8.9 Hz)

Example 9 (4)

Dichloromethane (930 μL) was added to the compound (62.0 mg, 45.5 mol) obtained in Example 9 (3), and the mixture was cooled to −20° C. At the same temperature, anisole (198 μL) and aluminum chloride (48.5 mg, 0.36 mmol) were sequentially added to the reaction mixture. The reaction mixture was stirred at the same temperature for 1 hour and 20 minutes. The reaction mixture was added to a mixture of acetonitrile (3 mL), water (3 mL), and trisodium citrate dihydrate (160 mg, 0.55 mmol) under ice cooling, and washed sequentially with acetonitrile (2 mL) and water (2 mL). Then, a saturated aqueous sodium hydrogen carbonate solution was added to the reaction mixture so as to adjust the pH to 5.4, and the aqueous layer was separated. The aqueous layer was purified by medium-pressure reverse-phase silica gel column chromatography [eluent; water:acetonitrile=100:0→75:25]. The high-polarity was lyophilized, thereby obtaining (3R,5R,6R)-6-((Z)-2-(2-aminothiazol-4-yl)-2-(((2-carboxypropan-2-yl))oxy)imino)acetamide)-3-((2-((Z)-2-(2-chloro-3,4-dihydroxyphenyl)-2-(morpholinoimino)acetamide)ethyl)thio)-7-oxo-4-thia-1-azabicyclo[3.2.0]heptane-3-carboxylic acid (7.3 mg) as light yellow solids.

$^1$H-NMR (400 MHz, D$_2$O) δ value: 1.47 (3H, s), 1.49 (3H, s), 2.93-3.30 (7H, m), 3.57-3.67 (2H, m), 3.85-3.98 (4H, m), 4.38 (1H, d, J=11.6 Hz), 5.35-5.41 (1H, m), 5.68-5.76 (1H, m), 6.88-7.05 (3H, m);

MS (ESI): 801.05 [M+H]$^+$, 799.20 [M−H]$^-$

Example 10

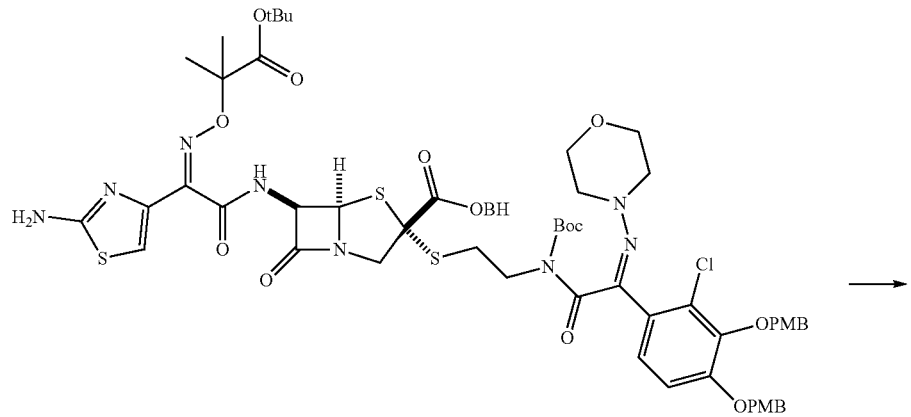

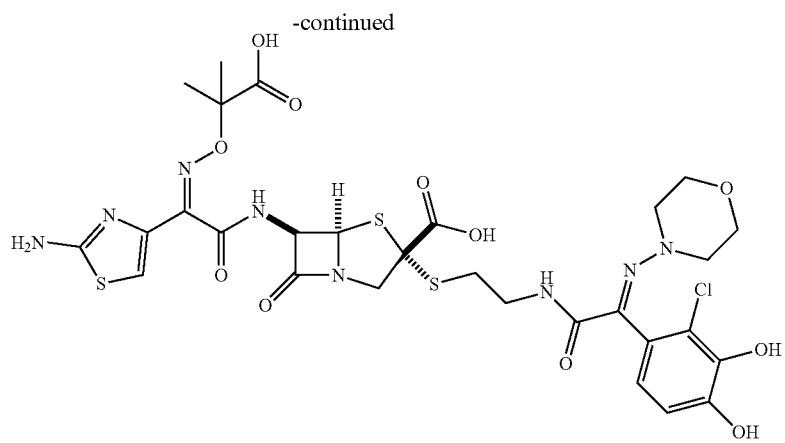

The low-polarity fraction obtained by the medium-pressure reverse-phase silica gel column chromatography in Example 9 (4) was lyophilized, thereby obtaining (3R,5R,6R)-6-((Z)-2-(2-aminothiazole-4-yl)-2-(((2-carboxypropan-2-yl)oxy)imino)acetamide)-3-((2-((E)-2-(2-chloro-3,4-dihydroxyphenyl)-2-(morpholinoimino)acetamide)ethyl)thio)-7-oxo-4-thia-1-azabicyclo[3.2.0]heptane-3-carboxylic acid (5.4 mg) as light yellow solids.

$^1$H-NMR (400 MHz, D$_2$O) δ value: 1.48 (3H, s), 1.50 (3H, s), 2.98 (2H, t, J=6.2 Hz), 3.15 (4H, t, J=4.7 Hz), 3.27 (1H, d, J=12.6 Hz), 3.44-3.65 (2H, m), 3.90 (4H, t, J=4.7 Hz), 4.39 (1H, d, J=12.6 Hz), 5.53 (1H, d, J=4.0 Hz), 5.74 (1H, d, J=4.0 Hz), 6.73 (1H, d, J=8.4 Hz), 6.90 (1H, d, J=8.4 Hz), 7.02 (1H, s);

MS (ESI): 801.05 [M+H]$^+$, 799.05 [M−H]$^−$

Example 11

Water (900 L), semicarbazide hydrochloride (4.6 mg, 41.1 mol), and a 5% aqueous sodium hydrogen carbonate solution (670 μL) were added to the compound (30 mg, 41.1 mol) obtained in Example 2, and the mixture was stirred at room temperature. The reaction mixture was purified by medium-pressure reverse-phase silica gel column chromatography [eluent; water:acetonitrile=100:0→90:10], and the aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamide)-3-((1-((Z)-2-(2-carbamoylhydrazono)-2-(2-chloro-3,4-dihydroxyphenyl)acetyl)azetidin-3-yl)thio)-7-oxo-4-thia-1-azabicyclo[3.2.0]heptane-3-carboxylic acid (7 mg) as yellow solids.

$^1$H-NMR (400 MHz, D$_2$O) δ value: 1.41-1.52 (6H, m), 3.17-3.28 (1H, m), 3.93-4.44 (4H, m), 4.54-4.66 (1H, m), 5.54-5.61 (1H, m), 5.71-5.77 (1H, m), 6.95-7.09 (3H, m);

MS (ESI): 786.00 [M+H]$^+$, 783.95 [M−H]$^−$

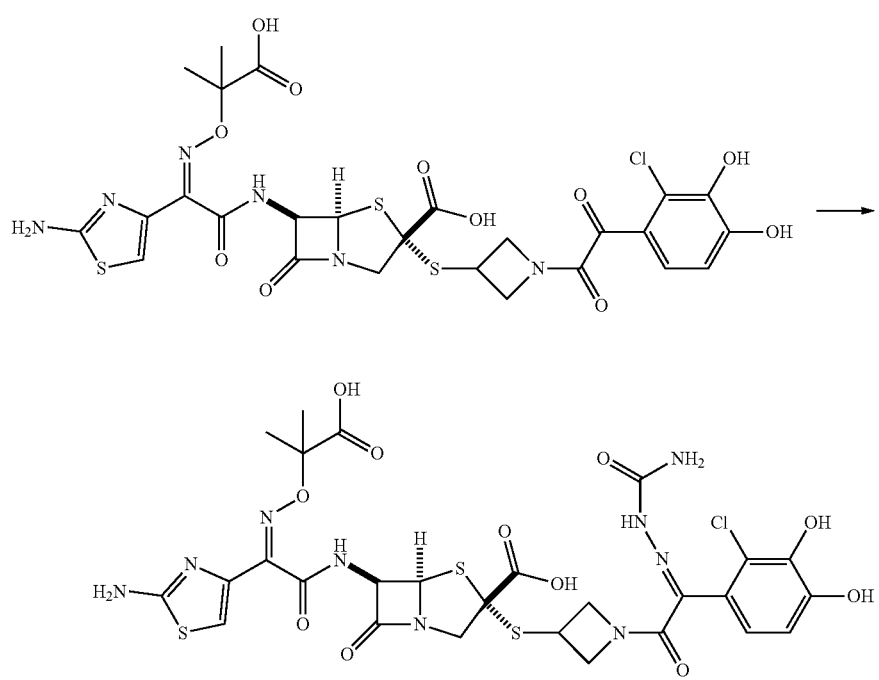

Example 12

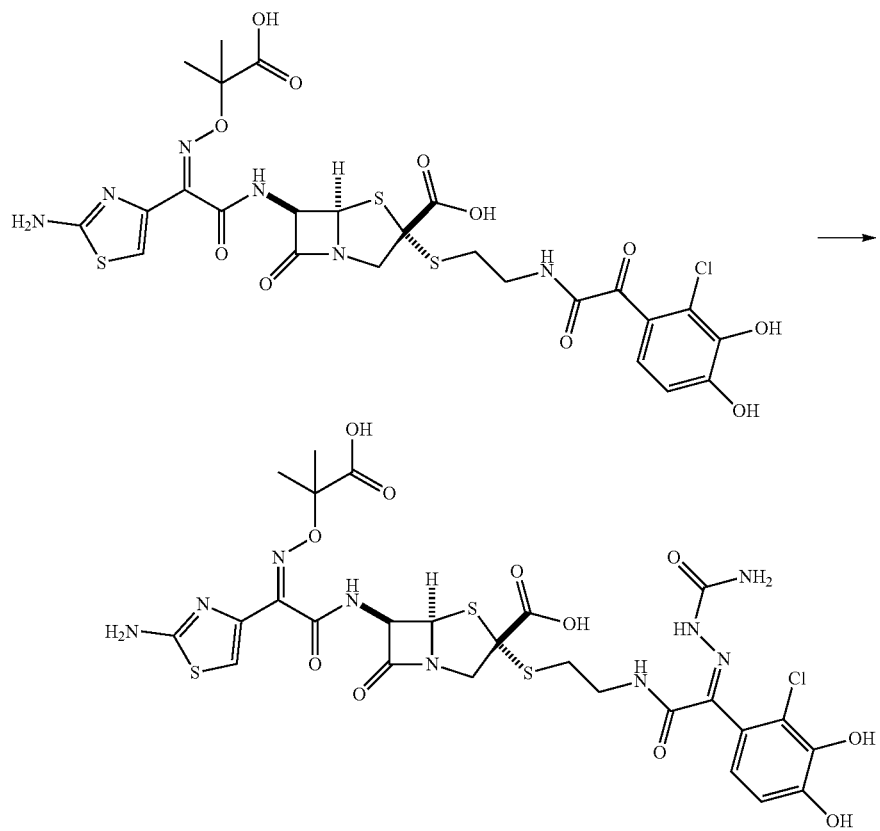

Water (3 mL) and semicarbazide hydrochloride (15 mg, 135 mol) were added to the compound (100 mg, 135 mol) obtained in Example 1, and the mixture was stirred. A saturated aqueous sodium hydrogen carbonate solution was added to the reaction mixture so as to adjust the pH to 4.3, and the mixture was stirred at room temperature overnight. A saturated aqueous sodium hydrogen carbonate solution was added to the reaction mixture so as to adjust the pH to 5.1, and the mixture was purified by medium-pressure reverse-phase silica gel column chromatography [eluent; water:acetonitrile=100:0→90:10]. The high-polarity fraction was lyophilized, thereby obtaining (3R,5R,6R)-6-((Z)-2-(2-aminothiazol-4-yl)-2-(((2-carboxypropan-2-yl)))oxy)imino)acetamide)-3-((2-((Z)-2-(2-carbamoylhydrazono)-2-(2-chloro-3,4-dihydroxyphenyl)acetamide)ethyl)thio)-7-oxo-4-thia-1-azabicyclo[3.2.0]heptane-3-carboxylic acid (12 mg) as light yellow solids.

$^1$H-NMR (400 MHz, D$_2$O) δ value: 1.47 (3H, s), 1.49 (3H, s), 2.94 (2H, t, J=6.0 Hz), 3.23 (1H, d, J=12.4 Hz), 3.51-3.57 (2H, m), 4.34 (1H, d, J=12.4 Hz), 5.36 (1H, d, J=4.0 Hz), 5.74 (1H, d, J=3.2 Hz), 6.99 (1H, d, J=8.4 Hz), 7.01 (1H, s), 7.05 (1H, d, J=8.4 Hz);

MS (ESI): 774.05 [M+H]$^+$, 771.85 [M−H]$^−$

Example 13

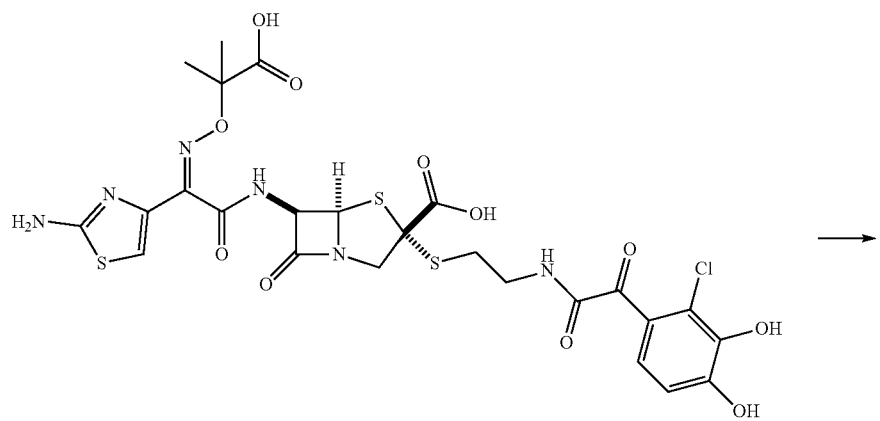

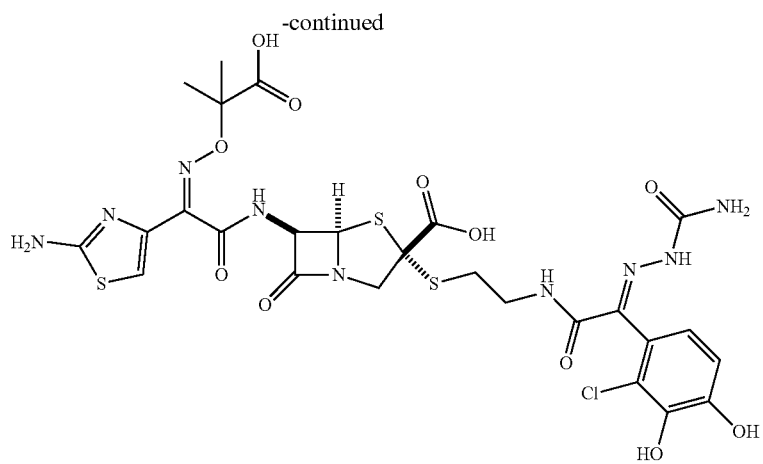

The low-polarity fraction obtained by medium-pressure reverse-phase silica gel column chromatography in Example 12 was lyophilized, thereby obtaining (3R,5R,6R)-6-((Z)-2-(2-aminothiazole-4-yl)-2-(((2-carboxypropan-2-yl)oxy)imino)acetamide)-3-((2-((E)-2-(2-carbamoylhydrazono)-2-(2-chloro-3,4-dihydroxyphenyl)acetamide)ethyl)thio)-7-oxo-4-thia-1-azabicyclo[3.2.0]heptane-3-carboxylic acid (6 mg) as light yellow solids.

$^1$H-NMR (400 MHz, D$_2$O) δ value: 1.47 (3H, s), 1.49 (3H, s), 2.94 (2H, t, J=6.0 Hz), 3.23 (1H, d, J=11.6 Hz), 3.53 (1H, dd, J=6.3, 2.1 Hz), 3.55 (1H, dd, J=6.3, 2.1 Hz), 4.34 (1H, d, J=12.4 Hz), 5.36 (1H, d, J=3.6 Hz), 5.74 (1H, d, J=3.6 Hz), 6.99 (1H, d, J=8.4 Hz), 7.01 (1H, s), 7.05 (1H, d, J=8.4 Hz);

MS (ESI): 774.10 [M+H]$^+$, 772.00 [M−H]$^−$

Example 14

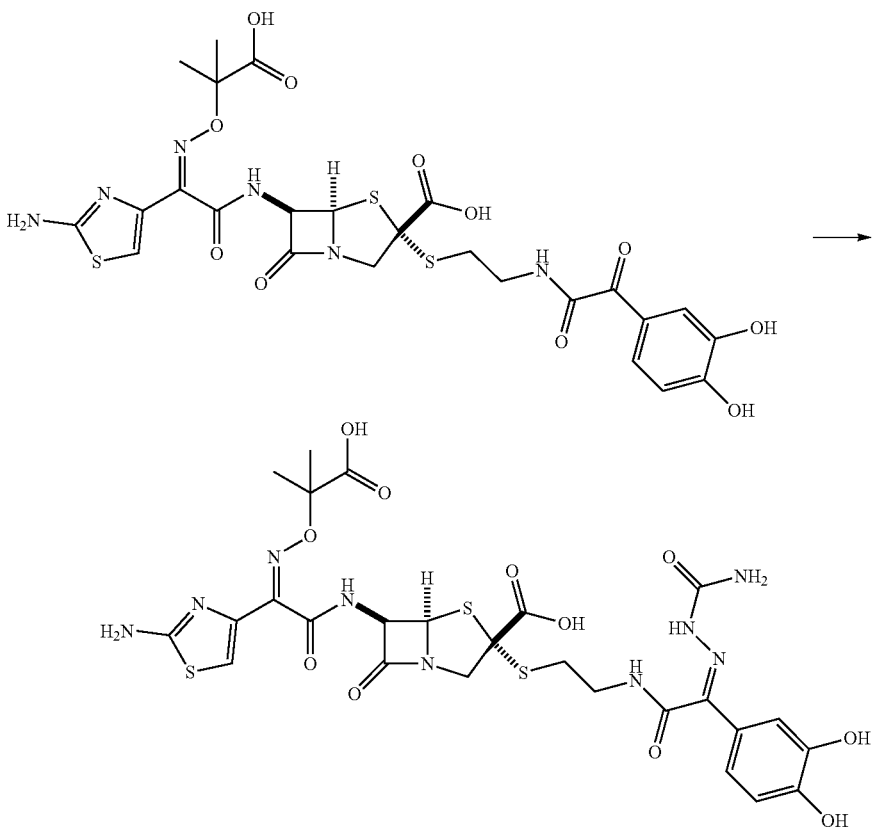

Water (1.5 mL) and semicarbazide hydrochloride (7.9 mg, 71.0 mol) were added to the compound (50 mg, 71.0 mol) obtained in Example 7, and the mixture was stirred. A saturated aqueous sodium hydrogen carbonate solution was added to the reaction mixture so as to adjust the pH to 4.1, and the mixture was stirred at room temperature for 3 days.

A saturated aqueous sodium hydrogen carbonate solution was added to the reaction mixture so as to adjust the pH to 5.2, and the mixture was purified by medium-pressure reverse-phase silica gel column chromatography [eluent; water:acetonitrile=100:0→90:10]. The aqueous solution containing a target substance was concentrated and lyophilized, thereby obtaining (3R,5R,6R)-6-((Z)-2-(2-aminothiazol-4-yl)-2-(((2-carboxypropane-2-yl)oxy)imino)acetamide)-3-((2-(2-(2-carbamoylhydrazono)-2-(3,4-dihydroxyphenyl)acetamide)ethyl)thio)-7-oxo-4-thia-1-azabicyclo[3.2.0]heptane-3-carboxylic acid (35 mg, light yellow solids) as a mixture of geometric isomers of a semicarbazone moiety.

$^1$H-NMR (400 MHz, D$_2$O) δ value: [1.45] 1.46 (3H, s), [1.48] 1.49 (3H, s), 2.99-3.09 (2H, m), 3.25-3.31 (1H, m), 3.45-3.72 (2H, m), [4.35] 4.42 (1H, d, J=12.6 Hz), [5.42] 5.51 (1H, d, J=4.0 Hz), [5.69] 5.72 (1H, d, J=3.0 Hz), [6.76] 7.18 (1H, dd, J=8.4, 2.2 Hz), [6.84]7.30 (1H, d, J=2.2 Hz), [6.97] 7.00 (1H, s), [6.98] 7.02 (1H, d, J=8.4 Hz);

MS (ESI): 761.05 [M+Na]$^+$, 758.80 [M+Na–H]$^-$

Example 15

Water (1.5 mL) and semicarbazide hydrochloride (7.1 mg, 63.8 mol) were added to the compound (50 mg, 63.8 mol) obtained in Example 6, and the mixture was stirred. A saturated aqueous sodium hydrogen carbonate solution was added to the reaction mixture so as to adjust the pH to 4.2, and the mixture was stirred at room temperature for 2 days. A saturated aqueous sodium hydrogen carbonate solution was added to the reaction mixture so as to adjust the pH to 5.3, and the mixture was purified by medium-pressure reverse-phase silica gel column chromatography [eluent; water:acetonitrile=100:0→92:8]. The high-polarity fraction was concentrated and then lyophilized, thereby obtaining (3R,5R,6R)-6-((Z)-2-(2-aminothiazol-4-yl)-2-(((2-carboxypropane-2-yl)oxy)imino)acetamide)-3-(((S)-3-((Z)-2-(2-carbamoylhydrazono)-2-(2-chloro-3,4-dihydroxyphenyl)acetamide)-2-methoxypropyl)thio)-7-oxo-4-thia-1-azabicyclo[3.2.0]heptane-3-carboxylic acid (1 mg) as light yellow solids.

$^1$H-NMR (400 MHz, D$_2$O) δ value: 1.46 (3H, s), 1.49 (3H, s), 2.90-2.99 (1H, m), 3.08 (1H, dd, J=13.8, 5.0 Hz), 3.27 (1H, d, J=11.6 Hz), 3.46 (3H, s), 3.53-3.60 (2H, m), 3.79-3.87 (1H, m), 4. (1), 4.40 (1H, d, J=12.4 Hz), 5.48-5.53 (1H, m), 5.72 (1H, d, J=3.6 Hz), 6.74 (1H, d, J=8.4 Hz), 6.98-7.02 (1H, m), 7.01 (1H, s);

MS (ESI): 818.05 [M+H]$^+$, 815.95 [M–H]$^-$

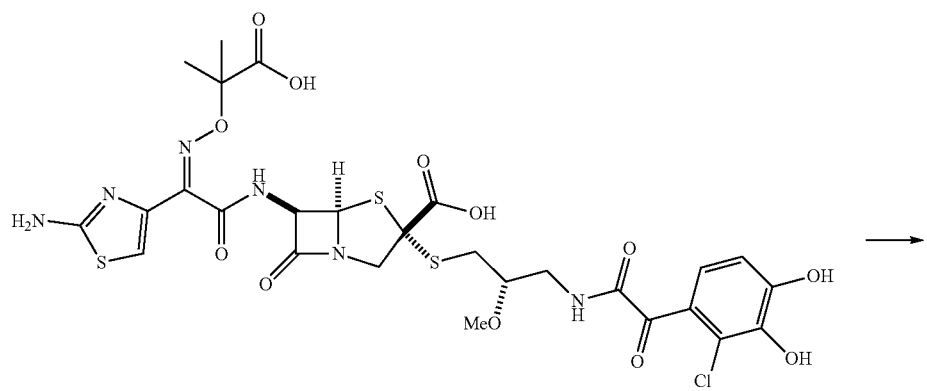

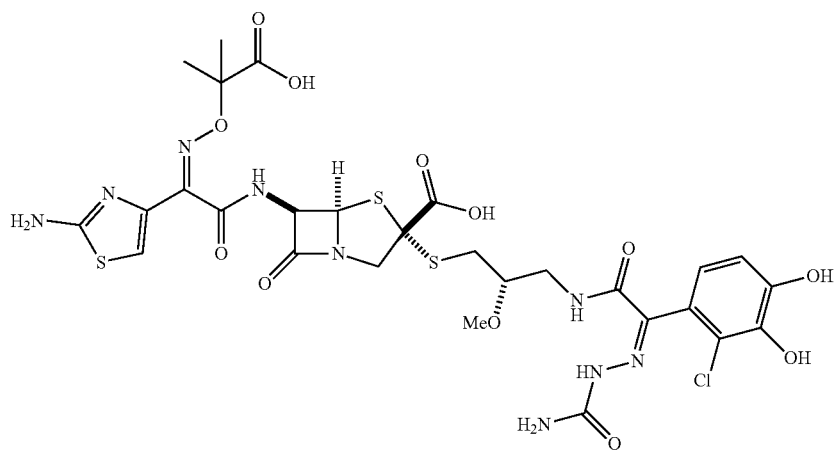

Example 16

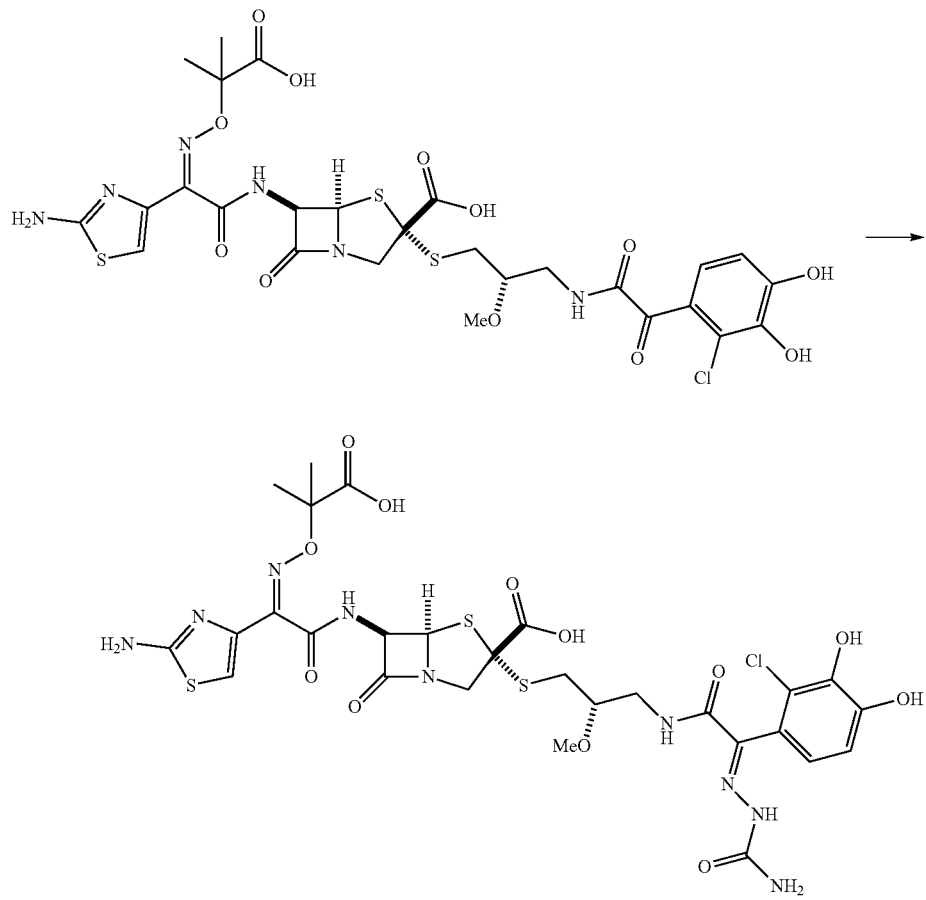

The low-polarity fraction obtained by medium-pressure reverse-phase silica gel column chromatography in Example 15 was lyophilized, thereby obtaining (3R,5R,6R)-6-((Z)-2-(2-aminothiazol-4-yl)-2-(((2-carboxypropan-2-yl)oxy)imino)acetamide)-3-(((S)-3-((E)-2-(2-carbamoylhydrazono)-2-(2-chloro-3,4-dihydroxyphenyl)acetamide)-2-methoxypropyl)thio)-7-oxo-4-thia-1-azabicyclo[3.2.0]heptane-3-carboxylic acid (12 mg) as light yellow solids.

$^1$H-NMR (400 MHz, D$_2$O) δ value: 1.47 (3H, s), 1.50 (3H, s), 2.91 (1H, dd, J=13.2, 5.6 Hz), 2.99 (1H, dd, J=13.2, 5.6 Hz), 3.21 (1H, dd, J=12.4, 1.2 Hz), 3.38-3.43 (1H, m), 3.40 (3H, s), 3.61 (1H, dd, J=14.0, 5.6 Hz), 3.74-3.80 (1H, m), 4.37 (1H, d, J=12.4 Hz), 5.45 (1H, d, J=4.0 Hz), 5.74 (1H, dd, J=4.0, 0.8 Hz), 6.97 (1H, d, J=8.4 Hz), 7.01 (1H, s), 7.04 (1H, d, J=8.4 Hz);

MS (ESI): 818.05 [M+H]$^+$, 816.00 [M−H]$^−$

Example 17

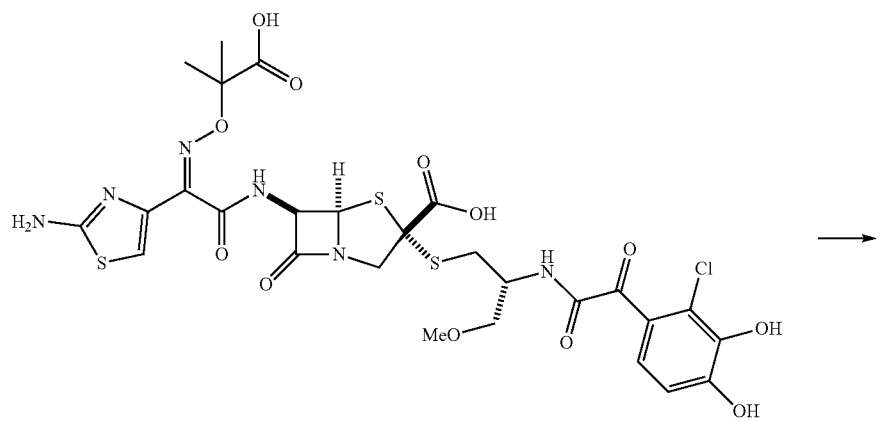

-continued

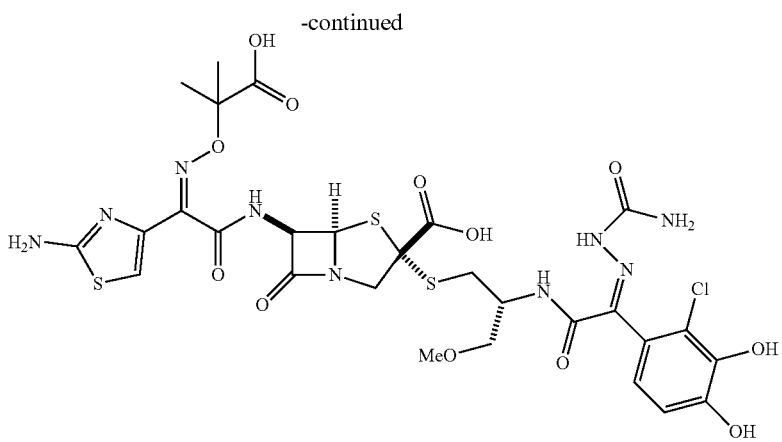

Water (1 mL) and semicarbazide hydrochloride (4.4 mg, 39.4 µmol) were added to the compound (10 mg, 13.1 µmol) obtained in Example 3, and the mixture was stirred. A saturated aqueous sodium hydrogen carbonate solution was added to the reaction mixture so as to adjust the pH to 4.1, and the mixture was stirred at room temperature for 20 hours. The reaction mixture was purified by medium-pressure reverse-phase silica gel column chromatography [eluent; water:acetonitrile=100:0→70:30]. The aqueous solution containing a target substance was concentrated and lyophilized, thereby obtaining (3R,5R,6R)-6-((Z)-2-(2-aminothiazol-4-yl)-2-(((2-carboxypropane-2-yl)oxy)imino)acetamide)-3-(((R)-2-(2-(2-carbamoylhydrazono)-2-(2-chloro-3,4-dihydroxyphenyl)acetamide)-3-methoxypropyl)thio)-7-oxo-4-thia-1-azabicyclo[3.2.0]heptane-3-carboxylic acid (2 mg, yellow solids) as a mixture of geometric isomers of a semicarbazone moiety.

$^1$H-NMR (400 MHz, D$_2$O) δ value: 1.36-1.47 (6H, m), [2.74-2.84] 2.97-3.07 (1H, m), [2.87-2.97] 3.16-3.25 (1H, m), [2.93] 3.13 (1H, d, J=12.4 Hz), [3.29] 3.33 (3H, s), [3.41-3.53] 3.53-3.64 (2H, m), 4.20-4.35 (1H, m), 4.35-4.45 (1H, m), [5.40] 5.48 (1H, d, J=3.8 Hz), [5.51] 5.66 (1H, d, J=3.8 Hz), 6.60-7.10 (3H, m);

MS (ESI): 818.05 [M+H]$^+$, 815.95 [M−H]$^-$

Example 18

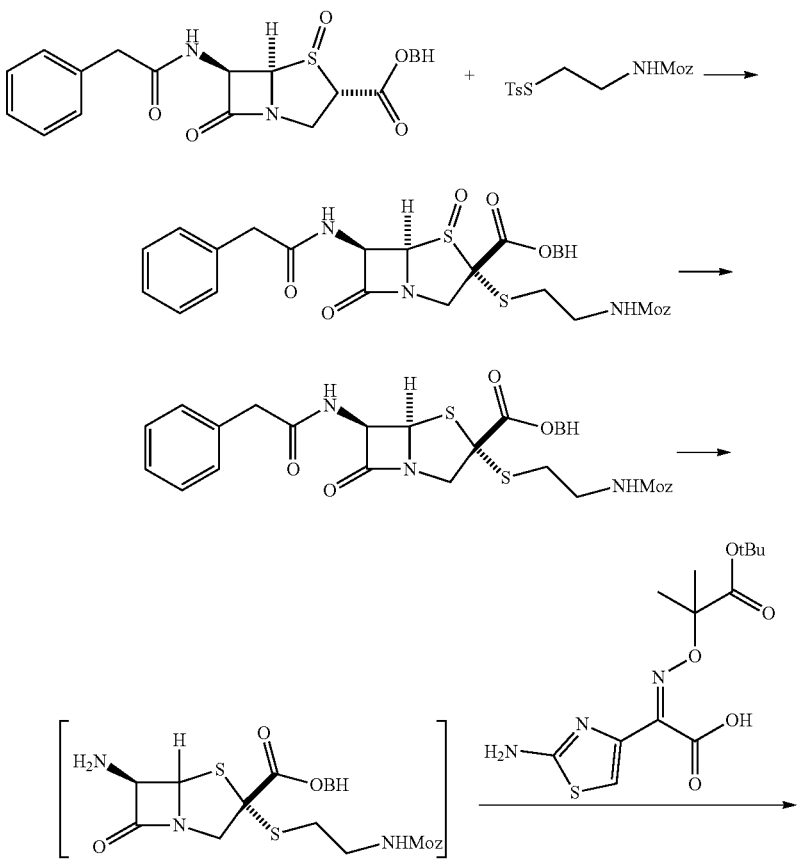

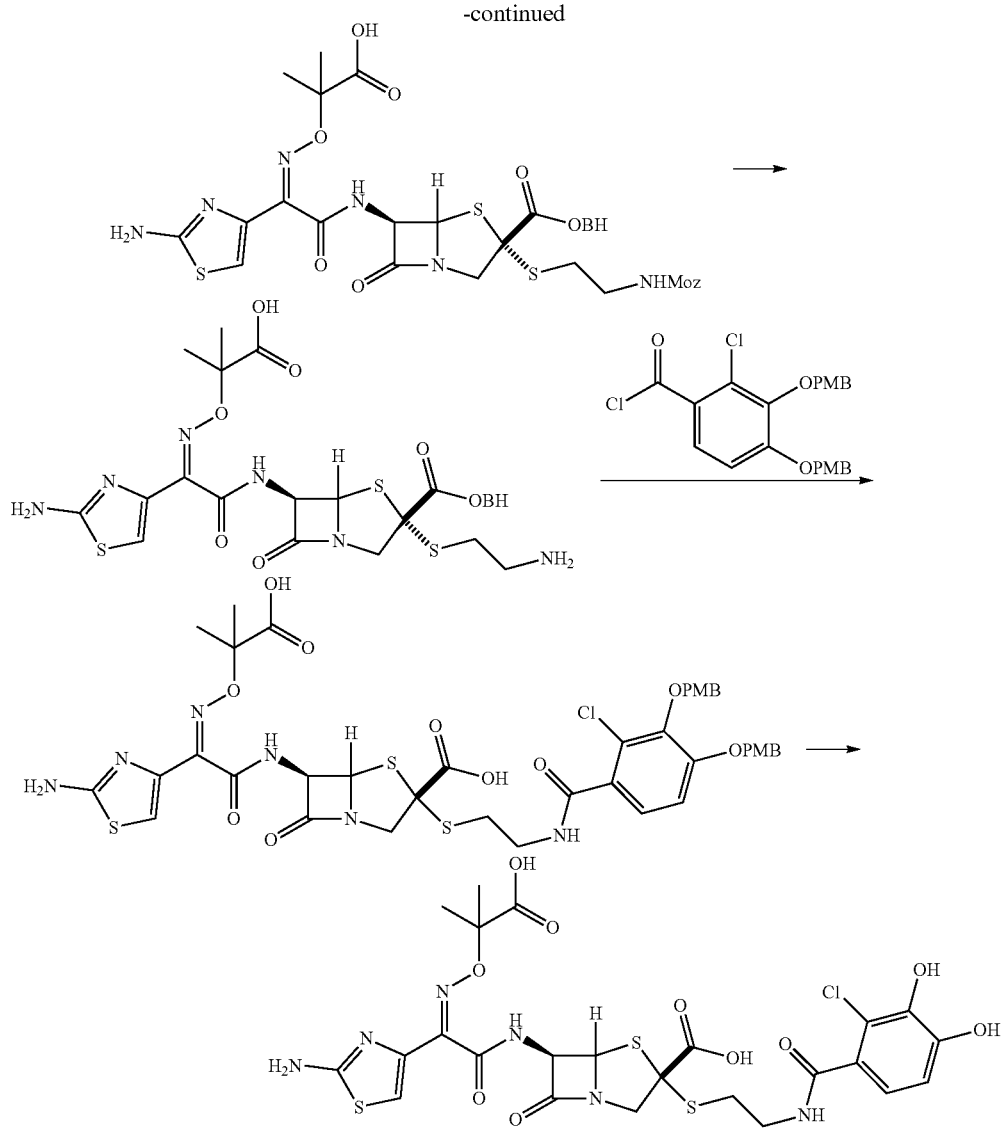

Example 18 (1)

S-(2-((((4-methoxybenzyl)oxy)carbonyl)amino)ethyl) 4-methylbenzenesulfonothioate (34.5 g, 87.2 mmol) and dichloromethane (370 mL) were added to benzhydryl (3 S,5R,6R)-7-oxo-6-(2-phenylacetamide)-4-thia-1-azabicyclo [3.2.0]heptane-3-carboxylate 4-oxide (37.2 g, 76.1 mmol), add the mixture was stirred. The reaction mixture was cooled on ice, and a solution of DBU (11.6 g, 76.1 mmol) in dichloromethane (80 mL) was added dropwise to the reaction mixture. The reaction mixture was stirred at the same temperature for 30 minutes. Then, the reaction mixture was added to a mixture of dichloromethane (380 mL), water (380 mL), and 1 mol/L hydrochloric acid (38 mL) under ice cooling. The organic layer was separated from the reaction mixture and washed sequentially with water (380 mL), a 5% aqueous sodium hydrogen carbonate solution (760 mL), and a saturated aqueous sodium chloride solution. The organic layer was dehydrated and dried over anhydrous magnesium sulfate, and then the solvent was distilled away under reduced pressure. The residue was purified by silica gel column chromatography [eluent; ethyl acetate:hexane=70:30], thereby obtaining a target substance (56.4 g) as white solids.

Example 18 (2)

DMF (837 mL) was added to the compound (60.9 g, 83.7 mmol) obtained in Example 18 (1), and the mixture was stirred. The reaction mixture was cooled to −10° C., and a solution of phosphorus tribromide (181 g, 669 mmol) in dichloromethane (200 mL) was added dropwise to the reaction mixture. The reaction mixture was stirred at −10° C. for 2 hours and 30 minutes. Under ice cooling, the reaction mixture was added dropwise to a 7% aqueous sodium hydrogen carbonate solution (4 L). Ethyl acetate (2 L) and hexane (50 mL) were added to the reaction mixture, and the organic layers were separated. The aqueous layer was extracted using ethyl acetate (1.5 L), the organic layers were combined and washed with water and a saturated aqueous sodium chloride solution. The organic layer was dehydrated and dried over anhydrous magnesium sulfate, and then the solvent was distilled away under reduced pressure. The residue was purified by silica gel column chromatography [eluent; ethyl acetate:hexane=50:50], thereby obtaining a target substance (35.4 g) as a yellow oily substance.

$^1$H-NMR (400 MHz, CDCl$_3$) δ value: 2.68 (2H, t, J=6.2 Hz), 3.10-3.25 (3H, m), 3.51 (2H, d, J=3.6 Hz), 3.80 (3H, s), 4.56 (1H, d, J=12.8 Hz), 4.70-4.80 (1H, m), 5.01 (2H, s), 5.38 (1H, d, J=3.7 Hz), 5.65 (1H, dd, J=8.8, 3.7 Hz), 6.30 (1H, d, J=8.8 Hz), 6.78 (1H, s), 6.85-6.91 (2H, m), 7.18-7.41 (17H, m)

Example 18 (3)

Dichloromethane (16 mL) was added to the compound (1.60 g, 2.25 mmol) obtained in Example 18 (2), and the mixture was stirred. The reaction mixture was cooled to −40° C., N,N-dimethylaniline (953 mg, 7.87 mmol) and phosphorus pentachloride (462 mg, 3.37 mmol) were sequentially added thereto, and the mixture was stirred at the same temperature for 15 minutes. Then, the reaction mixture was added to methanol (8 mL), stirred at room temperature for 8 minutes, and then stirred at −40° C. for 5 minutes. The reaction mixture was added to a mixture of ethyl acetate (64 mL) and an aqueous sodium hydrogen carbonate solution (2.64 g of sodium hydrogen carbonate/64 mL of water), and the organic layer was separated. The organic layer was washed sequentially with water and a saturated aqueous sodium chloride solution and then dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (889 mg, 2.70 mmol), HATU (1.05 g, 2.70 mmol), 2,6-lutidine (524 μL, 4.50 mmol), and DMF (13.4 mL) were added to the obtained ethyl acetate solution. The reaction mixture was stirred at room temperature under reduced pressure for 30 minutes, and then stirred at room temperature under normal pressure for 30 minutes. Ethyl acetate (40 mL), MTBE (20 mL), and water (50 mL) were added to the reaction mixture, and the organic layer was separated. The organic layer was washed sequentially with water and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=70:30], thereby obtaining benzhydryl (3R,5R,6R)-6-((Z)-2-(2-aminothiazol-4-yl-2-(((1-(tert-butoxy)-2-methyl-1-oxopropan-2-yl)oxy)imino)acetamide)-3-((2-((((4-methoxybenzyl)oxy)carbonyl)amino)ethyl)thio)-7-oxo-4-thia-1-azabicyclo[3.2.0]heptane-3-carboxylate (970 mg) as white solids.

$^1$H-NMR (400 MHz, CDCl$_3$) δ value: 1.35 (9H, s), 1.52 (3H, s), 1.53 (3H, s), 2.61-2.80 (2H, m), 3.06-3.34 (2H, m), 3.28 (1H, d, J=12.4 Hz), 3.80 (3H, s), 4.56 (1H, d, J=11.6 Hz), 4.67-4.78 (1H, m), 4.95-5.06 (2H, m), 5.47 (1H, d, J=3.6 Hz), 5.85 (1H, dd, J=8.4, 3.6 Hz), 6.47 (2H, s), 6.80 (1H, s), 6.84 (1H, s), 6.86-6.92 (2H, m), 7.23-7.44 (12H, m)

Example 18 (4)

Dichloromethane (14.6 mL) was added to the compound (970 mg, 1.07 mmol) obtained in Example 18 (3), and the mixture was cooled to −20° C. At the same temperature, anisole (4.67 mL), nitromethane (4.85 mL), and aluminum chloride (1.71 g, 12.9 mmol) were sequentially added to the reaction mixture. The reaction mixture was stirred at a temperature of −20° C. to −15° C. for 1 hour and 30 minutes. The reaction mixture was added to a mixture of acetonitrile (50 mL), water (30 mL), and trisodium citrate dihydrate (7.57 g, 25.7 mmol) under ice cooling, and washed sequentially with acetonitrile (5 mL) and water (5 mL). Then, 6 mol/L hydrochloric acid was added to the reaction mixture so as to adjust the pH to 2.6, and the aqueous layer was separated. The aqueous layer was purified by medium-pressure reverse-phase silica gel column chromatography [eluent; water:acetonitrile=100:0→75:25]. The aqueous solution containing a target substance was concentrated under reduced pressure and lyophilized, thereby obtaining (3R,5R,6R)-3-((2-aminoethyl)thio)-6-((Z)-2-(2-aminothiazole-4-yl)-2-(((2-carboxypropan-2-yl)oxy)imino)acetamide)-7-oxo-4-thia-1-azabicyclo[3.2.0]heptane-3-carboxylic acid (280 mg) as yellow solids.

Example 18 (5)

THF (2 mL) and water (4 mL) were added to the compound (100 mg, 0.19 mmol) obtained in Example 18 (4), and the mixture was stirred under ice cooling. At the same temperature, sodium hydrogen carbonate (32.4 mg, 386 mol), 2-chloro-3,4-bis ((4-methoxybenzyl) oxy) benzoyl chloride (103 mg, 232 mol), and THF (2 mL) were sequentially added to the reaction mixture. At the same temperature, a saturated aqueous sodium hydrogen carbonate solution was added to the reaction mixture, and the reaction mixture was stirred for 3 hours while maintaining the pH at 7.0. Ethyl acetate (10 mL), water (10 mL), and 1 mol/L hydrochloric acid were added to the reaction mixture so as to adjust the pH to 2.0. The organic layer was separated and washed with a saturated aqueous sodium chloride solution. The organic layer was dehydrated and dried over anhydrous sodium sulfate, and then the solvent was distilled away under reduced pressure, thereby obtaining a residue containing (3R,5R,6R)-6-((Z)-2-(2-aminothiazol-4-yl)-2-(((2-carboxypropan-2-yl)oxy)imino)acetamide)-3-((2-(2-chloro-3,4-bis((4-methoxybenzyl)oxy)benzamide)ethyl)thio)-7-oxo-4-thia-1-azabicyclo[3.2.0]heptane-3-carboxylic acid.

Example 18 (6)

Dichloromethane (2.70 mL) was added to the residue obtained in Example 18 (5), and the mixture was cooled to −20° C. At the same temperature, anisole (0.84 mL), nitromethane (0.89 mL), and aluminum chloride (206 mg, 1.54 mmol) were sequentially added to the reaction mixture. The reaction mixture was stirred at the same temperature for 30 minutes. Under ice cooling, the reaction mixture was added to a mixture of acetonitrile (10 mL), water (10 mL), and trisodium citrate dihydrate (907 mg, 3.09 mmol), and washed sequentially with acetonitrile (2 mL) and water (2 mL). The organic layer was separated, and 2 mol/L hydrochloric acid was added to the aqueous layer so as to adjust the pH to 2.0. The aqueous layer was purified by medium-pressure reverse-phase silica gel column chromatography [eluent; water:acetonitrile=100:0→75:25]. The aqueous solution containing a target substance was concentrated under reduced pressure and lyophilized, thereby obtaining (3R,5R,6R)-6-((Z)-2-(2-aminothiazol-4-yl)-2-(((2-carboxypropan-2-yl)oxy)imino)acetamide)-3-((2-(2-chloro-3,4-dihydroxybenzamide)ethyl)thio)-7-oxo-4-thia-1-azabicyclo [3.2.0]heptane-3-carboxylic acid (30 mg) as light yellow solids.

$^1$H-NMR (400 MHz, DMSO-d$_6$) δ value: 1.42 (3H, s), 1.43 (3H, s), 2.86-4.22 (5H, m), 4.32 (1H, d, J=12.4 Hz), 5.44-5.58 (1H, m), 5.62-5.76 (1H, m), 6.66-6.84 (4H, m), 7.28 (1H, s), 8.34 (1H, s), 9.23 (1H, s), 9.31 (1H, d, J=8.0 Hz), 10.01 (1H, s);

MS (ESI): 688.90 [M+H]$^+$, 686.95 [M−H]$^-$

Example 19
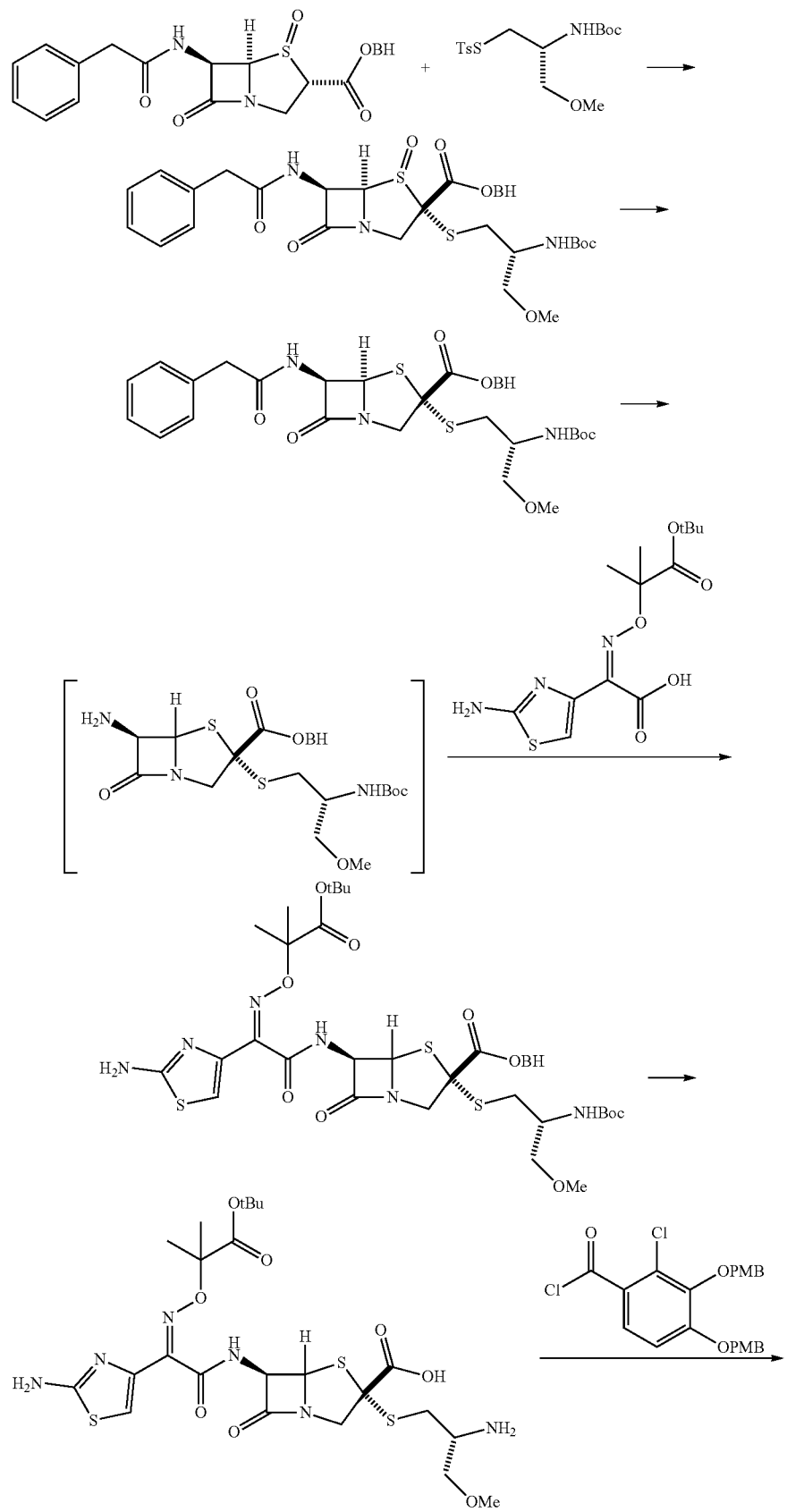

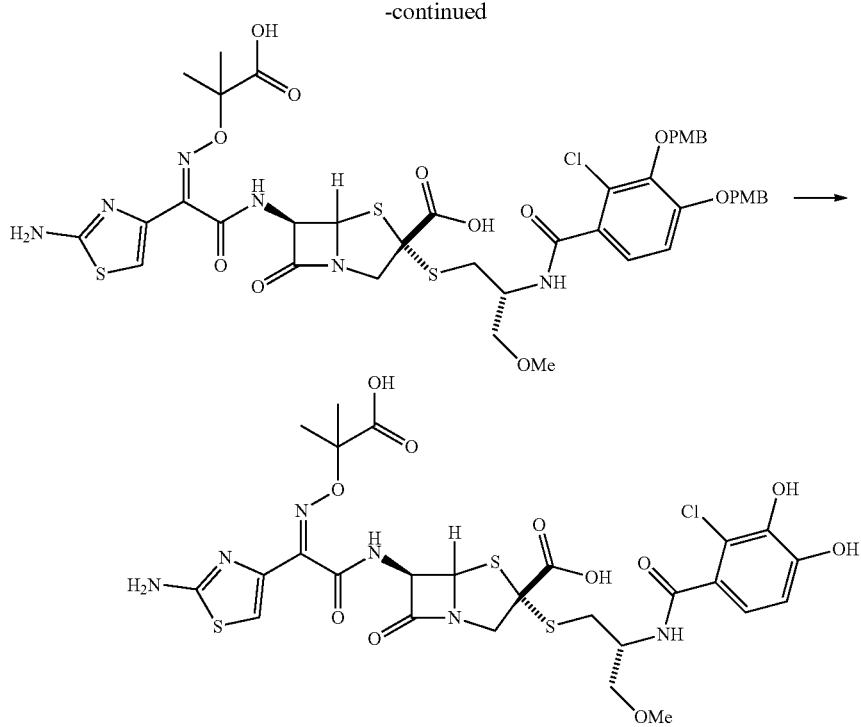

Example 19 (1)

(R)—S-(2-((tert-butoxycarbonyl)amino)-3-methoxypropyl) 4-methylbenzenesulfonothioate (16.1 g, 42.9 mmol) and dichloromethane (175 mL) were added to benzhydryl (3 S,5R,6R)-7-oxo-6-(2-phenylacetamide)-4-thia-1-azabicyclo [3.2.0]heptane-3-carboxylate 4-oxide (17.5 g, 35.8 mmol), and the mixture was stirred. Under ice cooling, a solution of DBU (5.45 g, 35.8 mmol) in dichloromethane (36 mL) was added dropwise to the reaction mixture. The reaction mixture was stirred at the same temperature for 30 minutes. The reaction mixture was added to a mixture of dichloromethane (180 mL), water (180 mL), and 1 mol/L hydrochloric acid (18 mL) under ice cooling. The organic layer was separated from the reaction mixture and washed sequentially with water (180 mL), a 5% aqueous sodium hydrogen carbonate solution (360 mL), and a saturated aqueous sodium chloride solution. The organic layer was dehydrated and dried over anhydrous magnesium sulfate, and then the solvent was distilled away under reduced pressure. The residue was purified by silica gel column chromatography [eluent; ethyl acetate:hexane=40:60], thereby obtaining a target substance (24.9 g) as white solids.

Example 19 (2)

Phosphorus tribromide (132 g, 486 mmol) was added to NMP (430 mL), and the mixture was cooled to −10° C. Then, a solution of the compound obtained in Example 19 (1) (43.0 g, 60.7 mmol) in NMP (215 mL) was added dropwise to the reaction mixture at the same temperature. After being stirred at −10° C., the reaction mixture was added dropwise to a mixture of ethyl acetate (1.08 L) and an aqueous potassium hydrogen carbonate solution (182 g of potassium hydrogen carbonate/1.18 L of water) under ice cooling. The organic layer was separated and washed twice with an aqueous sodium chloride solution (1 L, saturated aqueous sodium chloride solution:water=50:50). The organic layer was washed with a saturated aqueous sodium chloride solution and then dehydrated and dried over anhydrous sodium sulfate, and the solvent was distilled away under reduced pressure. The residue was purified by silica gel column chromatography [eluent; ethyl acetate: hexane=50:50], thereby obtaining a target substance (14.3 g) as a yellow oily substance.

$^1$H-NMR (400 MHz, CDCl$_3$) δ value: 1.44 (9H, s), 2.65-2.85 (2H, m), 3.17-3.41 (5H, m), 3.30 (3H, s), 3.78-3.99 (1H, m), 4.55 (1H, d, J=12.8 Hz), 4.71-4.85 (1H, m), 5.43 (1H, d, J=4.0 Hz), 5.66 (1H, dd, J=9.2, 3.6 Hz), 6.32 (1H, d, J=9.2 Hz), 6.80 (1H, s), 7.16-7.45 (15H, m)

Example 19 (3)

Dichloromethane (6 mL) was added to the compound (600 mg, 867 mol) obtained in Example 19 (2), and the mixture was stirred. The reaction mixture was cooled to −40° C., N,N-dimethylaniline (368 mg, 3.04 mmol) and phosphorus pentachloride (271 mg, 1.30 mmol) were sequentially added thereto, and the mixture was stirred at the same temperature for 30 minutes. Then, the reaction mixture was added to methanol (3 mL), stirred at room temperature for 8 minutes, and then stirred at −40° C. for 5 minutes. Ethyl acetate (24 mL) and an aqueous sodium hydrogen carbonate solution (1.02 g of sodium hydrogen carbonate/24 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (343 mg, 1.04 mmol), HATU (404 mg, 1.04 mmol), 2,6-lutidine (202 μL, 1.73 mmol), and DMF (5 mL) were added to the obtained ethyl acetate solution. The reaction mixture was stirred at room temperature under reduced pressure for 30 minutes, and then stirred at room temperature under normal pressure for 1 hour and 30 minutes. Water (40 mL) and ethyl acetate (40 mL) were added to the reaction mixture, and the organic layer was separated. The organic layer was washed sequentially with water and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=80:20], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-(((R)-2-((tert-butoxycarbonyl)amino)-3-methoxypropyl)thio)-7-oxo-4-thia-1-azabicyclo[3.2.0]heptane-3-carboxylate (489 mg) as white solids.

$^1$H-NMR (400 MHz, CDCl$_3$) δ value: 1.34 (9H, s), 1.44 (9H, s), 1.50-1.54 (6H, m), 2.71 (1H, dd, J=12.4, 7.2 Hz), 2.83 (1H, dd, J=12.4, 6.4 Hz), 3.22-3.38 (4H, m), 3.29 (3H, s), 3.82-3.94 (1H, m), 4.55 (1H, d, J=12.4 Hz), 4.70-4.80 (1H, m), 5.54 (1H, d, J=4.4 Hz), 5.87 (1H, dd, J=8.8, 4.4 Hz), 6.40 (2H, s), 6.82 (1H, s), 6.84 (1H, s), 7.24-7.44 (10H, m)

Example 19 (4)

Dichloromethane (7.2 mL) was added to the compound (480 mg, 0.54 mmol) obtained in Example 19 (3), and the mixture was cooled to −20° C. At the same temperature, anisole (7.1 mL), nitromethane (4.8 mL), and aluminum chloride (868 mg, 6.51 mmol) were sequentially added to the reaction mixture. The reaction mixture was stirred at the same temperature for 1 hour. Under ice cooling, the reaction mixture was added to a mixture of acetonitrile (19 mL), water (19 mL), and trisodium citrate (3.37 g, 13.0 mmol), and washed sequentially with acetonitrile (9 mL) and water (6 mL). Then, a saturated aqueous sodium hydrogen carbonate solution was added to the reaction mixture so as to adjust the pH to 6.0, and the aqueous layer was separated. The aqueous layer was concentrated under reduced pressure, and 2 mol/L hydrochloric acid was added thereto so as to adjust the pH to 2.9. The obtained aqueous solution was purified by medium-pressure reverse-phase silica gel column chromatography [eluent; water:acetonitrile=100:0→75:25]. The aqueous solution containing a target substance was concentrated under reduced pressure and lyophilized, thereby obtaining (3R,5R,6R)-3-(((R)-2-amino-3-methoxypropyl)thio)-6-((Z)-2-(2-aminothiazol-4-yl)-2-(((2-carboxypropan-2-yl)oxy)imino)acetamide)-7-oxo-4-thia-1-azabicyclo[3.2.0]heptane-3-carboxylic acid (160 mg) as white solids.

Example 19 (5)

THF (1.2 mL) and water (1.2 mL) were added to the compound (40 mg, 71 mol) obtained in Example 19 (4), and the mixture was stirred under ice cooling. At the same temperature, sodium hydrogen carbonate (13 mg, 150 μmol) and 2-chloro-3,4-bis((4-methoxybenzyl)oxy)benzoyl chloride (38 mg, 85 μmol) were sequentially added to the reaction mixture. A saturated aqueous sodium hydrogen carbonate solution was added to the reaction mixture, and the mixture was stirred at the same temperature for 3 hours and 30 minutes while maintaining the pH at 7.0. Ethyl acetate (20 mL) and water (20 mL) were added to the reaction mixture, and then 1 mol/L hydrochloric acid was added thereto so as to adjust the pH to 1.9. The organic layer was separated and washed with a saturated aqueous sodium chloride solution. The organic layer was dehydrated and dried over anhydrous sodium sulfate, and then the solvent was distilled away under reduced pressure, thereby obtaining a residue containing (3R,5R,6R)-6-((Z)-2-(2-aminothiazol-4-yl)-2-(((2-carboxypropan-2-yl)oxy)imino)acetamide)-3-(((R)-2-(2-chloro-3,4-bis((4-methoxybenzyl)oxy)benzamide)-3-methoxypropyl)thio)-7-oxo-4-thia-1-azabicyclo[3.2.0]heptane-3-carboxylic acid.

Example 19 (6)

Dichloromethane (4.1 mL) was added to the residue obtained in Example 19 (5), and the mixture was cooled to −20° C. At the same temperature, anisole (460 L), nitromethane (2.1 mL), and aluminum chloride (57 mg, 430 mol) were sequentially added to the reaction mixture, and the mixture was stirred at the same temperature for 30 minutes. Under ice cooling, the reaction mixture was added to a mixture of acetonitrile (6.9 mL), water (6.9 mL), and trisodium citrate (440 mg, 1.70 mmol), and washed sequentially with acetonitrile (9 mL) and water (6 mL). The aqueous layer was separated and concentrated under reduced pressure. Hydrochloric acid (2 mol/L) was added to the obtained aqueous solution so as to adjust the pH to 4.8. The aqueous solution was purified by medium-pressure reverse-phase silica gel column chromatography [eluent; water:acetonitrile=100:0→60:40]. The aqueous solution containing a target substance was concentrated under reduced pressure and lyophilized, thereby obtaining (3R,5R,6R)-6-((Z)-2-(2-aminothiazol-4-yl)-2-(((2-carboxypropan-2-yl)oxy)imino)acetamide)-3-(((R)-2-(2-chloro-3,4-dihydroxybenzamide)-3-methoxypropyl)thio)-7-oxo-4-thia-1-azabicyclo[3.2.0]heptane-3-carboxylic acid (16.6 mg) as white solids.

$^1$H-NMR (400 MHz, CDCl$_3$) δ value: 1.42-1.54 (6H, m), 3.00 (1H, dd, J=13.2, 8.0 Hz), 3.15 (1H, dd, J=13.2, 4.2 Hz), 3.30 (1H, d, J=12.4 Hz), 3.43 (3H, s), 3.58-3.70 (2H, m), 4.37 (1H, d, J=12.8 Hz), 4.46-4.58 (1H, m), 5.56 (1H, dd, J=4.0, 1.2 Hz), 5.74 (1H, d, J=4.0 Hz), 6.88-6.94 (1H, m), 6.98-7.04 (2H, m);

MS (ESI): 732.90 [M+H]$^+$, 730.85 [M−H]$^−$

Example 20

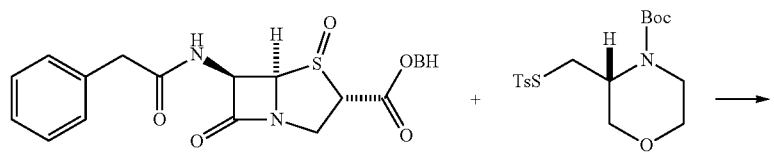

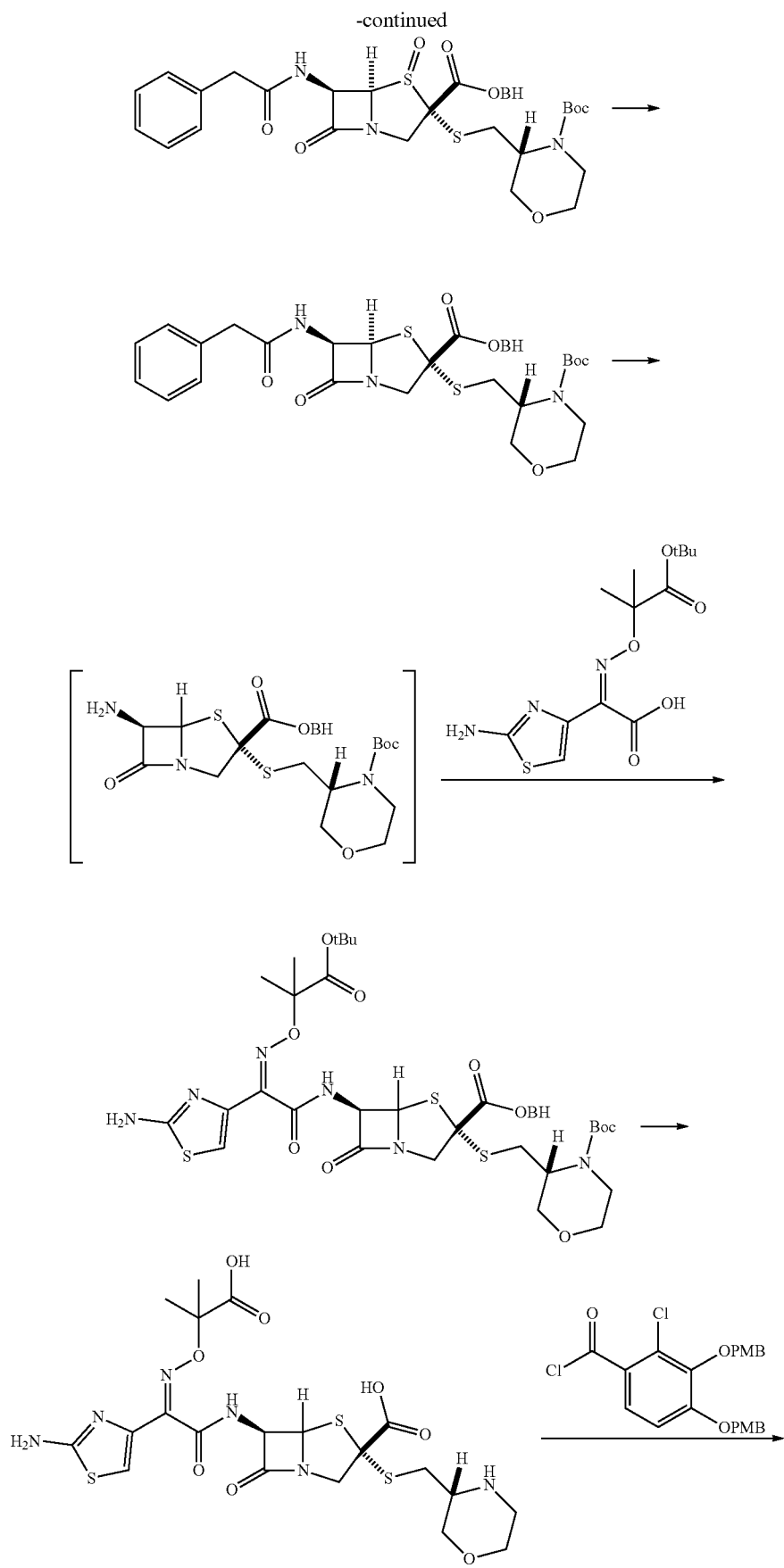

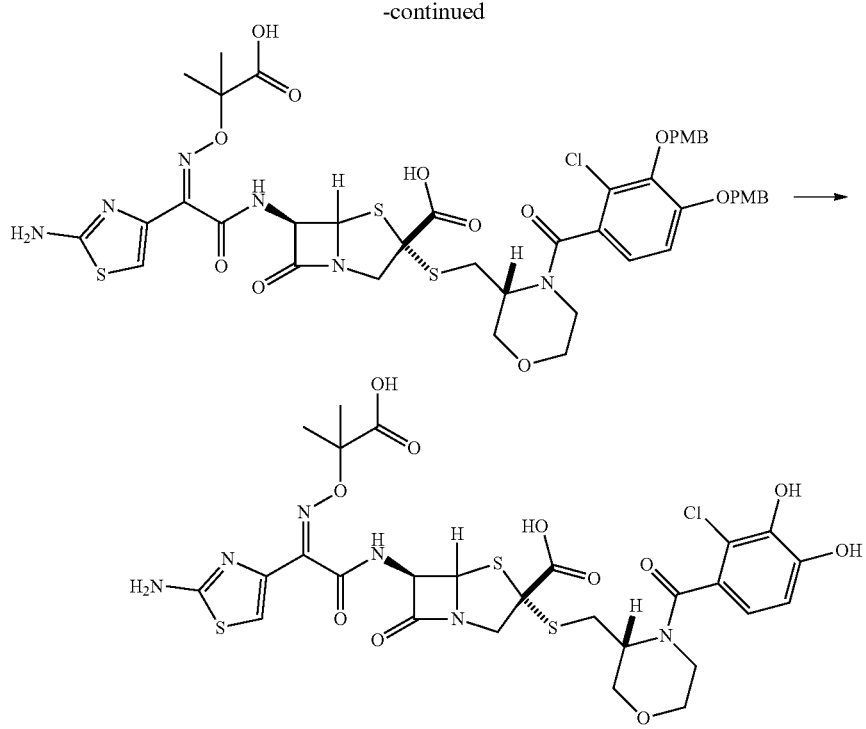

Example 20 (1)

Tert-butyl (R)-3-((tosylthio)methyl)morpholine-4-carboxylate (12.3 g, 31.7 mmol) and dichloromethane (141 mL) were added to benzhydryl (3 S, 5R,6R)-7-oxo-6-(2-phenylacetamide)-4-thia-1-azabicyclo[3.2.0]heptane-3-carboxylate 4-oxide (14.1 g, 28.9 mmol), and the mixture and stirred. The reaction mixture was cooled on ice, and a solution of DBU (4.31 g, 28.3 mmol) in dichloromethane (8 mL) was added dropwise thereto. The reaction mixture was stirred at the same temperature for 30 minutes. Under ice cooling, the reaction mixture was added to a mixture of chloroform (150 mL), water (150 mL), and 1 mol/L hydrochloric acid (15 mL). The organic layer was separated from the reaction mixture and washed sequentially with an aqueous sodium hydrogen carbonate solution, water, and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=50:50], thereby obtaining a target substance (18.9 g) as a colorless oily substance.

Example 20 (2)

Dichloromethane (31.4 mL) and NMP (157 mL) were added to the compound (11.3 g, 15.7 mmol) obtained in Example 20 (1), and the mixture was stirred. The reaction mixture was cooled to −20° C., and a solution of phosphorus tribromide (34.0 g, 126 mmol) in dichloromethane (21 mL) was added dropwise thereto. The reaction mixture was stirred at a temperature of −20° C. to −10° C. for 4 hours, and added dropwise to an aqueous sodium hydrogen carbonate solution (52.7 g of sodium hydrogen carbonate/120 mL of water) under ice cooling. Ethyl acetate (500 mL) was added to the reaction mixture, and the organic layer was separated and washed sequentially with an aqueous sodium hydrogen carbonate solution, an aqueous citric acid solution, and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate: hexane=45:55], thereby obtaining a target substance (4.43 g) as a light yellow oily substance.

$^1$H-NMR (400 MHz, CDCl$_3$) δ value: 1.46 (9H, s), 2.74 (1H, dd, J=12.0, 7.6 Hz), 2.90-3.07 (2H, m), 3.10-3.29 (1H, m), 3.33-3.54 (4H, m), 3.62-3.86 (3H, m), 3.90-4.05 (1H, m), 4.55 (1H, d, J=12.8 Hz), 5.39 (1H, d, J=4.0 Hz), 5.66 (1H, dd, J=9.2, 4.0 Hz), 6.36 (1H, d, J=9.2 Hz), 6.80 (1H, s), 7.18-7.42 (15H, m)

Example 20 (3)

Dichloromethane (5 mL) was added to the compound (500 mg, 0.71 mmol) obtained in Example 20 (2), and the mixture was stirred. The reaction mixture was cooled to −40° C., N,N-dimethylaniline (301 mg, 2.49 mmol) and phosphorus pentachloride (222 mg, 1.07 mmol) were sequentially added thereto, and the mixture was stirred at the same temperature for 30 minutes. Then, the reaction mixture was added to methanol (2.5 mL) at room temperature and cooled to −40° C. The reaction mixture was added to a mixture of ethyl acetate (15 mL) and an aqueous sodium hydrogen carbonate solution (835 mg of sodium hydrogen carbonate/15 mL of water), and the organic layer was separated. The organic layer was washed sequentially with water and a saturated aqueous sodium chloride solution and then dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (281 mg, 0.85 mmol), HATU (331 mg, 0.85 mmol), 2,6-lutidine (165 μL, 1.42 mmol), and DMF (4.2 mL) were added to the filtrate. The reaction mixture was stirred at room temperature under reduced pressure for 20 minutes and then stirred at room temperature under normal pressure for 40 minutes. The reaction mixture was diluted with ethyl acetate, and water was added thereto. A saturated aqueous sodium hydrogen carbonate solution was added to the reaction mixture so as to adjust the pH to 7.4, and then the organic layer was separated. The organic layer was washed sequentially with water and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=80:20], thereby obtaining tert-butyl (R)-3-((((3R,5R,6R)-6-((Z)-2-(2-aminothiazol-4-yl)-2-(((1-(tert-butoxy)-2-methyl-1-oxopropan-2-yl)oxy)imino)acetamide)-3-((benzhydryloxy)carbonyl)-7-oxo-4-thia-1-azabicyclo[3.2.0]heptane-3-yl)thio)methyl)morpholine-4-carboxylate (249 mg) as light yellow solids.

Example 20 (4)

Dichloromethane (7.5 mL) was added to the compound (249 mg, 0.28 mmol) obtained in Example 20 (3), and the mixture was cooled to −20° C. At the same temperature, anisole (3.6 mL), nitromethane (3.7 mL) and aluminum chloride (444 mg, 3.33 mmol) were sequentially added to the reaction mixture. The reaction mixture was stirred at the same temperature for 30 minutes. The reaction mixture was stirred at −10° C. for 1 hour, then added to a mixture of acetonitrile (12.5 mL), water (12.5 mL), and trisodium citrate dihydrate (1.72 g, 6.66 mmol) under ice cooling, and washed sequentially with dichloromethane (4 mL) and water (4 mL). A saturated aqueous sodium hydrogen carbonate solution was added to the reaction mixture so as to adjust the pH to 6.0, and then the aqueous layer was separated. The aqueous layer was concentrated under reduced pressure, and 1 mol/L hydrochloric acid was added to the obtained aqueous solution so as to adjust the pH to 2.8. The aqueous solution was purified by medium-pressure reverse-phase silica gel column chromatography [eluent; water:acetonitrile=100:0→50:50]. The aqueous solution containing a target substance was concentrated under reduced pressure and lyophilized, thereby obtaining (3R,5R,6R)-6-((Z)-2-(2-aminothiazol-4-yl)-2-(((2-carboxypropan-2-yl)oxy)imino)acetamide)-3-((((R)-morpholin-3-yl)methyl)thio)-7-oxo-4-thia-1-azabicyclo[3.2.0]heptane-3-carboxylic acid (83 mg) as white solids.

Example 20 (5)

THF (2.3 mL) and water (2.3 mL) were added to the compound (77 mg, 0.13 mmol) obtained in Example 20 (4), and the mixture was stirred under ice cooling. At the same temperature, sodium hydrogen carbonate (24 mg, 0.28 mmol), 2-chloro-3,4-bis((4-methoxybenzyl)oxy)benzoyl chloride (72 mg, 0.16 mmol), and THF (2.3 mL) were sequentially added to the reaction mixture. A saturated aqueous sodium hydrogen carbonate solution was added to the reaction mixture, and the mixture was stirred at the same temperature for 2 hours while maintaining the pH at 7.0. Ethyl acetate (20 mL) and water (20 mL) were added to the reaction mixture, and then 1 mol/L hydrochloric acid was added thereto so as to adjust the pH to 2.0. The organic layer was separated and washed with a saturated aqueous sodium chloride solution. The organic layer was dehydrated and dried over anhydrous sodium sulfate, and then the solvent was distilled away under reduced pressure, thereby obtaining a residue containing (3R,5R,6R)-6-((Z)-2-(2-aminothiazol-4-yl)-2-(((2-carboxypropan-2-yl)oxy)imino)acetamide)-3-((((R)-4-(2-chloro-3,4-bis((4-methoxybenzyl)oxy)benzoyl)morpholin-3-yl)methyl)thio)-7-oxo-4-thia-1-azabicyclo[3.2.0]heptane-3-carboxylic acid.

Example 20 (6)

Dichloromethane (7.7 mL) was added to the residue obtained in Example 20 (5), and the mixture was cooled to −20° C., and the mixture was stirred. Anisole (849 L), nitromethane (3.8 mL), and aluminum chloride (104 mg, 0.78 mmol) were sequentially added to the reaction mixture, and the mixture was stirred at the same temperature for 1 hour. Under ice cooling, the reaction mixture was added to a mixture of acetonitrile (12.8 mL), water (12.8 mL), and trisodium citrate (807 mg, 3.12 mmol), and washed sequentially with acetonitrile (9 mL) and water (6 mL). The aqueous layer was separated and concentrated under reduced pressure. Hydrochloric acid (2 mol/L) was added to the obtained aqueous solution so as to adjust the pH to 2.8. The aqueous solution was purified by medium-pressure reverse-phase silica gel column chromatography [eluent; water: acetonitrile=100:0→50:50]. The aqueous solution containing a target substance was concentrated under reduced pressure and lyophilized, thereby obtaining (3R,5R,6R)-6-((Z)-2-(2-aminothiazol-4-yl)-2-(((2-carboxypropan-2-yl)oxy)imino)acetamide)-3-((((R)-4-(2-chloro-3,4-dihydroxybenzoyl)morpholin-3-yl)methyl)thio)-7-oxo-4-thia-1-azabicyclo[3.2.0]heptane-3-carboxylic acid (24.3 mg) as white solids.

$^1$H-NMR (400 MHz, DMSO-$d_6$) δ value: 1.43 (3H, s), 1.44 (3H, s), 2.88-3.63 (7H, m), 3.64-3.80 (1H, m), 3.83-3.88 (1H, m), 4.20-4.40 (1H, m), 4.54-4.74 (1H, m), 5.50-5.76 (2H, m), 6.50-6.84 (4H, m), 7.22-7.36 (3H, m), 9.25-9.43 (2H, m), 9.90-10.10 (1H, m);

MS (ESI): 744.95 [M+H]$^+$, 742.80 [M−H]$^−$

Example 21

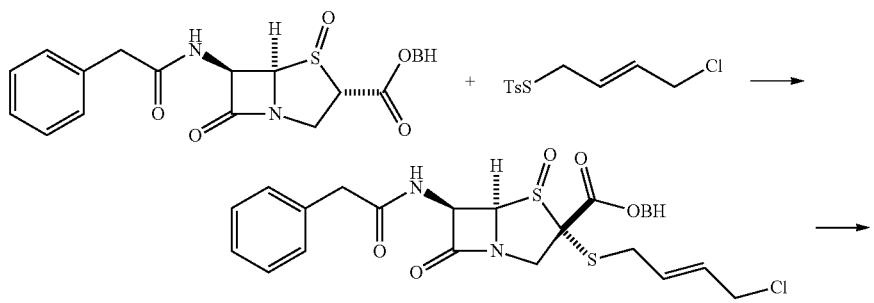

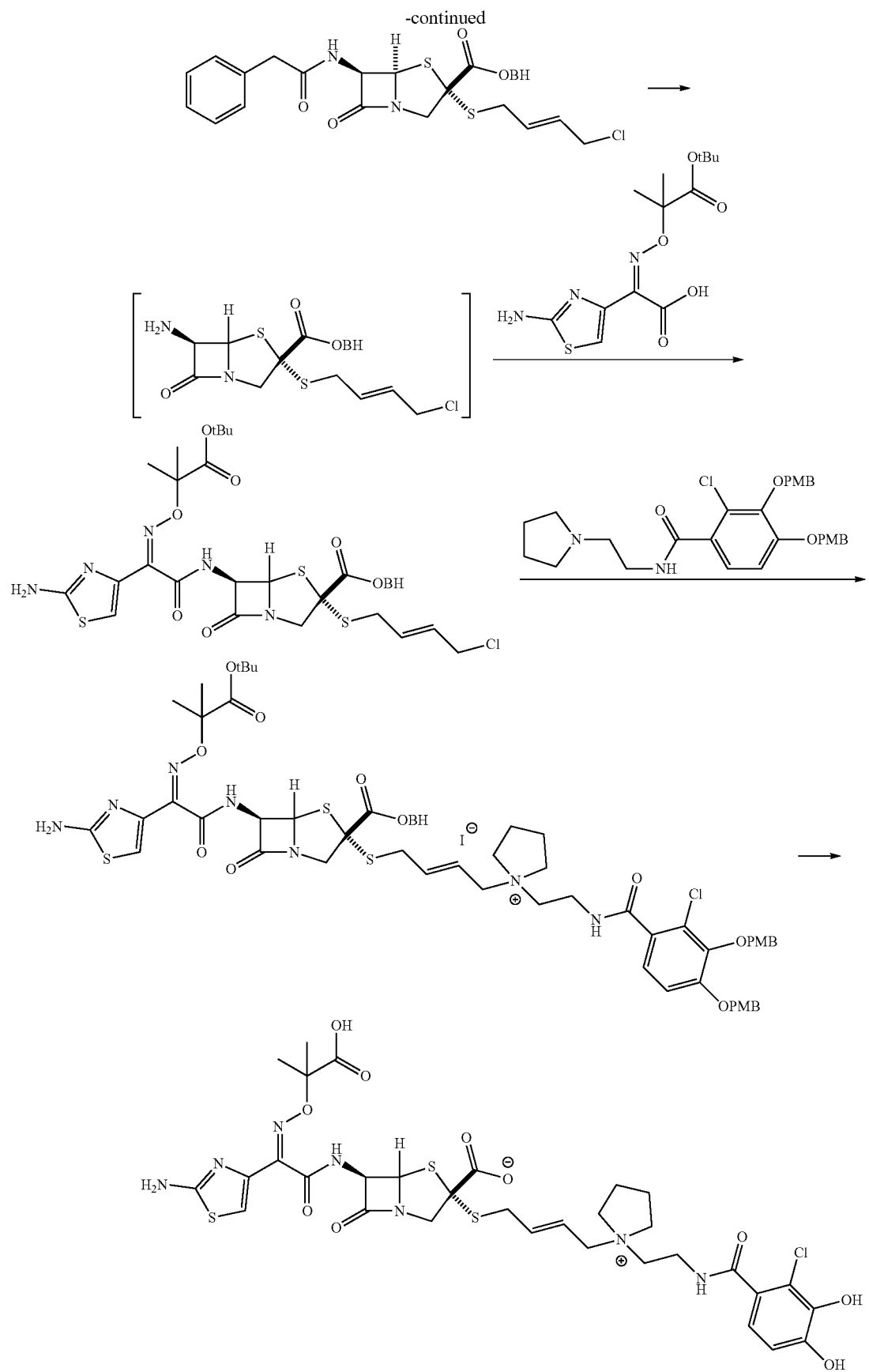

Example 21 (1)

(E)-S-(4-chlorobut-2-en-1l-yl) 4-methylbenzenesulfonothioate (1.95 g, 7.06 mmol) and dichloromethane (23 mL) were added to benzhydryl (3 S, 5R, 6R)-7-oxo-6-(2-phenylacetamide)-4-thia-1-azabicyclo[3.2.0]heptane-3-carboxylate 4-oxide (3.00 g, 6.14 mmol), and the mixture was stirred under ice cooling. At the same temperature, a solution of DBU (935 mg, 6.14 mmol) in dichloromethane (7 mL) was added dropwise to the reaction mixture. The reaction mixture was stirred at the same temperature for 1 hour. Under ice cooling, the reaction mixture was added to a mixture of chloroform (30 mL), water (30 mL), and 1 mol/L hydrochloric acid (3 mL). The organic layer was separated and washed sequentially with 0.1 mol/L hydrochloric acid, an aqueous sodium hydrogen carbonate solution, and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=40:60], thereby obtaining a target substance (3.27 g) as white solids.

Example 21 (2)

Dichloromethane (5 mL) and NMP (27 mL) were added to the compound (3.27 g, 5.37 mmol) obtained in Example 21 (1), and the mixture was stirred. The reaction mixture was cooled to −20° C., and a solution of phosphorus tribromide (11.6 g, 42.9 mmol) in dichloromethane (4 mL) cooled to −10° C. was added dropwise thereto. The reaction mixture was stirred at a temperature of −15° C. to −5° C. for 3 hours and 30 minutes. Under ice cooling, the reaction mixture was added dropwise to a mixture of an aqueous sodium hydrogen carbonate solution (18.0 g of sodium hydrogen carbonate/350 mL of water). Ethyl acetate (300 mL) was added to the reaction mixture, and the organic layers were separated. The aqueous layer was extracted using ethyl acetate (200 mL), the organic layers were combined, washed three times with a 0.5% aqueous citric acid solution, and then washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=30:70], thereby obtaining a target substance (1.63 g) as a colorless oily substance.

$^1$H-NMR (400 MHz, CDCl$_3$) δ value: 3.12-3.25 (3H, m), 3.51 (2H, d, J=2.8 Hz), 3.82-3.93 (2H, m), 4.59 (1H, d, J=12.8 Hz), 5.40 (1H, d, J=4.1 Hz), 5.53-5.60 (2H, m), 5.65 (1H, dd, J=9.1, 4.1 Hz), 6.36 (1H, d, J=9.1 Hz), 6.80 (1H, s), 7.18-7.45 (15H, m)

Example 21 (3)

Dichloromethane (4 mL) was added to the compound (400 mg, 0.67 mmol) obtained in Example 21 (2), and the mixture was stirred. The reaction mixture was cooled to −40° C., N,N-dimethylaniline (286 mg, 2.36 mmol) and phosphorus pentachloride (211 mg, 1.01 mmol) were sequentially added thereto, and the mixture was stirred at the same temperature for 20 minutes. Then, the reaction mixture was added to methanol (2 mL), stirred at room temperature for 5 minutes, and then stirred at −40° C. for 5 minutes. The reaction mixture was added to a mixture of ethyl acetate (16 mL) and an aqueous sodium hydrogen carbonate solution (793 mg of sodium hydrogen carbonate/16 mL of water), and the organic layer was separated. The organic layer was washed sequentially with water and a saturated aqueous sodium chloride solution and then dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (222 mg, 0.67 mmol), HATU (262 mg, 0.67 mmol), 2,6-lutidine (157 μL, 1.35 mmol), and DMF (3.2 mL) were added to the filtrate. The reaction mixture was stirred at room temperature for 1 hour and 30 minutes under reduced pressure, and then stirred for 1 hour and 30 minutes at room temperature under normal pressure. Water (40 mL) and ethyl acetate (40 mL) were added to the reaction mixture, and the organic layer was separated. The organic layer was washed sequentially with a 5% aqueous citric acid solution, water, and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=80:20], thereby obtaining benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-(((E)-4-chlorobut-2-en-1-yl)thio)-7-oxo-4-thia-1-azabicyclo[3.2.0]heptane-3-carboxylate (530 mg) as a colorless oily substance.

$^1$H-NMR (400 MHz, CDCl$_3$) δ value: 1.36 (9H, s), 1.52 (3H, s), 1.54 (3H, s), 3.14-3.36 (3H, m), 3.84-3.90 (2H, m), 4.58 (1H, d, J=12.8 Hz), 5.48-5.66 (3H, m), 5.86 (1H, dd, J=8.4, 4.0 Hz), 6.50 (2H, s), 6.83 (1H, s), 6.84 (1H, s), 7.24-7.41 (10H, m)

Example 21 (4)

THF (4.1 mL) was added to the compound (410 mg, 0.52 mmol) obtained in Example 21 (3), and the mixture was stirred at room temperature in a state of being shielded from light. Sodium iodide (782 mg, 5.21 mmol) was added to the reaction mixture, and the mixture was stirred at room temperature for 3 hours and 30 minutes in a state of being shielded from light. Ethyl acetate (20 mL) and water (20 mL) were added to the reaction mixture, and then a 10% aqueous sodium thiosulfate solution was added thereto. The organic layer was separated and washed sequentially with water and a saturated aqueous sodium chloride solution. The organic layer was dehydrated and dried over anhydrous sodium sulfate, and then solids were filtered. 2-Chloro-3,4-bis((4-methoxybenzyl)oxy)-N-(2-(pyrrolidin-1-yl)ethyl)benzamide (274 mg, 0.52 mmol) and DMF (4.1 mL) were added to the filtrate, and ethyl acetate was distilled away under reduced pressure. The reaction mixture was stirred at room temperature for 20 hours, ethyl acetate (20 mL) and water (20 mL) were then added thereto, and the organic layer was separated. The organic layer was washed sequentially with water and a saturated aqueous sodium chloride solution, and then dehydrated and dried over anhydrous sodium sulfate. The solvent was distilled away under reduced pressure, thereby obtaining yellow solids containing 1-((E)-4-(((3R,5R,6R)-6-((Z)-2-(2-aminothiazol-4-yl)-2-(((1-(tert-butoxy)-2-methyl-1-oxopropan-2-yl)oxy)imino)acetamide)-3-((benzhydryloxy)carbonyl)-7-oxo-4-thia-1-azabicyclo[3.2.0]heptan-3-yl)thio)but-2-en-1-yl)-1-(2-(2-chloro-3,4-bis((4-methoxybenzyl)oxy)benzamide)ethyl)pyrrolidin-1-ium iodide.

Example 21 (5)

Dichloromethane (14.6 mL) was added to the yellow solids obtained in Example 21 (4), and the mixture was cooled to −20° C. At the same temperature, anisole (6.81 mL) and aluminum chloride (834 mg, 6.25 mmol) were sequentially added to the reaction mixture. The reaction mixture was stirred at the same temperature for 1 hour and 30 minutes. Under ice cooling, the reaction mixture was added to a mixture of acetonitrile (29 mL), water (29 mL), and trisodium citrate (3.23 g, 12.5 mmol), and washed sequentially with acetonitrile (9 mL) and water (6 mL). A saturated aqueous sodium hydrogen carbonate solution was added to the reaction mixture so as to adjust the pH to 5.8, and the aqueous layer was separated. The aqueous layer was concentrated under reduced pressure, and 2 mol/L hydrochloric acid was added thereto so as to adjust the pH to 3.9. The aqueous solution was purified by medium-pressure reverse-phase silica gel column chromatography [eluent; water:acetonitrile=100:0→60:40]. The aqueous solution containing a target substance was concentrated and lyophilized, thereby obtaining (3R,5R,6R)-6-((Z)-2-(2-aminothiazol-4-yl)-2-(((2-carboxypropan-2-yl)oxy)imino)acetamide)-3-(((E)-4-(1-(2-(2-chloro-3,4-dihydroxybenzamide)ethyl)pyrrolidin-1-ium-1-yl)but-2-en-1-yl)thio)-7-oxo-4-thia-1-azabicyclo[3.2.0]heptane-3-carboxylic acid (102 mg) as white solids.

$^1$H-NMR (400 MHz, D$_2$O) δ value: 1.48 (3H, s), 1.49 (3H, s), 2.14-2.30 (4H, m), 3.23 (1H, d, J=12.4 Hz), 3.44-3.72 (8H, m), 3.80-3.90 (2H, m), 3.99 (2H, d, J=7.6 Hz), 4.39 (1H, d, J=12.4 Hz), 5.46 (1H, d, J=4.0 Hz), 5.63 (1H, d, J=3.6 Hz), 5.85-5.96 (1H, m), 6.20-6.32 (1H, m), 6.84-6.93 (1H, m), 6.95-7.02 (1H, m);

MS (ESI): 812.15 [M+H]$^+$, 809.95 [M−H]$^-$

Example 22

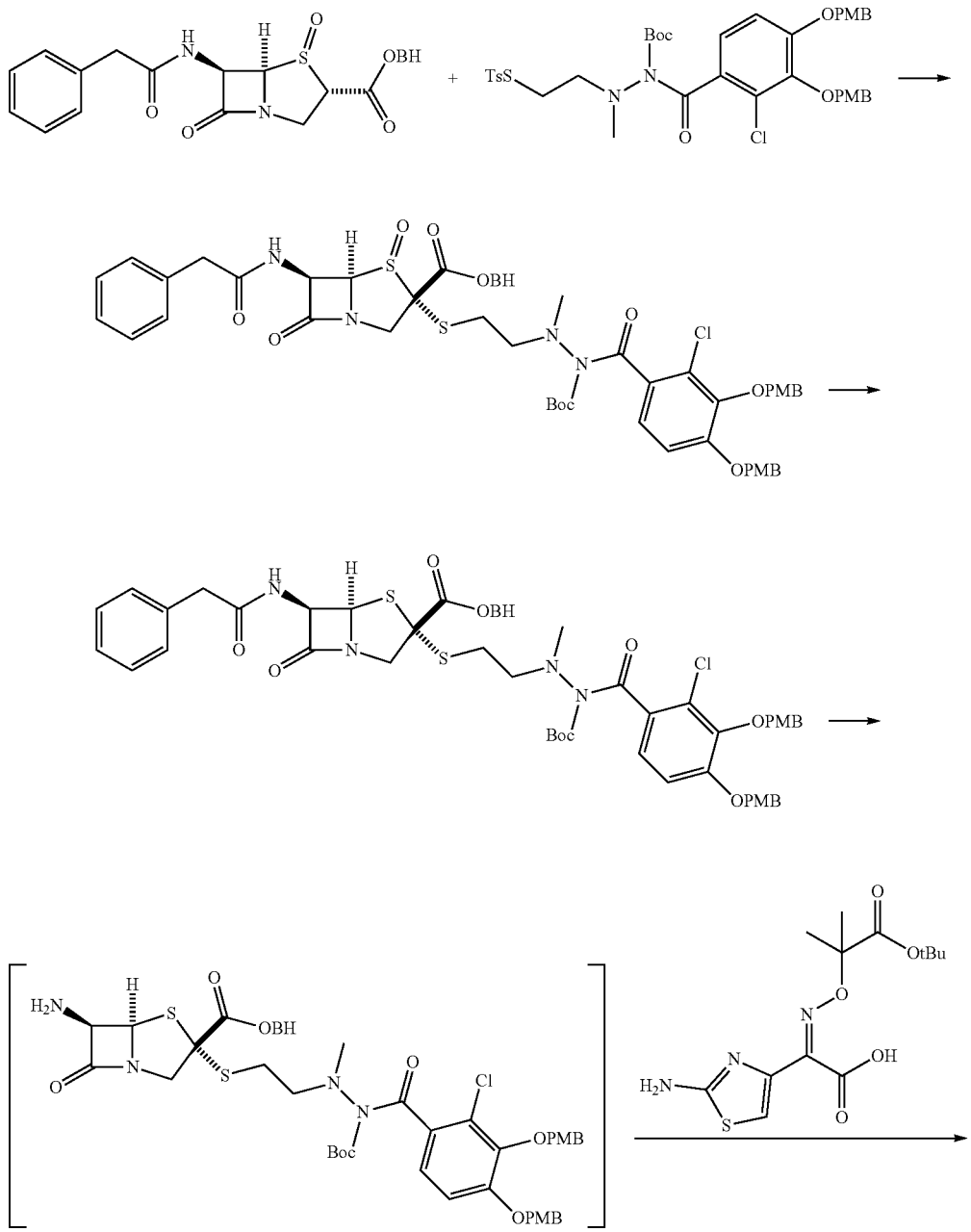

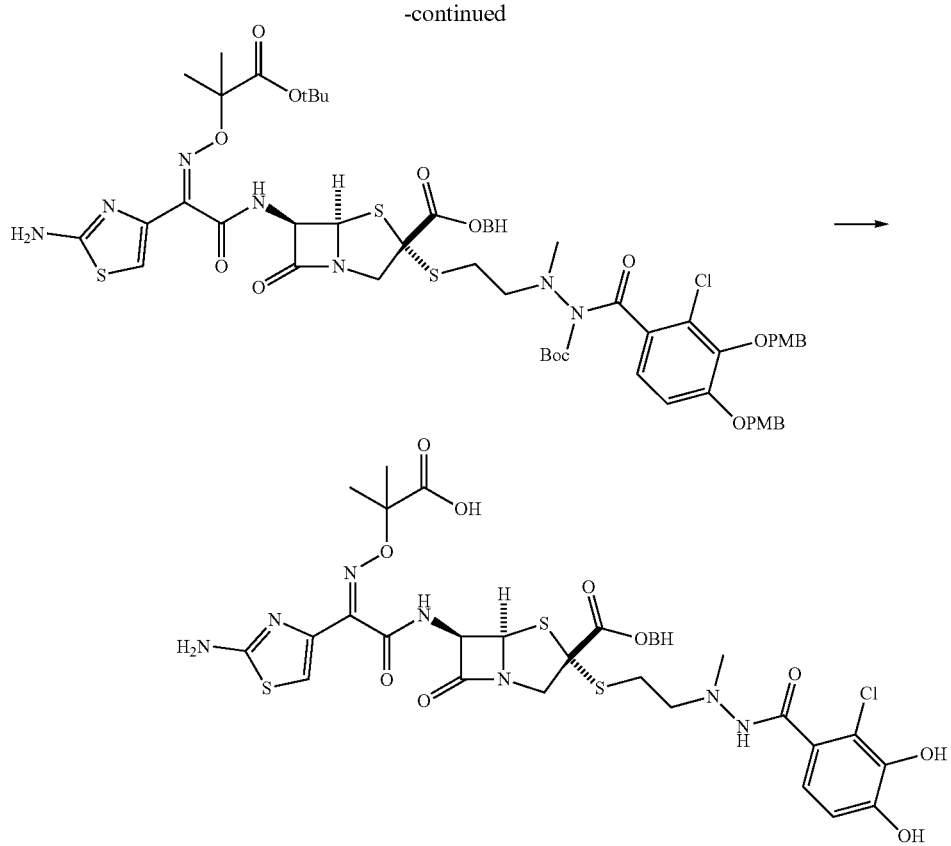

Example 22 (1)

Tert-butyl 1-(2-chloro-3,4-bis((4-methoxybenzyl)oxy)benzoyl)-2-methyl-2-(2-(tosylthio)ethyl)hydrazine-1-carboxylate (6.87 g, 8.91 mmol) and dichloromethane (40 mL) were added to benzhydryl (3 S,5R,6R)-7-oxo-6-(2-phenylacetamide)-4-thia-1-azabicyclo[3.2.0]heptane-3-carboxylate 4-oxide (4.00 g, 8.19 mmol), and the mixture was stirred. The reaction mixture was cooled to −20° C., and a solution of DBU (1.18 g, 7.78 mmol) in dichloromethane (8 mL) was added dropwise thereto. The reaction mixture was stirred at the same temperature for 30 minutes. Under ice cooling, the reaction mixture was added to a mixture of dichloromethane (50 mL), water (50 mL), and 1 mol/L hydrochloric acid (5 mL). The organic layer was separated from the reaction mixture and washed sequentially with water (50 mL), a 5% aqueous sodium hydrogen carbonate solution (50 mL), and a 10% aqueous sodium chloride solution (50 mL). The organic layer was dehydrated and dried over anhydrous sodium sulfate, and then the solvent was distilled away under reduced pressure. The residue was purified by silica gel column chromatography [eluent; ethyl acetate:hexane=50:50], thereby obtaining a target substance (7.77 g) as a colorless oily substance.

Example 22 (2)

Ethyl acetate (7 mL) and NMP (35 mL) were added to the compound (7.77 g, 7.04 mmol) obtained in Example 22 (1), and the mixture was stirred. The reaction mixture was cooled to −20° C., and a solution of phosphorus tribromide (15.2 g, 56.3 mmol) in ethyl acetate (4.7 mL) was added dropwise thereto. The reaction mixture was stirred at a temperature of −15° C. to −5° C. for 3 hours. Under ice cooling, the reaction mixture was added to a mixture of ethyl acetate (100 mL) and an aqueous potassium hydrogen carbonate solution (21.1 g of potassium hydrogen carbonate/94 mL of water). The organic layer was separated and washed twice with a 5% aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=50:50], thereby obtaining a target substance (4.81 g) as a colorless oily substance.

$^1$H-NMR (400 MHz, CDCl$_3$) δ value: 1.24 (9H, s), 2.64-2.75 (2H, m), 2.80 (3H, s), 3.19 (1H, d, J=12.8 Hz), 3.13-3.36 (2H, m), 3.49 (2H, d, J=2.8 Hz), 3.80 (3H, s), 3.82 (3H, s), 4.54 (1H, d, J=12.8 Hz), 4.93 (2H, s), 5.07 (2H, s), 5.39 (1H, d, J=4.0 Hz), 5.62 (1H, d, J=8.4 Hz), 6.32 (1H, d, J=9.2 Hz), 6.78 (1H, s), 6.80-6.86 (2H, m), 6.87-6.94 (3H, m), 7.01 (1H, d, J=8.4 Hz), 7.17-7.23 (3H, m), 7.24-7.41 (15H, m)

Example 22 (3)

Dichloromethane (3 mL) and N,N-dimethylaniline (122 μL, 0.97 mmol) were sequentially added to the compound (300 mg, 0.28 mmol) obtained in Example 22 (2), and the mixture was stirred. The reaction mixture was cooled to −50° C., phosphorus pentachloride (86 mg, 0.41 mmol) was added thereto, and the mixture was stirred at a temperature of −50° C. to −45° C. for 1 hour and 30 minutes. The reaction mixture was added to methanol (1.5 mL) and then stirred for 15 minutes under ice cooling. Ethyl acetate and an aqueous sodium hydrogen carbonate solution (301 mg of sodium hydrogen carbonate/9 mL of water) were added to the reaction mixture, and the organic layer was separated. The organic layer was washed sequentially with water and a saturated aqueous sodium chloride solution. The organic layer was dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (104 mg, 0.30 mmol), HATU (115 mg, 0.30 mmol), 2,6-lutidine (71 μL, 0.61 mmol), and DMF (3 mL) were added to the filtrate. The reaction mixture was stirred at room temperature under reduced pressure for 50 minutes until it became a solution. Water and ethyl acetate were added to the reaction mixture, and the organic layer was separated. Water and a saturated aqueous sodium hydrogen carbonate solution were added to the organic layer so as to adjust the pH to 7.5. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=60:40], thereby obtaining benzhydryl (3R,5R,6R)-6-((Z)-2-(2-aminothiazol-4-yl-2-(((1-(tert-butoxy)-2-methyl-1-oxopropan-2-yl)oxy)imino)acetamide)-3-((2-(2-(tert-butoxycarbonyl)-2-(2-chloro-3,4-bis((4-methoxybenzyl)oxy)benzoyl)-1-methylhydrazinyl)ethyl)thio)-7-oxo-4-thia-1-azabicyclo[3.2.0]heptane-3-carboxylate (122 mg) as a colorless amorphous solids.

$^1$H-NMR (400 MHz, DMSO-d$_6$) δ value: 1.17-1.21 (6H, m), 1.32-1.37 (18H, m), 2.62-2.74 (4H, m), 2.69 (3H, s), 3.37-3.45 (2H, m), 3.74 (3H, s), 3.77 (3H, s), 4.30 (1H, d, J=12.4 Hz), 4.88 (2H, s), 5.16 (2H, s), 5.48 (1H, s), 5.70-5.77 (1H, m), 6.70 (1H, s), 6.82 (1H, s), 6.86 (1H, d, J=8.8 Hz), 6.97 (1H, d, J=8.8 Hz), 7.05-7.45 (17H, m)

Example 22 (4)

Dichloromethane (1.8 mL) was added to the compound (120 mg, 0.09 mmol) obtained in Example 22 (3), and the mixture was cooled to −20° C. At the same temperature, anisole (408 L), nitromethane (600 L), and aluminum chloride (62 mg, 0.47 mmol) were sequentially added to the reaction mixture, and the mixture was stirred at a temperature of −25 to −20° C. for 2 hours. Under ice cooling, the reaction mixture was added to a mixture of acetonitrile (5 mL), water (5 mL), and trisodium citrate dihydrate (248 mg, 0.84 mmol), and washed with a 50% aqueous acetonitrile solution (15 mL). A saturated aqueous sodium hydrogen carbonate solution was added to the reaction mixture so as to adjust the pH to 6.0, and the aqueous layers were separated. The organic layer was extracted using water (4 mL). The aqueous layers were combined, 1 mol/L hydrochloric acid was added thereto so as to adjust the pH to 4.6, and the aqueous layer was concentrated under reduced pressure. The residue was purified by medium-pressure reverse-phase silica gel column chromatography [eluent; water:acetonitrile=100:0→75:25]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamide)-3-((2-(2-(2-chloro-3,4-dihydroxybenzoyl)-1-methylhydrazinyl)ethyl)thio)-7-oxo-4-thia-1-azabicyclo[3.2.0]heptane-3-carboxylic acid (75 mg) as yellow solids.

$^1$H-NMR (400 MHz, D$_2$O) δ value: 1.44 (3H, s) 1.46 (3H, s), 2.68 (3H, s), 2.92-3.12 (4H, m), 3.30 (1H, d, J=12.3 Hz), 4.37 (1H, d, J=12.3 Hz), 5.52 (1H, d, J=4.0 Hz), 5.71 (1H, d, J=4.0 Hz), 6.89 (1H, d, J=8.2 Hz), 6.97 (1H, s), 7.00 (1H, d, J=8.2 Hz), 7.46 (2H, s), 8.64 (1H, s);

MS (ESI): 717.95 [M+H]$^+$, 715.95 [M−H]$^-$

Example 23

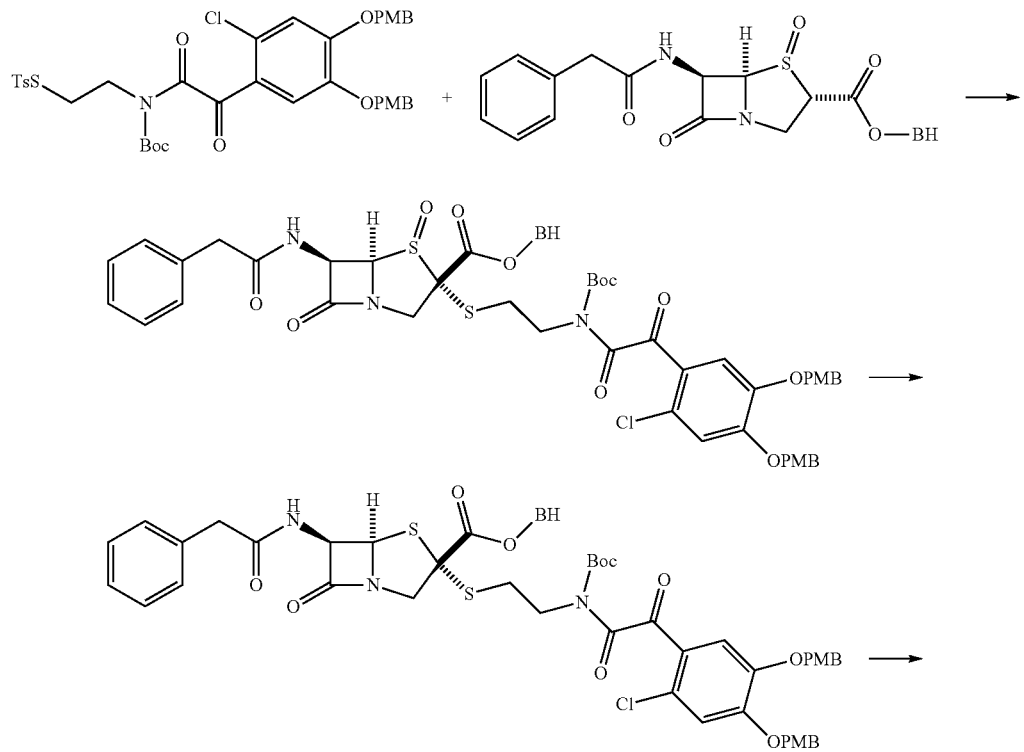

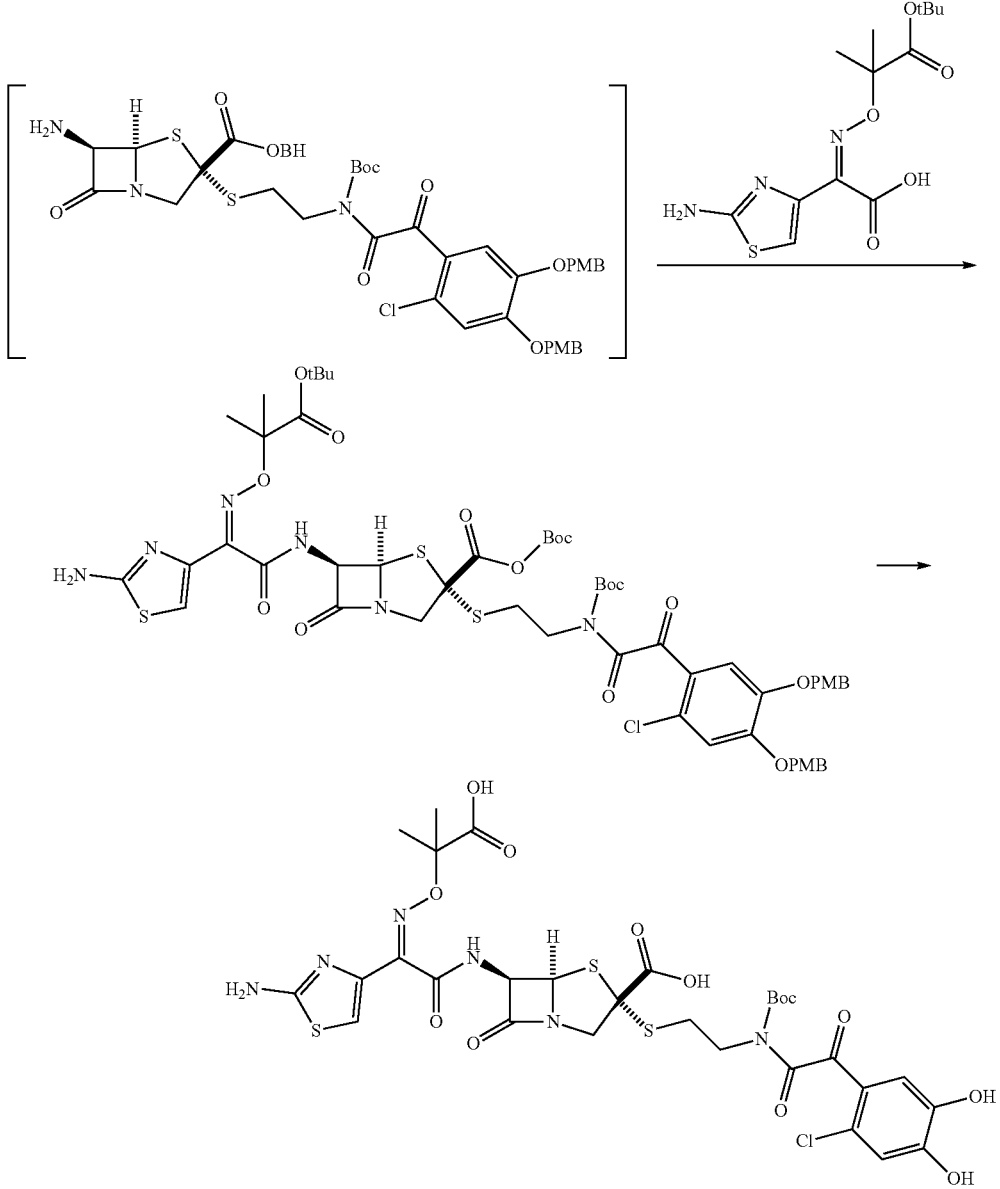

Example 23 (1)

By using S-(2-(N-(tert-butoxycarbonyl)-2-(2-chloro-4,5-bis((4-methoxybenzyl)oxy)phenyl)-2-oxoacetamide)ethyl) 4-methylbenzenesulfonothioate (12.3 g, 16.0 mmol) and benzhydryl (3 S,5R,6R)-7-oxo-6-(2-phenylacetamide)-4-thia-1-azabicyclo[3.2.0]heptane-3-carboxylate 4-oxide (7.8 g, 16.0 mmol), a target substance (14.5 g) was obtained as white solids in the same manner as in Example 1 (1).

Example 23 (2)

By using the compound (14.5 g, 13.2 mmol) obtained in Example 23 (1), a target substance (10.0 g) was obtained as white solids in the same manner as in Example 1 (2).

$^1$H-NMR (400 MHz, CDCl$_3$) δ value: 1.29 (9H, s), 2.60-2.70 (1H, m), 2.80-3.01 (3H, m), 3.24 (1H, d, J=12.0 Hz), 3.48-3.52 (2H, m), 3.80 (3H, s), 3.82 (3H, s), 4.56 (1H, d, J=13.2 Hz), 5.10 (2H, s), 5.13 (2H, s), 5.45 (1H, d, J=4.0 Hz), 5.67 (1H, dd, J=9.2, 4.0 Hz), 6.80 (1H, s), 6.85-6.95 (7H, m), 7.17-7.43 (17H, m), 7.65-7.70 (2H, m)

Example 23 (3)

By using the compound (10.0 g, 9.2 mmol) obtained in Example 23 (2), in the same manner as in Example 1 (3), benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-((2-(N-(tert-butoxycarbonyl)-2-(2-chloro-4,5-bis((4-methoxybenzyl)oxy)phenyl)-2-oxoacetamide)ethyl)thio)-7-oxo-4-thia-1-azabicyclo[3.2.0]heptane-3-carboxylate (5.0 g) was obtained as yellow solids.

$^1$H-NMR (400 MHz, CDCl$_3$) δ value: 1.28 (9H, s), 1.34 (6H, s), 1.39 (9H, s), 2.64-3.06 (4H, m), 3.34 (1H, d, J=12.4 Hz), 3.80 (3H, s), 3.81 (3H, s), 4.83 (1H, d, J=12.8 Hz), 5.10 (2H, s), 5.12 (2H, s), 5.56 (1H, dd, J=7.0, 4.2 Hz), 5.88 (1H, dd, J=8.2, 4.2 Hz), 6.79-6.99 (7H, m), 7.22-7.43 (15H, m), 7.58-7.70 (3H, m)

Example 23 (4)

By using the compound (1.5 g, 1.2 mmol) obtained in Example 23 (3), in the same manner as in Example 1 (4), (3R,5R,6R)-6-((Z)-2-(2-aminothiazol-4-yl)-2-(((2-carboxypropan-2-yl)oxy)imino)acetamide)-3-((2-(2-(2-chloro-4,5-dihydroxyphenyl)-2-oxoacetamide)ethyl)thio)-7-oxo-4-thia-1-azabicyclo[3.2.0]heptane-3-carboxylic acid (115 mg) was obtained as light yellow solids.

$^1$H-NMR (400 MHz, D$_2$O) δ value: 1.38 (3H, s), 1.41 (3H, s), 2.99 (2H, t, J=6.2 Hz), 3.22 (1H, dd, J=12.4, 1.2 Hz), 3.46-3.56 (1H, m), 3.56-3.68 (1H, m), 4.34 (1H, d, J=12.8 Hz), 5.50 (1H, d, J=4.0 Hz), 5.67 (1H, d, J=3.2 Hz), 6.92 (1H, s), 6.97 (1H, s), 7.26 (1H, s);

MS (ESI): 716.95 [M+H]$^+$, 714.95 [M−H]$^−$

Example 24

By using the compound obtained in Example 23 (40 mg, 55.8 mol), in the same manner as in Example 12, (3R,5R,6R)-6-((Z)-2-(2-aminothiazol-4-yl)-2-(((2-carboxypropan-2-yl)oxy)imino)acetamide)-3-((2-((Z)-2-(2-carbamoylhydrazinylidene)-2-(2-chloro-4,5-dihydroxyphenyl)acetamide)ethyl) thio)-7-oxo-4-thia-1-azabicyclo[3.2.0] heptane-3-carboxylic acid (9 mg) was obtained as white solids.

$^1$H-NMR (400 MHz, D$_2$O) δ value: 1.40 (3H, s), 1.44 (3H, s), 2.84-3.13 (2H, m), 3.19 (1H, d, J=12.4 Hz), 3.33-3.52 (1H, m), 3.52-3.65 (1H, m), 4.22-4.35 (1H, m), 5.42-5.53 (1H, m), 5.63-5.70 (1H, m), 6.71 (1H, s), 6.91 (1H, s), 7.02 (1H, s);

MS (ESI): 773.95 [M+H]$^+$, 771.95 [M−H]$^−$

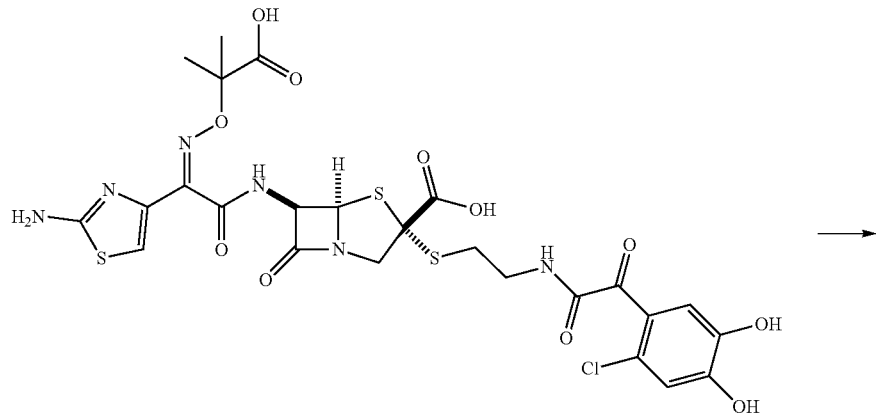

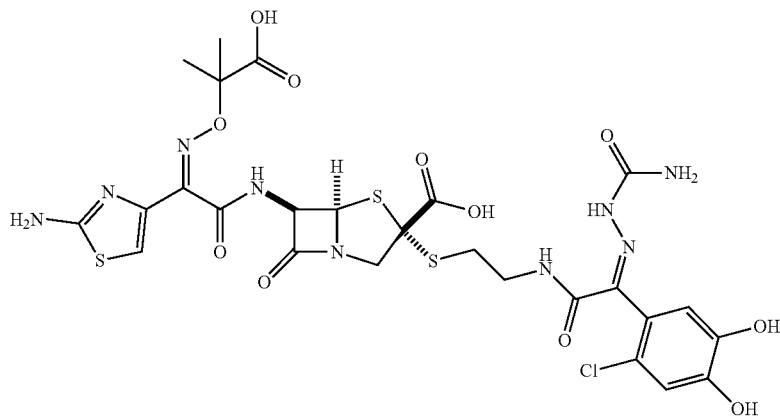 [SMILES: CN/N=C(\C(=O)NCCS[C@]1(C(=O)O)CN2C(=O)[C@@H](NC(=O)/C(=N\OC(C)(C)C(=O)O)c3csc(N)n3)[C@H]2S1)c1ccc(O)c(O)c1Cl]

Example 25
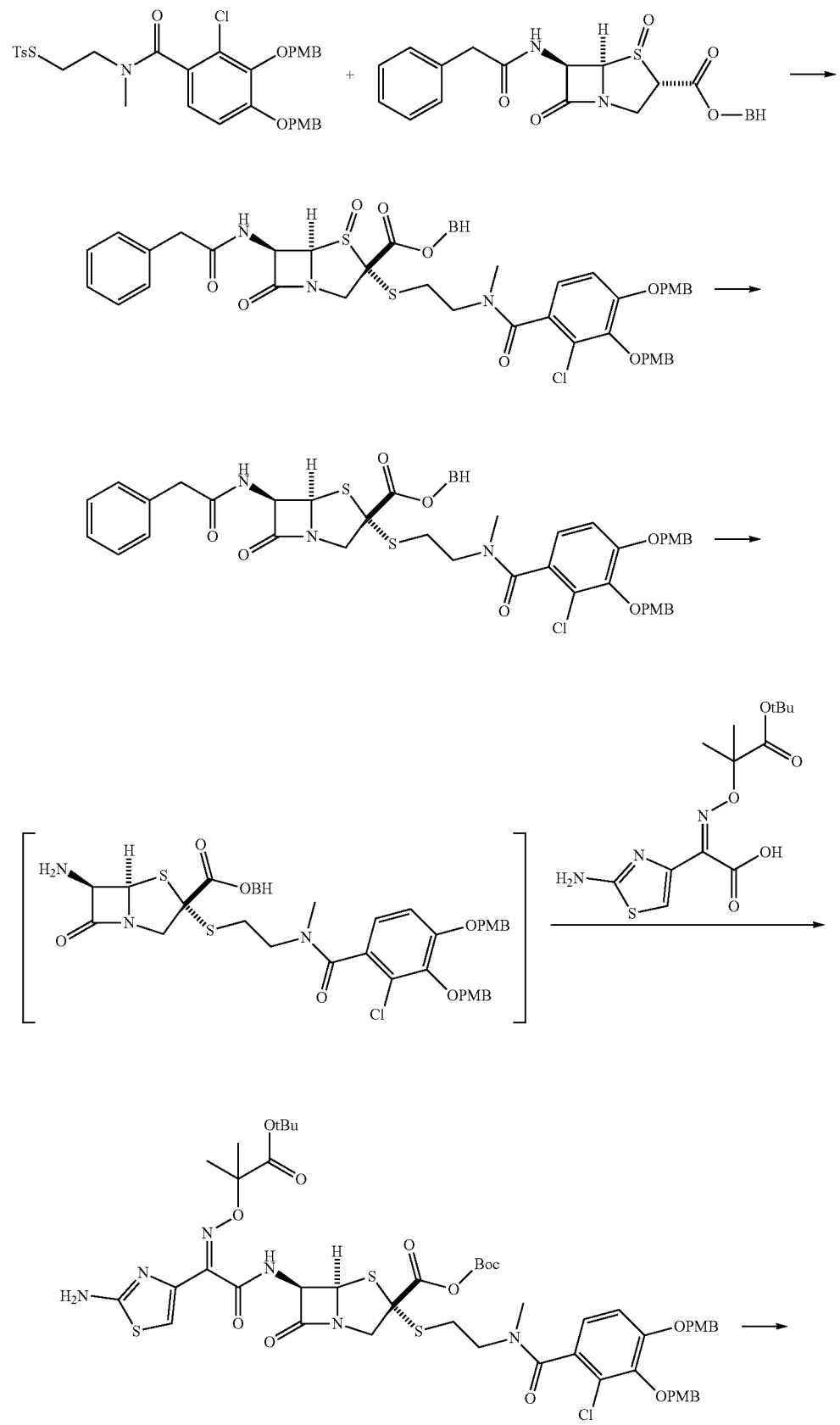

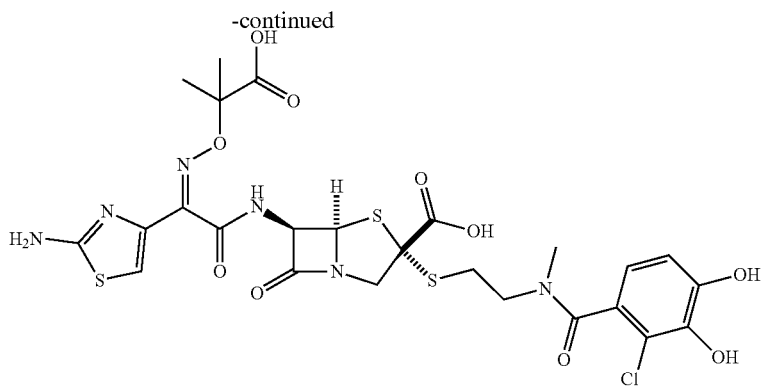

Example 25 (1)

By using S-(2-(2-chloro-3,4-bis((4-methoxybenzyl)oxy)-N-methylbenzamide)ethyl) 4-methylbenzenesulfonothioate (2.54 g, 3.87 mmol) and benzhydryl (3S,5R,6R)-7-oxo-6-(2-phenylacetamide)-4-thia-1-azabicyclo[3.2.0]heptane-3-carboxylate 4-oxide (1.80 g, 3.68 mmol), in the same manner as in Example 1 (1), a target substance (3.39 g) was obtained as white solids.

Example 25 (2)

By using the compound (3.39 g, 3.43 mmol) obtained in Example 25 (1), a target substance (1.70 g) was obtained as light yellow solids in the same manner as in Example 1 (2).

$^1$H-NMR (400 MHz, CDCl$_3$) δ value: 2.66 (3H, s), 2.78-2.91 (2H, m), 3.26 (1H, d, J=12.8 Hz), 3.41-3.56 (2H, m), 3.79 (3H, s), 3.82 (3H, s), 4.59 (1H, d, J=12.8 Hz), 4.85-5.12 (4H, m), 5.43 (1H, d, J=4.0 Hz), 5.66 (1H, dd, J=8.8, 4.0 Hz), 6.20-6.38 (2H, m), 6.65-7.00 (7H, m), 7.11-7.47 (19H, m)

Example 25 (3)

By using the compound (623 mg, 641 mol) obtained in Example 25 (2), in the same manner as in Example 1 (3), benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-((2-(2-chloro-3,4-bis((4-methoxybenzyl)oxy)-N-methylbenzamide)ethyl)thio)-7-oxo-4-thia-1-azabicyclo[3.2.0]heptane-3-carboxylate (370 mg) was obtained as light yellow solids.

$^1$H-NMR (400 MHz, CDCl$_3$) δ value: 1.35 (9H, s), 1.52 (3H, s), 1.53 (3H, s), 2.65 (3H, s), 2.79-3.21 (4H, m), 3.36 (1H, d, J=12.8 Hz), 3.87-3.96 (6H, m), 4.58 (1H, d, J=12.8 Hz), 4.90-5.10 (4H, m), 5.35-5.56 (1H, m), 5.78-5.90 (1H, m), 6.07 (2H, s), 6.79-6.96 (10H, m), 7.24-7.40 (13H, m)

Example 25 (4)

By using the compound (370 mg, 317 mol) obtained in Example 25 (3), in the same manner as in Example 1 (4), (3R,5R,6R)-6-((Z)-2-(2-aminothiazol-4-yl)-2-(((2-carboxypropan-2-yl)oxy)imino)acetamide)-3-((2-(2-chloro-3,4-dihydroxy-N-methylbenzamide)ethyl)thio)-7-oxo-4-thia-1-azabicyclo[3.2.0]heptane-3-carboxylic acid (58 mg) was obtained as white solids.

$^1$H-NMR (400 MHz, D$_2$O) δ value: 1.47 (3H, s), 1.50 (3H, s), 2.81-3.18 (6H, m), 3.29-3.89 (2H, m), 4.25-4.47 (1H, m), 5.25-5.78 (2H, m), 6.79-7.05 (3H, m);
MS (ESI): 703.05 [M+H]$^+$, 701.00 [M−H]$^-$

Example 26

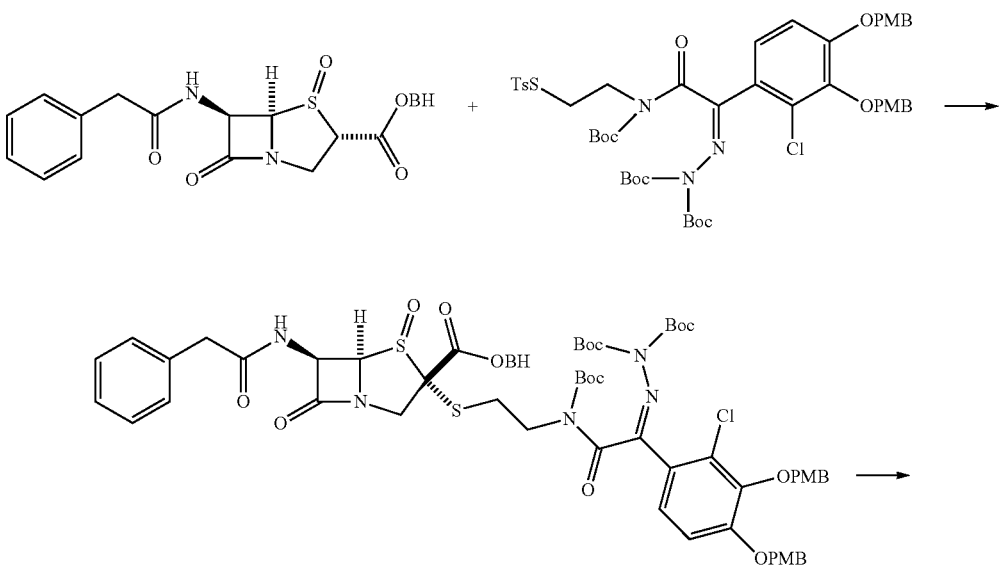

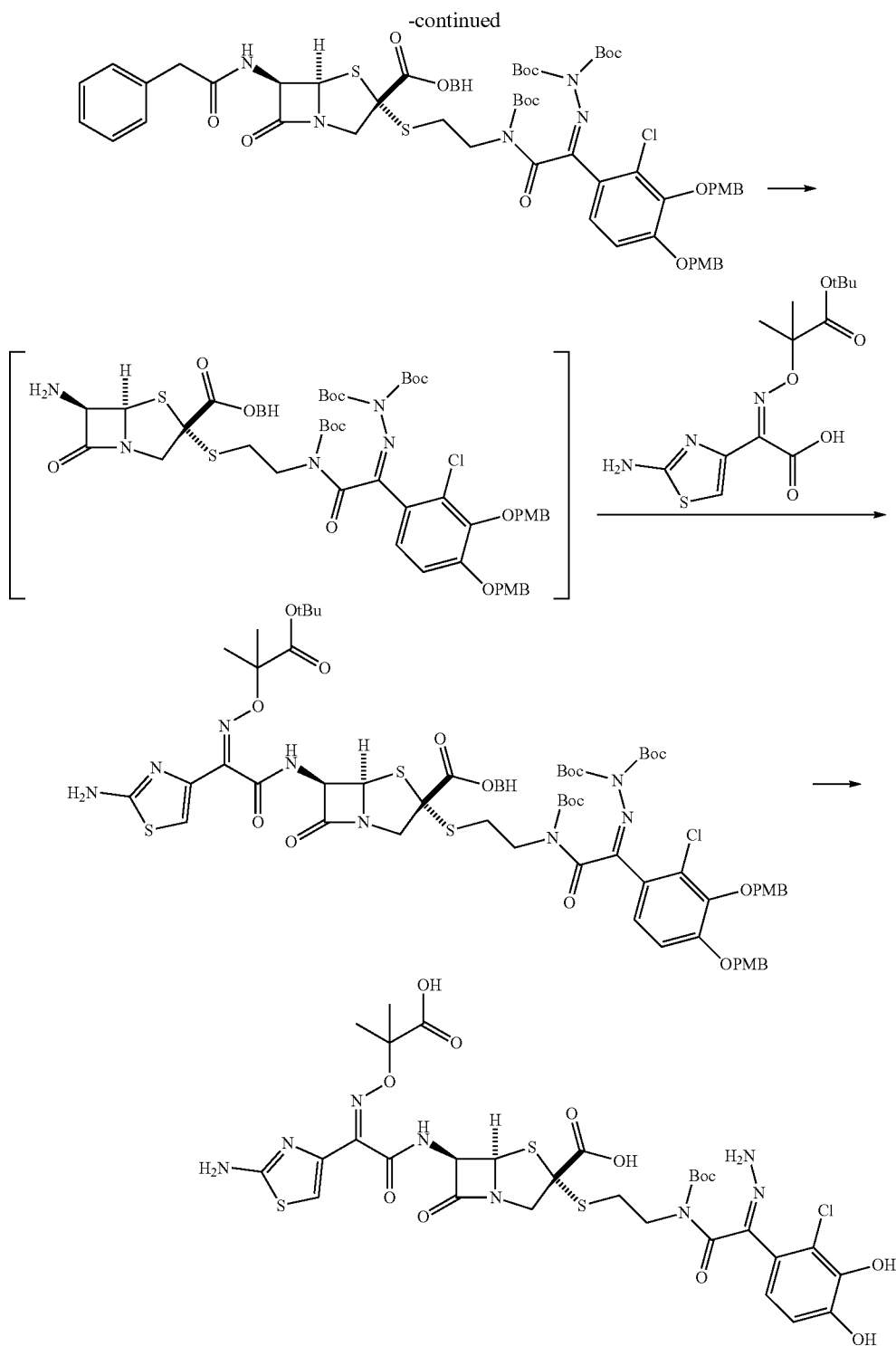

Example 26 (1)

By using benzhydryl (3 S,5R,6R)-7-oxo-6-(2-phenylacetamide)-4-thia-1-azabicyclo[3.2.0]heptane-3-carboxylate 4-oxide (450 mg, 921 mol) and di-tert-butyl (Z)-2-(2((tert-butoxycarbonyl)(2-(tosylthio)ethyl)amino)-1-(2-chloro-3,4-bis((4-methoxybenz yl)oxy)phenyl)-2-oxoethylidene)hydrazine-1,1-dicarboxylate (983 mg, 998 mol), in the same manner as in Example 8 (1), a target substance (1.12 g) was obtained as a colorless oily substance.

Example 26 (2)

By using the compound (1.12 g, 852 mol) obtained in Example 26 (1), a target substance (864 mg) was obtained as a colorless oily substance in the same manner as in Example 8 (2).

¹H-NMR (400 MHz, CDCl₃) δ value: 1.30 (9H, s), 1.48 (18H, s), 2.81-2.97 (2H, m), 3.26 (1H, d, J=13.2 Hz), 3.44-3.50 (2H, m), 3.78 (3H, s), 3.84 (3H, s), 4.56 (1H, d, J=13.2 Hz), 4.91 (2H, s), 5.11 (2H, s), 5.48 (1H, d, J=4.0 Hz), 5.65 (1H, dd, J=9.2, 4.0 Hz), 6.39 (1H, d, J=9.2 Hz), 6.77-6.84 (3H, m), 6.89-7.00 (4H, m), 7.15-7.43 (20H, m), 8.09 (1H, d, J=9.2 Hz)

Example 26 (3)

By using the compound (780 mg, 600 mol) obtained in Example 26 (2), in the same manner as in Example 8 (3), di-tert-butyl (Z)-2-(2-((2-(((3R,5R,6R)-6-((Z)-2-(2-aminothiazol-4-yl)-2-(((1-(tert-butoxy)-2-methyl-1-oxo propane-2-yl)oxy)imino)acetamide)-3-((benzhydryloxy)carbonyl)-7-oxo-4-thia-1-azabicyclo[30.2.0]heptan-3-yl)thio) ethyl)(tert-butoxycarbonyl)amino)-1-(2-chloro-3,4-bis((4-methoxybenzyl)oxy)phenyl)-2-oxoethylidene)hydrazine-1,1-dicarboxylate (317 mg) was obtained as light yellow solids.

¹H-NMR (400 MHz, CDCl₃) δ value: 1.30 (9H, s), 1.35 (9H, s), 1.49 (18H, s), 1.51 (3H, s), 1.52 (3H, s), 2.83-2.97 (2H, m), 3.35 (1H, d, J=12.8 Hz), 3.75-3.86 (8H, m), 4.58 (1H, d, J=12.8 Hz), 4.91 (2H, s), 5.11 (2H, s), 5.58 (1H, d, J=4.0 Hz), 5.85 (1H, dd, J=9.2, 4.0 Hz), 6.24 (2H, s), 6.77-7.02 (8H, m), 7.21-7.53 (14H, m), 8.07 (1H, d, J=9.2 Hz)

Example 26 (4)

By using the compound (317 mg, 0.21 mmol) obtained in Example 26 (3), in the same manner as in Example 8 (4), (3R,5R,6R)-6-((Z)-2-(2-aminothiazol-4-yl)-2-(((2-carboxypropan-2-yl)oxy)imino)acetamide)-3-((2-((Z)-2-(2-chloro-3,4-dihydroxyphenyl)-2-hydrazinylideneacetamide)ethyl)thio)-7-oxo-4-thia-1-azabicyclo[3.2.0]heptane-3-carboxylic acid (70 mg) was obtained as light yellow solids.

¹H-NMR (400 MHz, D₂O) δ value: 1.48 (3H, s), 1.50 (3H, s), 2.88-3.05 (2H, m), 3.18-3.31 (1H, m), 3.43-3.66 (2H, m), 4.30-4.40 (1H, m), 5.31-5.57 (1H, m), 5.72-5.78 (1H, m), 6.67-7.03 (3H, m);
MS (ESI): 731.05 [M+H]⁺, 729.10 [M−H]⁻

Example 27

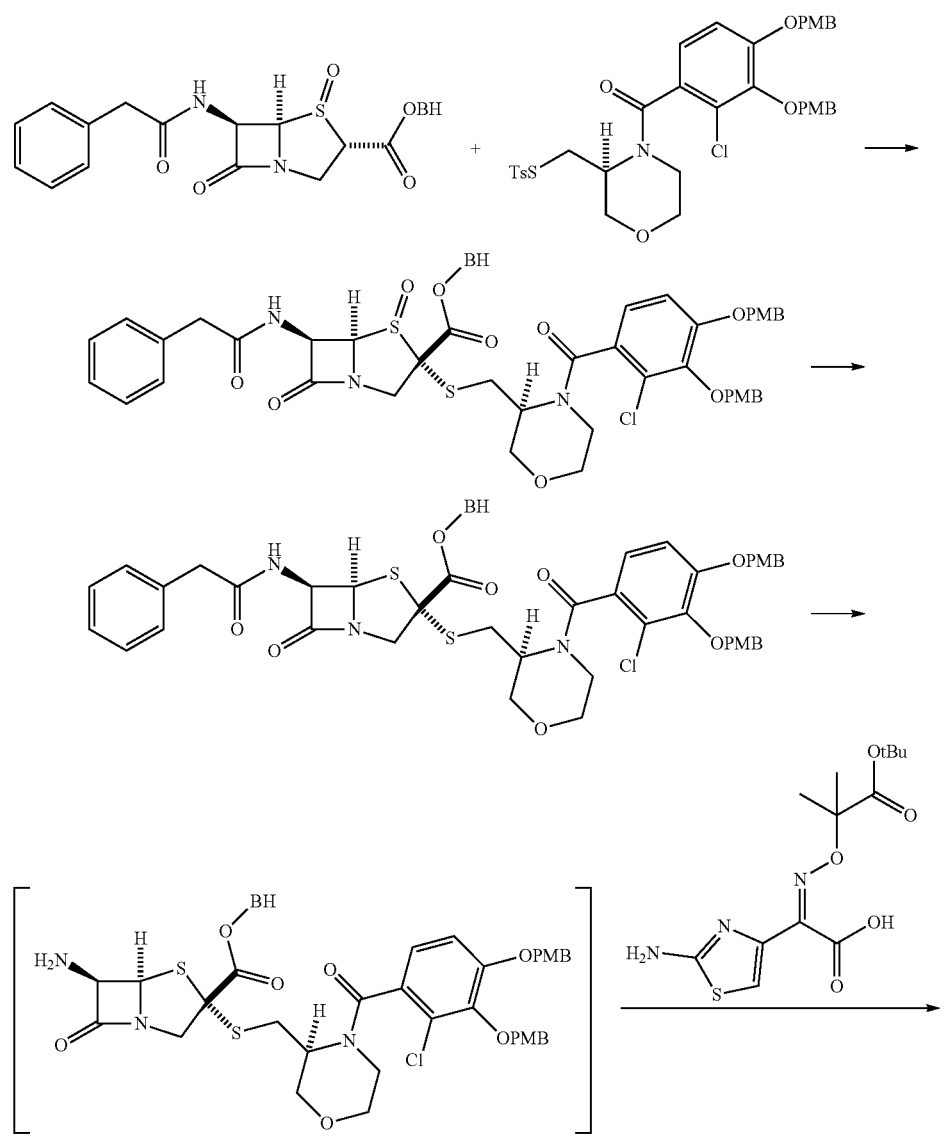

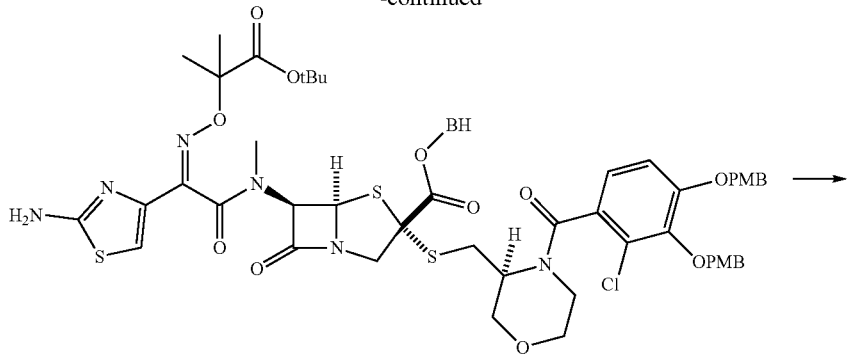

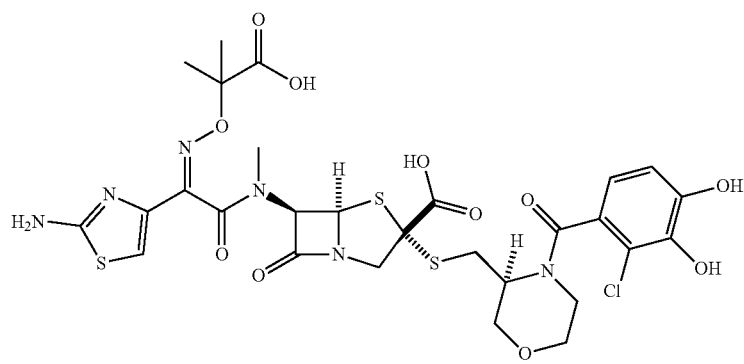 [SMILES: CN(C(=O)/C(=N\OC(C)(C)C(=O)O)c1csc(N)n1)[C@@H]1C(=O)N2C[C@](SC[C@@H]3COCCN3C(=O)c3ccc(O)c(O)c3Cl)(C(=O)O)S[C@H]12]

Example 27 (1)

By using (S)—S-((4-(2-chloro-3,4-bis((4-methoxybenzyl)oxy)benzoyl)morpholin-3-yl)methyl) 4-methylbenzenesulfonothioate (7.24 g, 10.4 mmol) and benzhydryl (3 S,5R, 6R)-7-oxo-6-(2-phenylacetamide)-4-thia-1-azabicyclo[3.2.0]heptane-3-carboxylate 4-oxide (4.83 g, 9.88 mmol), a target substance (9.85 g) was obtained as white solids in the same manner as in Example 1 (1).

Example 27 (2)

By using the compound (9.85 g, 9.56 mmol) obtained in Example 27 (1), a target substance (5.15 g) was obtained as yellow solids in the same manner as in Example 1 (2).

$^1$H-NMR (400 MHz, CDCl$_3$) δ value: 2.64-2.76 (1H, m), 2.84-3.36 (4H, m), 3.38-3.74 (5H, m), 3.74-3.94 (7H, m), 4.34-4.70 (2H, m), 4.92-5.12 (4H, m), 5.26-5.49 (1H, m), 5.60-5.70 (1H, m), 6.26-6.43 (1H, m), 6.70-7.00 (8H, m), 7.16-7.46 (18H, m)

Example 27 (3)

By using the compound (800 mg, 788 mol) obtained in Example 27 (2), in the same manner as in Example 1 (3), benzhydryl (3R,5R,6R)-6-((Z)-2-(2-aminothiazol-4-yl)-2-(((1-(tert-butoxy)-2-methyl-1-oxopropan-2-yl)oxy)imino)acetamide)-3-((((S)-4-(2-chloro-3,4-bis((4-methoxybenzyl)oxy)benzoyl)morpholin-3-yl)methyl)thio)-7-oxo-4-thia-1-azabicyclo[3.2.0]heptane-3-carboxylate (404 mg) was obtained as light yellow solids.

$^1$H-NMR (400 MHz, CDCl$_3$) δ value: 1.35 (9H, s), 1.51-1.54 (6H, m), 2.66-2.74 (1H, m), 2.83-3.34 (4H, m), 3.37-3.70 (4H, m), 3.77-3.85 (6H, m), 4.40 [4.49] (1H, d, J=13.0 Hz), 4.56-4.71 (1H, m), 4.92-5.15 (4H, m), 5.31-5.58 (1H, m), 5.80 [5.85] (1H, dd, J=8.6, 3.8 Hz), 6.18-6.33 (2H, m), 6.71-7.04 (10H, m), 7.22-7.41 (12H, m), 7.56 [7.61] (1H, d, J=8.6 Hz)

Example 27 (4)

By using the compound (404 mg, 334 μmol) obtained in Example 27 (3), in the same manner as in Example 1 (4), (3R,5R,6R)-6-((Z)-2-(2-aminothiazol-4-yl)-2-(((2-carboxypropan-2-yl)oxy)imino)acetamide)-3-((((S)-4-(2-chloro-3,4-dihydroxybenzoyl)morpholin-3-yl)methyl)thio)-7-oxo-4-thia-1-azabicyclo[3.2.0]heptane-3-carboxylic acid (102 mg) was obtained as light yellow solids.

$^1$H-NMR (400 MHz, D$_2$O) δ value: 1.45-1.52 (6H, m), 3.00-4.40 (1H, m), 5.43-5.58 (1H, m), 5.69-5.77 (1H, m), 6.82-7.06 (3H, m);

MS (ESI): 745.05 [M+H]+, 743.10 [M−H]$^−$

Example 28

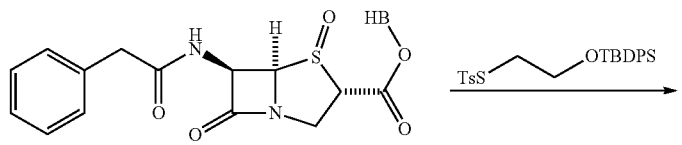

143 144
-continued
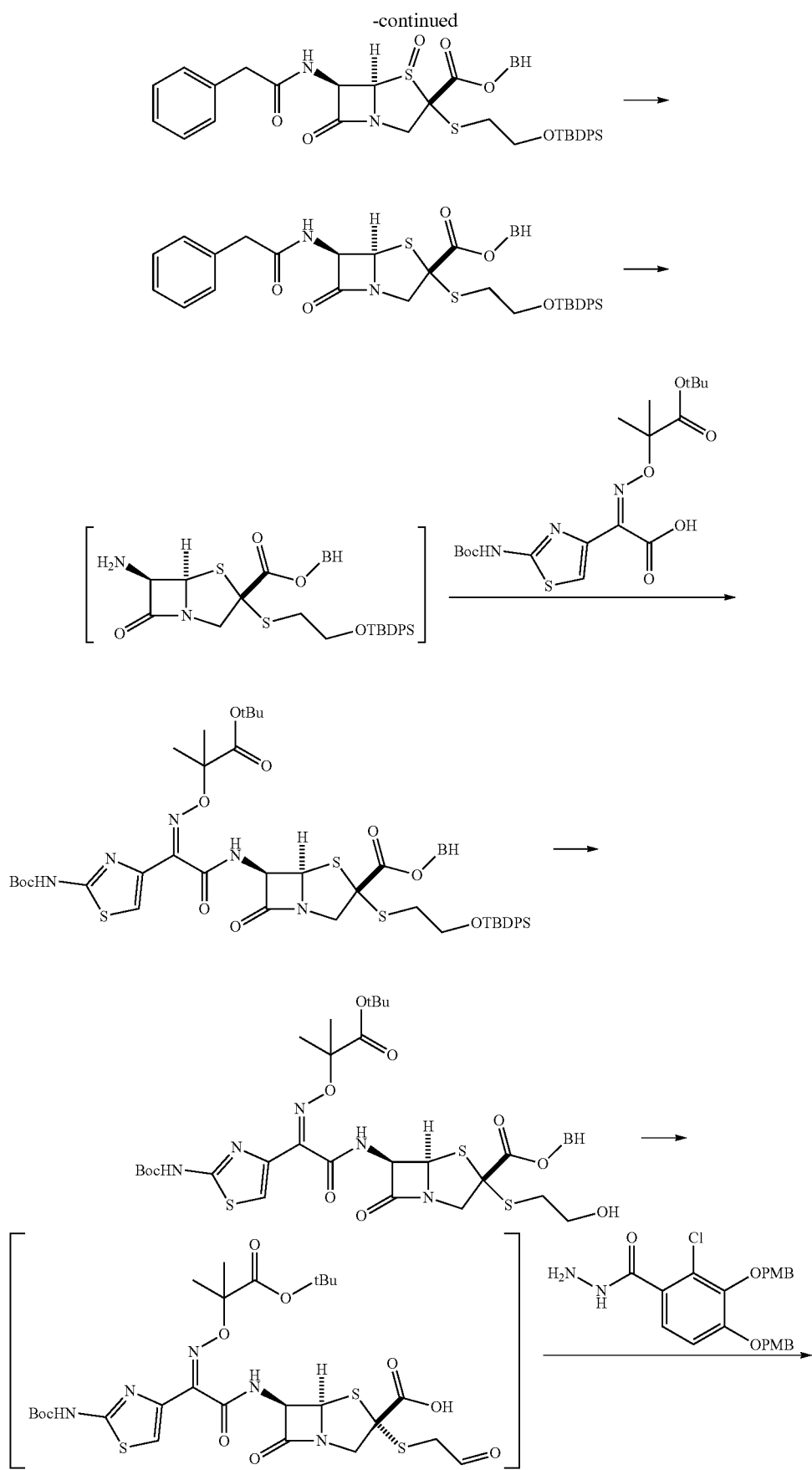

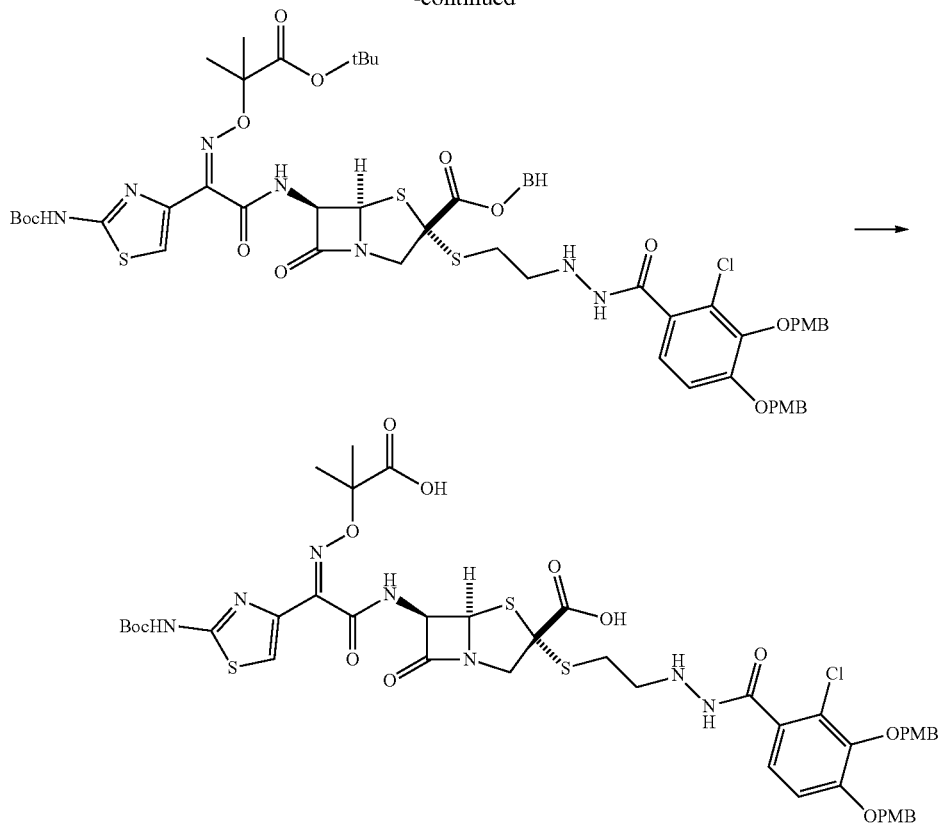

Example 28 (1)

Benzhydryl (3S,5R,6R)-7-oxo-6-(2-phenylacetamide)-4-thia-1-azabicyclo[30.2.0]heptane-3-carboxylate 4-oxide (9.18 g, 18.8 mmol) and dichloromethane (70 mL) were added to S-(2-((tert-butyldiphenyl silyl)oxy)ethyl) 4-methylbenzenesulfonothioate (10.6 g, 22.5 mmol), and the mixture was stirred under ice cooling. At the same temperature, a solution of DBU (2.86 g, 18.8 mmol) in dichloromethane (20 mL) was added dropwise to the reaction mixture. The reaction mixture was stirred at the same temperature for 40 minutes. The reaction mixture was then added to a mixture of chloroform (100 mL), water (100 mL), and 1 mol/L hydrochloric acid (10 mL). The organic layer was separated from the reaction mixture and washed sequentially with a saturated aqueous sodium hydrogen carbonate solution and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=30:70], thereby obtaining a target substance (14.4 g) as a white foamy substance.

Example 28 (2)

Ethyl acetate (3 mL) and NMP (15 mL) were added to the compound (2.41 g, 3.0 mmol) obtained in Example 28 (1), and the mixture was stirred. The reaction mixture was cooled to −20° C., and a solution of phosphorus tribromide (6.50 g, 24.0 mmol) in ethyl acetate (2 mL) was added dropwise to the reaction mixture at the same temperature. The reaction mixture was stirred at a temperature of −20° C. to −5° C. for 3 hours. Then, the reaction mixture was added to an ice-cooled aqueous potassium hydrogen carbonate solution (9.01 g of potassium hydrogen carbonate/40 mL of water). Ethyl acetate (50 mL) was added to the reaction mixture, and the organic layer was separated. The organic layer was washed sequentially with water and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=50:50], thereby obtaining a target substance (1.63 g) as white solids.

$^1$H-NMR (400 MHz, CDCl$_3$) δ value: 1.04 (9H, s), 2.68-2.80 (2H, m), 3.13 (1H, dd, J=12.8, 0.8 Hz), 3.50 (2H, d, J=3.6 Hz), 3.70 (2H, t, J=6.4 Hz), 4.50 (1H, d, J=13.2 Hz), 5.31 (1H, d, J=4.0 Hz), 5.63 (1H, dd, J=9.2, 4.0 Hz), 6.37 (1H, d, J=9.2 Hz), 6.75 (1H, s), 7.16-7.46 (20H, m), 7.59-7.66 (5H, m)

Example 28 (3)

Dichloromethane (64 mL) was added to the compound (6.40 g, 8.13 mmol) obtained in Example 28 (2), and the mixture was cooled to −30° C. At the same temperature, N,N-dimethylaniline (3.45 g, 28.5 mmol) and phosphorus pentachloride (2.54 g, 12.2 mmol) were sequentially added to the reaction mixture, and the mixture was stirred at a temperature equal to or lower than −30° C. for 40 minutes. Then, the reaction mixture was then added to ice-cooled methanol (32 mL) and stirred for 15 minutes. Ethyl acetate (300 mL) and an aqueous sodium hydrogen carbonate solution (8.88 g of sodium hydrogen carbonate/150 mL of water) were added to the reaction mixture, and the organic layer was separated. The organic layer was washed sequentially with water and a saturated aqueous sodium chloride solution and then dehydrated and dried over anhydrous sodium sulfate, and solids were filtered. (Z)-2-(((1-(tert-butoxy)-2-methyl-1-oxopropan-2-yl)oxy)imino)-2-(2-tert-butoxycarbonyl)amino)thiazol-4-yl)acetic acid (3.84 g, 8.94 mmol), HATU (3.40 g, 8.94 mmol), 2,6-lutidine (1.92 g, 17.9 mmol), and DMF (64 mL) were added to the filtrate. The reaction mixture was stirred at room temperature under reduced pressure until it became a solution. Ethyl acetate (300 mL) and water (200 mL) were added to the reaction mixture, and the organic layer was separated. Water (200 mL) and a saturated aqueous sodium hydrogen carbonate solution were added to the organic layer so as to adjust the pH to 7.1. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=30: 70], thereby obtaining benzhydryl (3R,5R,6R)-6-((Z)-2-(((1-(tert-butoxy)-2-methyl-1-oxopropan-2-yl)oxy)imino)-2-(2-((tert-but oxycarbonyl)amino)thiazol-4-yl)acetamide)-3-((2-((tert-butyldiphenylsilyl)oxy)ethyl)thio)-7-oxo-4-thia-1-azabicyclo[3.2.0]heptane-3-carboxylate (2.79 g) as light yellow solids.

$^1$H-NMR (400 MHz, CDCl$_3$) δ value: 1.03 (6H, s), 1.04 (6H, s), 1.34 (9H, s), 1.52 (9H, s), 2.54-2.85 (2H, m), 3.28 (1H, ddd, J=12.7, 6.4, 1.0 Hz), 3.55 (1H, t, J=6.0 Hz), 3.68 (1H, t, J=6.2 Hz), 4.51 (1H, t, J=13.2 Hz), 5.36-5.46 (1H, m), 5.87 (1H, dt, J=9.0, 4.0 Hz), 6.78 (1H, d, J=10.8 Hz), 7.18-7.45 (18H, m), 7.56-7.65 (6H, m), 7.84 (1H, d, J=8.8 Hz), 8.16 (1H, s)

Example 28 (4)

THF (14.2 mL) was added to the compound (2.56 g, 2.37 mmol) obtained in Example 28 (3), and the mixture was stirred under ice cooling for 6 hours. Acetic acid (1.42 g, 23.7 mmol) and a solution of 1 mol/L tetrabutylammonium fluoride in THF (14.2 mL, 14.2 mmol) were added to the reaction mixture at the same temperature. The reaction mixture was stirred at the same temperature for 6 hours. Ethyl acetate (60 mL) and water (60 mL) were added to the reaction mixture, and the pH was adjusted to 6.5 by adding a saturated aqueous sodium hydrogen carbonate solution. The organic layer was separated and washed with a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=50:50], thereby obtaining benzhydryl (3R,5R,6R)-6-((Z)-2-(((1-(tert-butoxy))-2-methyl-1-oxopropan-2-yl)oxy)imino)-2-(2-((tert-but oxycarbonyl)amino)thiazol-4-yl)acetamide)-3-((2-hydroxyethyl)thio)-7-oxo-4-thia-1-azabicyclo[3.2.0]heptane-3-carboxylate (1.44 g) as light yellow solids.

$^1$H-NMR (400 MHz, CDCl$_3$) δ value: 1.35 (9H, s), 1.53 (9H, s), 1.54 (3H, s), 1.55 (3H, s), 2.55-2.90 (2H, m), 3.29-3.38 (1H, m), 3.49-3.63 (2H, m), 4.56 (1H, dd, J=12.8, 6.8 Hz), 5.51 (1H, dd, J=6.0, 4.0 Hz), 5.87 (1H, dd, J=8.6, 3.0 Hz), 6.82 (1H, s), 7.24-7.42 (12H, m), 7.87-7.92 (1H, m), 8.33 (1H, s)

Example 28 (5)

Ethyl acetate (3.6 mL) was added to the compound (300 mg, 356 μmol) obtained in Example 28 (4), and the mixture was stirred under ice cooling. At the same temperature, sodium hydrogen carbonate (150 mg, 1.78 mmol) and Dess-Martin periodinane (302 mg, 713 μmol) were sequentially added to the reaction mixture. The reaction mixture was stirred at the same temperature for 2 hours and 30 minutes. Ethyl acetate, water, and a 1 mol/L aqueous sodium thiosulfate solution were sequentially added to the reaction mixture, and the organic layer was separated. The organic layer was washed with a saturated aqueous sodium chloride solution. The organic layer was dehydrated and dried over anhydrous sodium sulfate, and then the solvent was distilled away under reduced pressure. Dichloromethane (3.6 mL) and 2-chloro-3,4-bis ((4-methoxybenzyl) oxy) benzohydrazide (158 mg, 356 μmol) were added to the residue, and the mixture was stirred for 1 hour under ice cooling. At the same temperature, p-toluenesulfonic acid monohydrate (95 mg, 499 μmol) and a borane-2-picoline complex (56 mg, 445 μmol) were sequentially added to the reaction mixture, and the mixture was stirred for 1 hour. Ethyl acetate and water were added to the reaction mixture, and a saturated aqueous sodium hydrogen carbonate solution was added thereto so as to adjust the pH to 5.5. The organic layer was separated and washed with a saturated aqueous sodium chloride solution. The organic layer was dehydrated and dried over anhydrous sodium sulfate, and then the solvent was distilled away under reduced pressure, thereby obtaining benzhydryl (3R,5R,6R)-6-((Z)-2-(((1-(tert-butoxy)-2-methyl-1-oxopropan-2-yl)oxy)imino)-2-(2-((tert-but oxycarbonyl)amino)thiazol-4-yl)acetamide)-3-((2-(2-(2-chloro-3,4-bis((4-methoxybenzyl)oxy) benzoyl)hydradienyl)ethyl)thio)-7-oxo-4-thia-1-azabicyclo[3.2.0]heptane-3-carboxylate as a light yellow oily substance.

Example 28 (6)

Dichloromethane (7 mL) was added to the light yellow oily substance obtained in Example 28 (5), and the mixture was cooled to −20° C. At the same temperature, anisole (1.6 mL) and aluminum chloride (480 mg, 3.6 mmol) were sequentially added to the reaction mixture. The reaction mixture was stirred at the same temperature for 30 minutes. Aluminum chloride (240 mg, 1.8 mmol) was added to the reaction mixture at the same temperature. The reaction mixture was stirred at the same temperature for 1 hour. The reaction mixture was added to a mixture of acetonitrile (20 mL), water (20 mL), and trisodium citrate dihydrate (2.4 g, 8.1 mmol) and washed sequentially with acetonitrile (1 mL) and water (1 mL). A saturated aqueous sodium hydrogen carbonate solution was added to the reaction mixture so as to adjust the pH to 5.2, and then the aqueous layer was separated. The aqueous layer was concentrated under reduced pressure, and the residue was purified twice by medium-pressure reverse-phase silica gel column chromatography [eluent; water:acetonitrile=100:0→80:20]. The eluent containing a target substance was lyophilized, thereby obtaining (3R,5R,6R)-6-((Z)-2-(2-aminothiazol-4-yl)-2-(((2-carboxypropan-2-yl)oxy)imino)acetamide)-3-((2-(2-(2-chloro-3,4-dihydroxybenzoyl)hydradienyl)ethyl)thio)-7-oxo-4-thia-1-azabicyclo[3.2.0]heptane-3-carboxylic acid (14 mg) as light yellow solids.

$^1$H-NMR (400 MHz, D$_2$O) δ value: 1.44 (3H, s), 1.46 (3H, s), 3.01 (2H, t, J=7.2 Hz), 3.22 (2H, dt, J=6.9, 2.6 Hz), 3.31 (1H, dd, J=12.4, 1.2 Hz), 4.41 (1H, d, J=12.4 Hz), 5.56 (1H, d, J=3.6 Hz), 5.72 (1H, d, J=4.0 Hz), 6.89 (1H, d, J=8.0 Hz), 6.98 (1H, s), 7.00 (1H, d, J=8.4 Hz);

MS (ESI): 704.05 [M+H]$^+$, 702.05 [M−H]$^−$

Test Example 1 Antibacterial Activity Evaluation Test (MIC)

The minimum inhibitory concentration (MIC) was measured according to the Clinical and Laboratory Standards Institute (CLSI) standard method by using the following broth microdilution method.

As bacteria, a *Pseudomonas aeruginosa* strain ATCC 27853, a *Pseudomonas aeruginosa* AmpC derepression mutant strain S-3028, and a *Pseudomonas aeruginosa* IMP-1-producing strain S-2838 were used.

Among the above bacteria, the AmpC derepression mutant strain S-3028 exhibits resistance to antibacterial agents including cephalosporin by the overexpression of class C lactamase AmpC on chromosome, and the IMP-1-producing strain exhibits resistance to antibacterial drugs including carbapenem by the expression of class B lactamase IMP-1.

The *Pseudomonas aeruginosa* AmpC-derepression mutant strain S-3028 or the *Pseudomonas aeruginosa* IMP-1-producing strain S-2838 was cultured on a Mueller Hinton agar medium overnight, thereby preparing test bacterial cells. The obtained test bacterial cells were scraped off, suspended to yield 0.5 McFarland equivalence, and diluted 10-fold to obtain an inoculum. A cation-adjusted Mueller Hinton medium containing a test compound was inoculated with 0.0005 mL of the inoculum, and the cells were cultured at 35° C. for 16 to 20 hours. The minimum drug concentration at which the growth of bacteria was not visually observed was defined as MIC.

The MIC of the *Pseudomonas aeruginosa* ATCC strain 27853 was measured in the same manner as described above by using a cation-adjusted Mueller-Hinton medium supplemented with 20 M of apotransferrin as a final concentration.

The results are shown in Tables 1 and 2.

TABLE 1

| Example No. | MIC (µg/mL) | | |
| --- | --- | --- | --- |
| | *Pseudomonas aeruginosa* strain ATCC 27853 | *Pseudomonas aeruginosa* strain S-3028 | *Pseudomonas aeruginosa* strain S-2838 |
| 1 | 0.125 | 128 | 2 |
| 2 | ≤0.0625 | 4 | 16 |
| 3 | ≤0.0625 | 0.5 | 1 |
| 4 | ≤0.0625 | 8 | 32 |
| 5 | ≤0.0625 | 8 | 16 |
| 6 | 0.25 | 4 | 2 |
| 7 | 0.125 | 16 | 4 |
| 8 | ≤0.0625 | 2 | 0.25 |
| 10 | 1 | >128 | 32 |
| 11 | ≤0.0625 | 1 | 2 |
| 12 | ≤0.0625 | 16 | 4 |
| 13 | ≤0.0625 | 16 | 8 |
| 14 | 0.25 | 32 | 1 |
| 16 | 0.5 | 16 | 8 |
| 17 | ≤0.0625 | 8 | 8 |
| 18 | 0.125 | 2 | 4 |
| 19 | 0.125 | 1 | 1 |
| 20 | 0.5 | 4 | 4 |
| 22 | 0.125 | 8 | 2 |

TABLE 2

| Example No. | MIC (µg/mL) | | |
| --- | --- | --- | --- |
| | *Pseudomonas aeruginosa* strain ATCC 27853 | *Pseudomonas aeruginosa* strain S-3028 | *Pseudomonas aeruginosa* strain S-2838 |
| 23 | 1 | 2 | 4 |
| 24 | 0.5 | 8 | 4 |
| 25 | 1 | 2 | 1 |
| 26 | 0.5 | 8 | 1 |
| 27 | 1 | 0.5 | 0.5 |
| 28 | 1 | 1 | 1 |

The compound represented by General Formula [1] or a salt thereof has a strong antibacterial activity against Gram-negative bacteria such as *Pseudomonas aeruginosa* and drug-resistant Gram-negative bacteria including multidrug-resistant *Pseudomonas aeruginosa*. Therefore, the compound or a salt thereof is useful as an antibacterial agent.

What is claimed is:

1. A compound represented by General Formula [1] or a salt thereof,

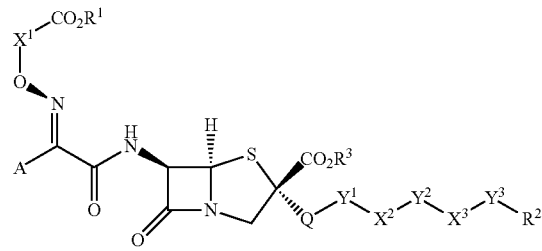

[1]

General Formula [1]
in the formula, $R^1$ represents a hydrogen atom or a carboxyl protecting group;
$R^2$ represents an aryl group which may be substituted or a heterocyclic group which may be substituted;
$R^3$ represents a hydrogen atom or a carboxyl protecting group;
$X^1$ represents a $C_{1-6}$ alkylene group which may be substituted, a $C_{2-6}$ alkenylene group which may be substituted, a $C_{2-6}$ alkynylene group which may be substituted, a divalent cyclic hydrocarbon group which may be substituted, or a divalent monocyclic saturated heterocyclic group which may be substituted;
A represents a heterocyclic group which may be substituted;
Q represents a thio group;
$Y^1$ represents a $C_{1-6}$ alkylene group which may be substituted, a $C_{2-6}$ alkenylene group which may be substituted, a $C_{2-6}$ alkynylene group which may be substituted, a group represented by Formula —N=CH—CH=N—, or a bond;
$X^2$ represents a group represented by General Formula —NR$^4$— (where, $R^4$ represents a hydrogen atom, a $C_{1-6}$ alkyl group which may be substituted, or a hydroxyl group which may be protected), a group represented by General Formula —N$^+$R$^5$R$^6$— (where, $R^5$ and $R^6$ are the same as or different from each other and each represent a $C_{1-6}$ alkyl group which may be substituted, or in combination represent a $C_{2-6}$ alkylene group which may be substituted or a $C_{2-6}$ alkenylene group which may be substituted), a group represented by General Formula —NR$^7$—C(=O)—NR$^8$— (where, R$^7$ and R$^8$ are the same as or different from each other and each represent a hydrogen atom, a C$_{1-6}$ alkyl group which may be substituted, or a hydroxyl group which may be protected), a divalent cyclic amino group which may be substituted, or a bond;

Y$^2$ represents a C$_{1-6}$ alkylene group which may be substituted, a C$_{2-6}$ alkenylene group which may be substituted, a C$_{2-6}$ alkynylene group which may be substituted, or a bond;

X$^3$ represents a group represented by General Formula —NR$^9$— (where, R$^9$ represents a hydrogen atom, a C$_{1-6}$ alkyl group which may be substituted or a hydroxyl group which may be protected) or a bond; and Y$^3$ represents a group represented by —C(=O)— or —C(=O)—C(=O)—, a group represented by General Formula —C(=O)—C(=NR$^{10}$)— (where, R$^{10}$ represents a hydrogen atom, a C$_{1-6}$ alkyl group which may be substituted, a C$_{1-6}$ alkoxy group which may be substituted, a C$_{1-6}$ alkylamino group which may be substituted, a di(C$_{1-6}$ alkyl)amino group which may be substituted, a cyclic amino group which may be substituted, an amino group which may be substituted, an amino group which may be protected, or a hydroxyl group which may be protected), or a divalent heterocyclic group which may be substituted.

2. The compound or a salt thereof according to claim 1, wherein R$^2$ represents an aryl group which may be substituted.

3. The compound or a salt thereof according to claim 1, wherein A represents a monocyclic heterocyclic group which may be substituted.

4. The compound or a salt thereof according to claim 1, wherein X$^1$ represents a C$_{1-6}$ alkylene group which may be substituted.

5. The compound or a salt thereof according to claim 1, wherein Y$^1$ represents a C$_{1-6}$ alkylene group which may be substituted, a C$_{2-6}$ alkenylene group which may be substituted, a group represented by Formula —N=CH—CH=N—, or a bond.

6. The compound or a salt thereof according to claim 1, wherein X$^2$ represents a group represented by General Formula —NR$^{4a}$— (where, R$^{4a}$ represents a hydrogen atom), a group represented by General Formula —N$^+$R$^{5a}$R$^{6a}$— (where, R$^{5a}$ and R$^{6a}$ in combination represent a C$_{2-6}$ alkylene group which may be substituted), a group represented by General Formula —NR$^{7a}$—C(=O)—NR$^{8a}$— (where, R$^{7a}$ and R$^{8a}$ are the same as or different from each other and each represent a hydrogen atom or a hydroxyl group which may be protected), a divalent cyclic amino group which may be substituted, or a bond.

7. The compound or a salt thereof according to claim 1, wherein Y$^2$ represents a C$_{1-6}$ alkylene group which may be substituted or a bond.

8. The compound or a salt thereof according to claim 1, wherein X$^3$ represents a group represented by General Formula —NR$^{9a}$— (where, R$^{9a}$ represents a hydrogen atom) or a bond.

9. The compound or a salt thereof according to claim 1, wherein Y$^3$ represents a group represented by Formula —C(=O)— or —C(=O)—C(=O)—, a group represented by General Formula —C(=O)—C(=NR$^{10a}$)— (where, R$^{10a}$ represents a C$_{1-6}$ alkylamino group which may be substituted, a cyclic amino group which may be substituted, an amino group which may be substituted, or a hydroxyl group which may be protected), or a divalent heterocyclic group which may be substituted.

10. The compound or a salt thereof according to claim 1, wherein R$^3$ represents a hydrogen atom.

11. The compound or a salt thereof according to claim 1, wherein R$^1$ represents a hydrogen atom.

12. The compound or a salt thereof according to claim 1, wherein R$^2$ represents a phenyl group which may be substituted;

A represents a monocyclic nitrogen and sulfur-containing heterocyclic group which may be substituted;

X$^1$ represents a C$_{1-3}$ alkylene group which may be substituted;

Y$^1$ represents a C$_{1-6}$ alkylene group which may be substituted a C$_{2-6}$ alkenylene group which may be substituted, or a bond;

X$^2$ represents a group represented by General Formula —NR$^{4a}$— (where, R$^{4a}$ represents a hydrogen atom), a group represented by General Formula —N$^+$R$^{5a}$R$^{6a}$— (where, R$^{5a}$ and R$^{6a}$ in combination represent a C$_{2-6}$ alkylene group which may be substituted), a divalent cyclic amino group which may be substituted, or a bond; and Y$^2$ represents a C$_{1-3}$ alkylene group or a bond.

13. A pharmaceutical composition comprising:
the compound or a salt thereof according to claim 1.

14. A method for treating infections caused by Gram-negative bacteria or drug-resistant Gram-negative bacteria, comprising:
administering the compound or a salt thereof according to claim 1.

* * * * *